(12) United States Patent
Moon et al.

(10) Patent No.: US 10,886,474 B2
(45) Date of Patent: *Jan. 5, 2021

(54) ORGANIC ELECTROLUMINESCENT COMPOUND, AND ORGANIC ELECTROLUMINESCENT MATERIAL AND ORGANIC ELECTROLUMINESCENT DEVICE COMPRISING THE SAME

(71) Applicant: Rohm and Haas Electronic Materials Korea Ltd., Cheonan (KR)

(72) Inventors: Doo-Hyeon Moon, Hwaseong (KR); Jeong-Eun Yang, Suwon (KR); Hee-Ryong Kang, Seoul (KR); Young-Mook Lim, Cheonan (KR); Ji-Song Jun, Hwaseong (KR); Hee-Choon Ahn, Seoul (KR); Jin-Ri Hong, Cheonan (KR); Su-Hyun Lee, Suwon (KR); Bitnari Kim, Cheonan (KR); Tae-Jin Lee, Seoul (KR)

(73) Assignee: Rohm and Haas Electronic Materials Korea Ltd, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/509,590

(22) PCT Filed: Sep. 25, 2015

(86) PCT No.: PCT/KR2015/010261
§ 371 (c)(1),
(2) Date: Mar. 8, 2017

(87) PCT Pub. No.: WO2016/048109
PCT Pub. Date: Mar. 31, 2016

(65) Prior Publication Data
US 2017/0294590 A1 Oct. 12, 2017

(30) Foreign Application Priority Data

Sep. 26, 2014 (KR) .................. 10-2014-0129455
Sep. 24, 2015 (KR) .................. 10-2015-0135889

(51) Int. Cl.
| | | |
|---|---|---|
| C07D 209/56 | (2006.01) |
| C07D 209/88 | (2006.01) |
| C07D 209/86 | (2006.01) |
| C07D 209/82 | (2006.01) |
| C07D 405/02 | (2006.01) |
| C07D 405/10 | (2006.01) |
| C07D 405/04 | (2006.01) |
| C07D 409/02 | (2006.01) |
| C07D 409/10 | (2006.01) |
| C09K 11/06 | (2006.01) |
| H01L 51/00 | (2006.01) |
| C07D 409/04 | (2006.01) |
| H01L 51/50 | (2006.01) |

(52) U.S. Cl.
CPC ........ *H01L 51/0072* (2013.01); *C07D 209/56* (2013.01); *C07D 209/82* (2013.01); *C07D 209/86* (2013.01); *C07D 209/88* (2013.01); *C07D 405/02* (2013.01); *C07D 405/04* (2013.01); *C07D 405/10* (2013.01); *C07D 409/02* (2013.01); *C07D 409/04* (2013.01); *C07D 409/10* (2013.01); *C09K 11/06* (2013.01); *H01L 51/0052* (2013.01); *H01L 51/0054* (2013.01); *H01L 51/0056* (2013.01); *H01L 51/0074* (2013.01); *C09K 2211/1007* (2013.01); *C09K 2211/1011* (2013.01); *C09K 2211/1014* (2013.01); *C09K 2211/1018* (2013.01); *C09K 2211/1029* (2013.01); *C09K 2211/1059* (2013.01); *C09K 2211/1088* (2013.01); *C09K 2211/1092* (2013.01); *H01L 51/0067* (2013.01); *H01L 51/0085* (2013.01); *H01L 51/5016* (2013.01); *H01L 51/5056* (2013.01); *H01L 2251/5384* (2013.01)

(58) Field of Classification Search
CPC .. C07D 209/56; C07D 209/88; C07D 209/86; C07D 209/82; C07D 405/02; C07D 405/10; C07D 405/04; C07D 409/02; C07D 409/10; C07D 409/04; C09K 11/06
See application file for complete search history.

(56) References Cited

U.S. PATENT DOCUMENTS

| | | |
|---|---|---|
| 10,186,669 B2 | 1/2019 | Kang et al. |
| 2003/0186077 A1 | 10/2003 | Chen |
| 2008/0122344 A1 | 5/2008 | Shin et al. |
| 2014/0100367 A1 | 4/2014 | Yoon et al. |
| 2017/0077423 A1* | 3/2017 | Ahn .............. H01L 51/0072 |
| 2017/0207396 A1* | 7/2017 | Park .............. H01L 51/0085 |

(Continued)

FOREIGN PATENT DOCUMENTS

| | | |
|---|---|---|
| KR | 2010-0108924 A | 10/2010 |
| KR | 2012-0116272 A | 10/2012 |

(Continued)

OTHER PUBLICATIONS

Lee et al., 2012, caplus an 2012:176846.*

(Continued)

*Primary Examiner* — Sun Jae Yoo
(74) *Attorney, Agent, or Firm* — S. Matthew Cairns

(57) ABSTRACT

The present disclosure relates to an organic electroluminescent compound, and an organic electroluminescent material and an organic electroluminescent device comprising the same. The organic electroluminescent compound of the present disclosure has excellent color purity, solubility, and thermal stability. By comprising the organic electroluminescent compound and the organic electroluminescent material of the present disclosure, an organic electroluminescent device showing low driving voltage, excellent current and power efficiencies, and significantly improved lifespan can be provided.

4 Claims, No Drawings

(56) References Cited

U.S. PATENT DOCUMENTS

2017/0256722 A1 9/2017 Shim et al.
2018/0033975 A1* 2/2018 Kim .................. C07D 403/10

FOREIGN PATENT DOCUMENTS

| KR | 2013-0106255 A | 9/2013 |
| KR | 2014-0015259 A | 2/2014 |
| KR | 2014-0128892 A | 11/2014 |
| KR | 2015-0004099 A | 1/2015 |
| KR | 2015-0115226 A | 10/2015 |
| WO | 2012/011756 A1 | 1/2012 |
| WO | 2012/141499 A1 | 10/2012 |
| WO | 2012/165832 A1 | 12/2012 |
| WO | 2012/169821 A1 | 12/2012 |
| WO | 2014/129764 A1 | 8/2014 |
| WO | 2015/111888 A1 | 7/2015 |
| WO | 2015/126090 A1 | 8/2015 |
| WO | 2015/130069 A1 | 9/2015 |

OTHER PUBLICATIONS

Kwon et al., 2014, caplus an 2014:1319590.*
Yoon et al., 2012, caplus an 2012:1826426.*
Hanaki et al., 2015, caplus an 2015:1369822.*
Lee et al. 2, caplus an 2012:176846, 2012.*
Shin et al., caplus an 2014:1891645, 2014.*
Shin et al. 2, caplus an 2014:1891644, 2014.*
Lee et al 3, caplus an 2012:1875905, 2012.*
Park et al., 2014, caplus an 2016:149911.*
Lee et al. 2, 2015, caplus an 2016:1316701.*
Lee et al., 2015, caplus an 2016:1338351.*
Kim et al., 2015, caplus an 2016:1533875.*
Search Report for Chinese application No. 201580050211.9; dated Sep. 25, 2015.

* cited by examiner

ORGANIC ELECTROLUMINESCENT COMPOUND, AND ORGANIC ELECTROLUMINESCENT MATERIAL AND ORGANIC ELECTROLUMINESCENT DEVICE COMPRISING THE SAME

TECHNICAL FIELD

The present disclosure relates to an organic electroluminescent compound, and an organic electroluminescent material and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

The most important factor determining luminous efficiency in the organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, phosphorescent light-emitting materials have been widely researched. Iridium(III) complexes have been widely known as phosphorescent materials, including bis(2-(2'-benzothienyl)-pyridinato-N,C-3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red-, green-, and blue-emitting materials, respectively.

At present, 4,4'-N,N'-dicarbazol-biphenyl (CBP) is the most widely known host material for phosphorescent materials. Recently, Pioneer (Japan) et al., developed a high performance organic EL device using bathocuproine (BCP) and aluminum(III) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum. (2) The power efficiency of the organic EL device is given by [(π/voltage)× current efficiency], and the power efficiency is inversely proportional to the voltage. Although the organic EL device comprising phosphorescent host materials provides higher current efficiency (cd/A) than one comprising fluorescent materials, a significantly high driving voltage is necessary. Thus, there is no merit in terms of power efficiency (lm/W). (3) Furthermore, the operational lifespan of the organic EL device is short, and luminous efficiency is still required to be improved.

Korean Patent Application Laying-open No. 10-2010-0108924 and Korean Patent Application Laying-open No. 10-2014-0015259 disclose a compound having a dibenzocarbazole backbone. However, they fail to specifically disclose a compound having a structure in which a carbazole is connected to a dibenzocarbazole backbone.

DISCLOSURE OF INVENTION

Technical Problem

The objective of the present disclosure is to provide an organic electroluminescent compound, which can provide an organic electroluminescent device showing long lifespan, low driving voltage, and excellence in luminous efficiency such as current efficiency and power efficiency, color purity, solubility, and thermal stability. Another objective of the present disclosure is to provide an organic electroluminescent material and an organic electroluminescent device comprising the organic electroluminescent compound.

Solution to Problems

The present inventors found that the above objectives can be achieved by an organic electroluminescent compound represented by the following formula 1.

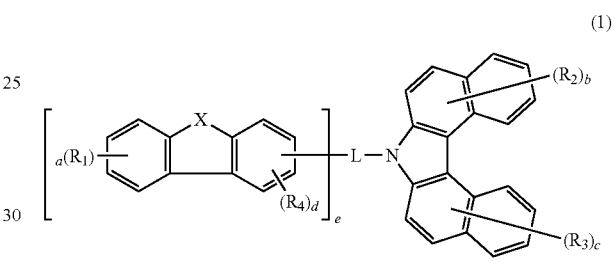

(1)

wherein

L represents a single bond, or a substituted or unsubstituted (C6-C30)arylene;

X represents —O—, —S—, —CR$_{11}$R$_{12}$—, or —NR$_{13}$—;

R$_{11}$ and R$_{12}$, each independently, represent a substituted or unsubstituted (C1-C30)alkyl, a substituted or unsubstituted (C6-C30)aryl, or a substituted or unsubstituted 5- to 30-membered heteroaryl, or may be linked to an adjacent substituent(s) to form a substituted or unsubstituted, (C3-C30), mono- or polycyclic, alicyclic or aromatic ring, whose carbon atom(s) may be replaced with at least one hetero atom selected from nitrogen, oxygen, and sulfur;

R$_{13}$ represents a substituted or unsubstituted (C6-C30) aryl, or a substituted or unsubstituted 5- to 30-membered heteroaryl;

R$_1$ to R$_4$, each independently, represent hydrogen, deuterium, a halogen, a cyano, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

R$_1$ and R$_4$, each independently, may be linked to an adjacent substituent(s) to form a substituted or unsubstituted, (C3-C30), mono- or polycyclic, alicyclic or aromatic ring, whose carbon atom(s) may be replaced with at least one hetero atom selected from nitrogen, oxygen and sulfur;

a represents an integer of 0 to 4; where a is 2 or more, each of $R_1$ may be the same or different;

b and c, each independently, represent an integer of 0 to 6; where b or c is 2 or more, each of $R_2$ or $R_3$ may be the same or different;

d represents an integer of 0 to 3; where d is 2 or more, each of $R_4$ may be the same or different;

e represents 0 or 1; provided that where e is 0, b+c=1 or more, and at least one of $R_2$ and $R_3$ represents a substituted or unsubstituted 5- to 30-membered heteroaryl; and the heteroaryl contains at least one hetero atom selected from B, N, O, S, Si, and P.

Advantageous Effects of Invention

The organic electroluminescent compound of the present disclosure has good color purity, solubility, and thermal stability. By comprising the organic electroluminescent compound or an organic electroluminescent material comprising the compound of the present disclosure, an organic electroluminescent device showing low driving voltage, excellent current and power efficiencies, and significantly improved lifespan can be provided.

MODE FOR THE INVENTION

Hereinafter, the present disclosure will be described in detail. However, the following description is intended to explain the invention, and is not meant in any way to restrict the scope of the invention.

The present disclosure provides the organic electroluminescent compound represented by formula 1 above, an organic electroluminescent material comprising the organic electroluminescent compound, and an organic electroluminescent device comprising the compound.

The details of the organic electroluminescent compound of formula 1 are as follows.

Herein, "alkyl" includes methyl, ethyl, n-propyl, isopropyl, n-butyl, isobutyl, tert-butyl, etc. "Cycloalkyl" includes cyclopropyl, cyclobutyl, cyclopentyl, cyclohexyl, etc. Furthermore, "aryl(ene)" indicates a monocyclic or fused ring radical derived from an aromatic hydrocarbon, and includes a spiro compound in which two rings are connected through one atom. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "3- to 30-membered heteroaryl(ene)" indicates an aryl group having 3 to 30 ring backbone atoms including at least one, preferably 1 to 4, hetero atom selected from the group consisting of B, N, O, S, Si, and P, preferably O, S, and N; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, dihydroacridinyl, etc. Furthermore, "halogen" includes F, Cl, Br, and I.

Herein, "substituted" in the expression, "substituted or unsubstituted," means that a hydrogen atom in a certain functional group is replaced with another atom or group, i.e. a substituent. In the present disclosure, the substituents for the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, and the substituted alkylarylamino in L, $R_1$ to $R_4$, and $R_{11}$ to $R_{13}$, each independently, may be at least one selected from the group consisting of deuterium, a halogen, a cyano, a carboxy, a nitro, a hydroxy, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl; and preferably at least one selected from the group consisting of deuterium, a halogen, a (C1-C20)alkyl, a halo(C1-C20)alkyl, a 6- to 20-membered heteroaryl unsubstituted or substituted with a (C6-C20)aryl, a (C6-C20)aryl unsubstituted or substituted with a 6- to 20-membered heteroaryl, a tri(C6-C20)arylsilyl, a di(C1-C20)alkyl(C6-C20)arylsilyl, a (C1-C20)alkyldi(C6-C20)arylsilyl, a mono- or di-(C6-C20)arylamino, a (C1-C20)alkyl(C6-C20)arylamino, a (C6-C20)aryl(C1-C20)alkyl, and a (C1-C20)alkyl(C6-C20)aryl.

Preferably, L may represent a single bond or a substituted or unsubstituted (C6-C20)arylene. Specifically, L may represent a single bond, a substituted or unsubstituted phenylene, a substituted or unsubstituted naphthylene, a substituted or unsubstituted biphenylene, a substituted or unsubstituted anthracenylene, a substituted or unsubstituted phenanthrenylene, a substituted or unsubstituted terphenylene, a substituted or unsubstituted tetracenylene, a substituted or unsubstituted chrysenylene, a substituted or unsubstituted pyrenylene, a substituted or unsubstituted triphenylenylene, or a substituted or unsubstituted fluoranthenylene. For the substituted arylene of L, the substituent may be preferably, a (C1-C20)alkyl, a (C6-C20)aryl unsubstituted or substituted with a 6- to 20-membered heteroaryl, or a 6- to 20-membered heteroaryl unsubstituted or substituted with a (C6-C20)aryl; and more preferably, a (C1-C6)alkyl, phenyl, naphthyl, biphenyl, carbazolyl unsubstituted or substituted with phenyl, or phenyl substituted with carbazolyl unsubstituted or substituted with phenyl.

X represents —O—, —S—, —$CR_{11}R_{12}$—, or —$NR_{13}$—. X may represent specifically, —O—, —S—, or —$NR_{13}$—, and more specifically —$NR_{13}$—.

Preferably, $R_{11}$ and $R_{12}$, each independently, may represent a substituted or unsubstituted (C1-C20)alkyl, or a substituted or unsubstituted (C6-C20)aryl, or may be linked to each other to form a substituted or unsubstituted (C3-

C20), mono- or polycyclic aromatic ring. Specifically, $R_{11}$ and $R_{12}$, each independently, may represent a substituted or unsubstituted (C1-C10)alkyl, a substituted or unsubstituted phenyl, a substituted or unsubstituted biphenyl, or a substituted or unsubstituted naphthyl, or may be linked to each other to form spirobifluorenyl along with the ring containing X. Preferably, $R_{11}$ and $R_{12}$ may be unsubstituted groups.

Preferably, $R_{13}$ may represent a substituted or unsubstituted (C6-C20)aryl. Specifically, $R_{13}$ may represent a substituted or unsubstituted phenyl, a substituted or unsubstituted naphthyl, a substituted or unsubstituted biphenyl, a substituted or unsubstituted phenyl-naphthyl, a substituted or unsubstituted naphthyl-phenyl, a substituted or unsubstituted anthracenyl, a substituted or unsubstituted phenanthrenyl, a substituted or unsubstituted terphenyl, a substituted or unsubstituted tetracenyl, a substituted or unsubstituted chrysenyl, a substituted or unsubstituted pyrenyl, a substituted or unsubstituted triphenylenyl, or a substituted or unsubstituted fluoranthenyl. Preferably, $R_{13}$ may be an unsubstituted group.

Preferably, $R_1$ and $R_4$, each independently, may represent hydrogen, a substituted or unsubstituted (C1-C20)alkyl, a substituted or unsubstituted (C6-C20)aryl, or a substituted or unsubstituted 5- to 20-membered heteroaryl, or may be linked to an adjacent substituent(s) to form a substituted or unsubstituted (C3-C20), mono- or polycyclic aromatic ring. Specifically, $R_1$ and $R_4$, each independently, may represent hydrogen, a substituted or unsubstituted phenyl, a substituted or unsubstituted biphenyl, or a substituted or unsubstituted naphthyl, or may be linked to an adjacent substituent(s) to form a substituted or unsubstituted benzene ring or a substituted or unsubstituted naphthalene ring. Preferably, $R_1$ and $R_4$ may be unsubstituted groups.

Preferably, $R_2$ and $R_3$, each independently, may represent hydrogen, a substituted or unsubstituted (C1-C20)alkyl, a substituted or unsubstituted (C6-C20)aryl, or a substituted or unsubstituted 5- to 20-membered heteroaryl, provided that where e is 0, b+c=1 or more, and at least one of $R_2$ and $R_3$ may represent a substituted or unsubstituted 13- to 25-membered heteroaryl. Specifically, $R_2$ and $R_3$, each independently, may represent hydrogen, a substituted or unsubstituted phenyl, a substituted or unsubstituted naphthyl, a substituted or unsubstituted biphenyl, a substituted or unsubstituted dibenzofuranyl, a substituted or unsubstituted dibenzothiophenyl, a substituted or unsubstituted carbazolyl, a substituted or unsubstituted benzocarbazolyl, or a substituted or unsubstituted dibenzocarbazolyl, provided that where e is 0, b+c=1 or more, and at least one of $R_2$ and $R_3$ may represent a substituted or unsubstituted dibenzofuranyl, a substituted or unsubstituted dibenzothiophenyl, a substituted or unsubstituted carbazolyl, a substituted or unsubstituted benzocarbazolyl, or a substituted or unsubstituted dibenzocarbazolyl. Specifically, $R_2$ and $R_3$, each independently, may be selected from hydrogen and the following formulae 2-1 to 2-3. In particular, where e is 0, b+c=1 or more, and at least one of $R_2$ and $R_3$ may be preferably selected from the following formulae 2-1 to 2-3.

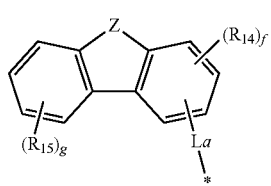

(2-1)

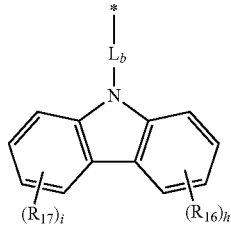

(2-2)

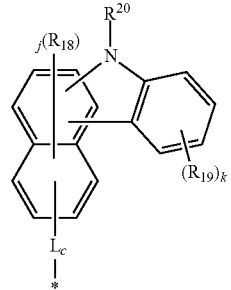

(2-3)

wherein $L_a$, $L_b$, and $L_c$, each independently, represent a single bond, or a substituted or unsubstituted (C6-C30)arylene;

Z represents —S—, —O—, —NR$_{23}$—, or —CR$_{24}$R$_{25}$—;

$R_{20}$, and $R_{23}$ to $R_{25}$, each independently, represent a substituted or unsubstituted (C1-C30)alkyl, a substituted or unsubstituted (C6-C30)aryl, or a substituted or unsubstituted 3- to 30-membered heteroaryl, or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur;

$R_{14}$ to $R_{19}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur;

f represents an integer of 0 to 3; g, h, i, and k, each independently, represent an integer of 0 to 4; j represents an integer of 0 to 5; where f, g, h, i, j, or k is 2 or more, each of $R_{14}$, $R_{15}$, $R_{16}$, $R_{17}$, $R_{18}$, or $R_{19}$ may be the same or different;

the heteroaryl contains at least one hetero atom selected from N, O, and S; and

* represents a bonding site.

Specifically, $L_a$ to $L_c$, each independently, may represent a single bond, or a substituted or unsubstituted (C6-C18) arylene. More specifically, $L_a$ to $L_c$, each independently, may represent a single bond, a substituted or unsubstituted phenylene, a substituted or unsubstituted biphenylene, or a substituted or unsubstituted naphthylene.

Specifically, Z may represent —NR$_{23}$—.

Specifically, R$_{20}$ and R$_{23}$ to R$_{25}$, each independently, may represent a substituted or unsubstituted (C1-C10)alkyl, or a substituted or unsubstituted (C6-C18)aryl, or may be linked to an adjacent substituent(s) to form a substituted or unsubstituted (C3-C30), mono- or polycyclic aromatic ring. More specifically, R$_{20}$ and R$_{23}$ to R$_{25}$, each independently, may represent a substituted or unsubstituted (C1-C6)alkyl, a substituted or unsubstituted phenyl, a substituted or unsubstituted biphenyl, or a substituted or unsubstituted naphthyl.

Specifically, R$_{14}$ to R$_{19}$, each independently, may represent hydrogen, a substituted or unsubstituted (C1-C10)alkyl, or a substituted or unsubstituted (C6-C18)aryl, or may be linked to an adjacent substituent(s) to form a substituted or unsubstituted (C3-C30) mono- or polycyclic aromatic ring, whose carbon atom(s) may be replaced with one to three hetero atom(s) selected from nitrogen, oxygen, and sulfur. More specifically, R$_{14}$ to R$_{19}$, each independently, may represent hydrogen, a substituted or unsubstituted phenyl, a substituted or unsubstituted biphenyl, or a substituted or unsubstituted naphthyl, or may be linked to an adjacent substituent(s) to form a benzene ring or a naphthalene ring.

According to another embodiment of the present disclosure, L may represent a single bond, or a substituted or unsubstituted (C6-C20)arylene; X may represent —O—, —S—, —CR$_{11}$R$_{12}$—, or —NR$_{13}$—; R$_{11}$ and R$_{12}$, each independently, may represent a substituted or unsubstituted (C1-C20)alkyl, or a substituted or unsubstituted (C6-C20)aryl, or may be linked to each other to form a substituted or unsubstituted (C3-C20), mono- or polycyclic aromatic ring; R$_{13}$ may represent a substituted or unsubstituted (C6-C20)aryl; R$_1$ and R$_4$, each independently, may represent hydrogen, a substituted or unsubstituted (C1-C20)alkyl, a substituted or unsubstituted (C6-C20)aryl, or a substituted or unsubstituted 5- to 20-membered heteroaryl, or may be linked to an adjacent substituent(s) to form a substituted or unsubstituted, (C3-C20), mono- or polycyclic aromatic ring; R$_2$ and R$_3$, each independently, may represent hydrogen, a substituted or unsubstituted (C1-C20)alkyl, a substituted or unsubstituted (C6-C20)aryl, or a substituted or unsubstituted 5- to 20-membered heteroaryl; provided that where e is 0, b+c=1 or more, and at least one of R$_2$ and R$_3$ may represent a substituted or unsubstituted 13- to 25-membered heteroaryl; and the heteroaryl may contain at least one hetero atom selected from N, O, and S.

According to another embodiment of the present disclosure, e may represent 1; X may represent —O—, —S—, or —NR$_{13}$—; R$_{13}$ may represent a substituted or unsubstituted phenyl, a substituted or unsubstituted naphthyl, a substituted or unsubstituted biphenyl, a substituted or unsubstituted phenyl-naphthyl, a substituted or unsubstituted naphthyl-phenyl, a substituted or unsubstituted anthracenyl, a substituted or unsubstituted phenanthrenyl, a substituted or unsubstituted terphenyl, a substituted or unsubstituted tetracenyl, a substituted or unsubstituted chrysenyl, a substituted or unsubstituted pyrenyl, a substituted or unsubstituted triphenylenyl, or a substituted or unsubstituted fluoranthenyl; and R$_1$ and R$_4$, each independently, may represent hydrogen, a substituted or unsubstituted phenyl, a substituted or unsubstituted biphenyl, or a substituted or unsubstituted naphthyl, or may be linked to an adjacent substituent(s) to form a substituted or unsubstituted benzene or naphthalene ring.

According to another embodiment of the present disclosure, e may represent 0; L may represent a substituted or unsubstituted (C6-C20)arylene; b+c=1 or more; and at least one of R$_2$ and R$_3$ may be selected from formulae 2-1 to 2-3.

More specifically, the organic electroluminescent compound of formula 1 includes the following, but is not limited thereto:

H-1

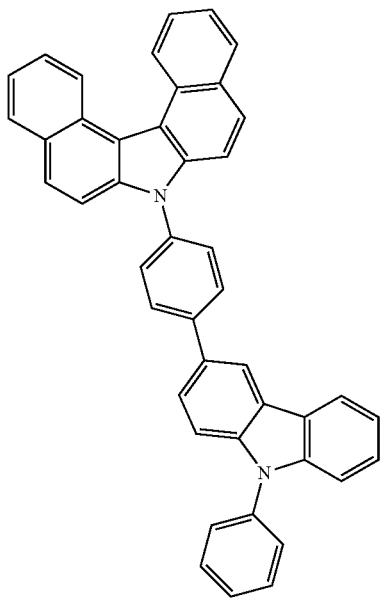

H-2

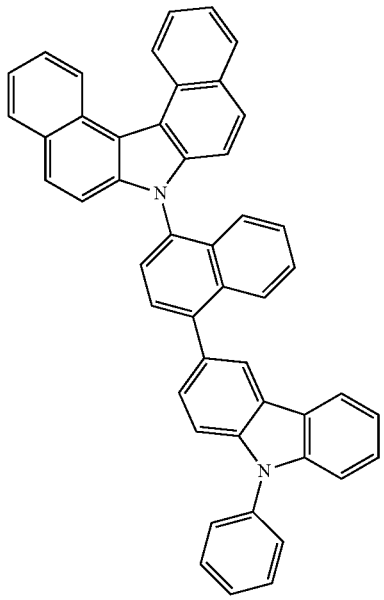

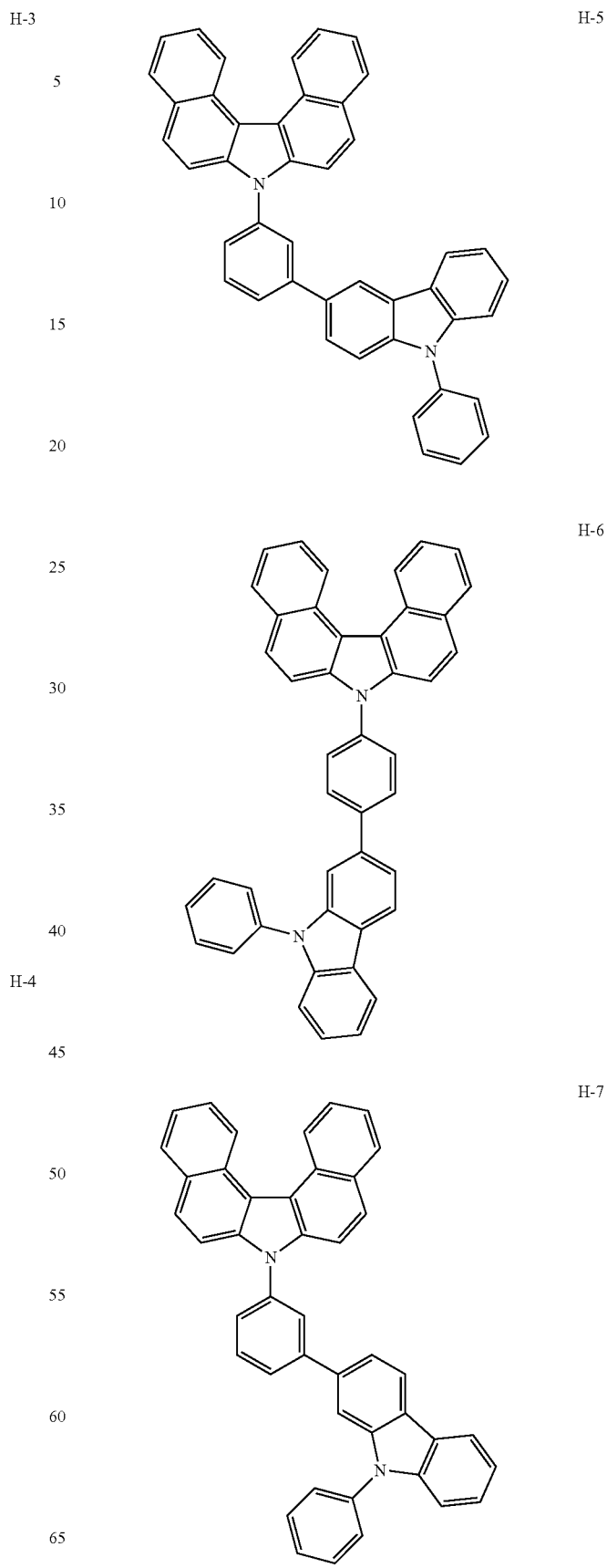

H-8
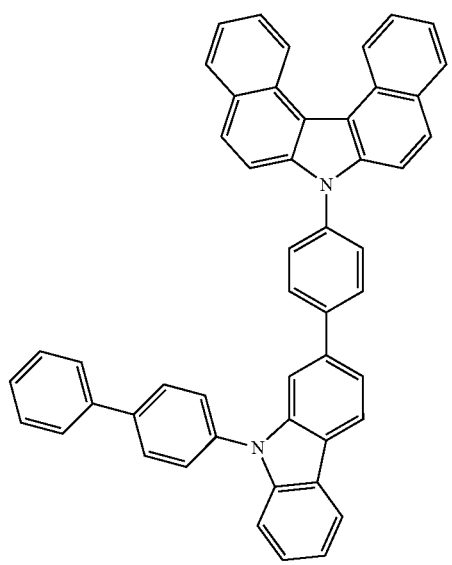
H-9
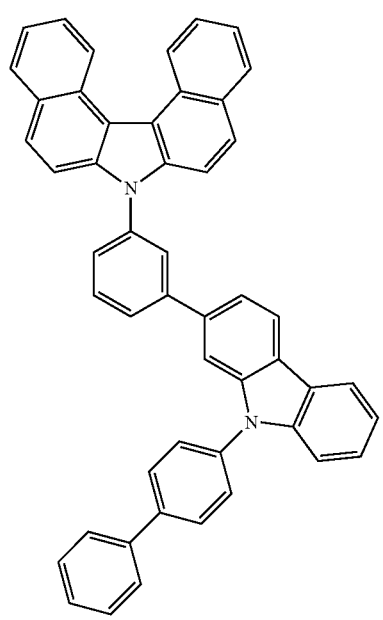
H-10
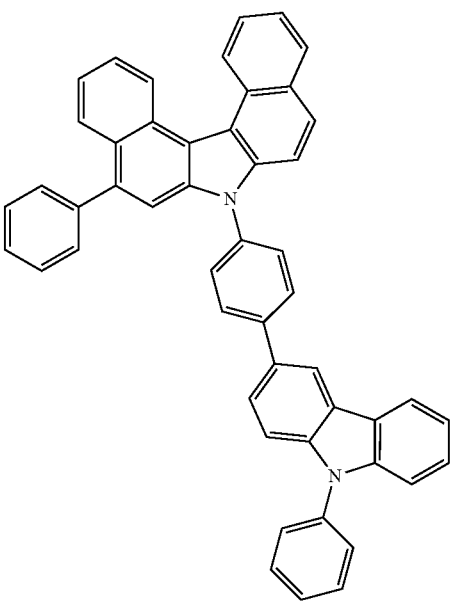
H-11
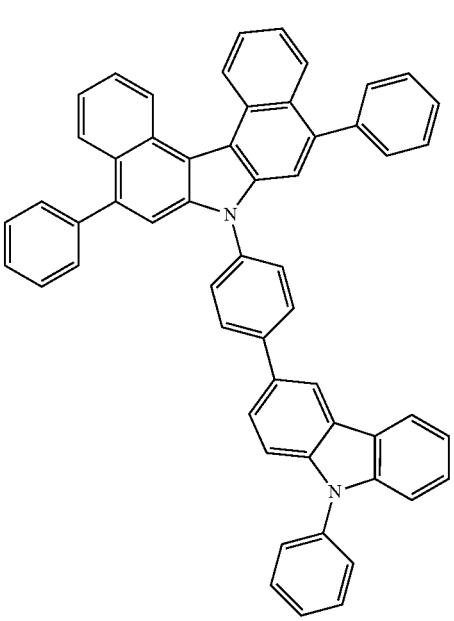

H-12
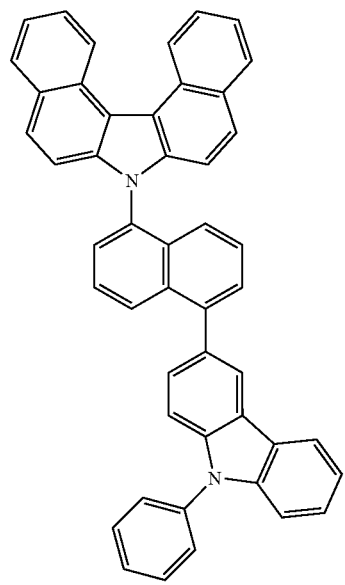
H-13
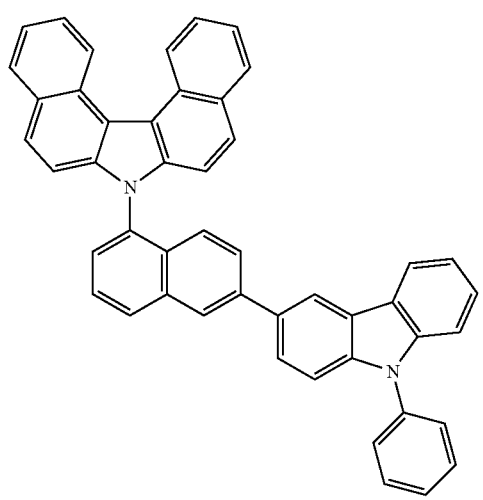
H-14
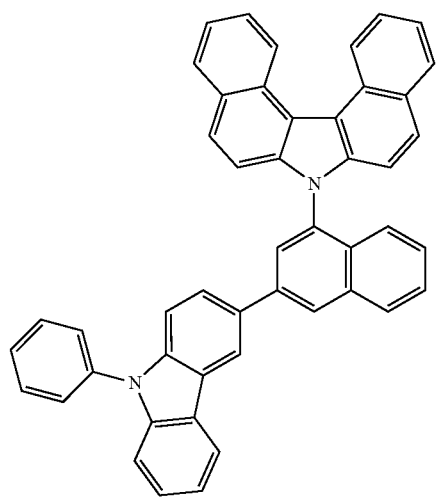
H-15
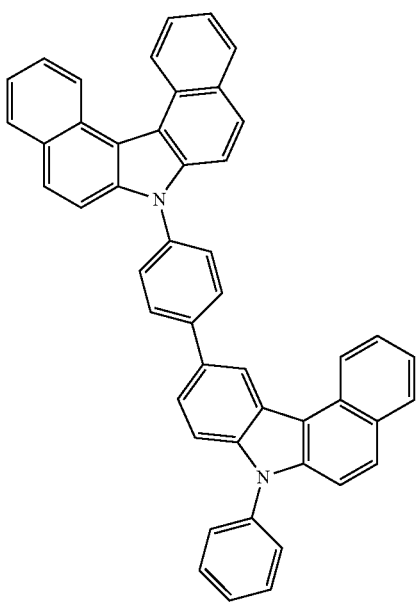
H-16
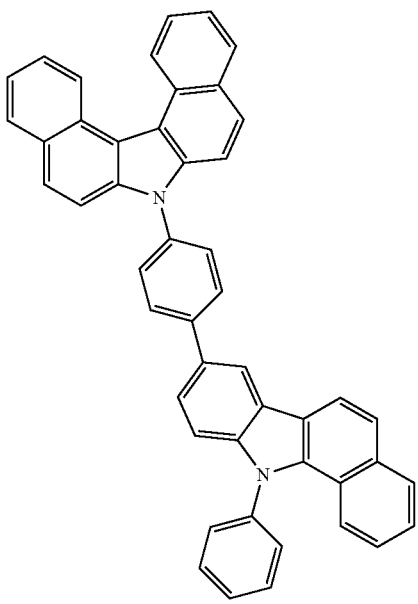

H-17
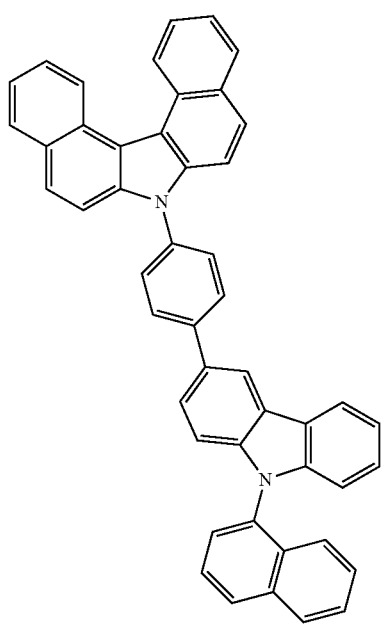
H-18
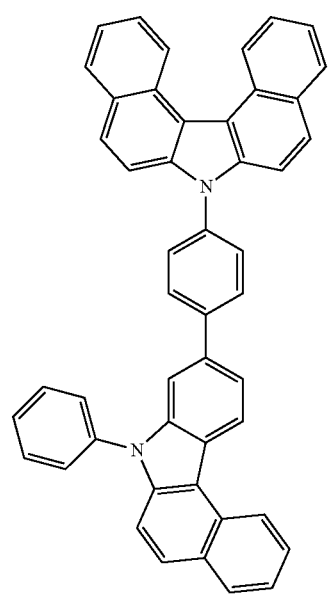
H-19
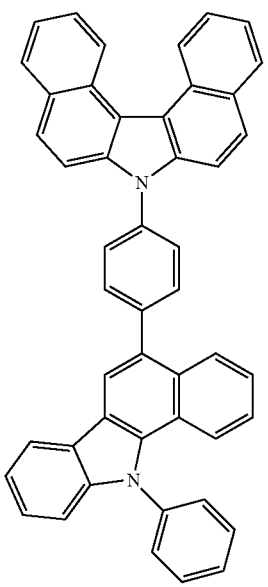
H-20
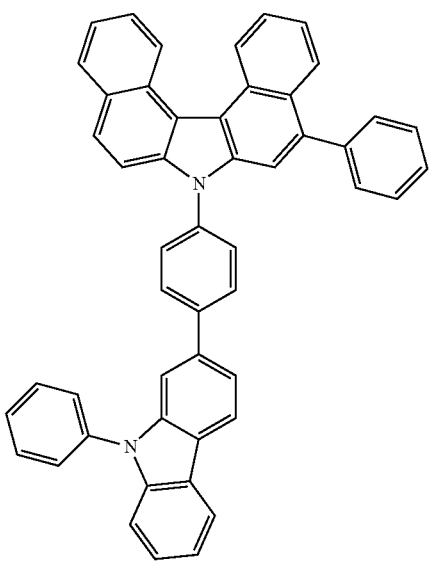

H-21
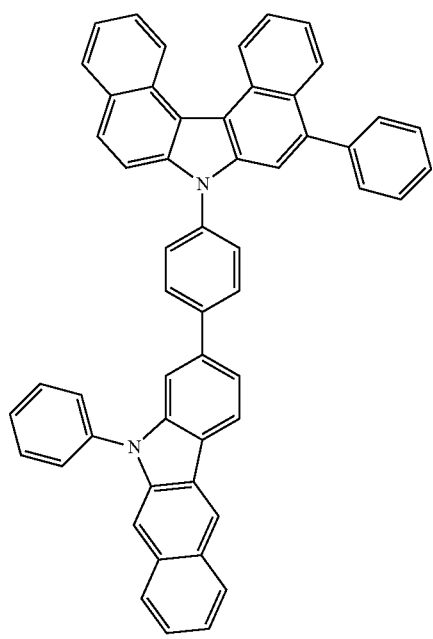
H-23
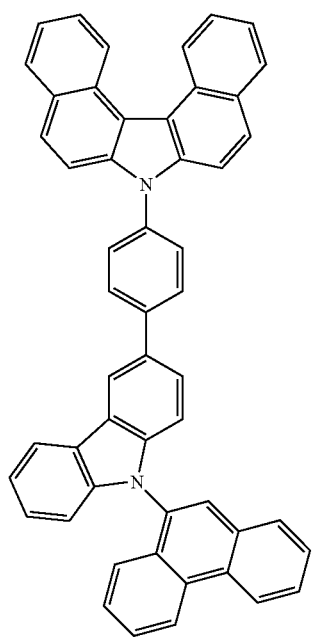
H-22
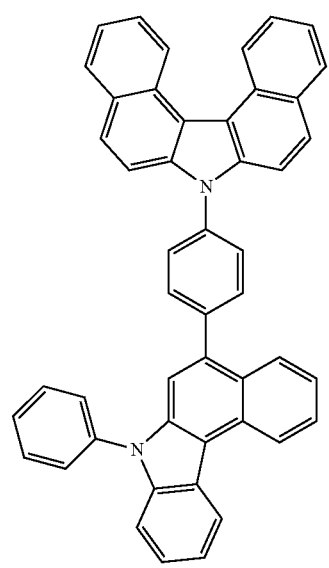
H-24
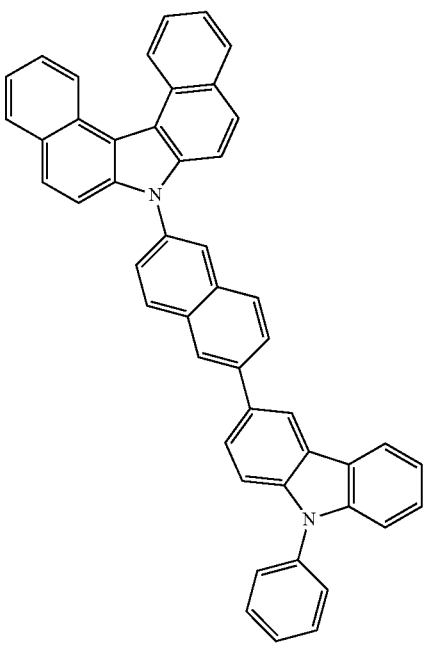

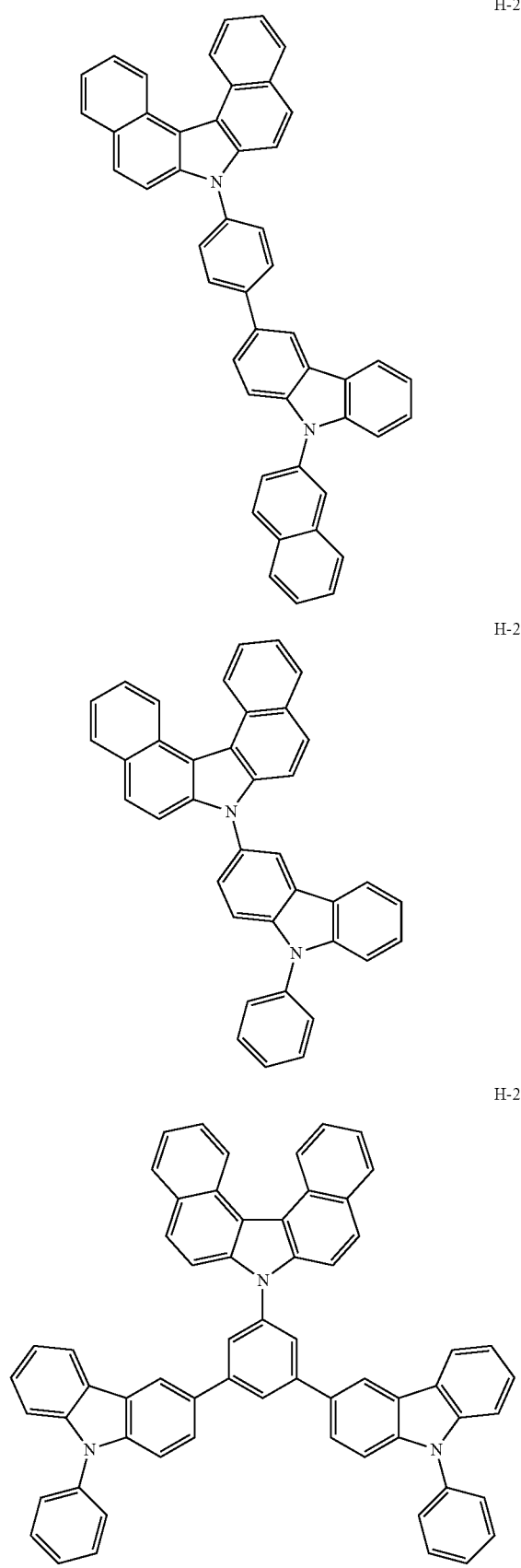
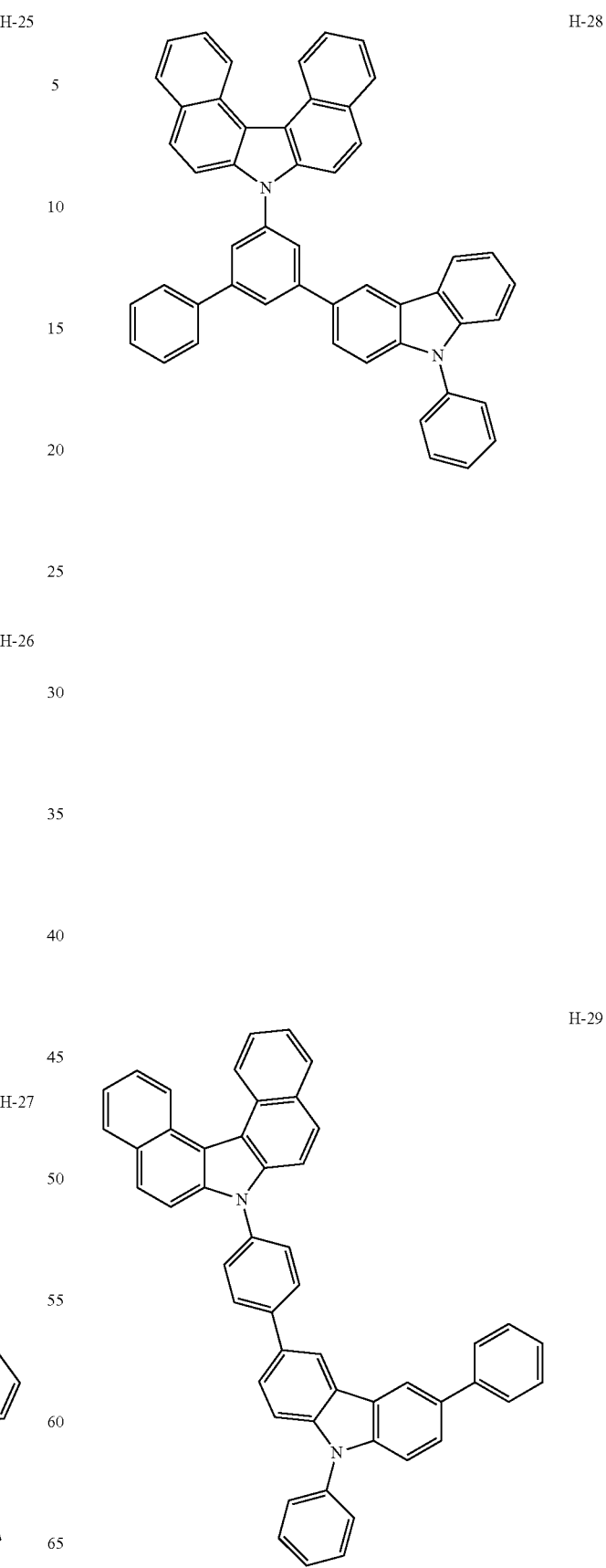

H-30
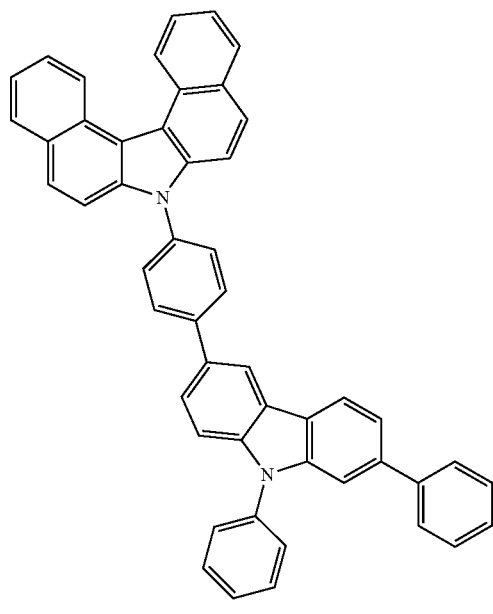
H-33
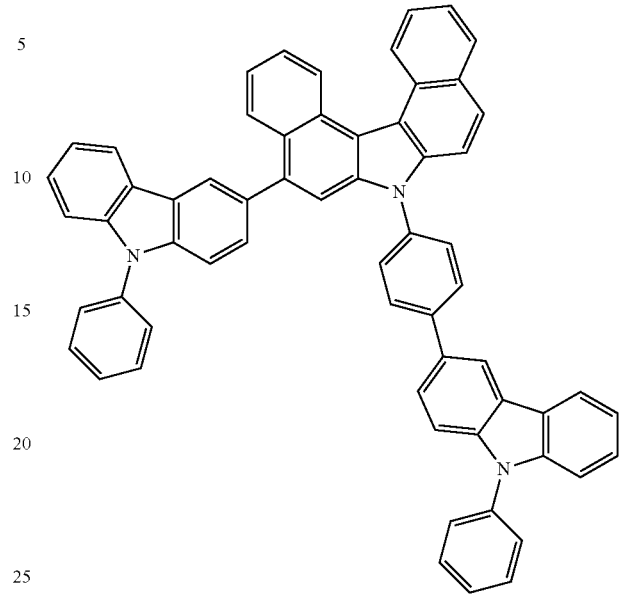
H-31
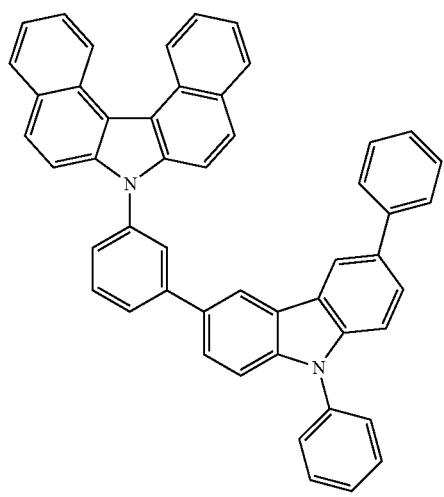
H-34
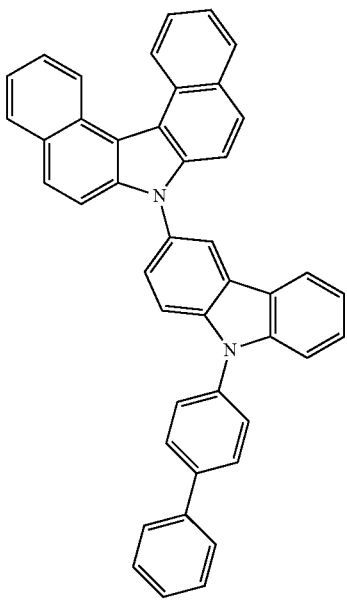
H-32
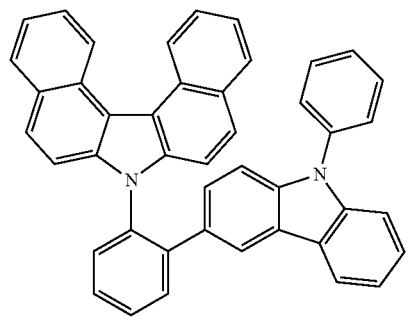

H-35
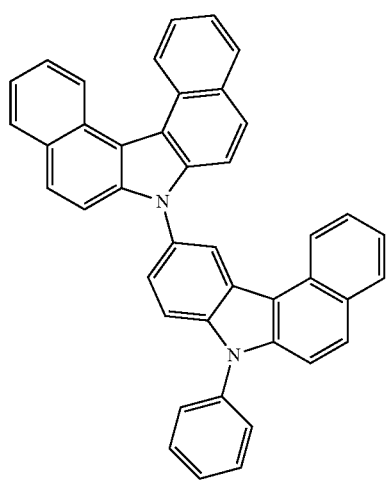
H-38
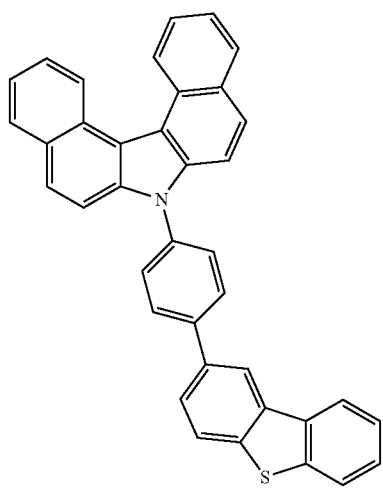
H-36
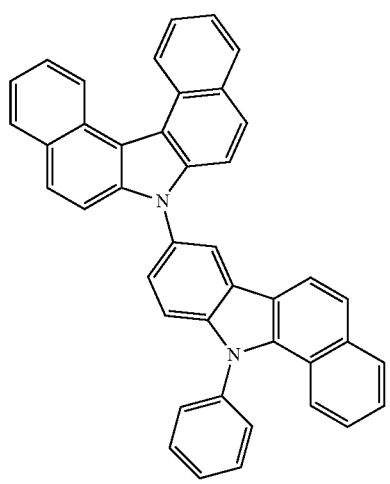
H-39
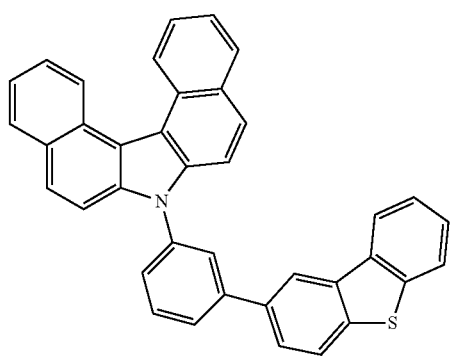
H-37
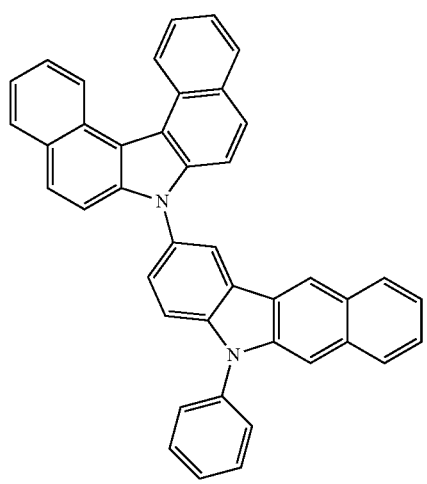
H-40
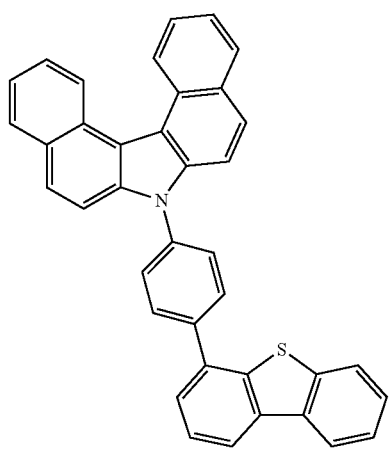

H-41
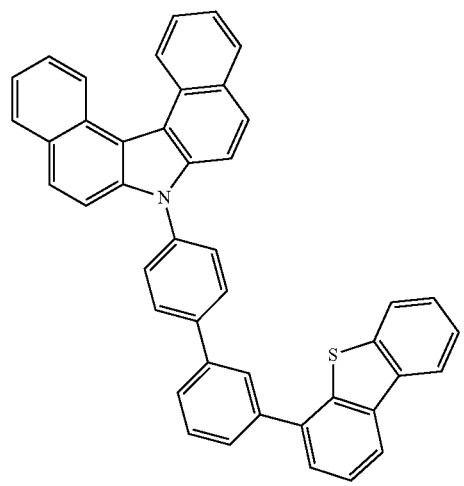
H-42
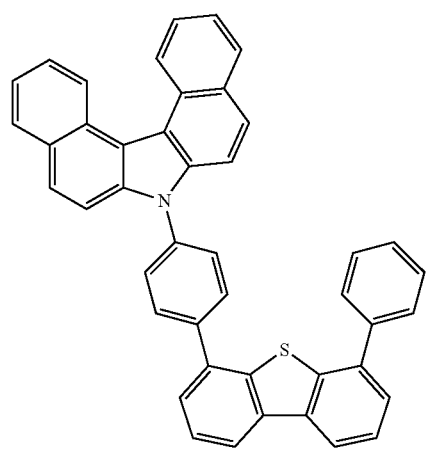
H-43
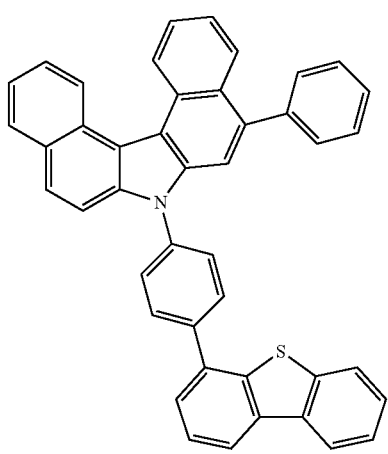
H-44
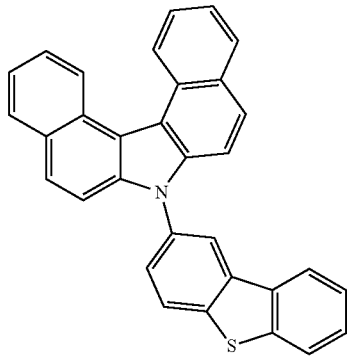
H-45
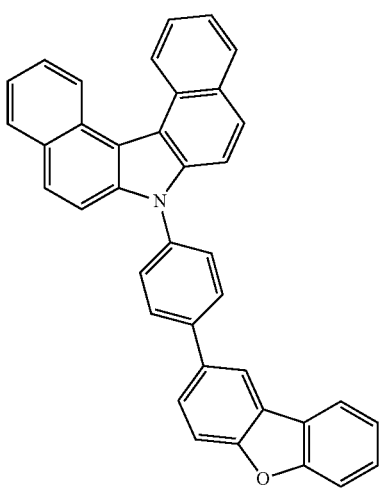
H-46
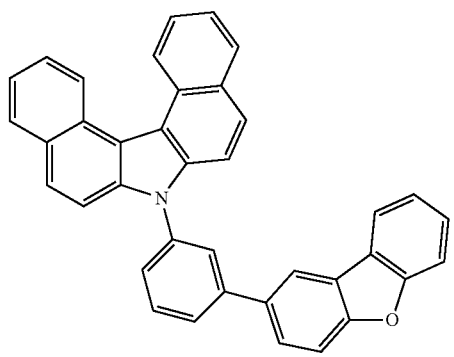
H-47
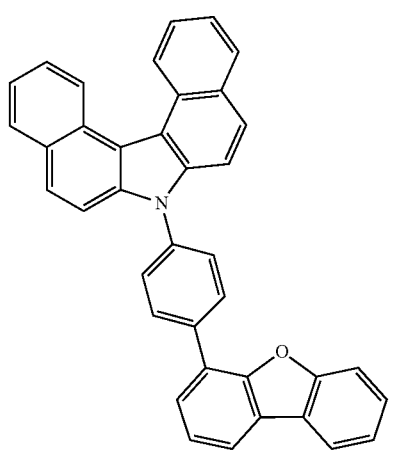

H-48
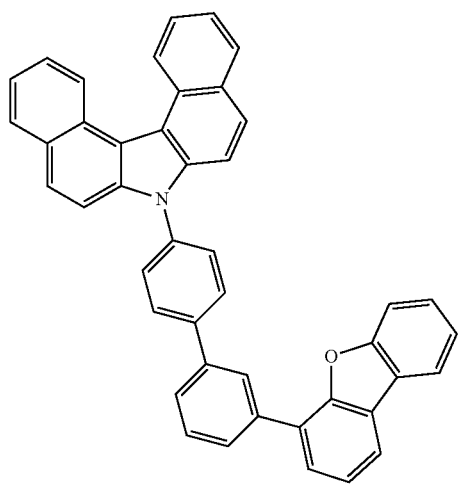
H-49
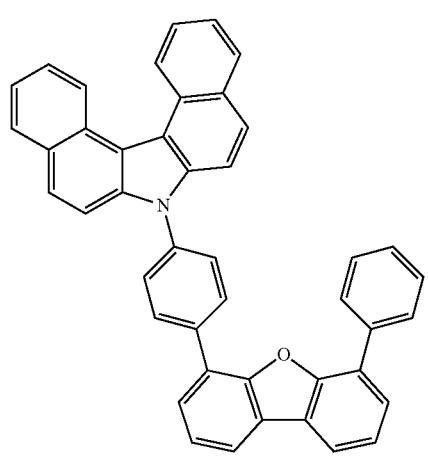
H-50
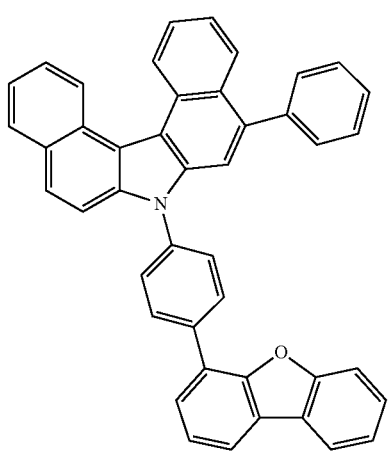
H-51
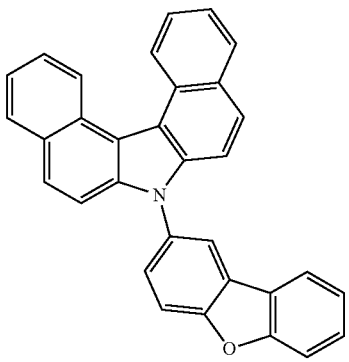
H-52
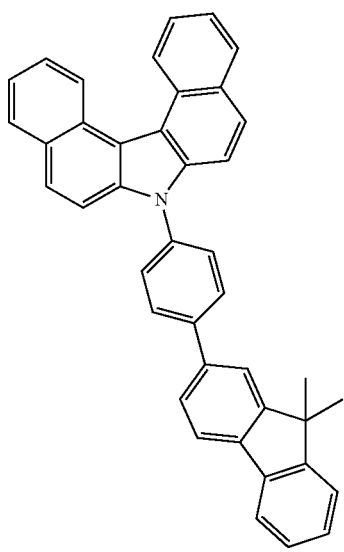
H-53
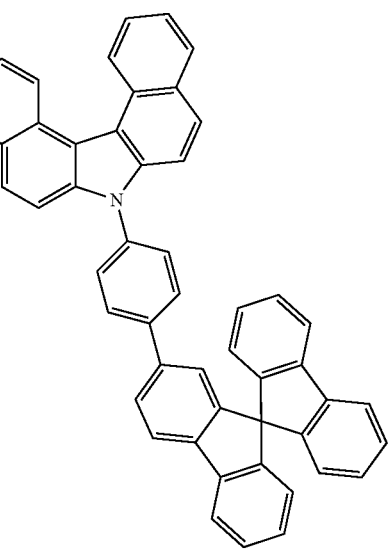

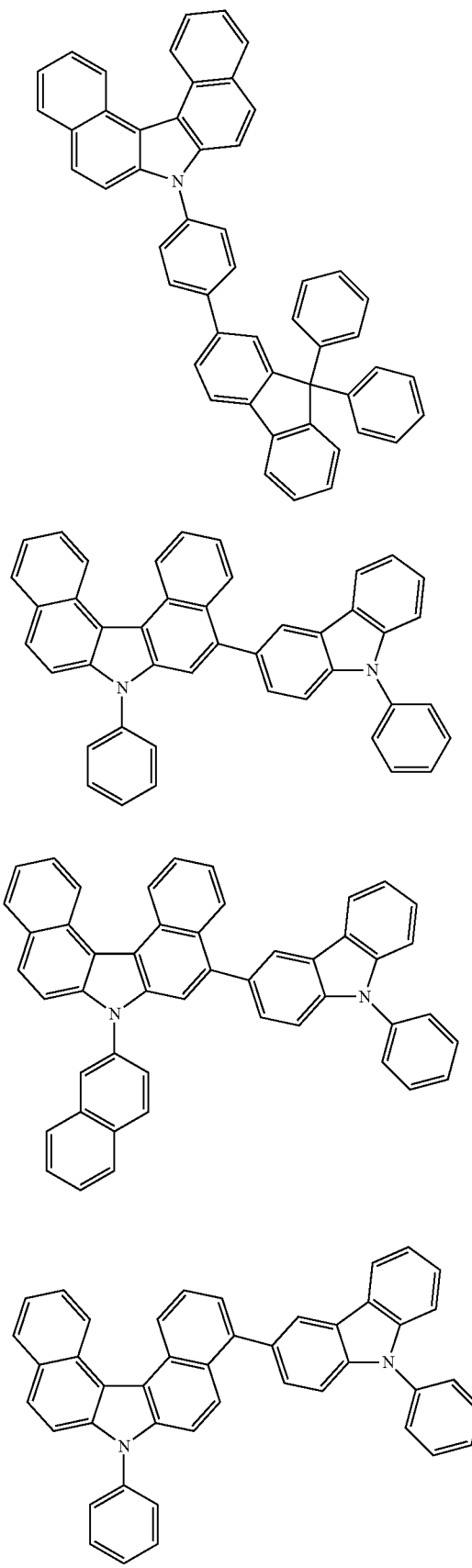
H-54
H-55
H-56
H-57
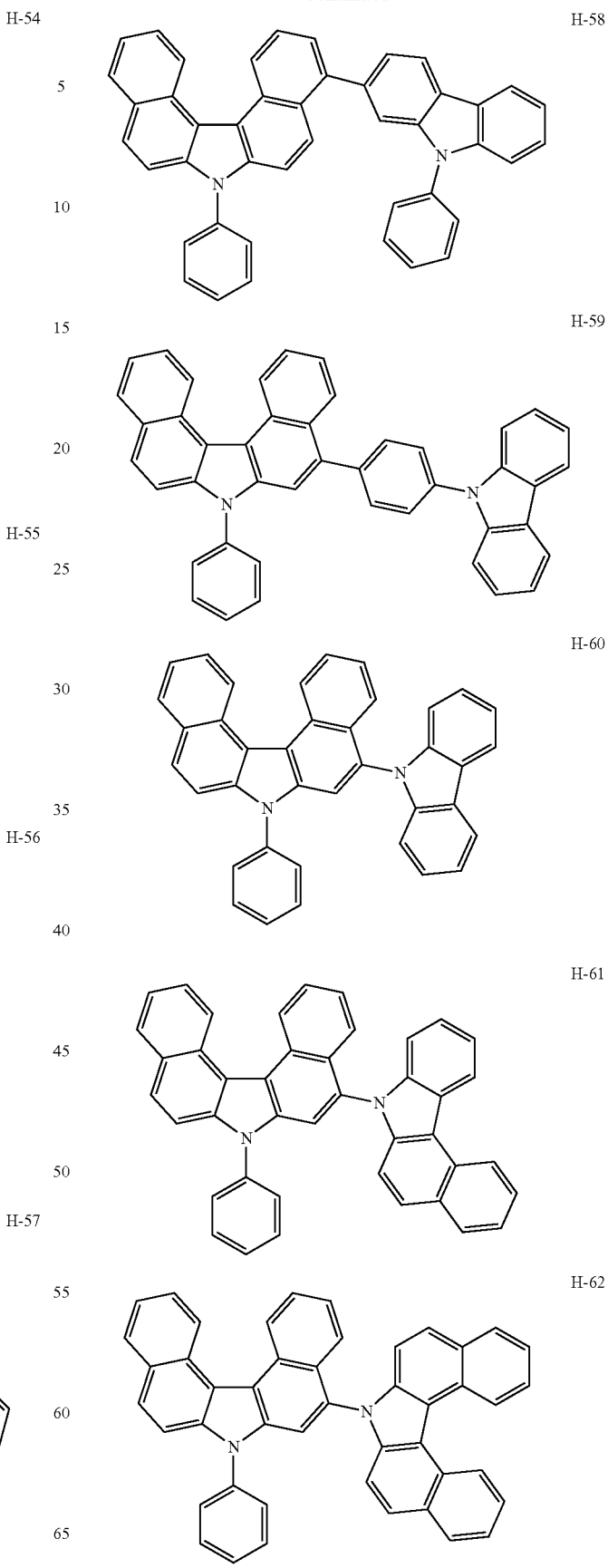
H-58
H-59
H-60
H-61
H-62

H-63
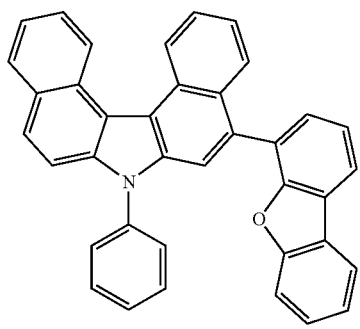
H-64
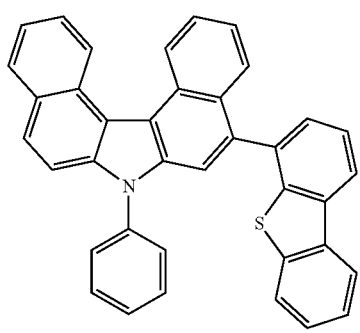
H-65
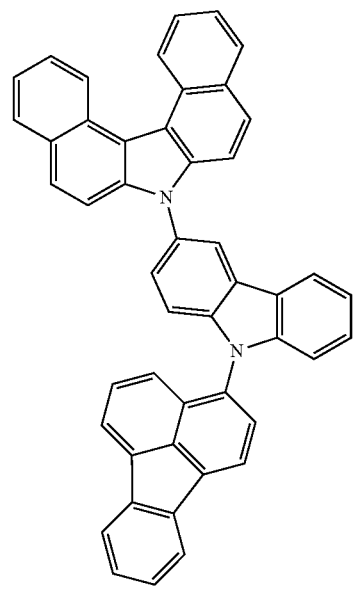
H-66
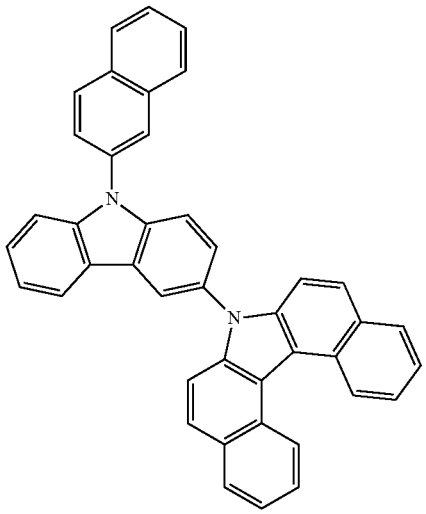
H-67
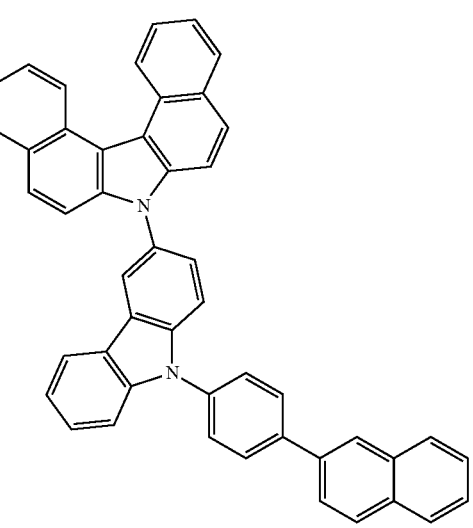
H-68
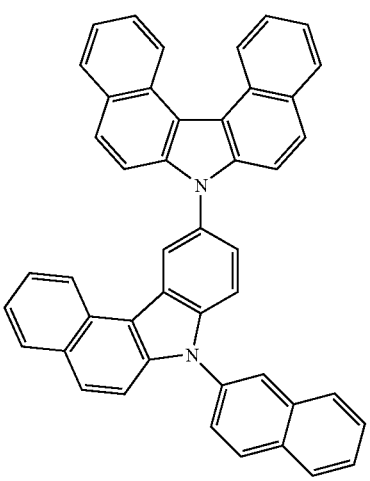
The organic electroluminescent compound of the present disclosure can be prepared by a synthetic method known to one skilled in the art. For example, it can be prepared according to any of the following reaction scheme 1 or 2.

[Reaction Scheme 1]

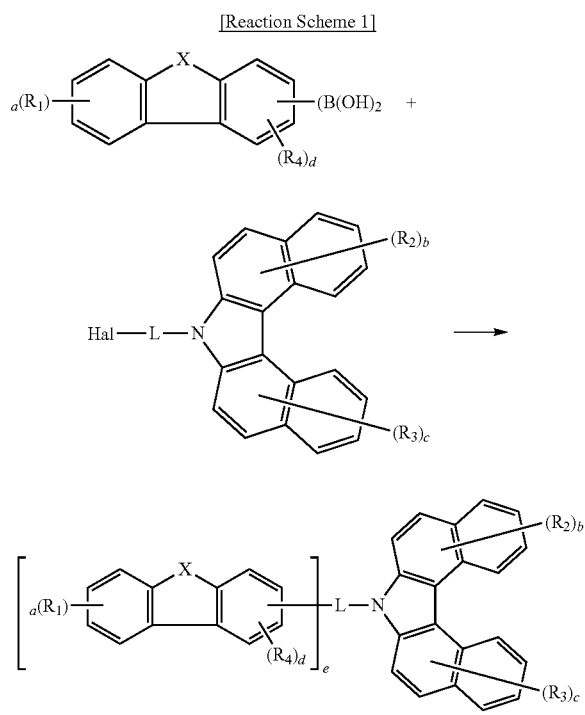

[Reaction Scheme 2]

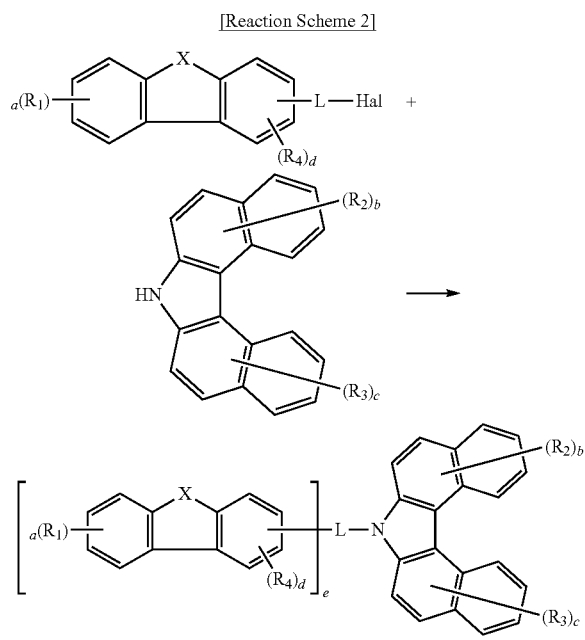

wherein X, $R_1$ to $R_4$, L, a, b, c, d, and e are as defined in formula 1 above, and Hal represents a halogen.

According to another embodiment of the present disclosure, an organic electroluminescent material comprising the organic electroluminescent compound of formula 1, and an organic electroluminescent device comprising the material are provided.

The material may consist of the organic electroluminescent compound of the present disclosure. Otherwise, the material may further comprise a conventional compound(s) which has been comprised for an organic electroluminescent material.

Herein, the organic electroluminescent material indicates a material which is used for an organic electroluminescence. The organic electroluminescent material may be a material for an organic electroluminescent device, which is used for preparing an organic electroluminescent device.

The organic electroluminescent material may be preferably, a material to be used for a light-emitting layer of an organic electroluminescent device, more preferably, a host material to be combined with a dopant material in a light-emitting layer of an organic electroluminescent device, and even more preferably a phosphorescent host material. The host material may further comprise a compound represented by the following formula 3. When the host material further comprises the compound of formula 3, the weight ratio between the compound of formula 1 and the compound of formula 3 may be in the range of 1:99 to 99:1, and specifically 30:70 to 70:30.

Preferably, the organic electroluminescent material may be a hole transport material. More preferably, the organic electroluminescent material may be a material to be used for a hole transport layer of an organic electroluminescent device.

The organic electroluminescent device of the present disclosure may comprise a first electrode, a second electrode, and at least one organic layer disposed between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron injection layer, an interlayer, a hole blocking layer, an electron buffering layer, and an electron blocking layer.

The organic electroluminescent compound of formula 1 of the present disclosure may be comprised in the light-emitting layer. When used in the light-emitting layer, the organic electroluminescent compound of formula 1 of the present disclosure may be comprised as a host material, preferably a phosphorescent host material, and more preferably a phosphorescent red light-emitting host material. Preferably, the light-emitting layer may further comprise at least one or more dopants, and, if necessary, a second host material other than the compound of formula 1 of the present disclosure. The weight ratio between the first host material and the second host material is in the range of 1:99 to 99:1 and specifically 30:70 to 70:30.

The second host material may be from any of the known phosphorescent hosts. The compound selected from the group consisting of compounds of formula 3 is preferably the second host material in view of luminous efficiency.

According to another embodiment of the present disclosure, an organic electroluminescent device comprising an anode, a cathode, and an organic layer between the anode and the cathode, wherein the organic layer comprises one or more light-emitting layers; at least one of the one or more light-emitting layers comprises one or more dopant compounds and two or more host compounds; a first host compound of the host compounds is represented by formula 1; and a second host compound is represented by formula 3 is provided.

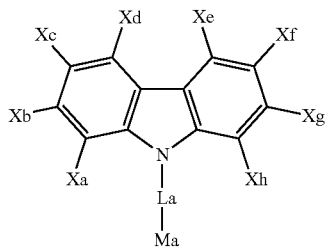

(3)

wherein

Ma represents a substituted or unsubstituted nitrogen-containing 5- to 11-membered heteroaryl;

La represents a single bond, or a substituted or unsubstituted (C6-C30)arylene;

Xa to Xh, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur; and the heteroaryl contains at least one hetero atom selected from B, N, O, S, Si, and P.

In formula 3, specifically, Ma may represent a substituted or unsubstituted pyrrolyl, a substituted or unsubstituted imidazolyl, a substituted or unsubstituted pyrazolyl, a substituted or unsubstituted triazinyl, a substituted or unsubstituted tetrazinyl, a substituted or unsubstituted triazolyl, a substituted or unsubstituted tetrazolyl, a substituted or unsubstituted pyridyl, a substituted or unsubstituted pyrazinyl, a substituted or unsubstituted pyrimidinyl, a substituted or unsubstituted pyridazinyl, a substituted or unsubstituted benzimidazolyl, a substituted or unsubstituted isoindolyl, a substituted or unsubstituted indolyl, a substituted or unsubstituted indazolyl, a substituted or unsubstituted quinolyl, a substituted or unsubstituted isoquinolyl, a substituted or unsubstituted cinnolinyl, a substituted or unsubstituted quinazolinyl, a substituted or unsubstituted naphthyridinyl, or a substituted or unsubstituted quinoxalinyl. More specifically, Ma may represent a substituted or unsubstituted triazinyl, a substituted or unsubstituted pyrimidinyl, a substituted or unsubstituted pyridyl, a substituted or unsubstituted quinolyl, a substituted or unsubstituted isoquinolyl, a substituted or unsubstituted quinazolinyl, a substituted or unsubstituted naphthyridinyl, or a substituted or unsubstituted quinoxalinyl. Specifically, the substituents for the substituted nitrogen-containing 5- to 11-membered heteroaryl of Ma may be a (C6-C18)aryl unsubstituted or substituted with a cyano, a halogen, a (C1-C10)alkyl, or a tri(C6-C12)arylsilyl.

In formula 3, specifically, La may represent a single bond, a substituted or unsubstituted phenylene, a substituted or unsubstituted naphthylene, or a substituted or unsubstituted biphenylene.

In formula 3, specifically, Xa to Xh, each independently, may represent hydrogen, a cyano, a substituted or unsubstituted (C6-C15)aryl, a substituted or unsubstituted 6- to 20-membered heteroaryl, or a substituted or unsubstituted tri(C6-C15)arylsilyl, or may be linked to an adjacent substituent(s) to form a substituted or unsubstituted 6- to 20-membered, mono- or polycyclic, aromatic ring, whose carbon atom(s) may be replaced with at least one hetero atom selected from nitrogen, oxygen, and sulfur. Specifically, the formed mono- or polycyclic aromatic ring may be a substituted or unsubstituted benzene, a substituted or unsubstituted indole, a substituted or unsubstituted benzindole, a substituted or unsubstituted indene, a substituted or unsubstituted benzofuran, or a substituted or unsubstituted benzothiophene.

Specifically, the second host material includes the following, but is not limited thereto:

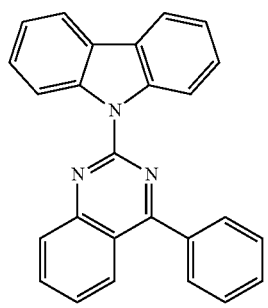

H2-1

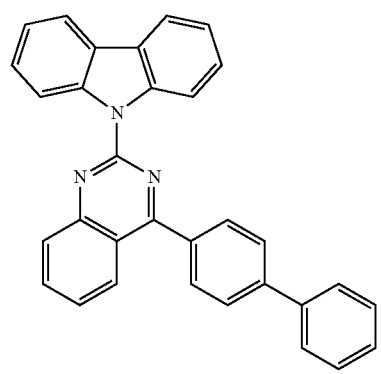

H2-2

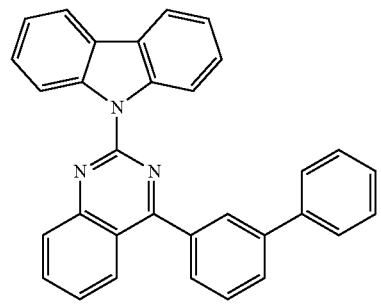

H2-3

-continued
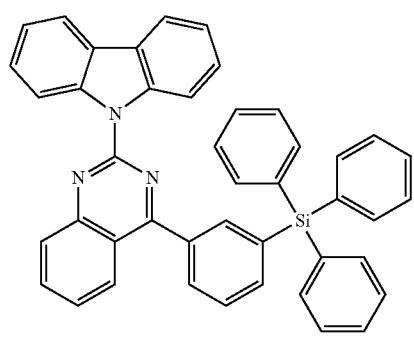
H2-4
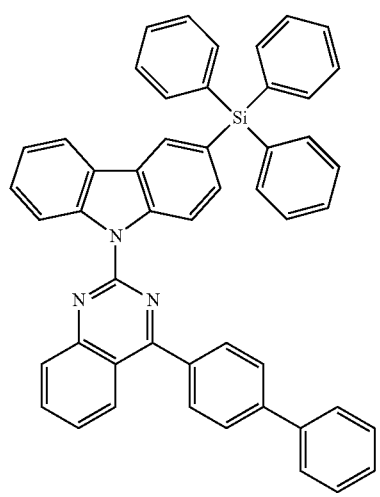
H2-5
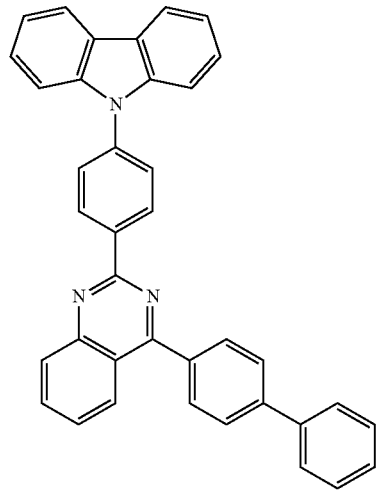
H2-6
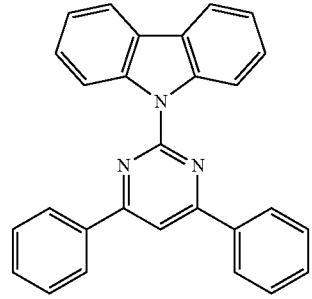
H2-7
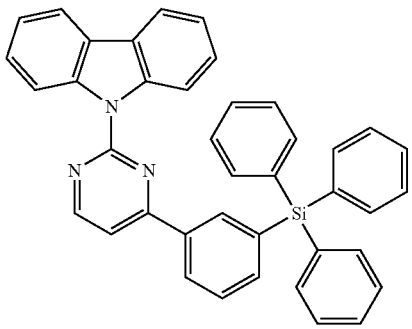
H2-8
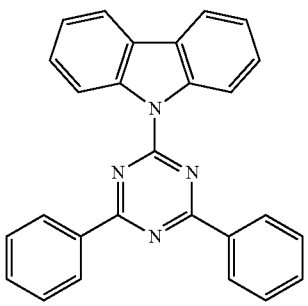
H2-9
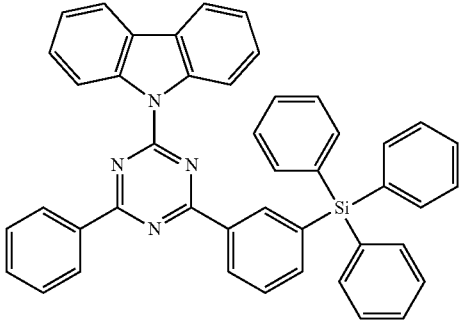
H2-10
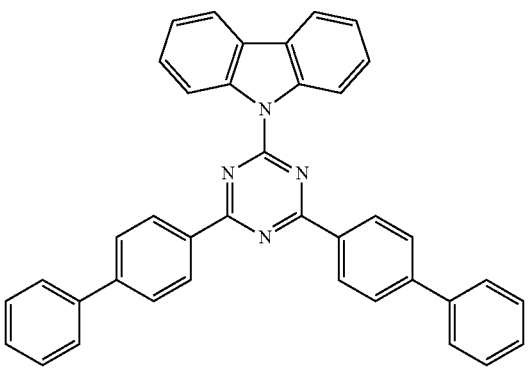
H2-11

H2-12
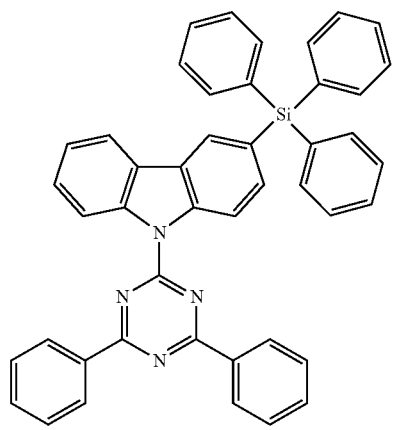
H2-13
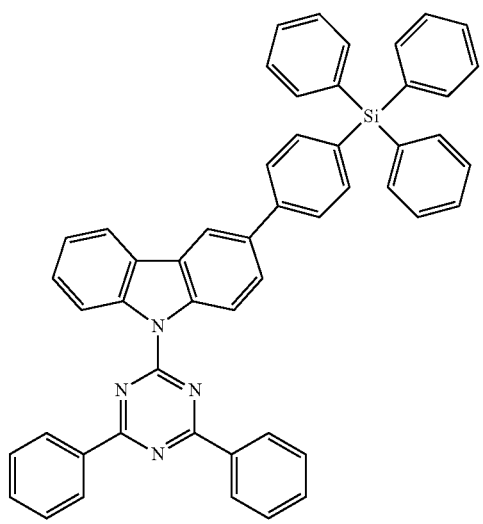
H2-14
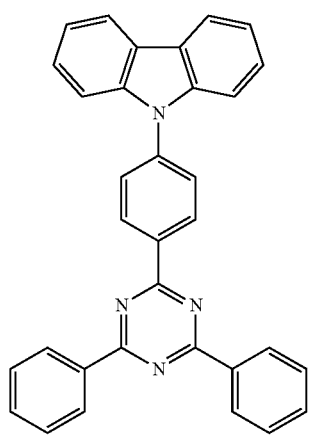
H2-15
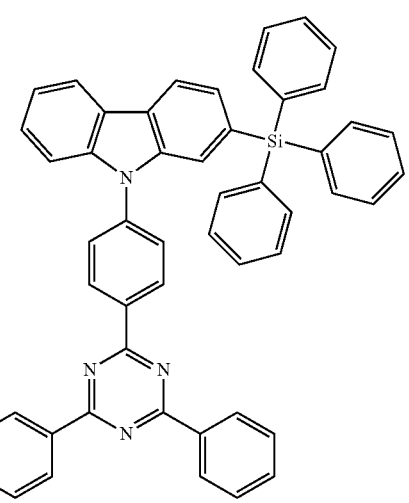
H2-16
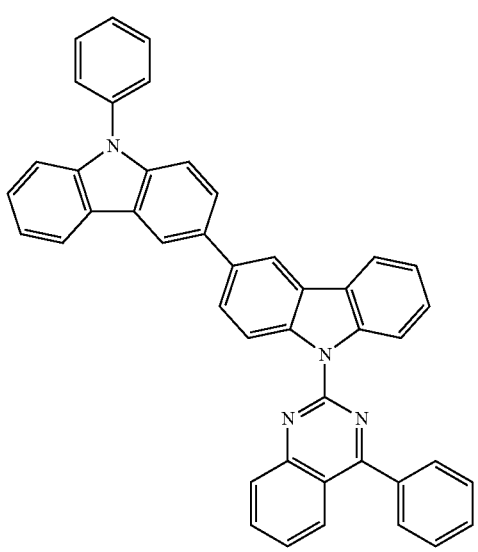
H2-17
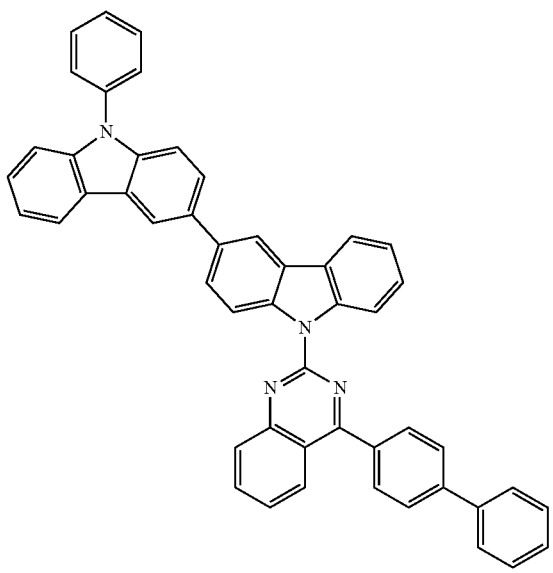

H2-18
H2-19
H2-20
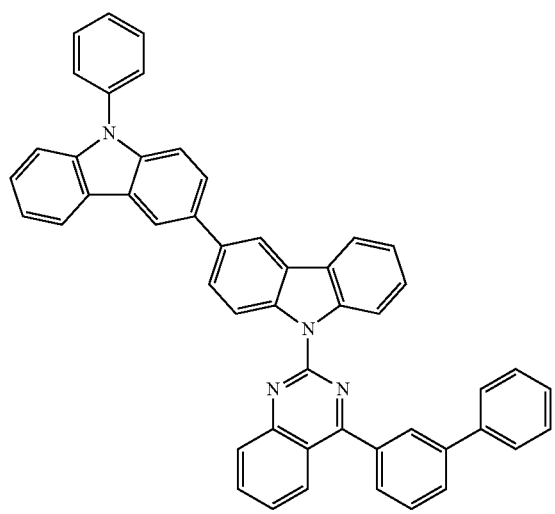
H2-21
H2-22
H2-23
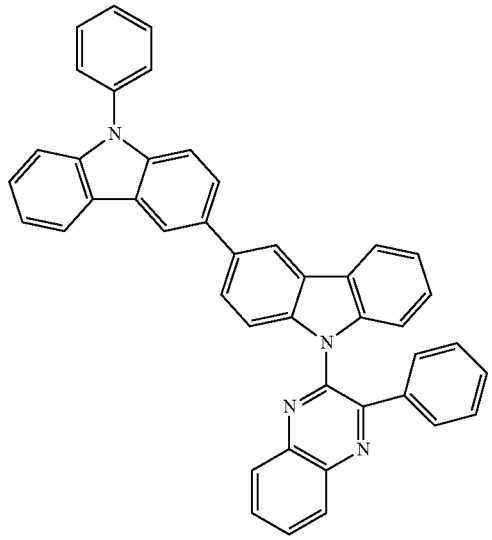
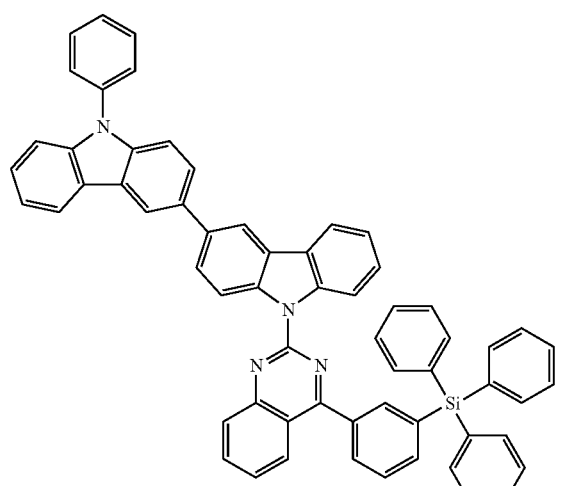
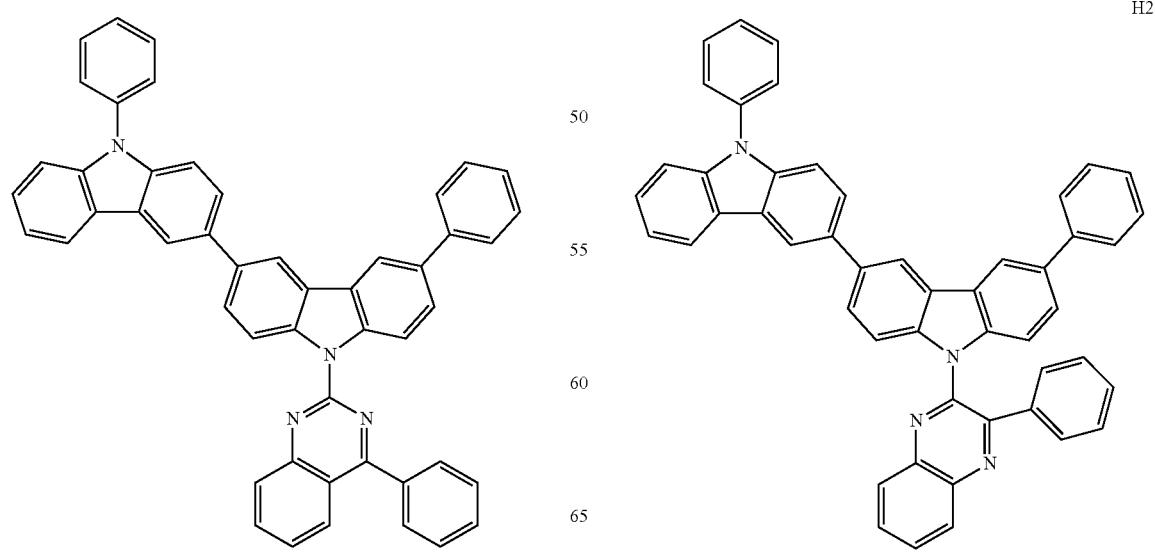

H2-24
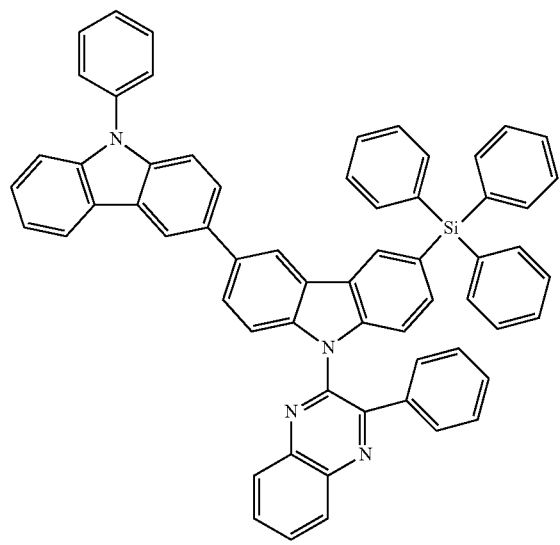
H2-26
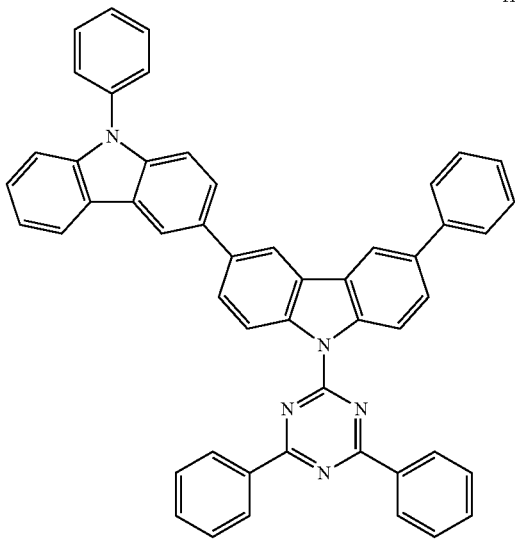
H2-25
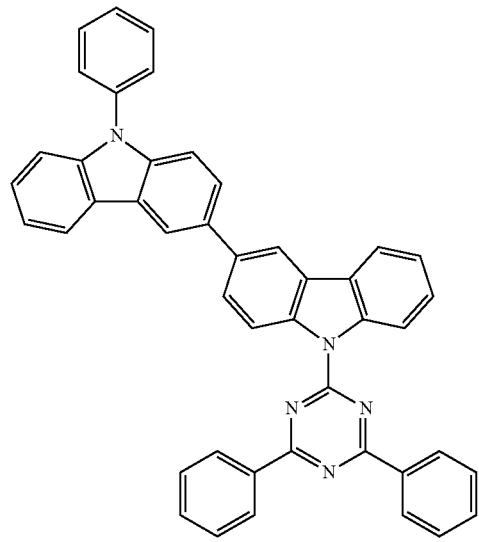
H2-27

H2-28
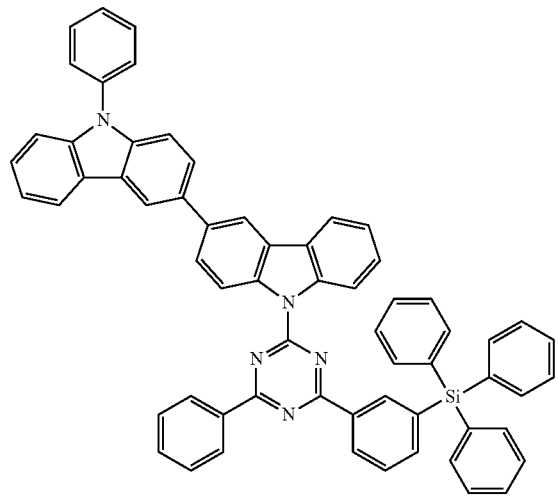
H2-29
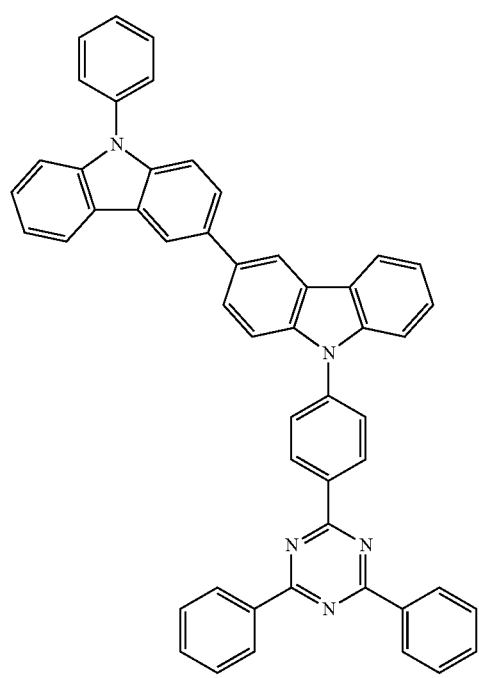
H2-30
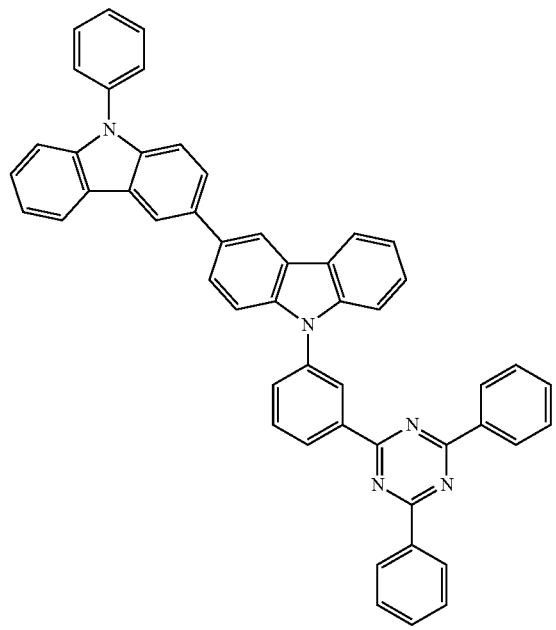
H2-31
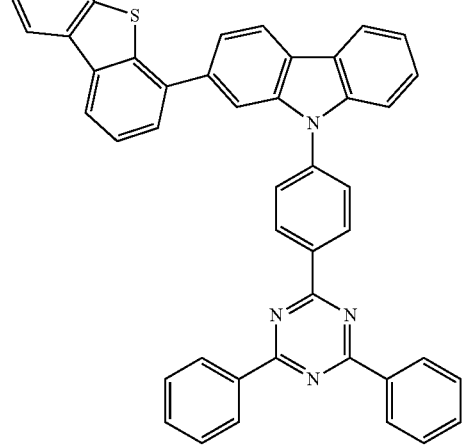
H2-32
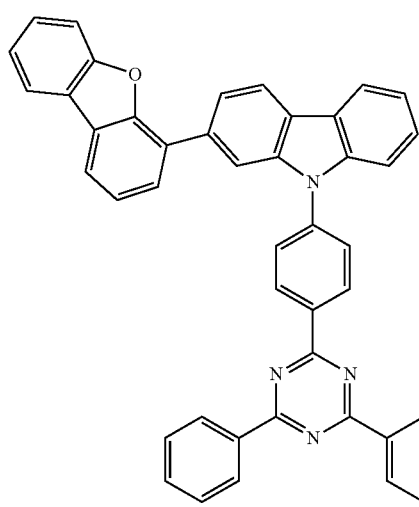

H2-33
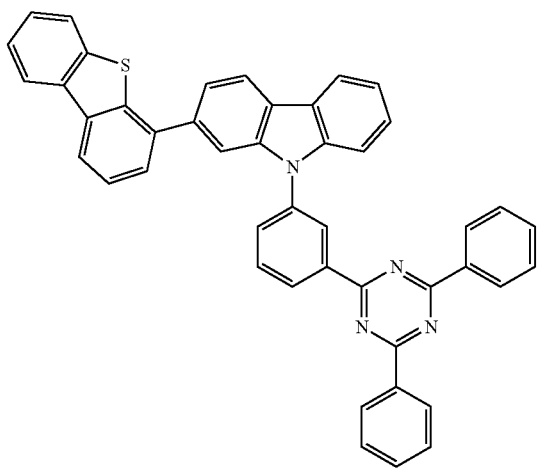
H2-34
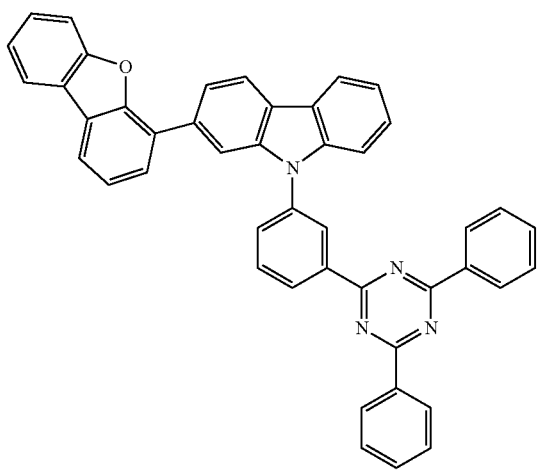
H2-35
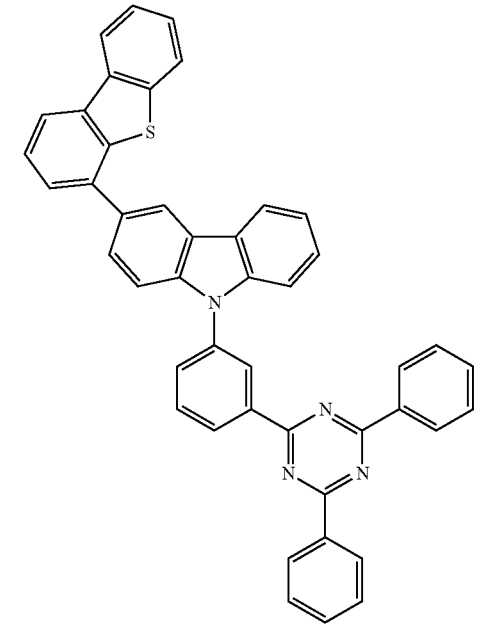
H2-36
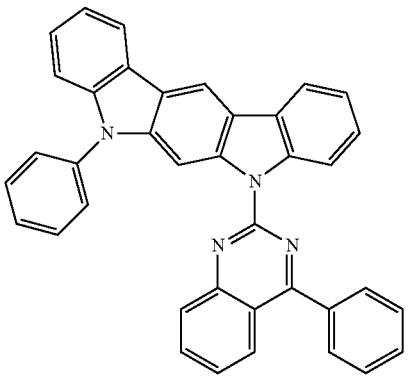
H2-37
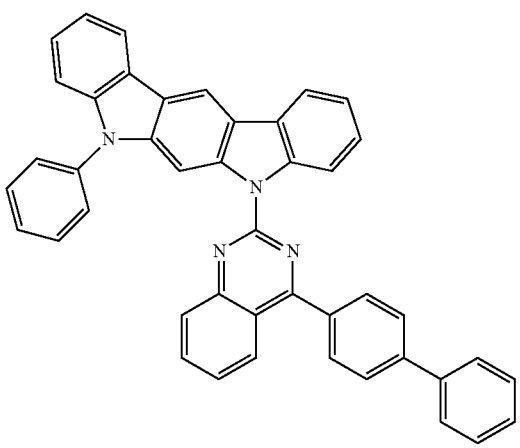
H2-38
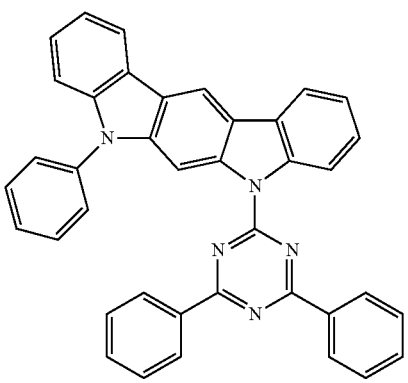
H2-39
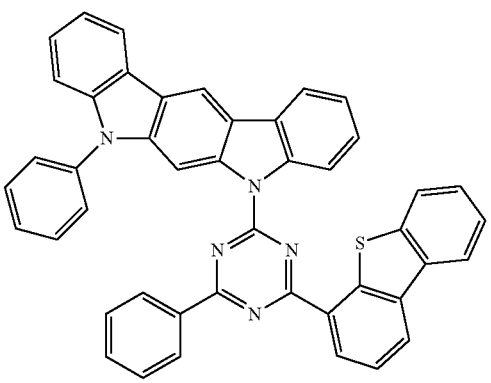

H2-40
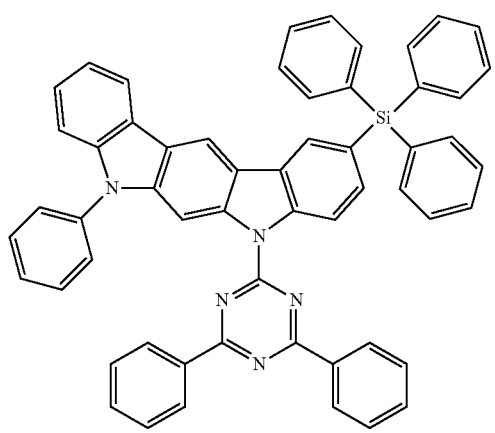
H2-41
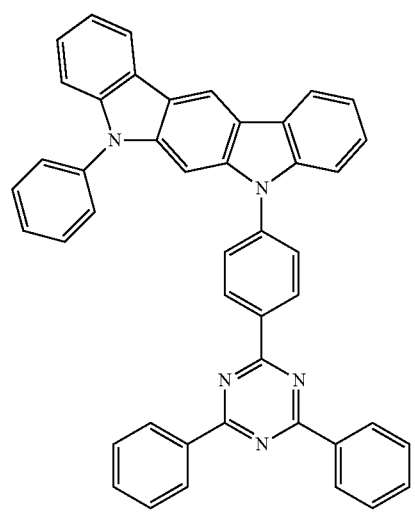
H2-42
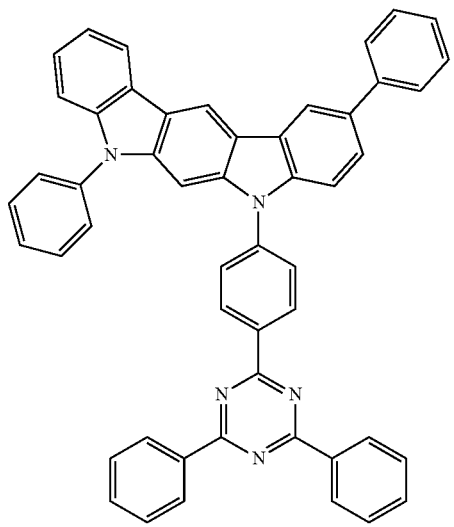
H2-43
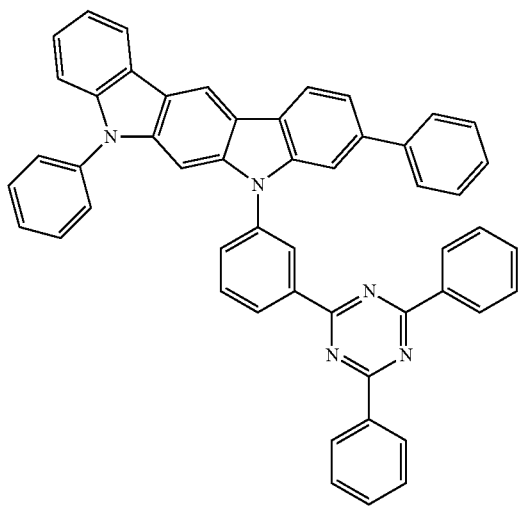
H2-44
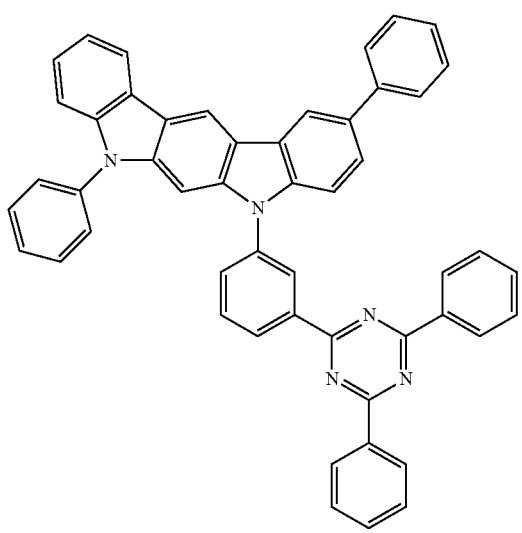
H2-45
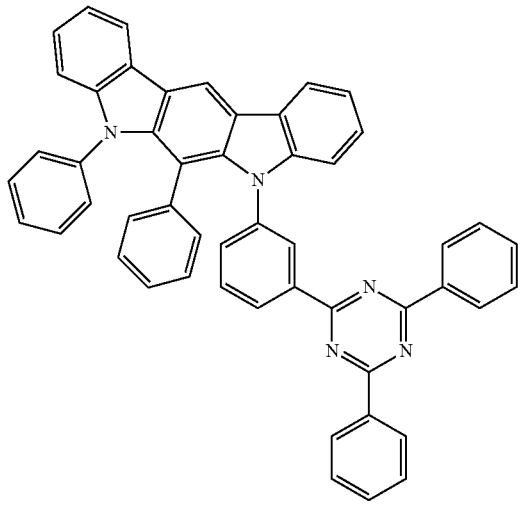

H2-46
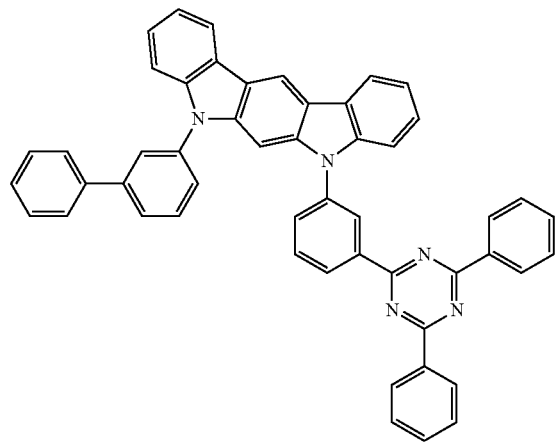
H2-47
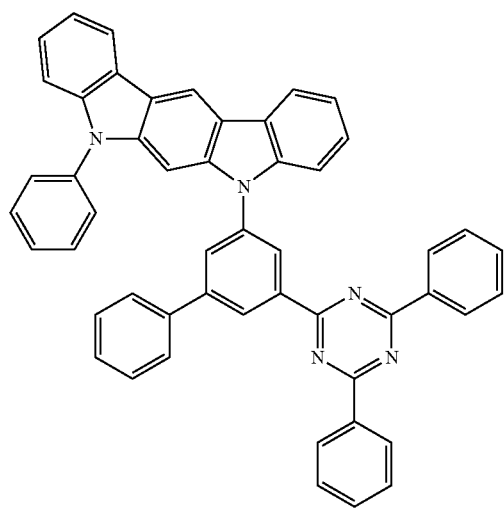
H2-48
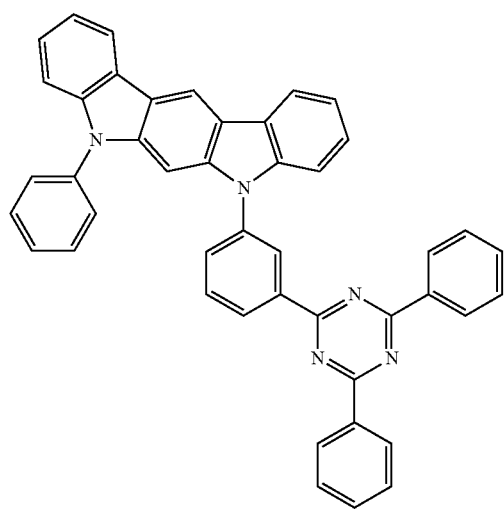
H2-49
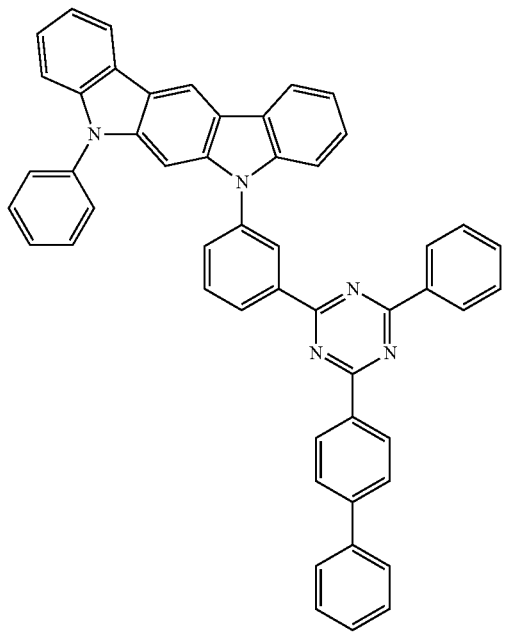
H2-50
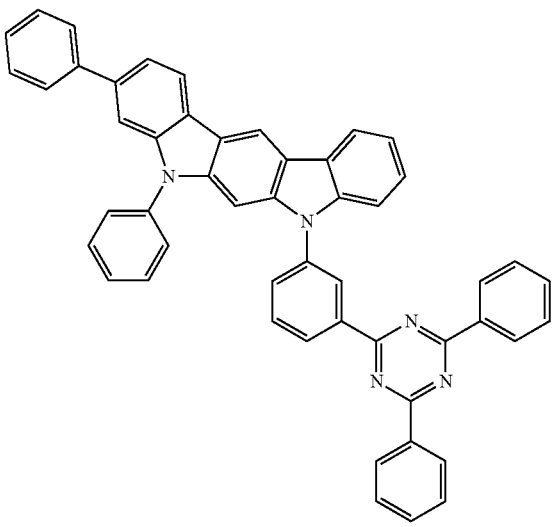

H2-51
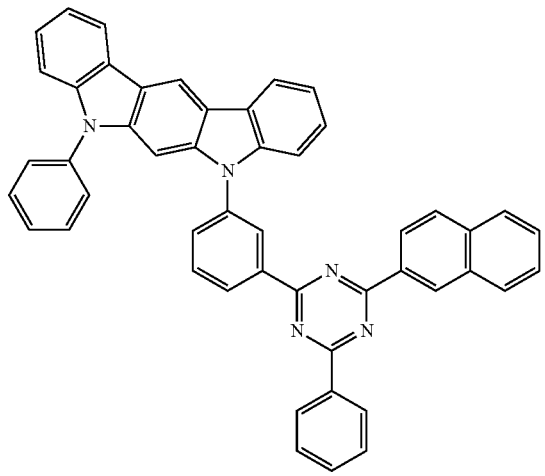
H2-52
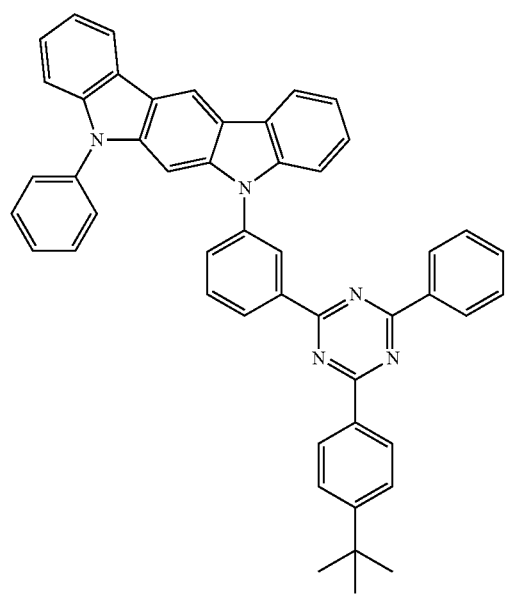
H2-53
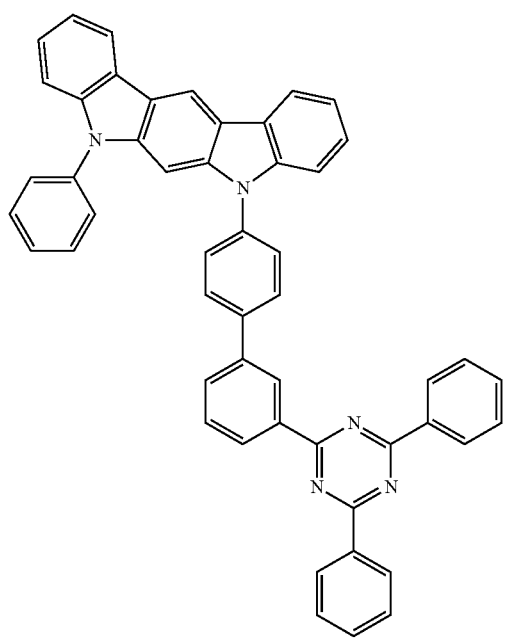
H2-54
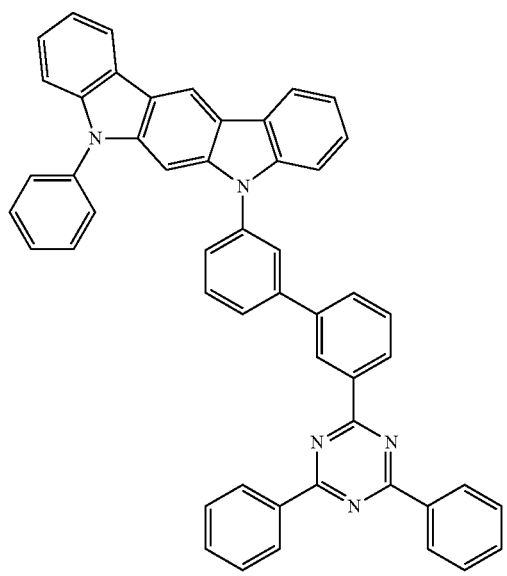

H2-55
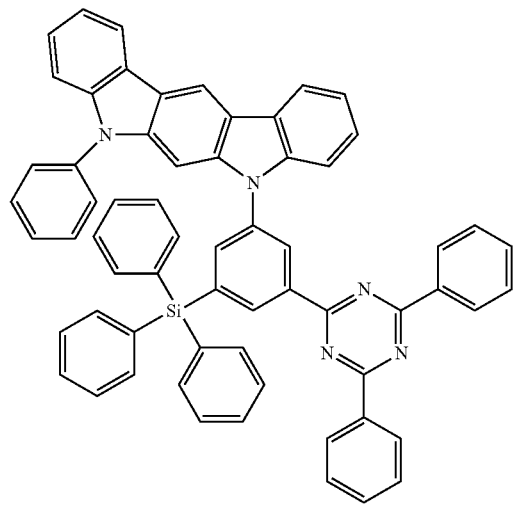
H2-56
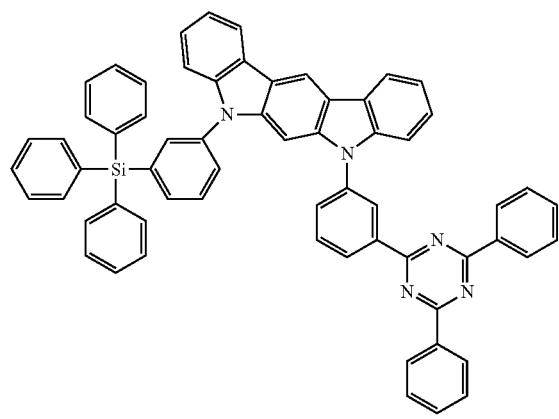
H2-57
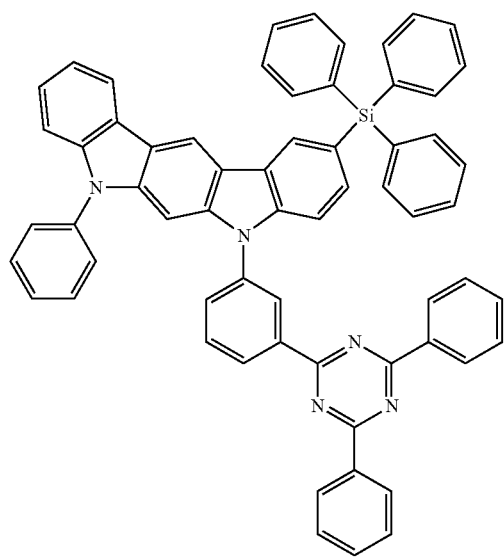
H2-58
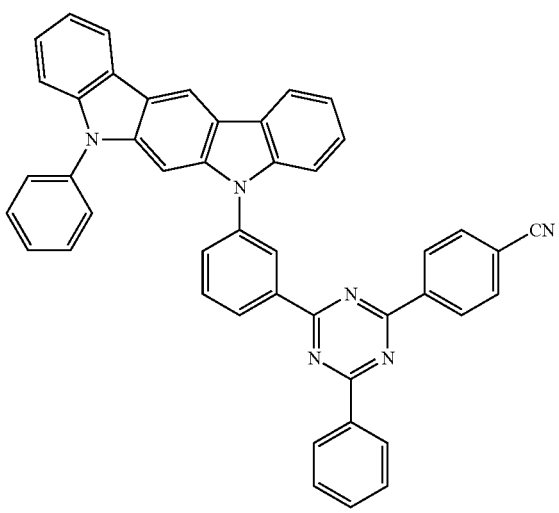
H2-59
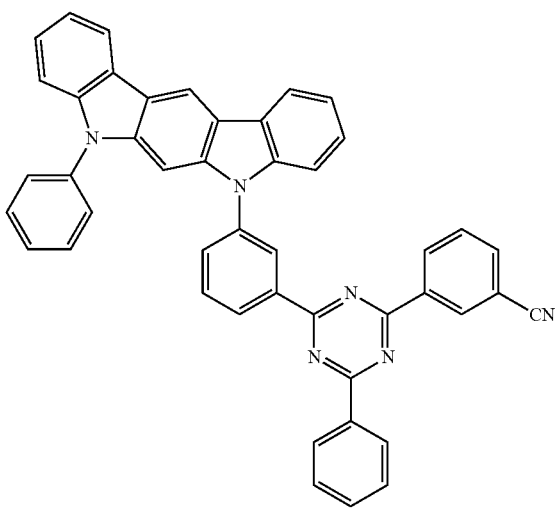
H2-60
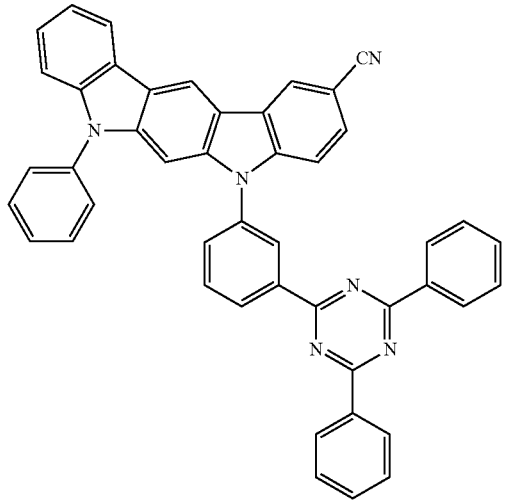

H2-61
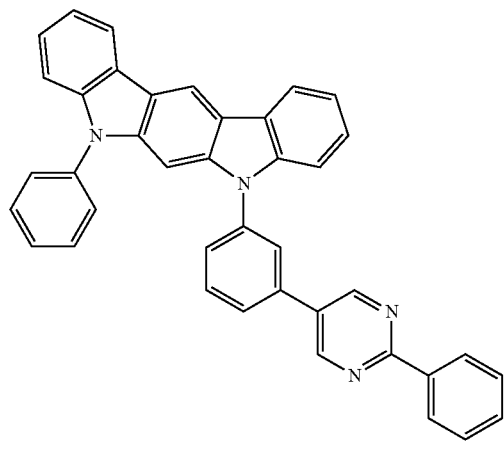
H2-62
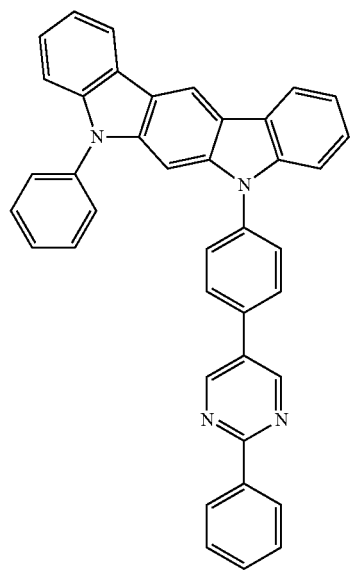
H2-63
H2-64
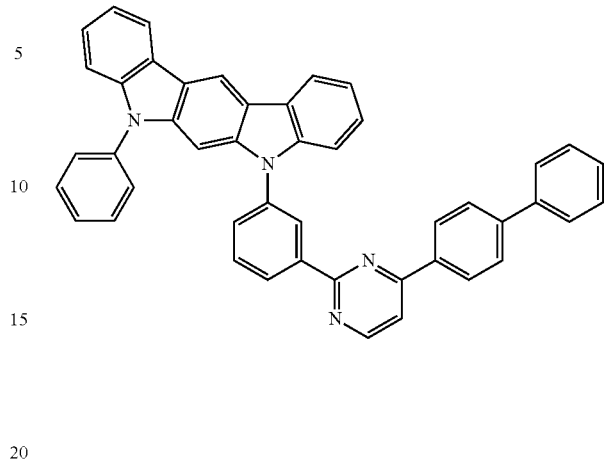
H2-65
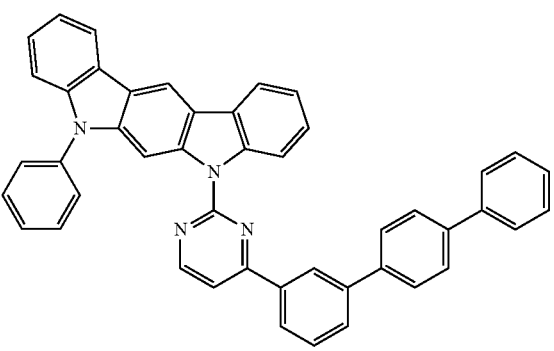
H2-66
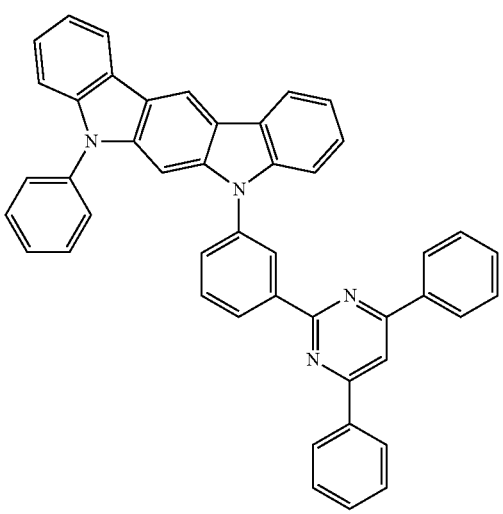

H2-67
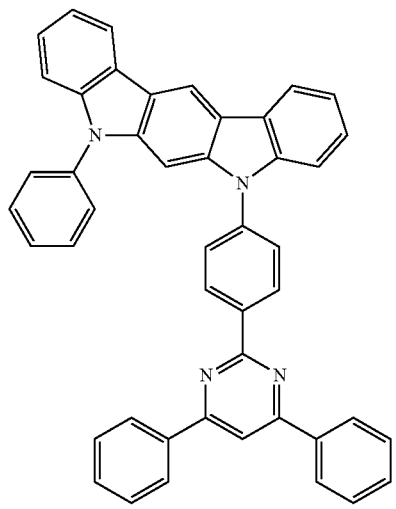
H2-68
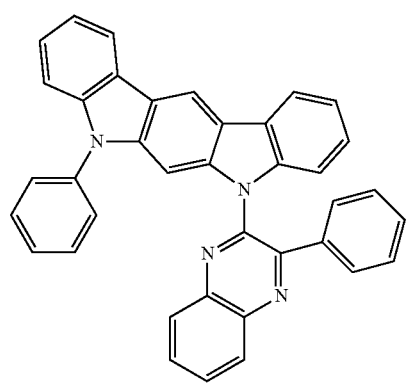
H2-69
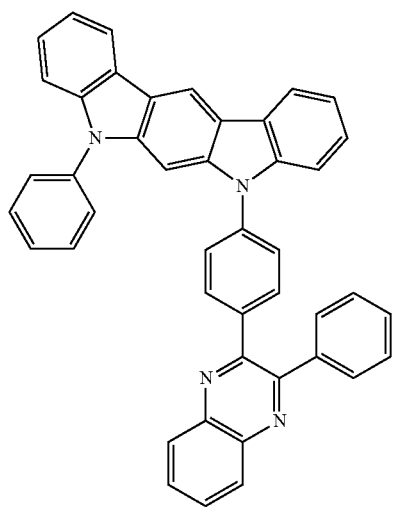
H2-70
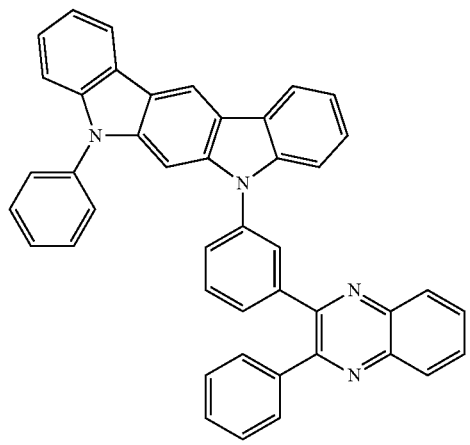
H2-71
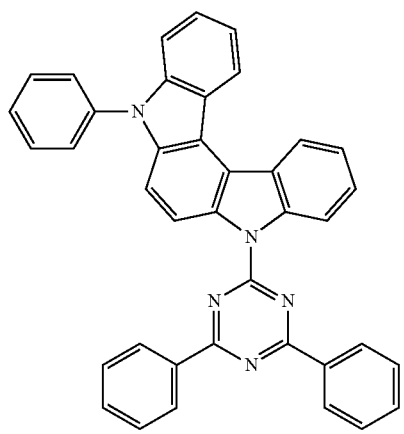
H2-72
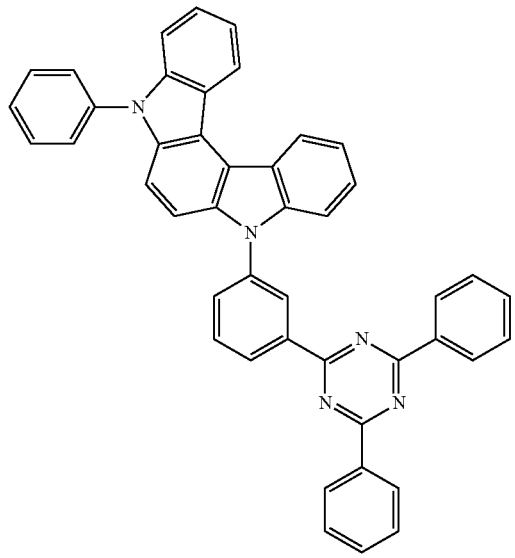

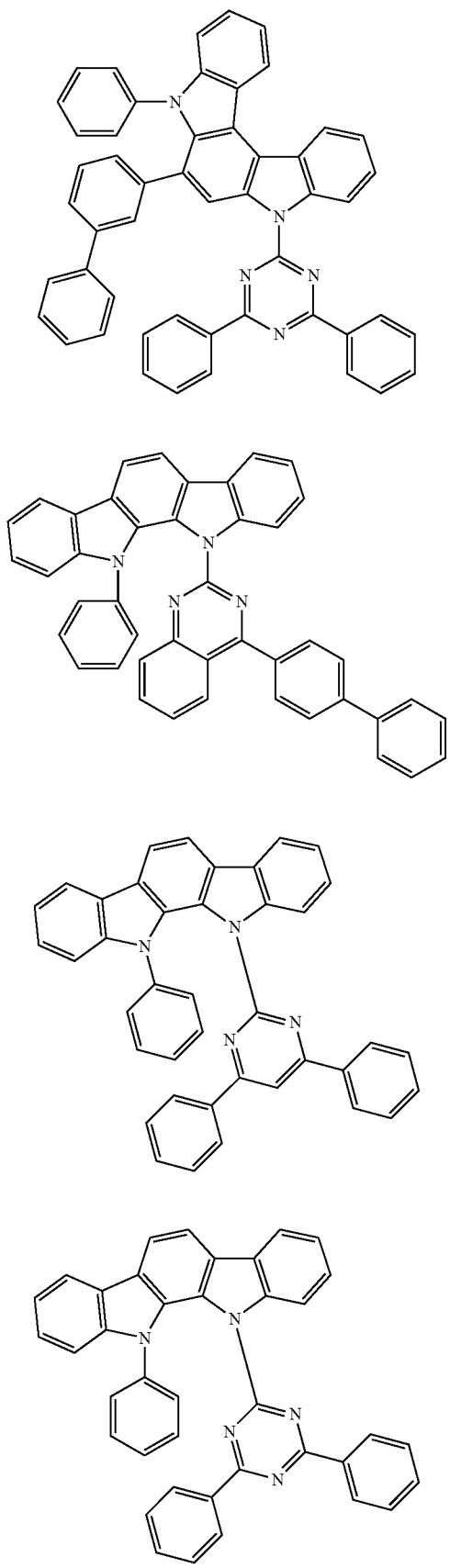
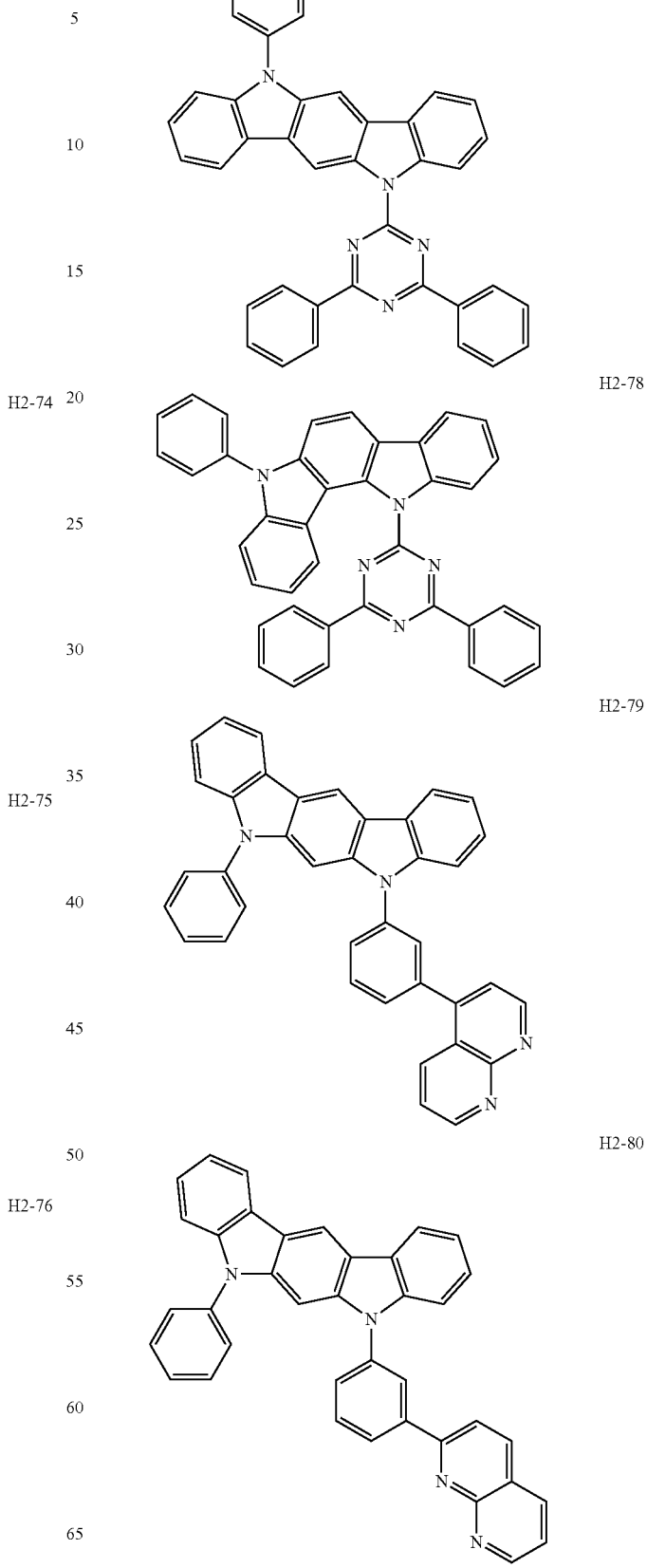

H2-81
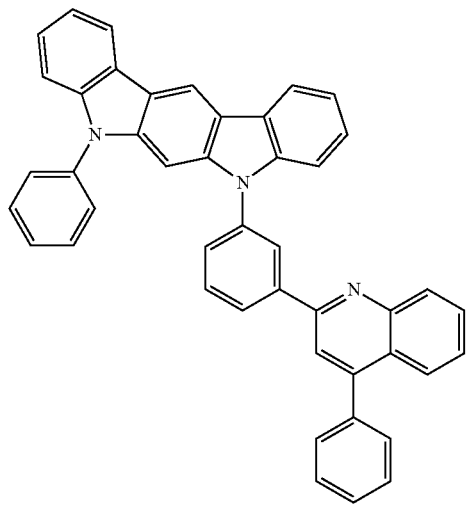
H2-82
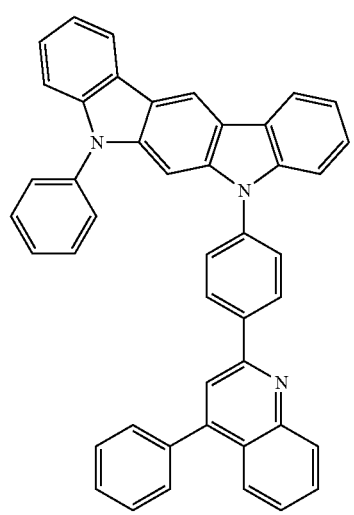
H2-83
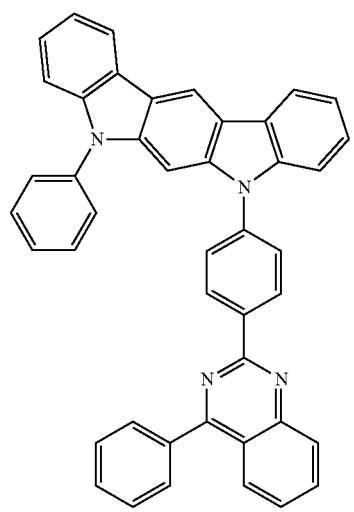
H2-84
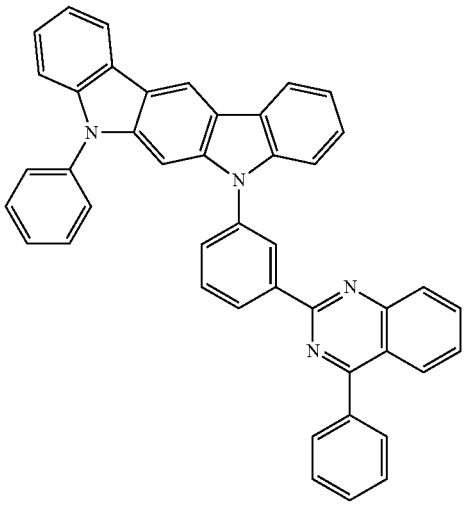
H2-85
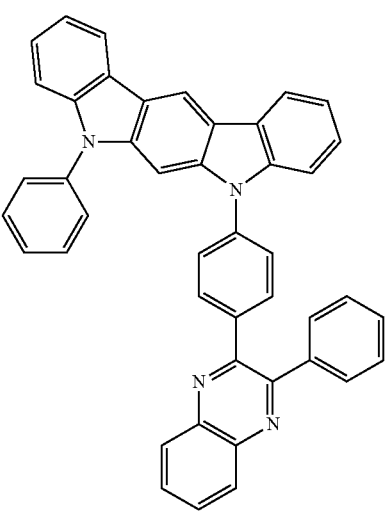
H2-86
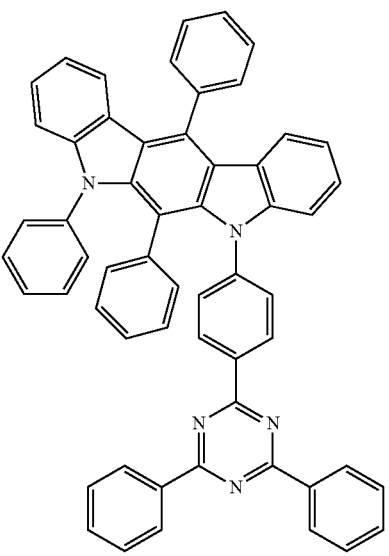

H2-87
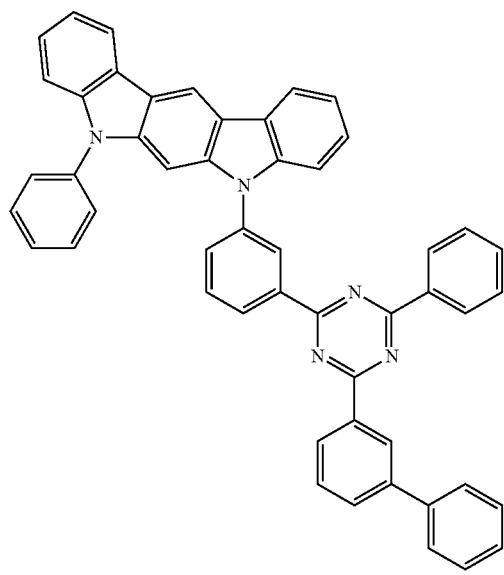
H2-89
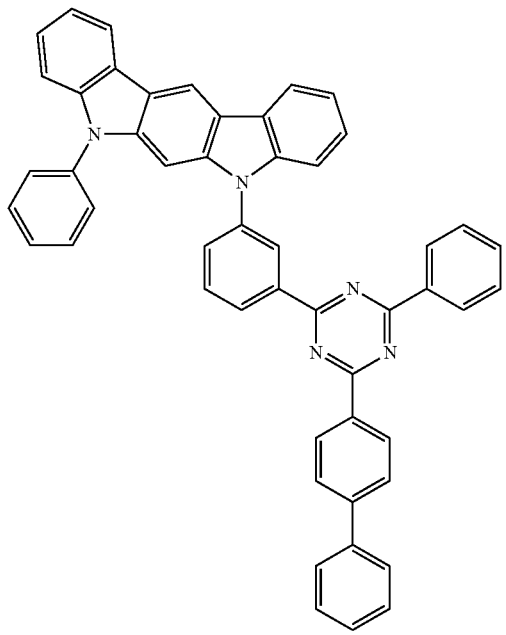
H2-88
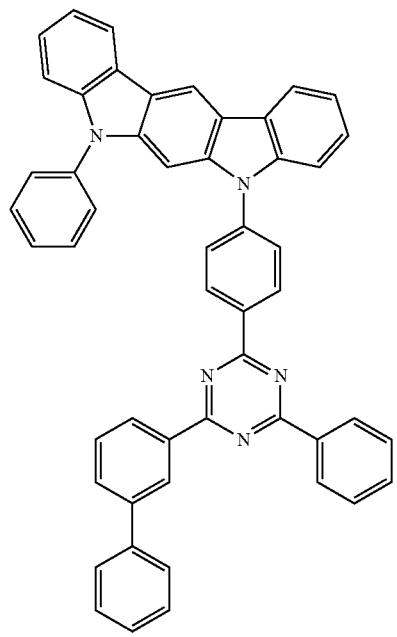
H2-90
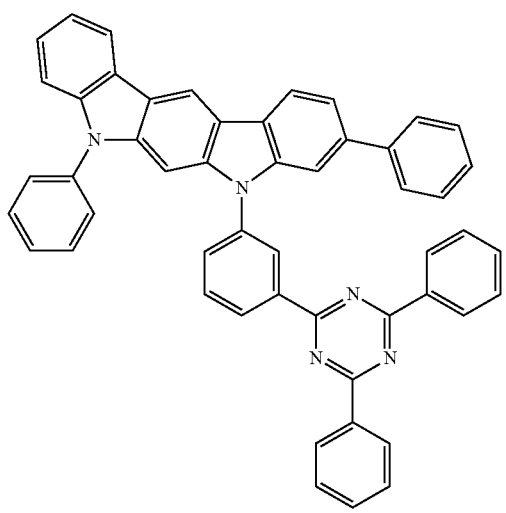

H2-91
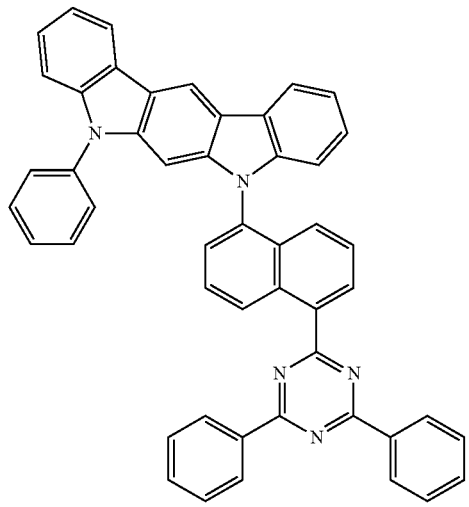
H2-92
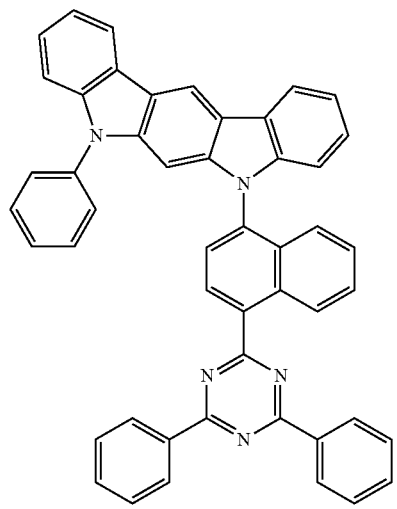
H2-93
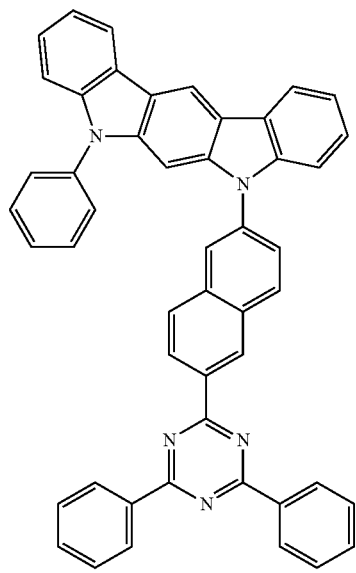
H2-94
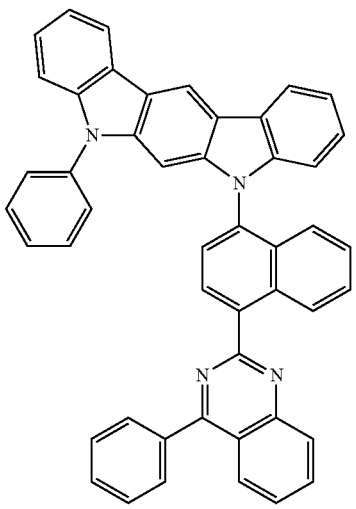
H2-95
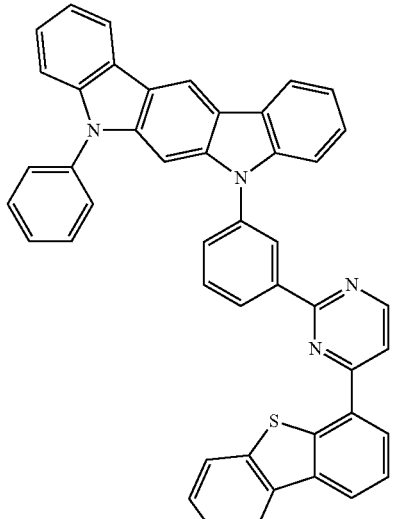
H2-96
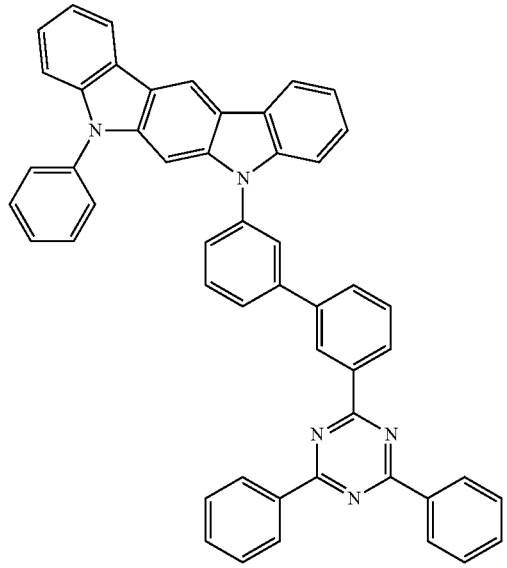

-continued
H2-97
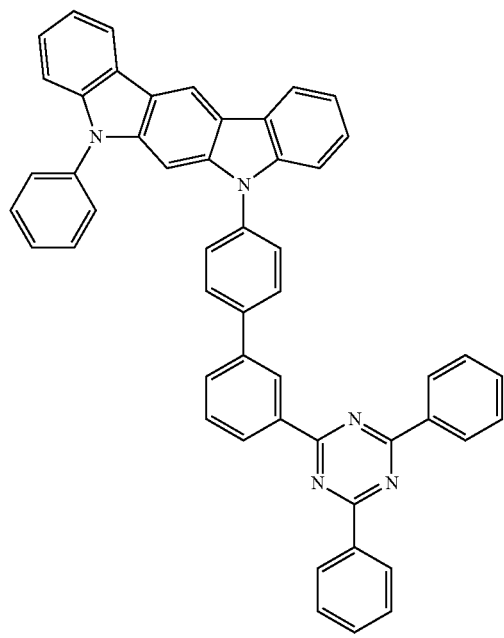
H2-98
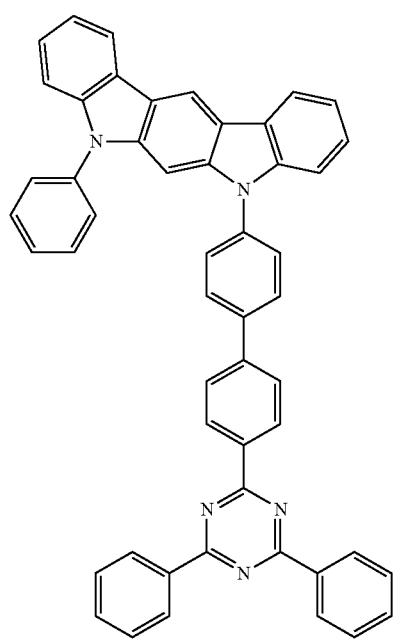
H2-99
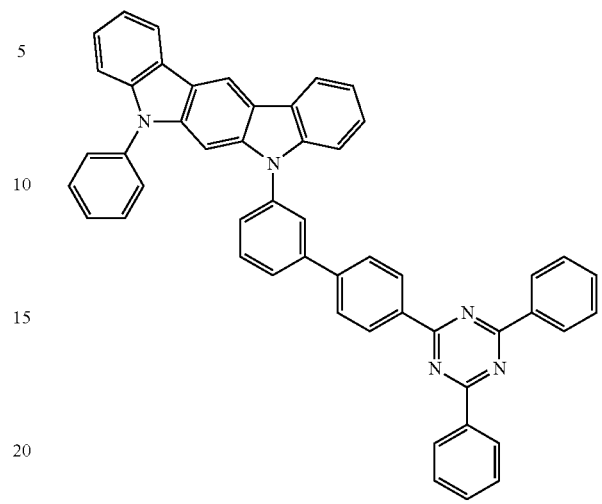
H2-100
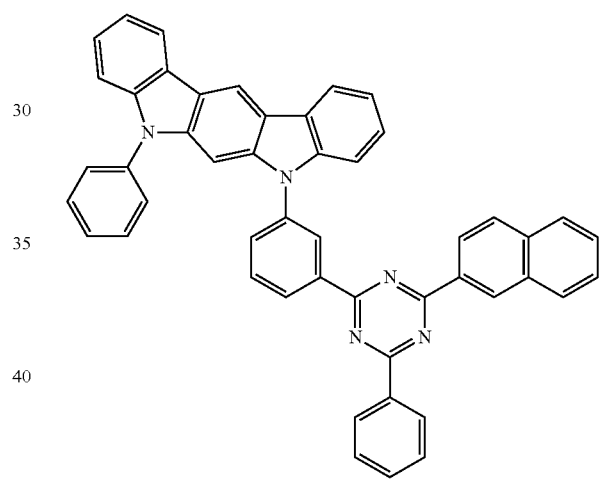
H2-101
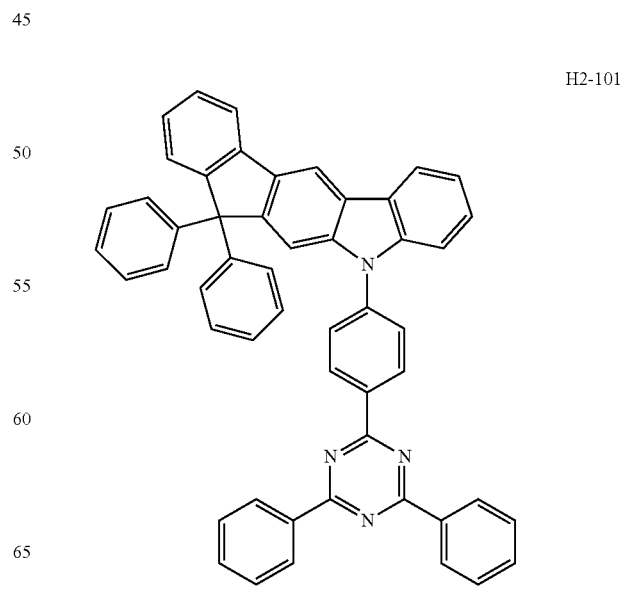

H2-102
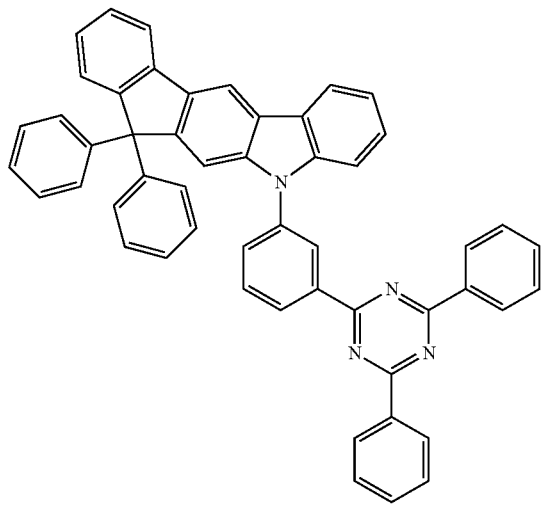
H2-105
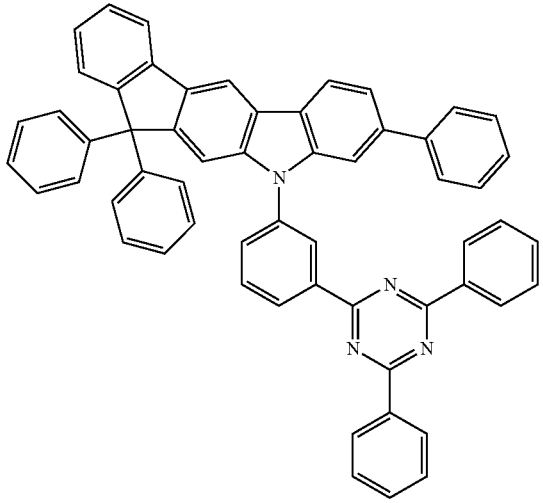
H2-103
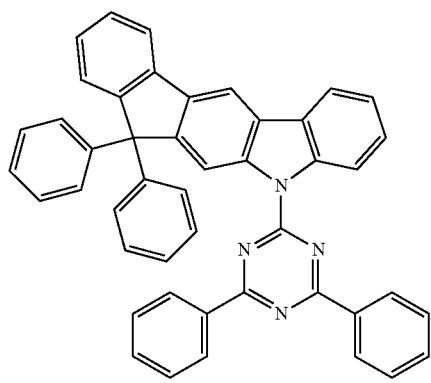
H2-106
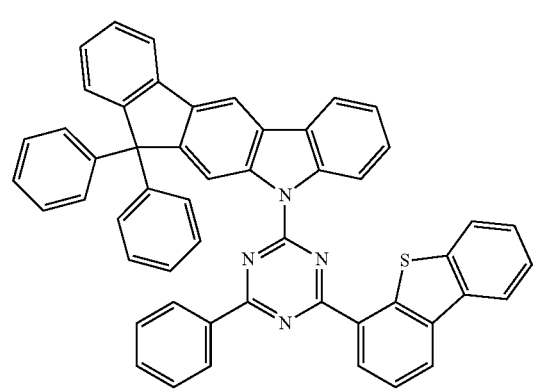
H2-104
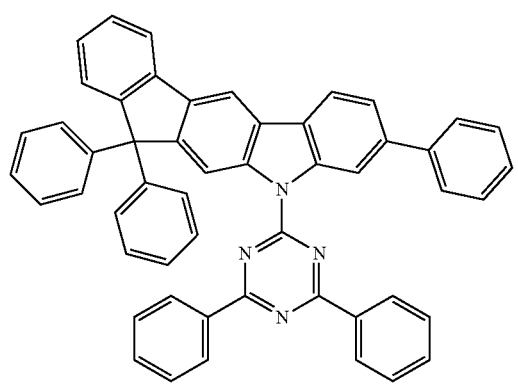
H2-107
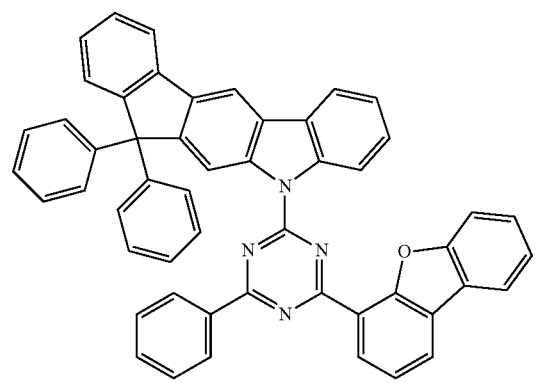

H2-108
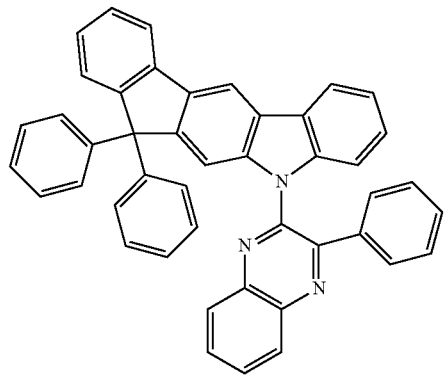
H2-109
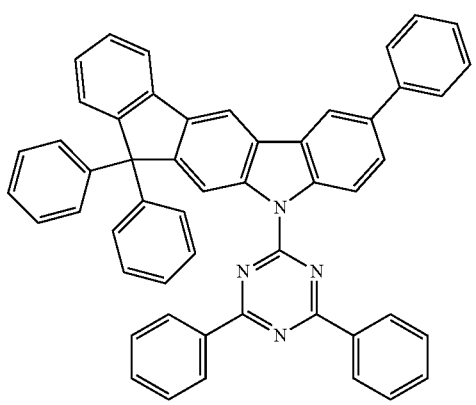
H2-110
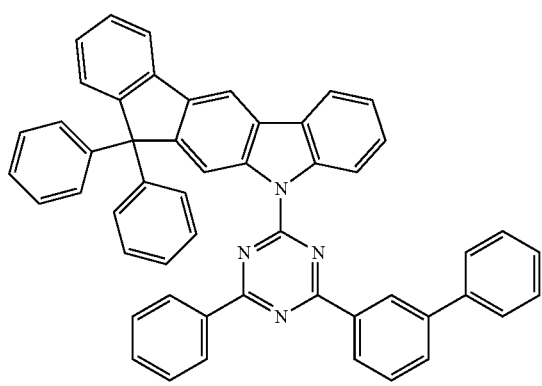
H2-111
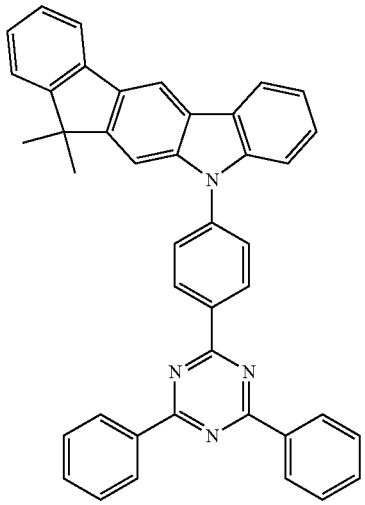
H2-112
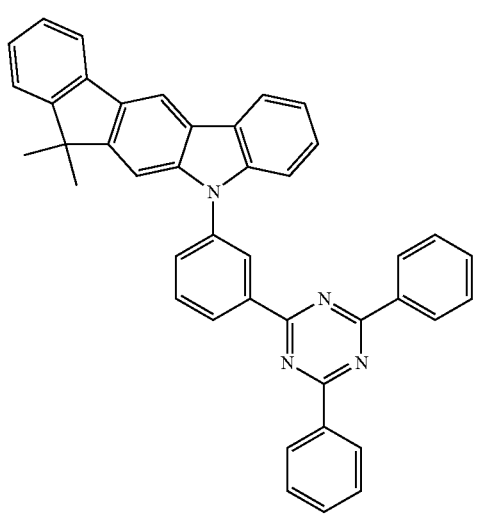
H2-113
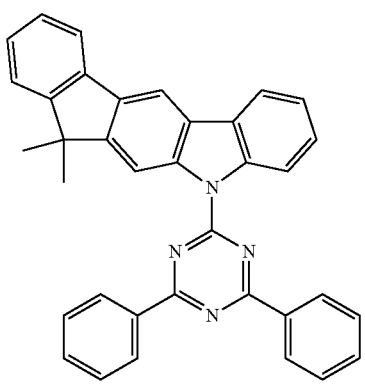

H2-114
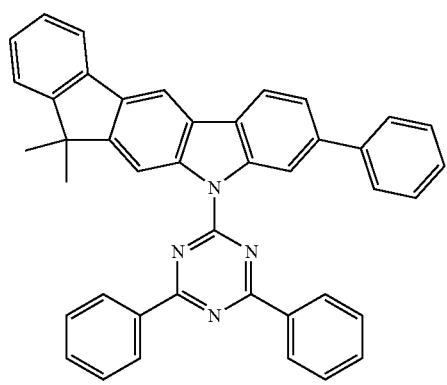
H2-115
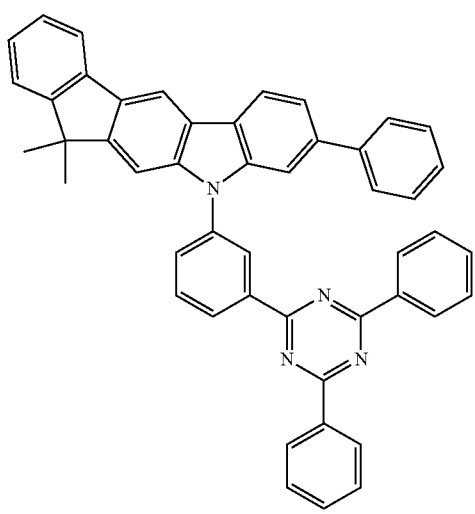
H2-116
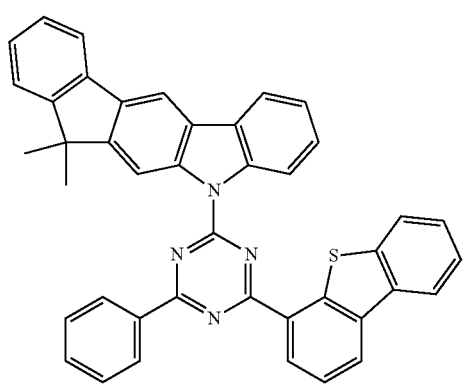
H2-117
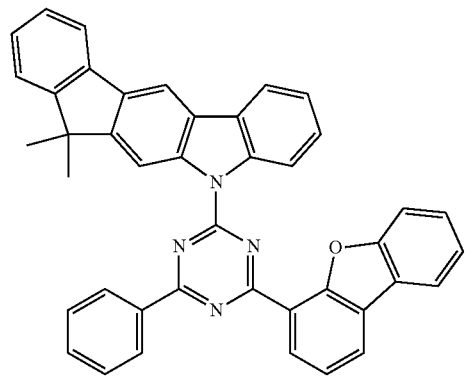
H2-118
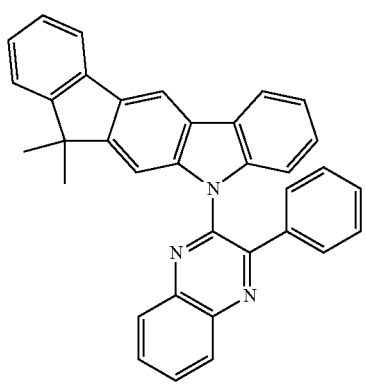
H2-119
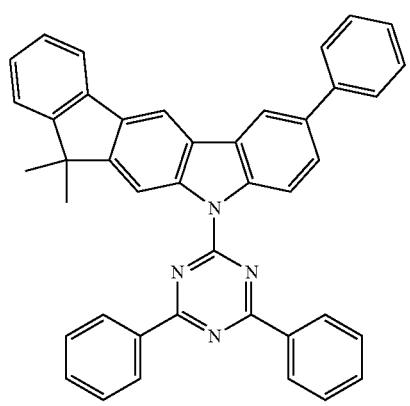
H2-120
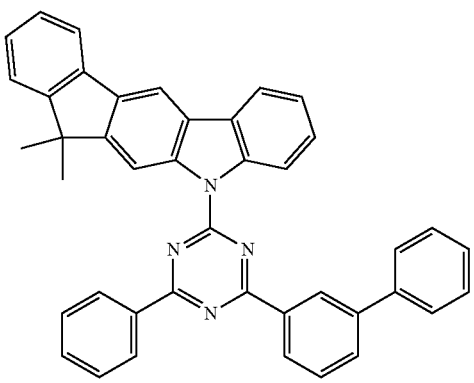

H2-121
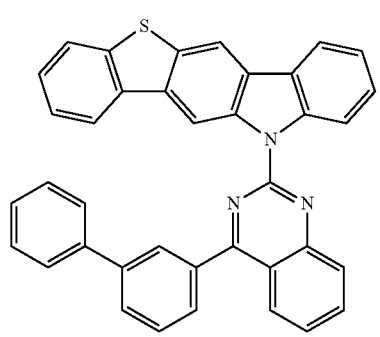
H2-122
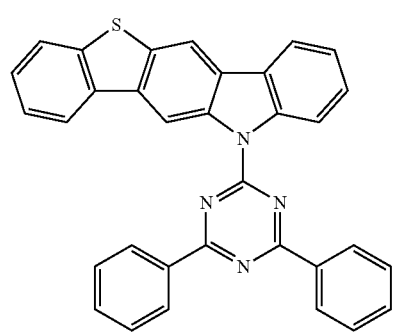
H2-123
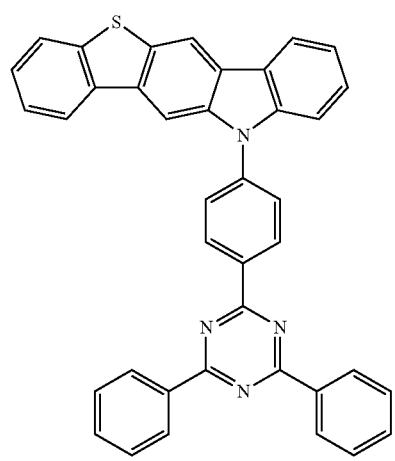
H2-124
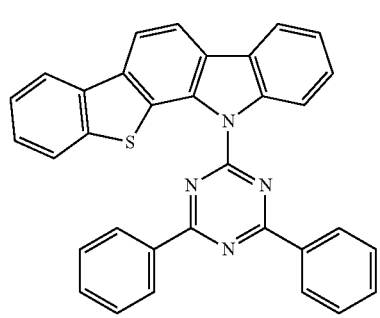
H3-125
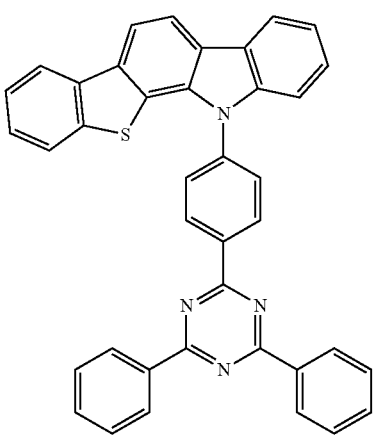
H2-126
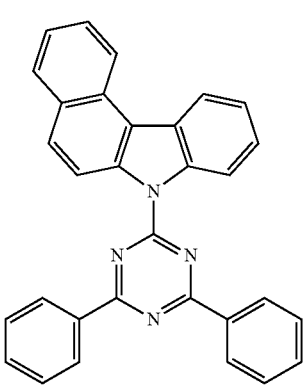
H2-127
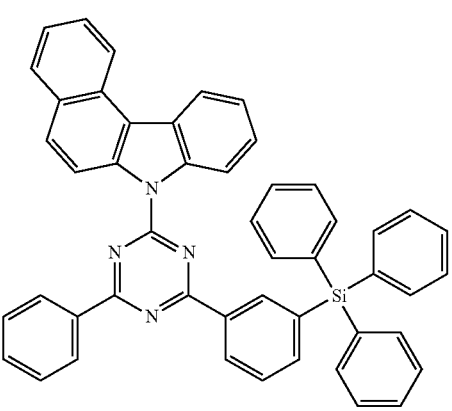
H2-128
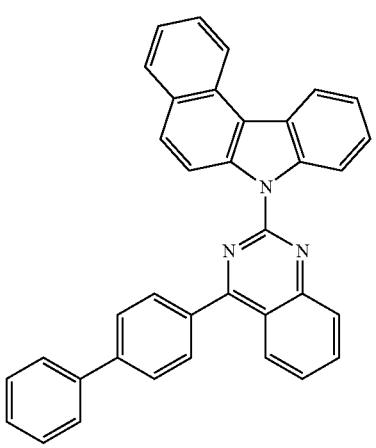

H2-129
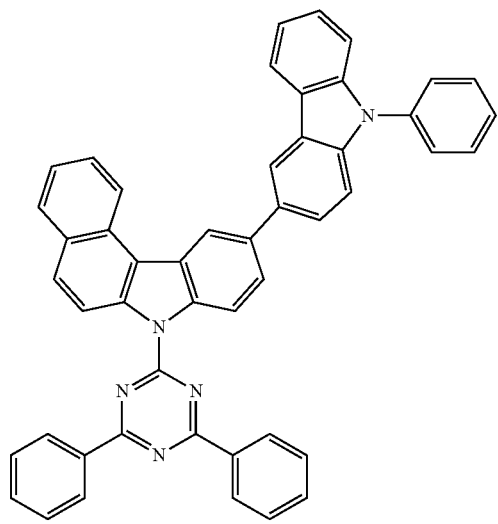
H2-131
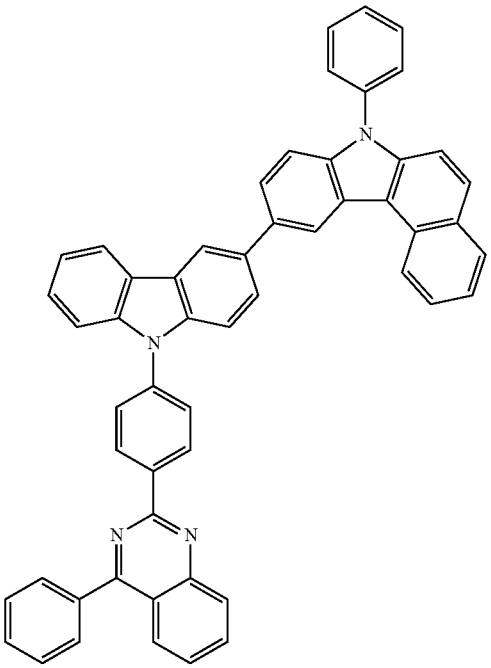
H2-130
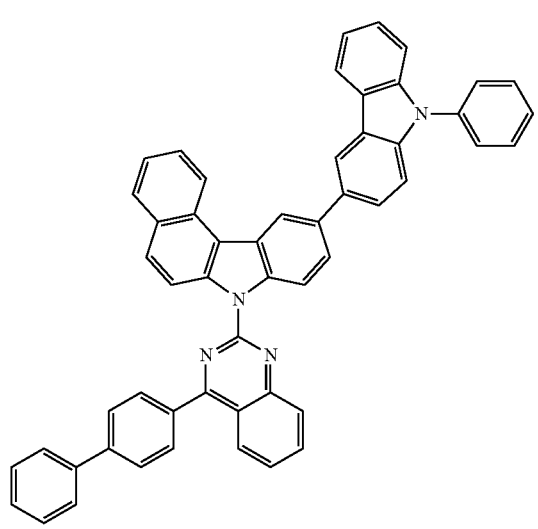
H2-132
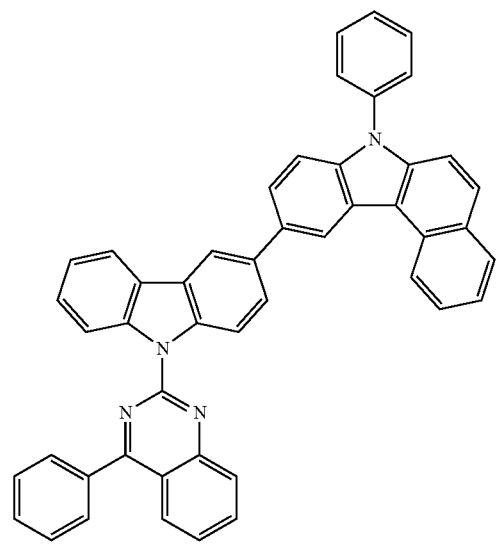

H2-133
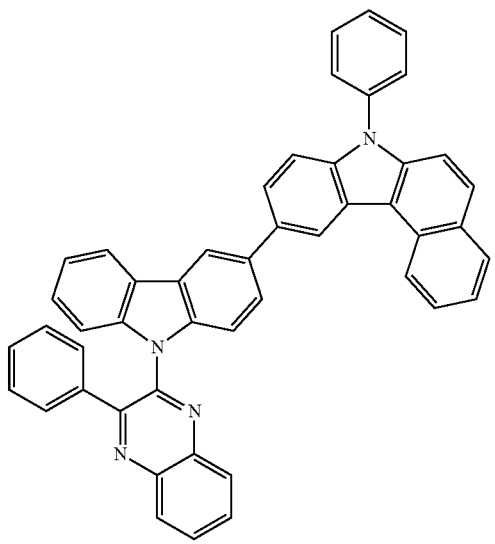
H2-135
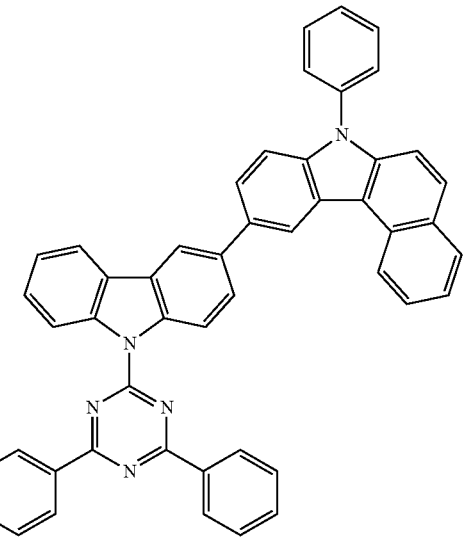
H2-136
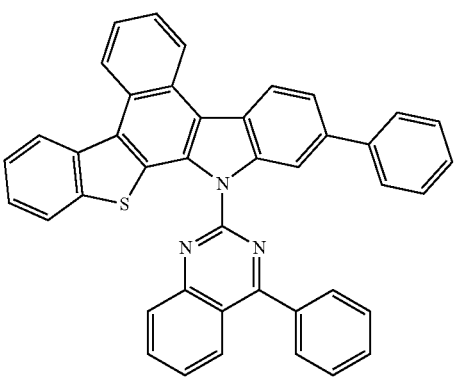
H2-134
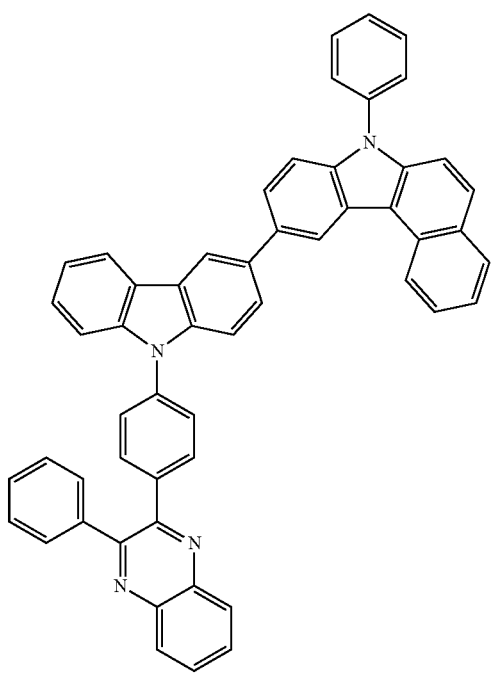
H2-137
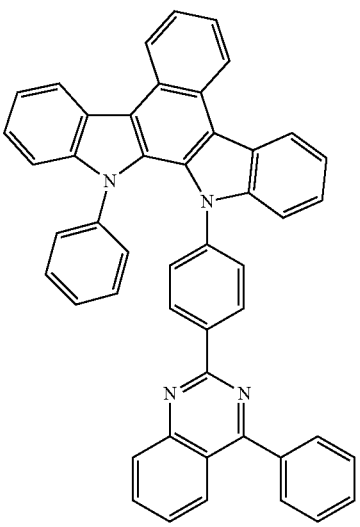

H2-138
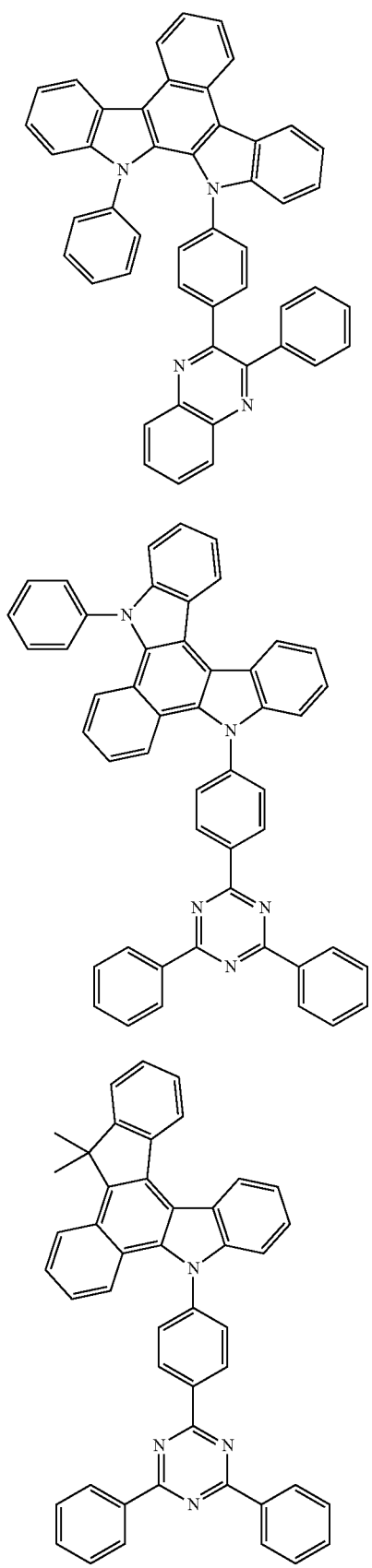
H2-139
H2-140
H2-141
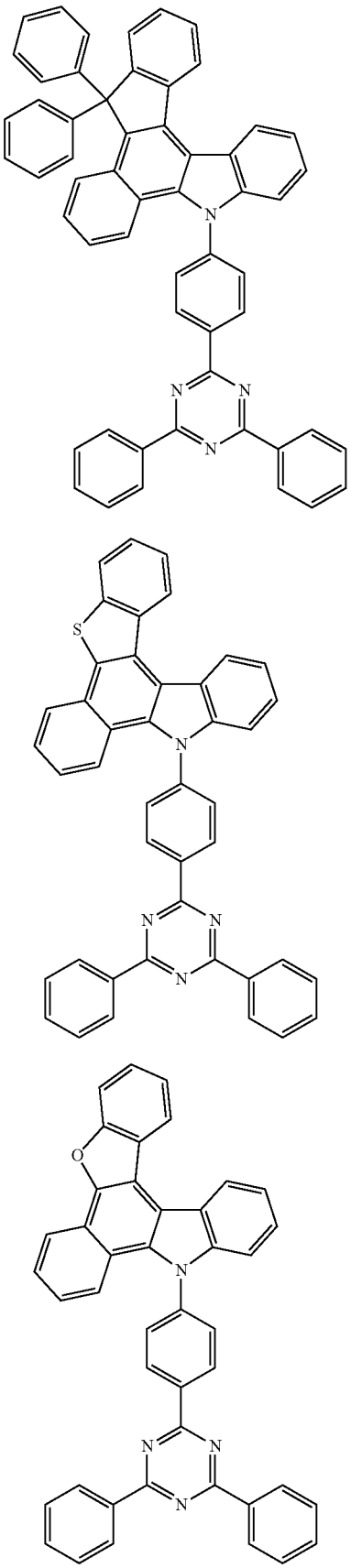
H2-142
H2-143

H2-144
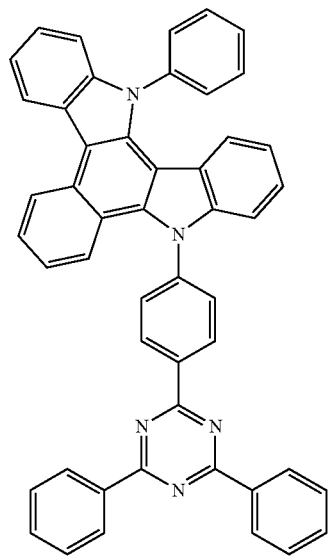
H2-146
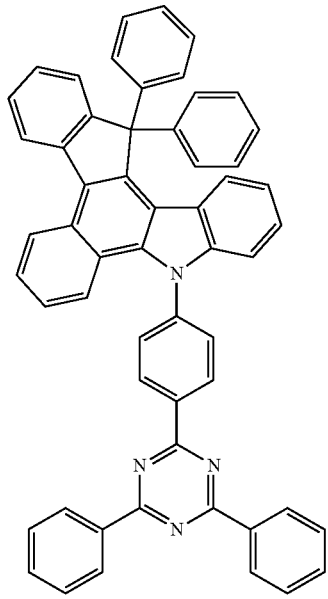
H2-145
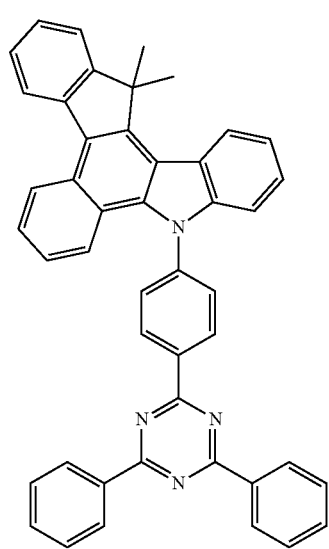
H2-147
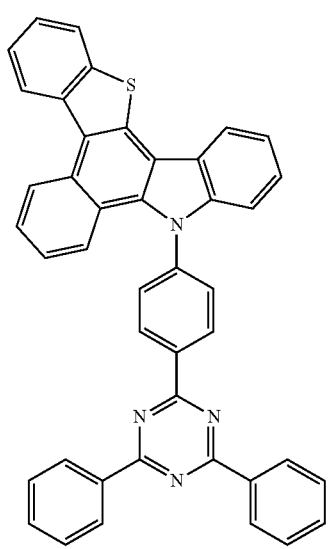

H2-148
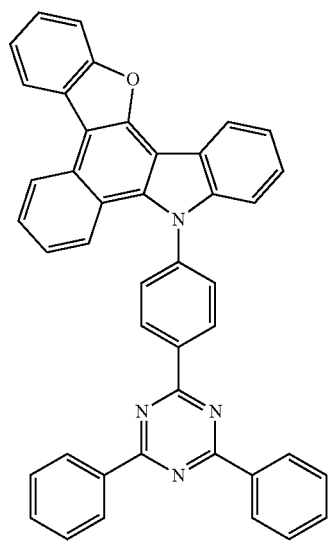
H2-149
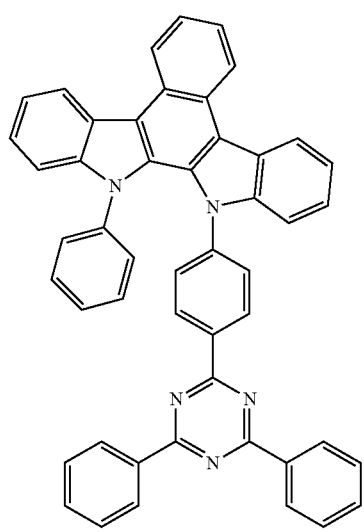
H2-150
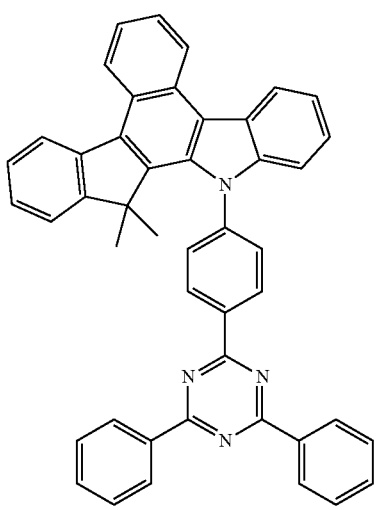
H2-151
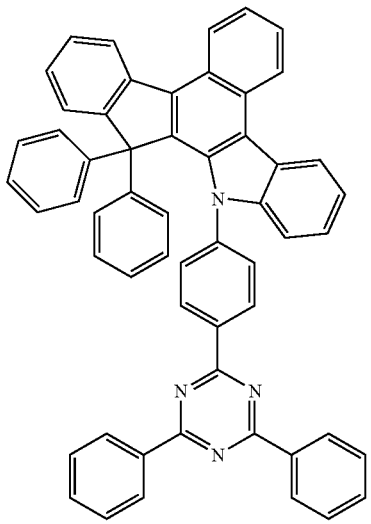
H2-152
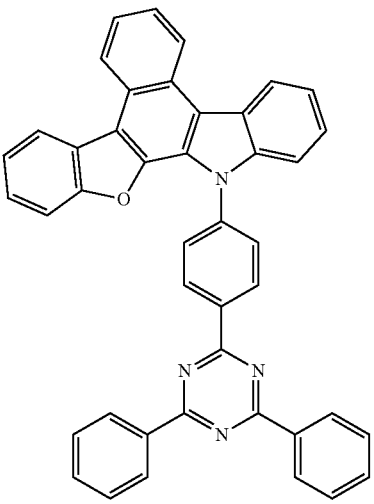
H2-153
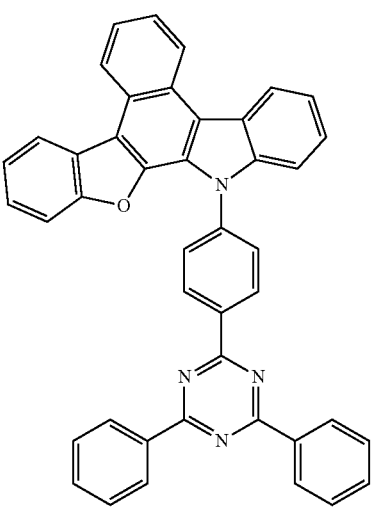

H2-154
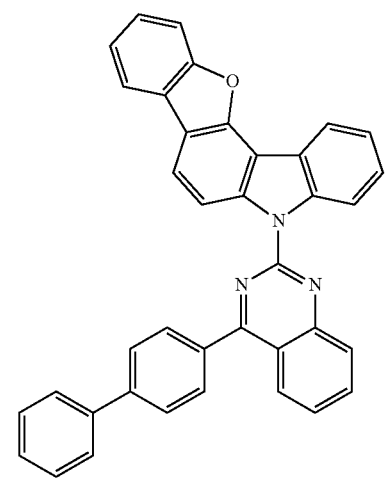
H2-155
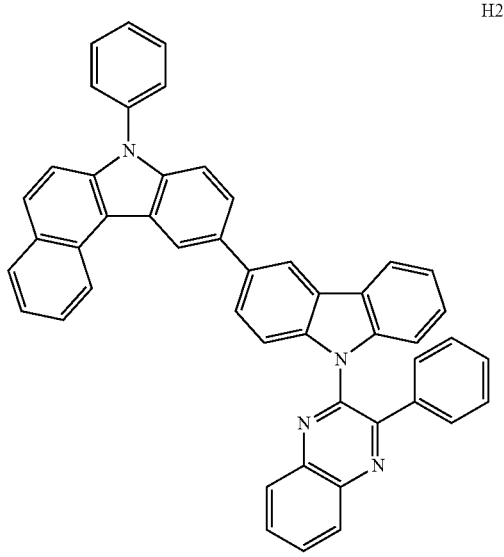
H2-156
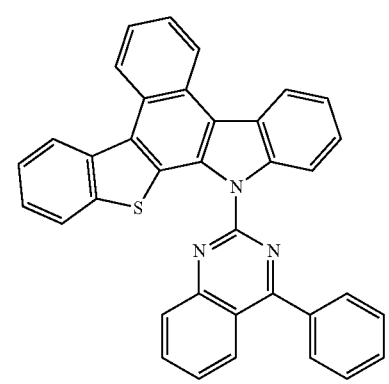
H2-157
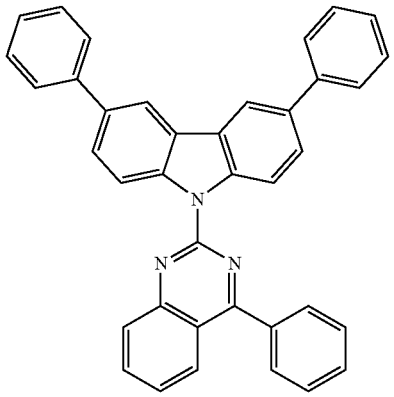
H2-158
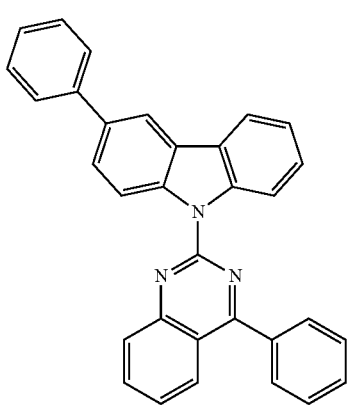
H2-159
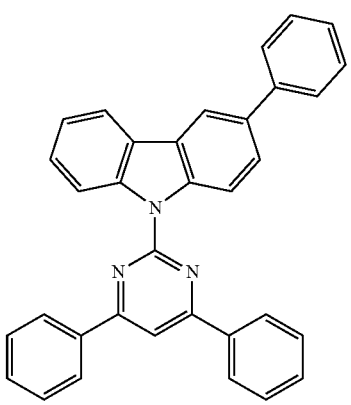
H2-160
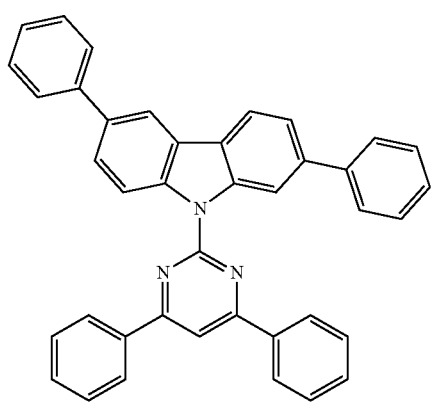

H2-161
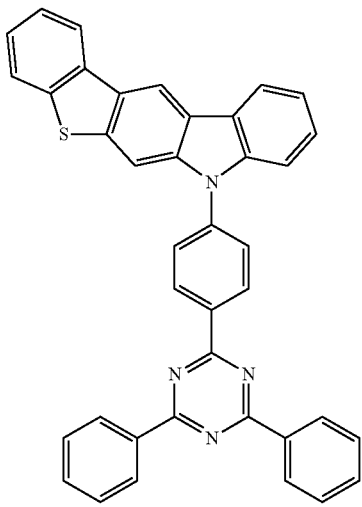
H2-164
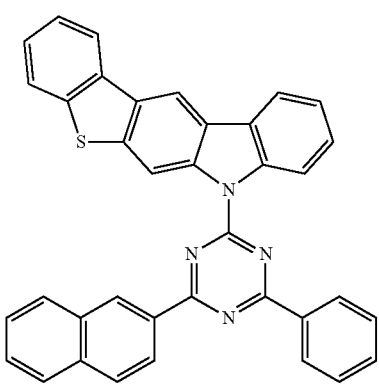
H2-162
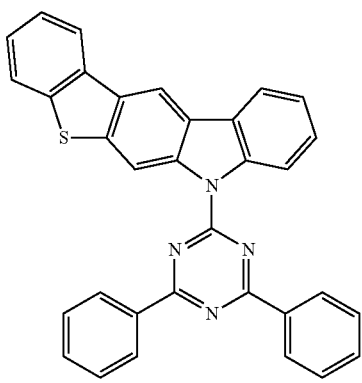
H2-165
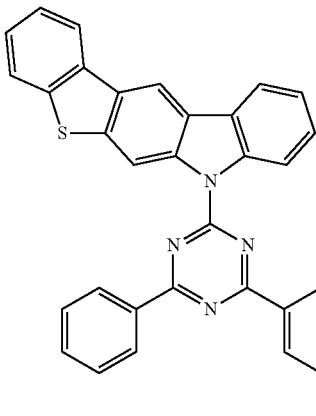
H2-163
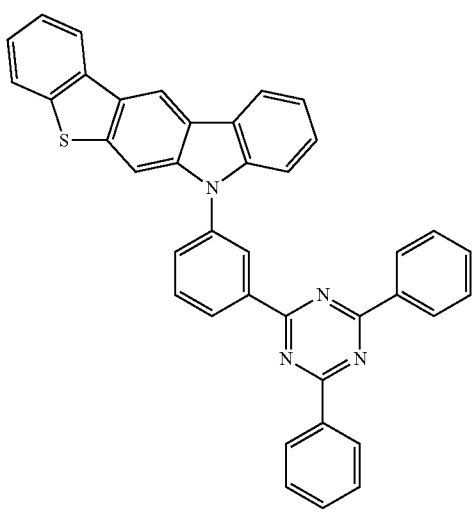
H2-166
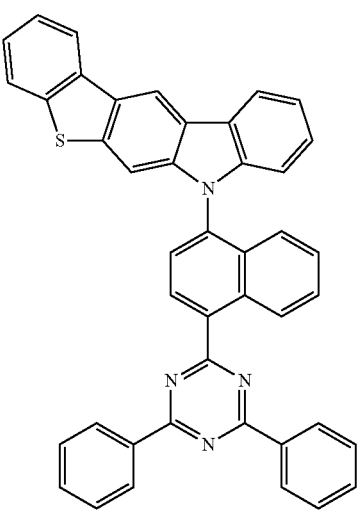

H2-167
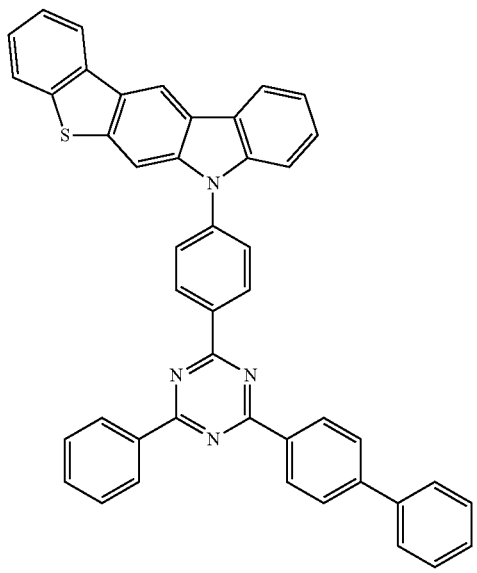
H2-168
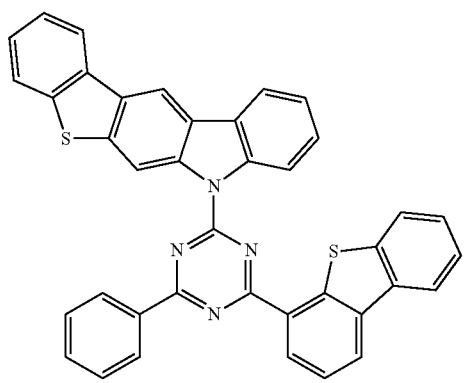
H2-169
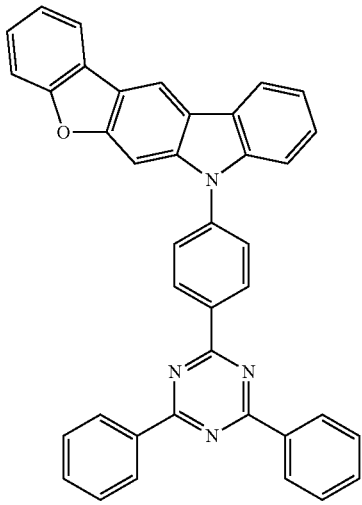
H2-170
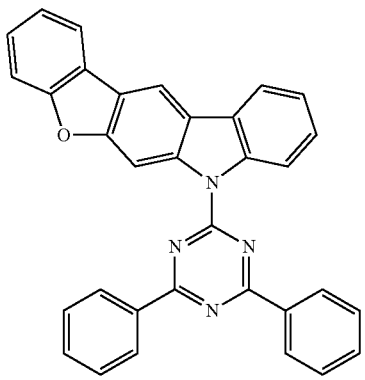
H2-171
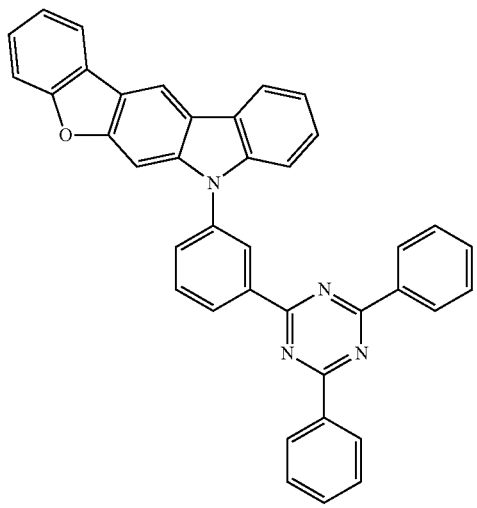
H2-172
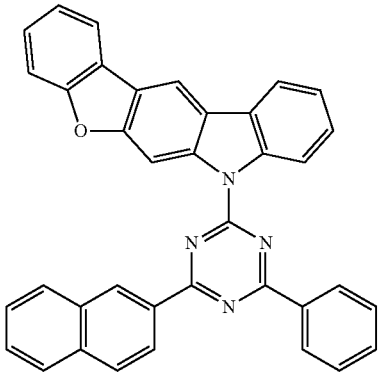

H2-173
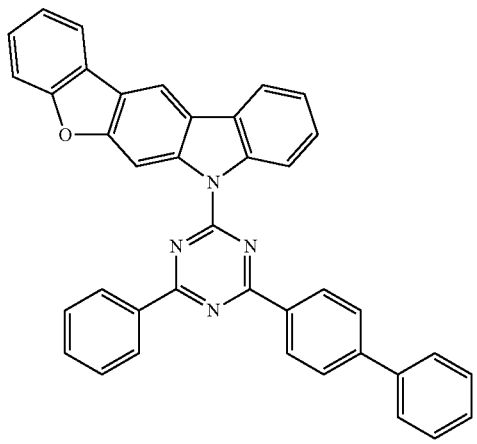
H2-176
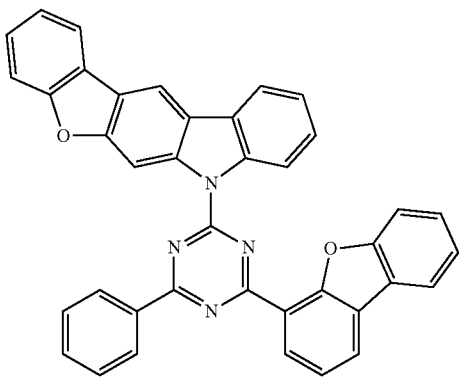
H2-174
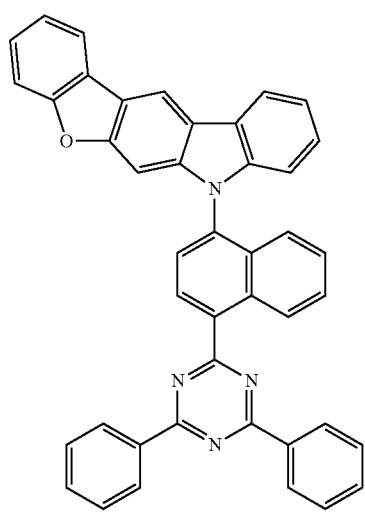
H2-177
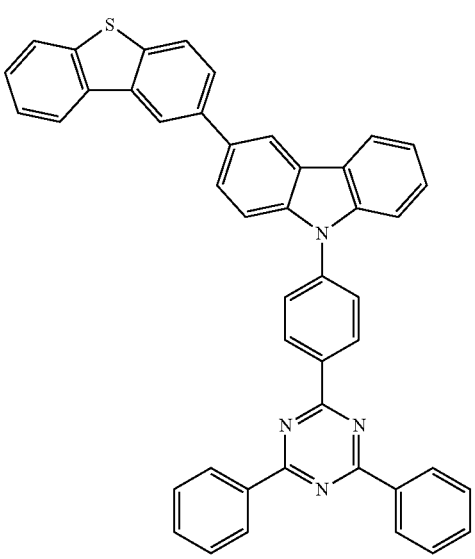
H2-175
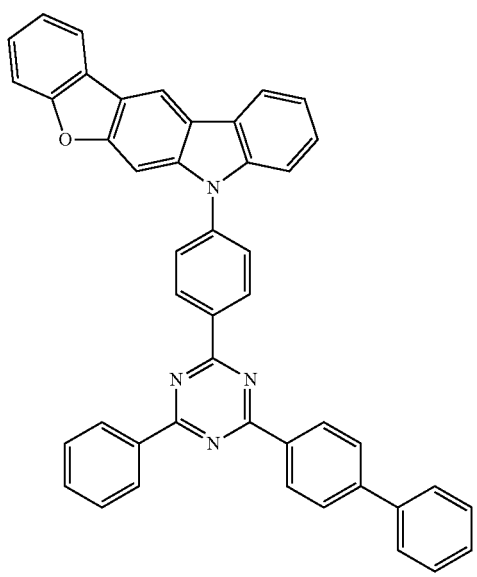
H2-178
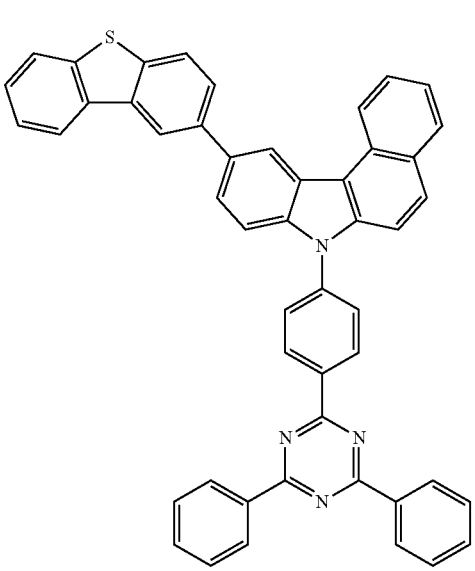

H2-179
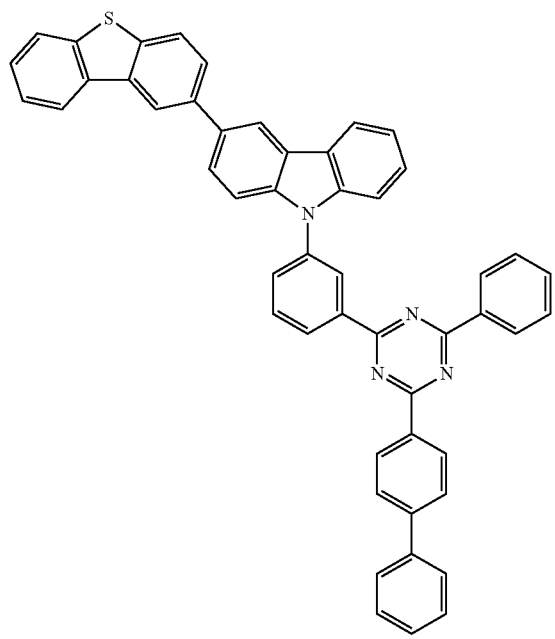
H2-180
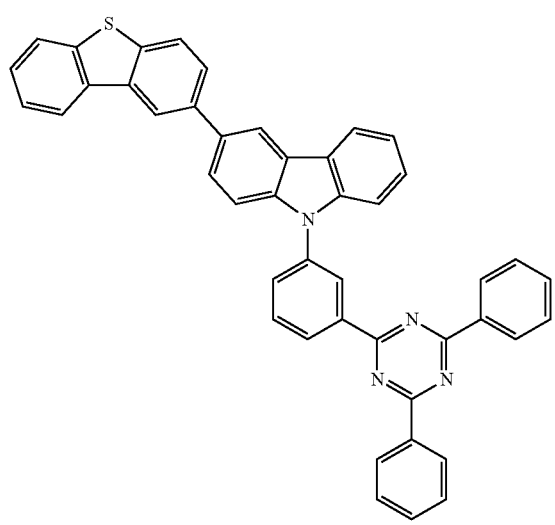
H2-181
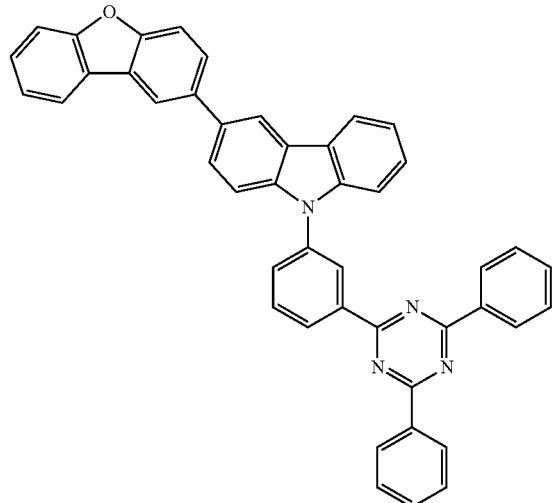
H2-182
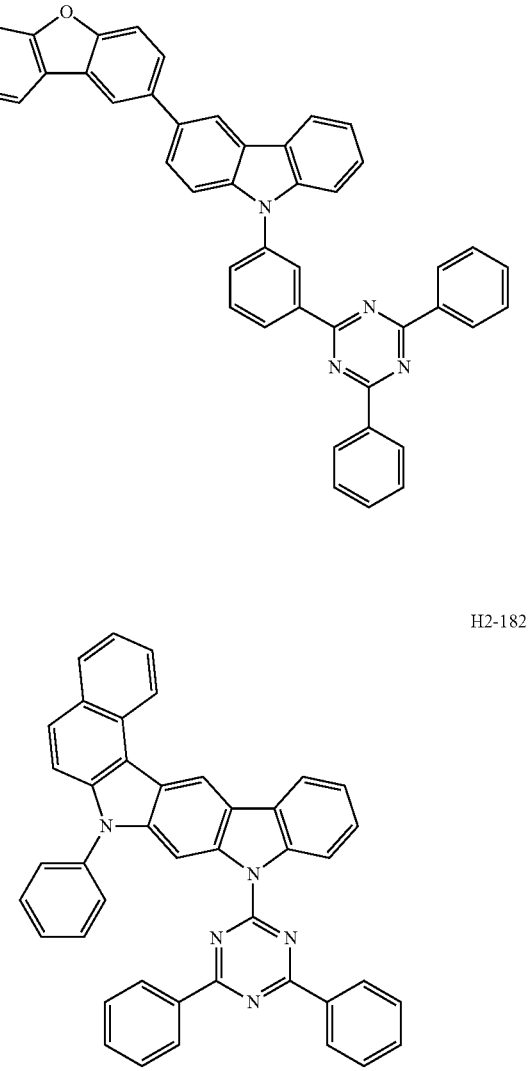
H2-183
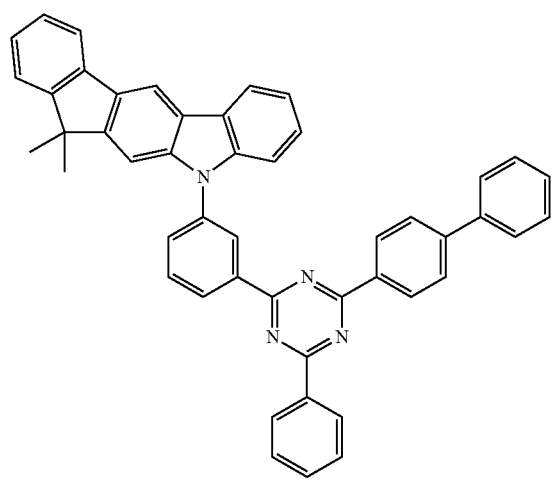

H2-184
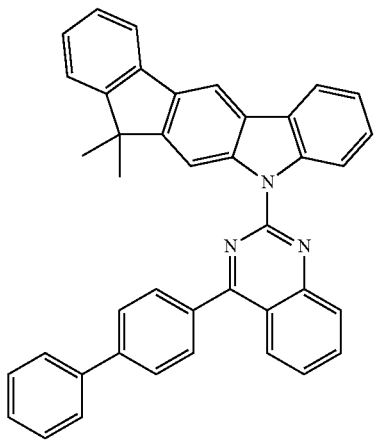
H2-185
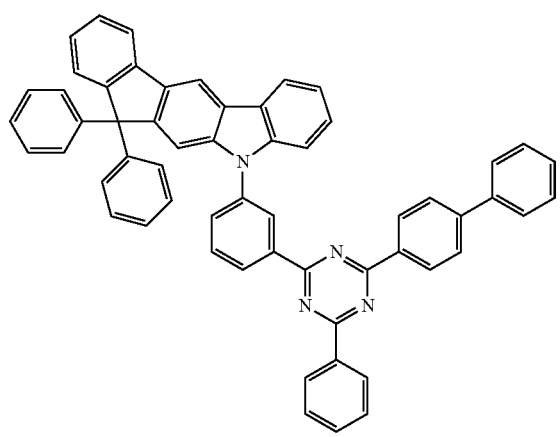
H2-186
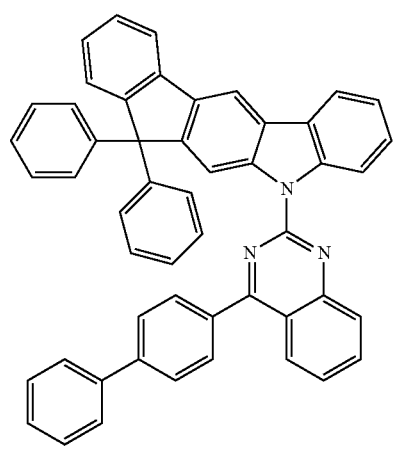
H2-187
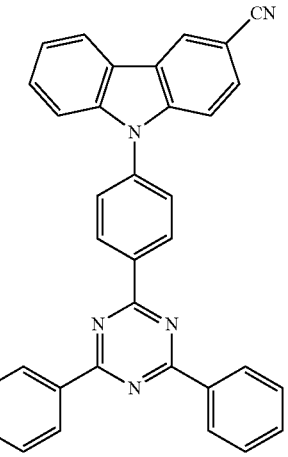
H2-188
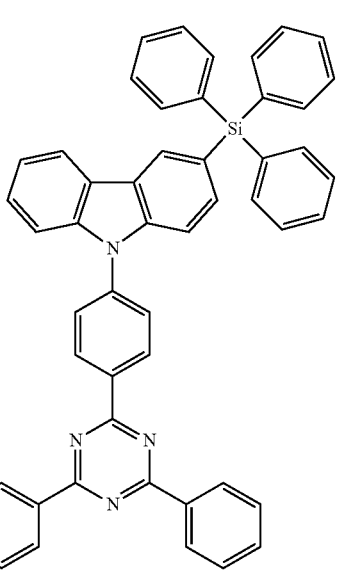
H2-189
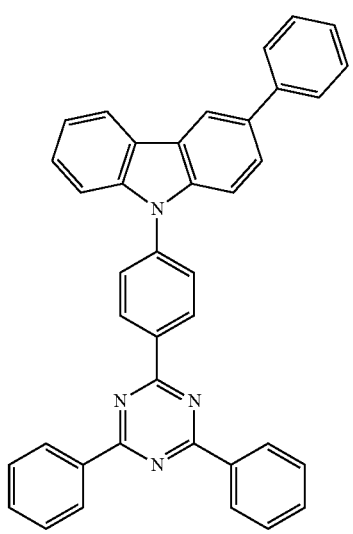

H2-190
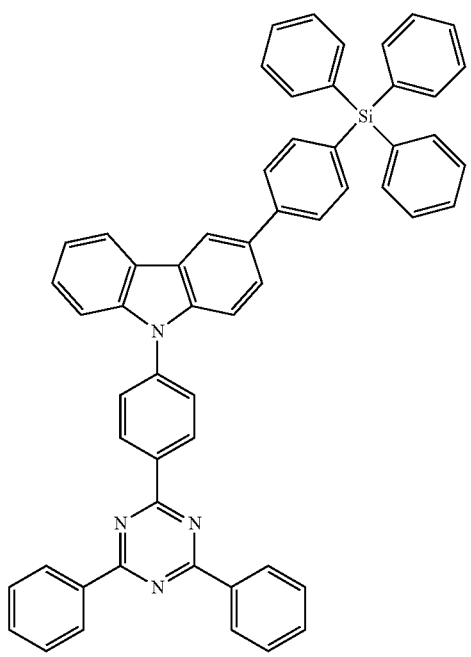
H2-191
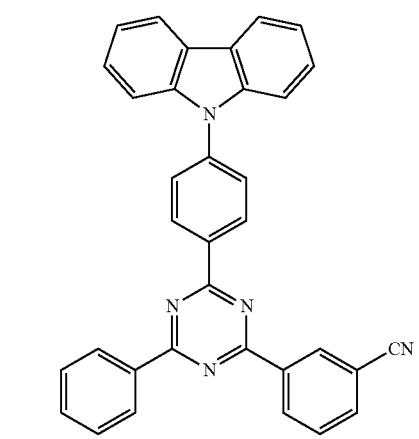
H2-192
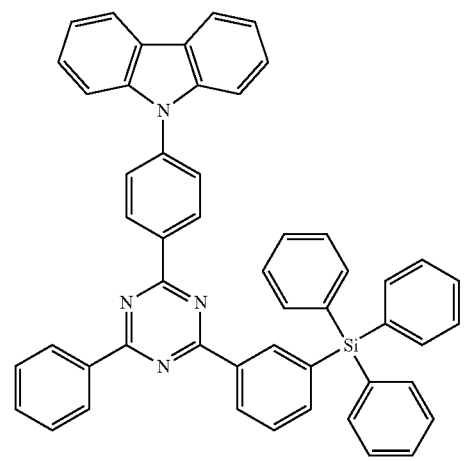
H2-193
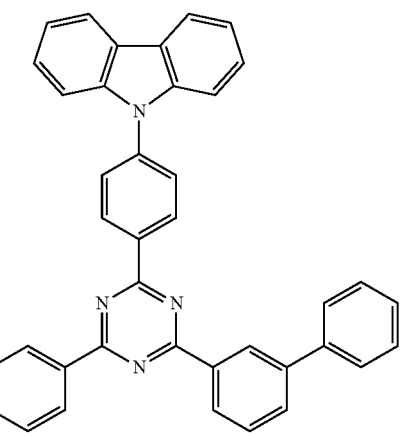
H2-194
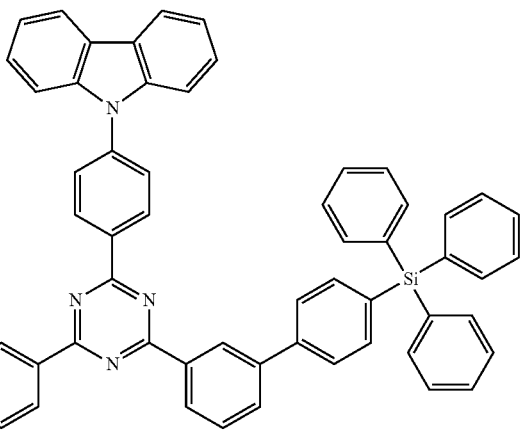
H2-195
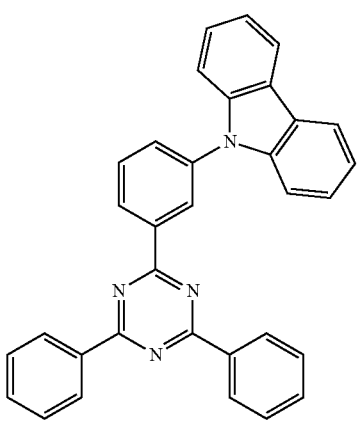

H2-196
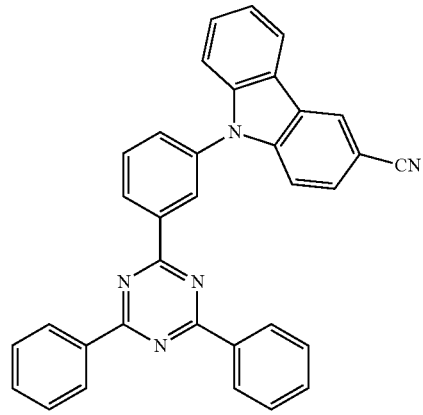
H2-197
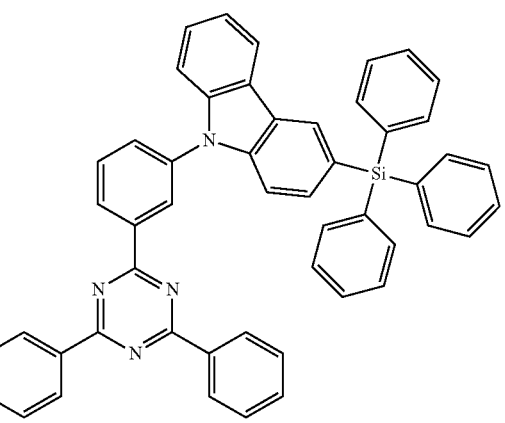
H2-198
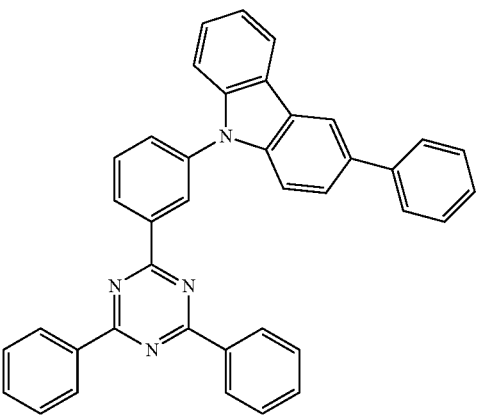
H2-199
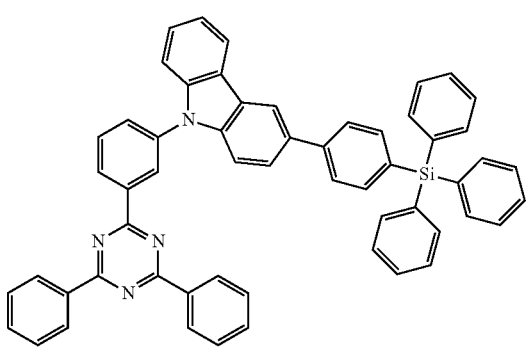
H2-200
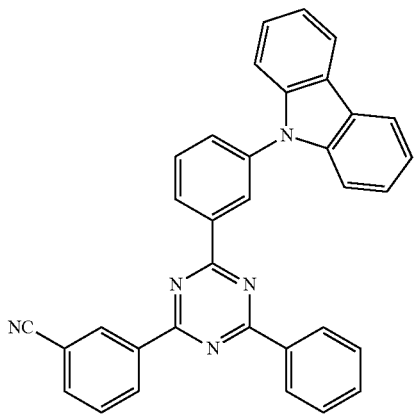
H2-201
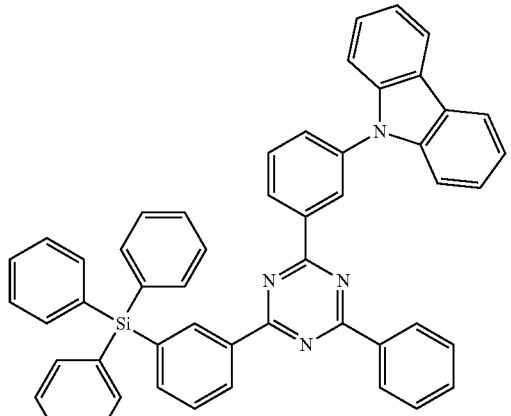
H2-202
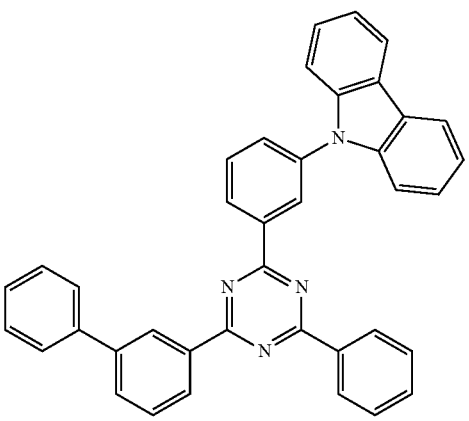

-continued
H2-203
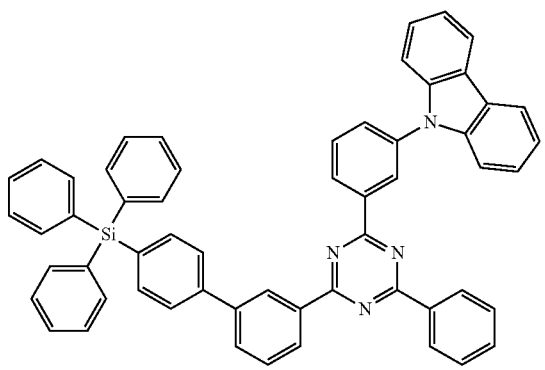
H2-204
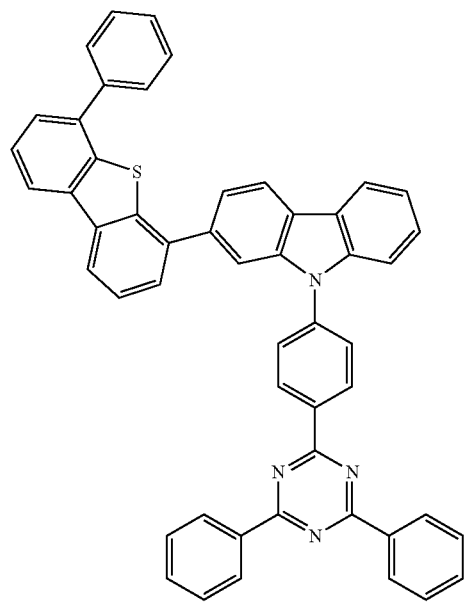
H2-205
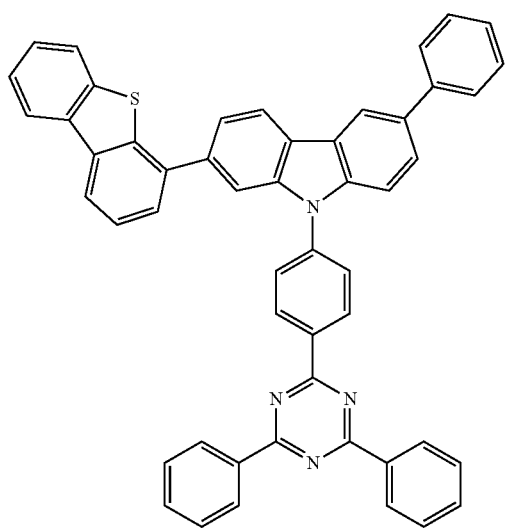
-continued
H2-206
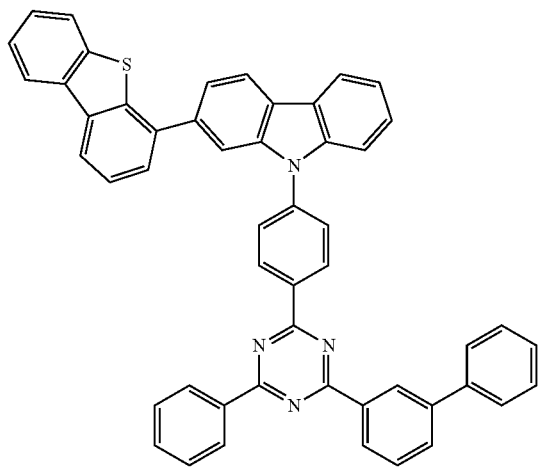
H2-207
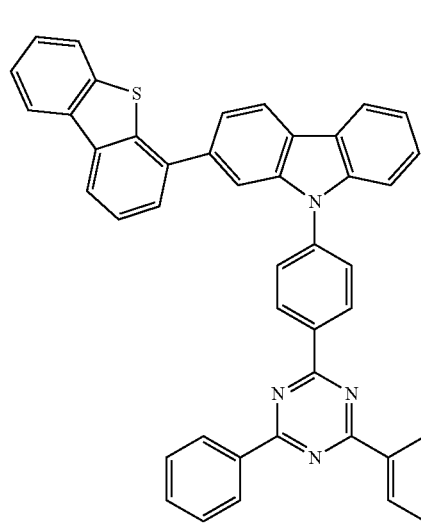
H2-208
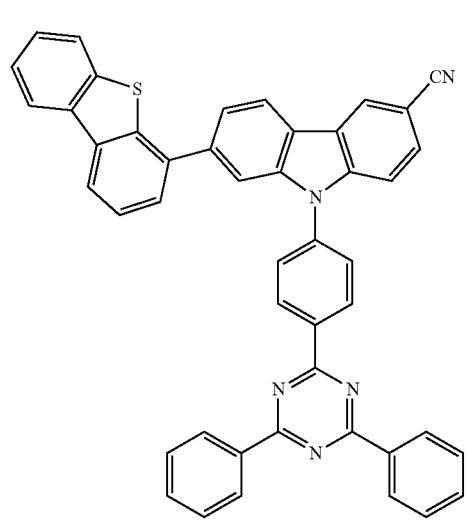

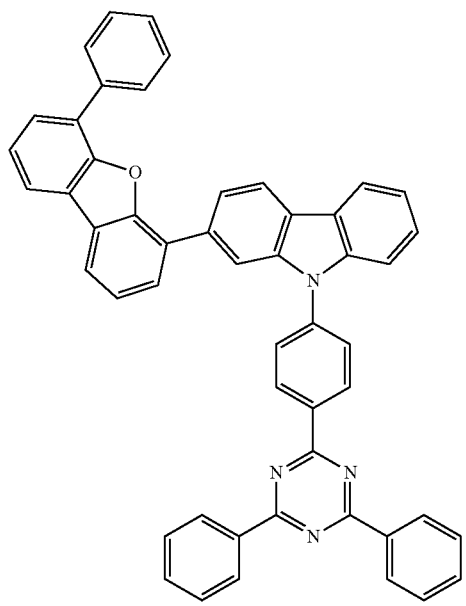
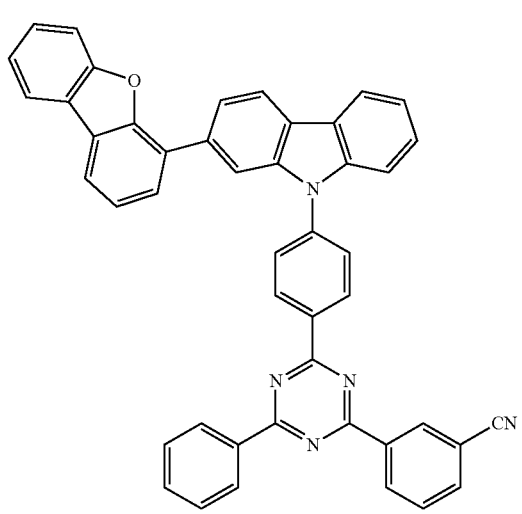

H2-215
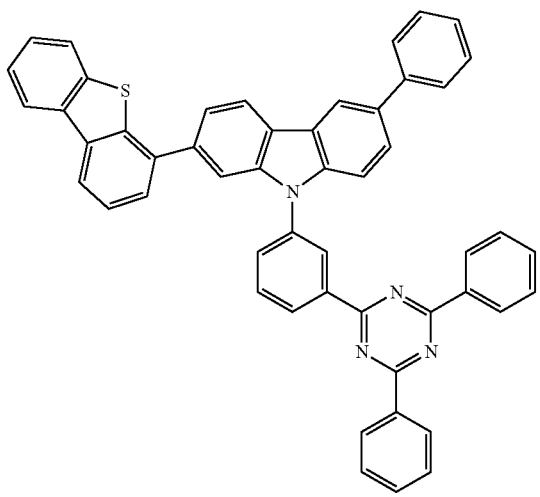
H2-216
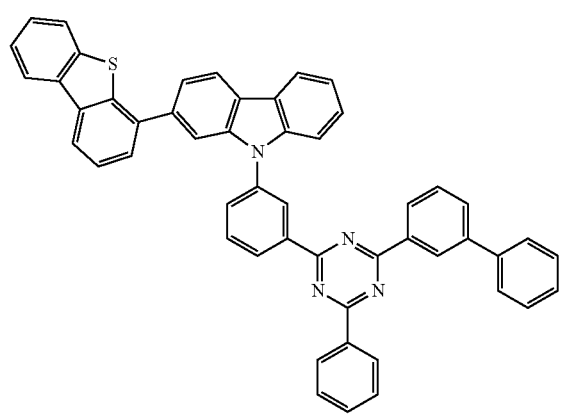
H2-217
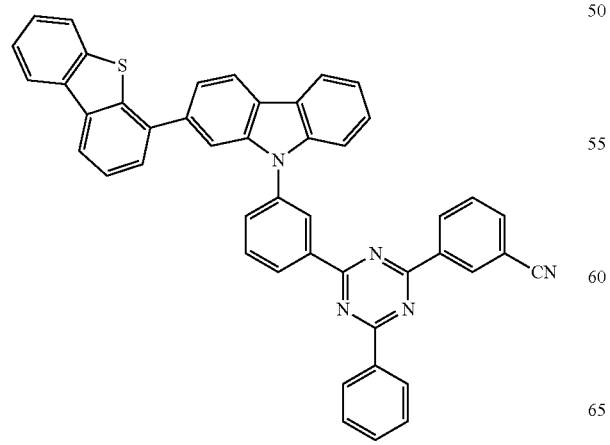
H2-218
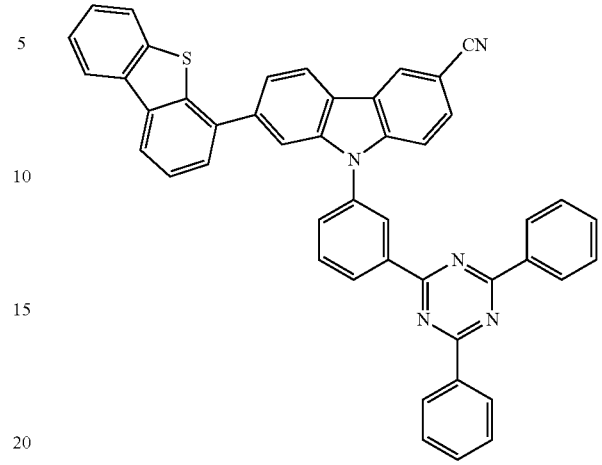
H2-219
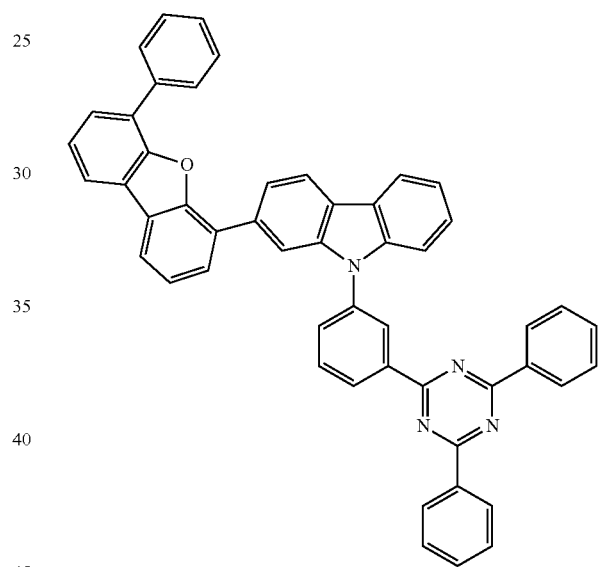
H2-220
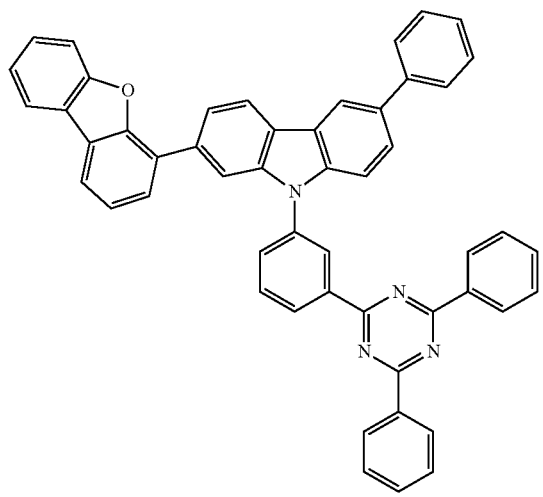

H2-221
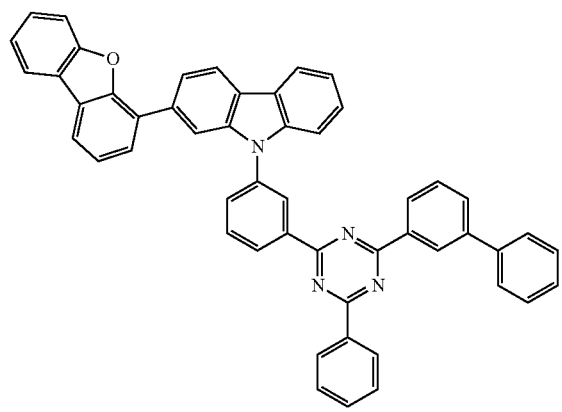
H2-222
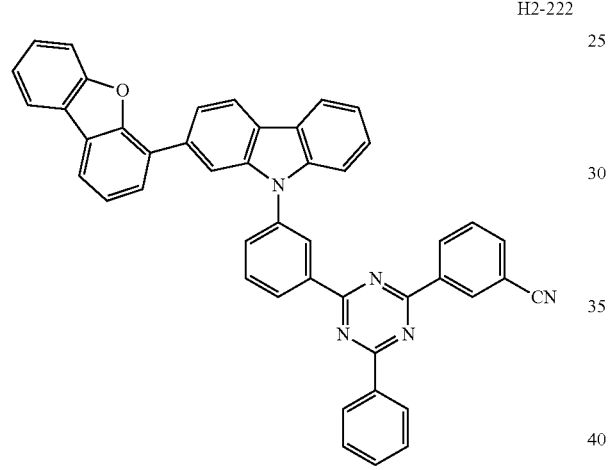
H2-223
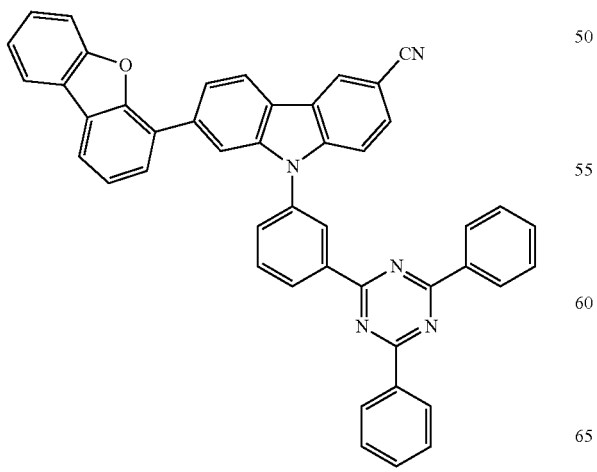
H2-224
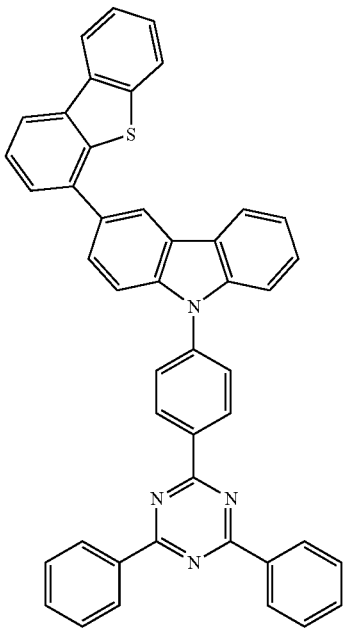
H2-225
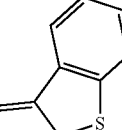

H2-226
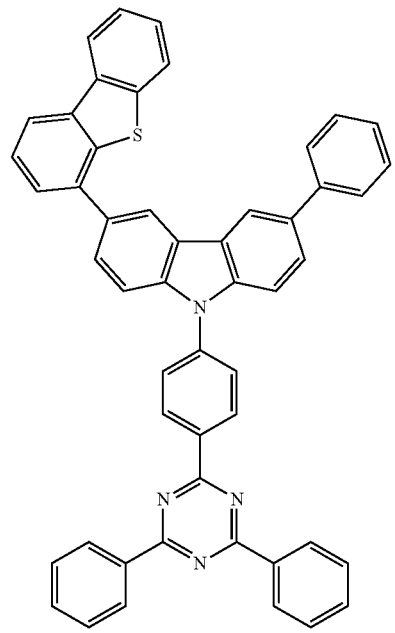
H2-228
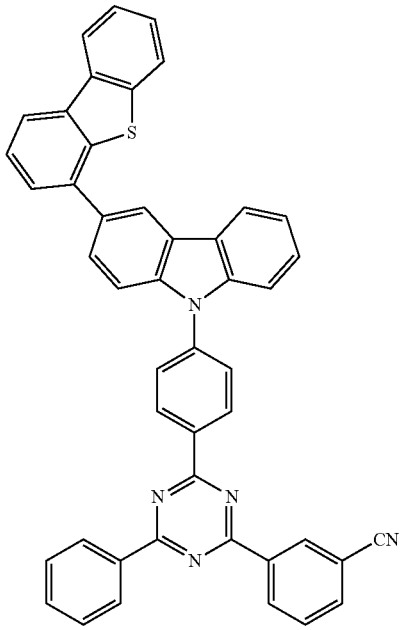
H2-227
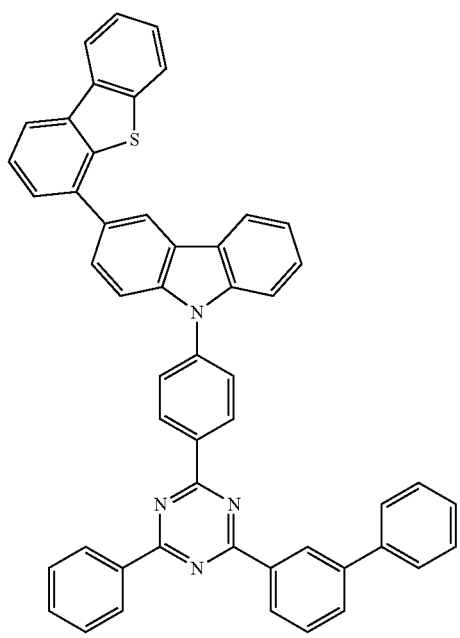
H2-229
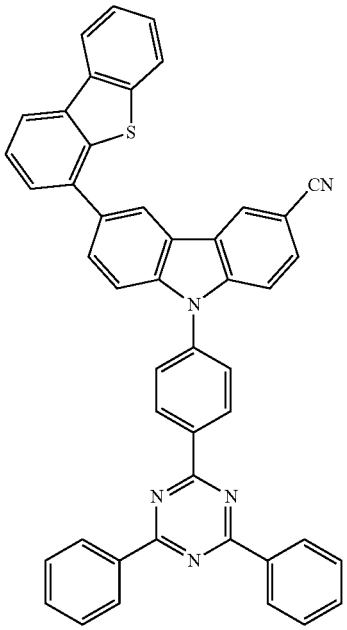

H2-230
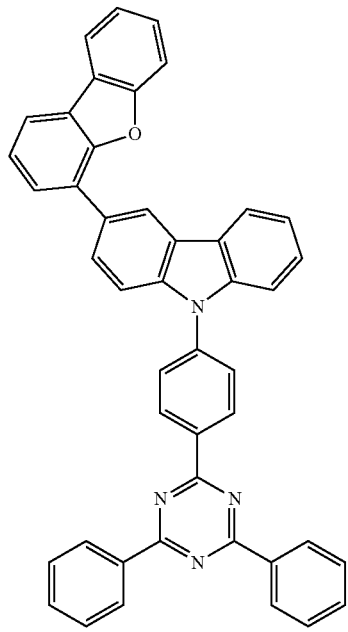
H2-231
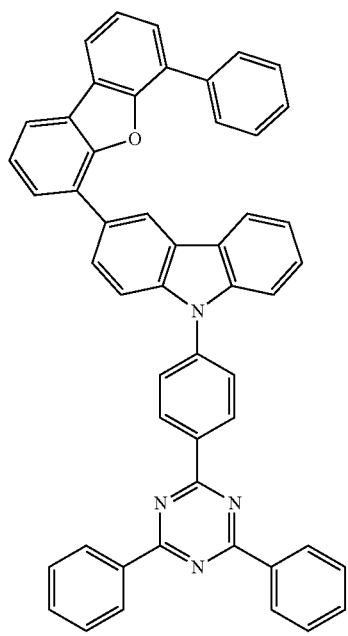
H2-232
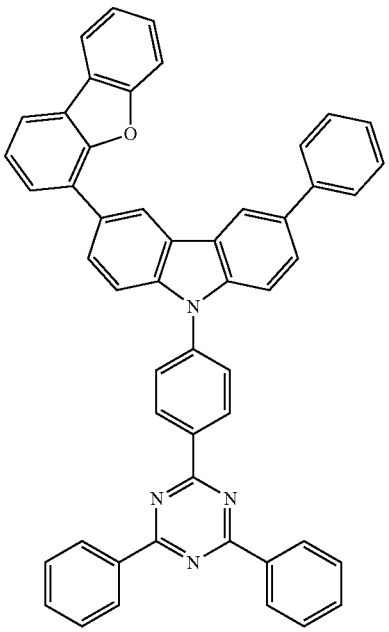
H2-233
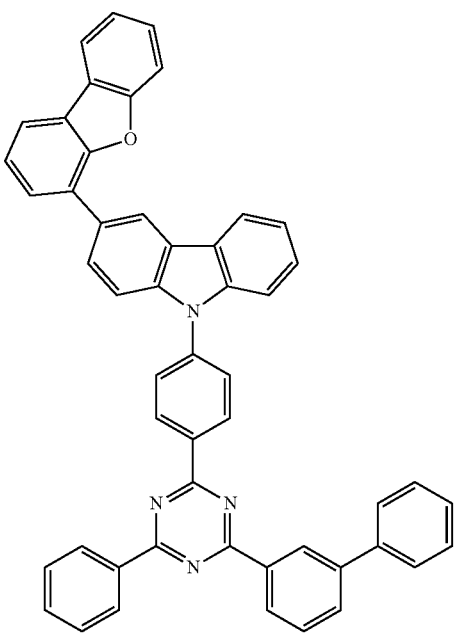

H2-234
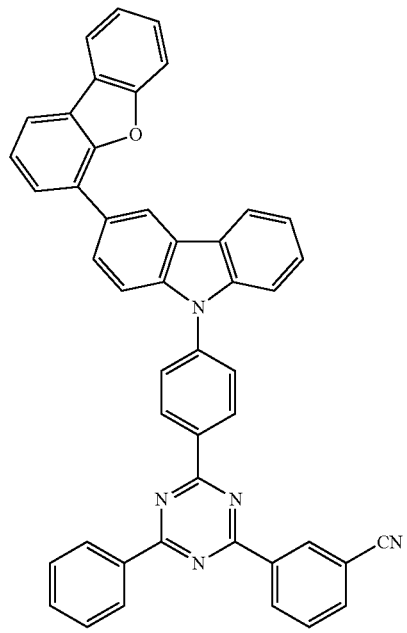
H2-235
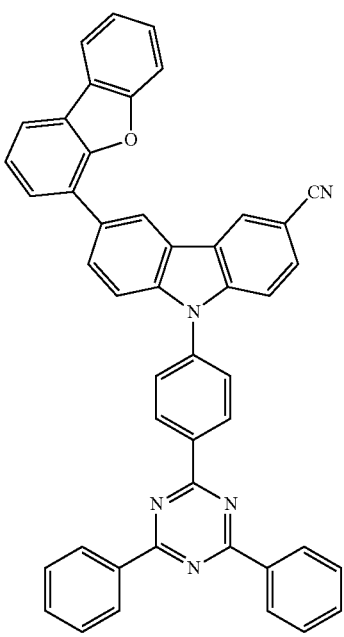
H2-236
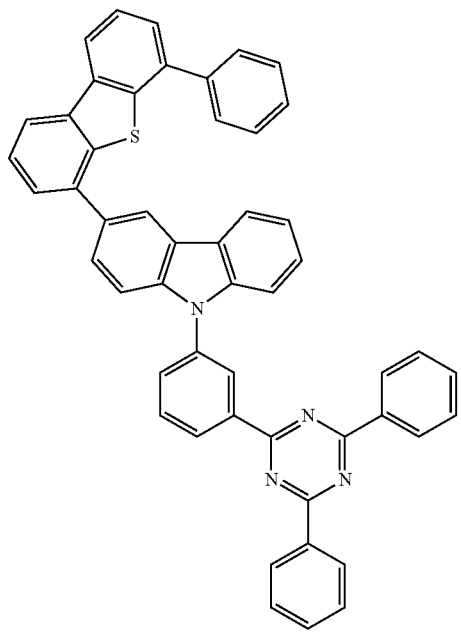
H2-237
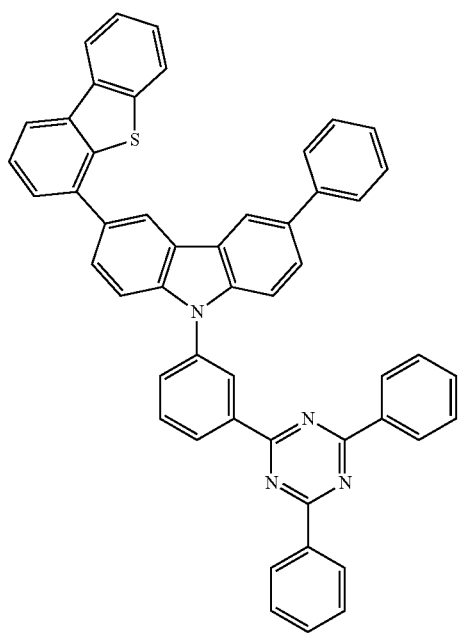

H2-238
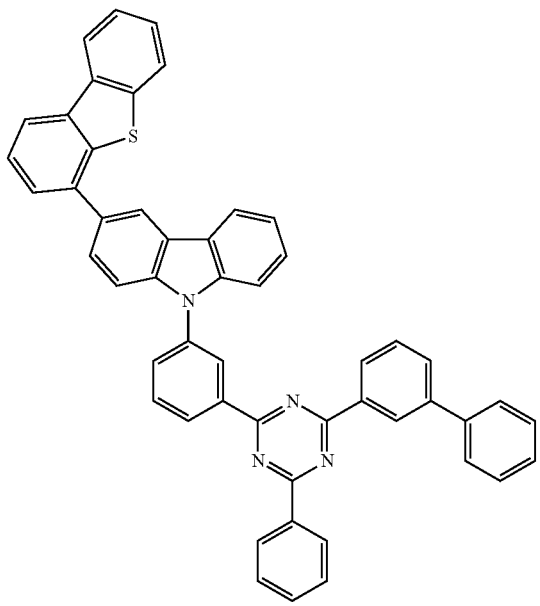
H2-240
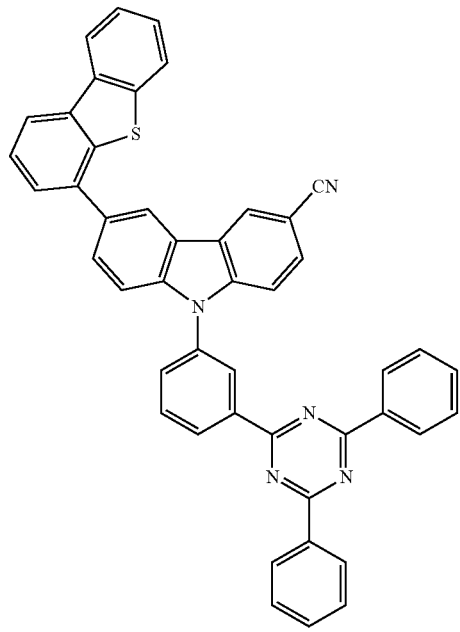
H2-239
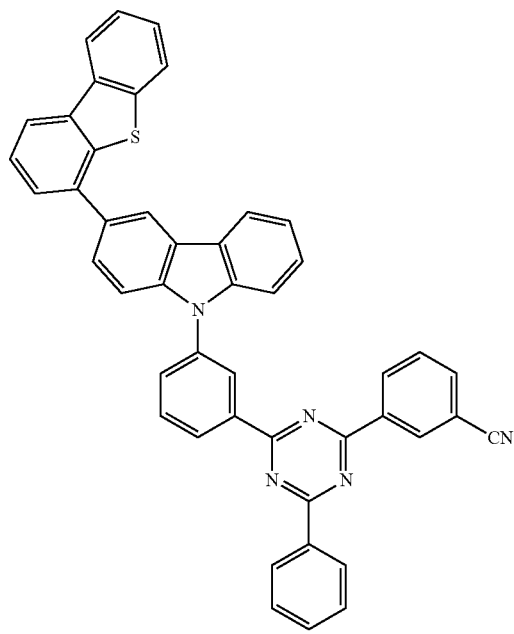
H2-241
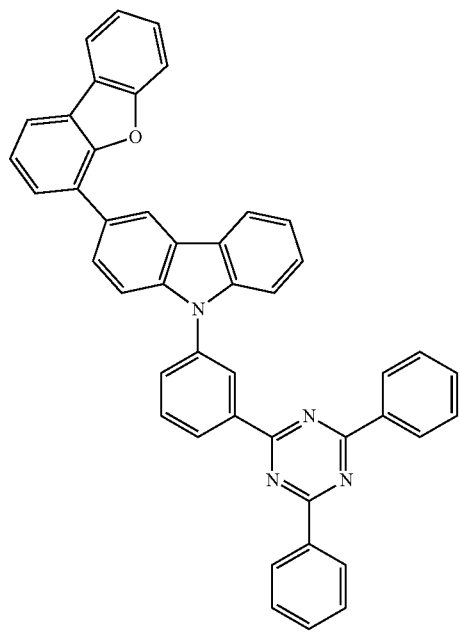

H2-242
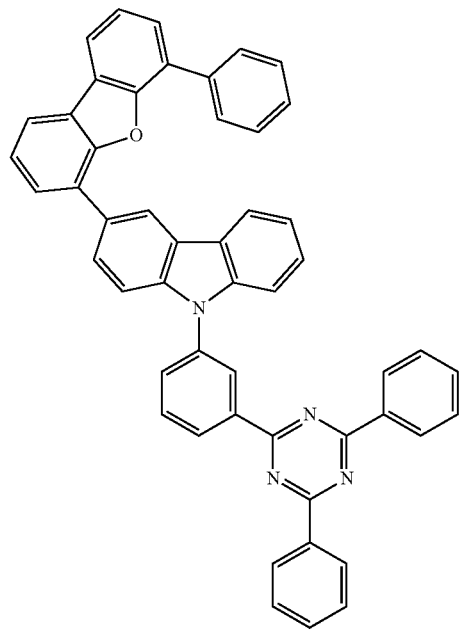
H2-244
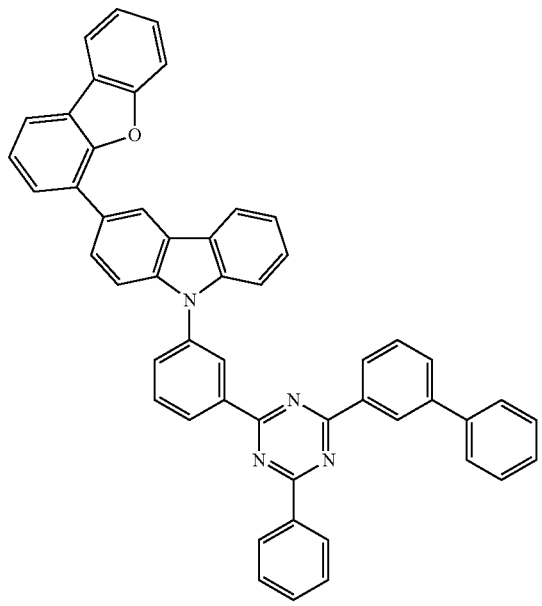
H2-243
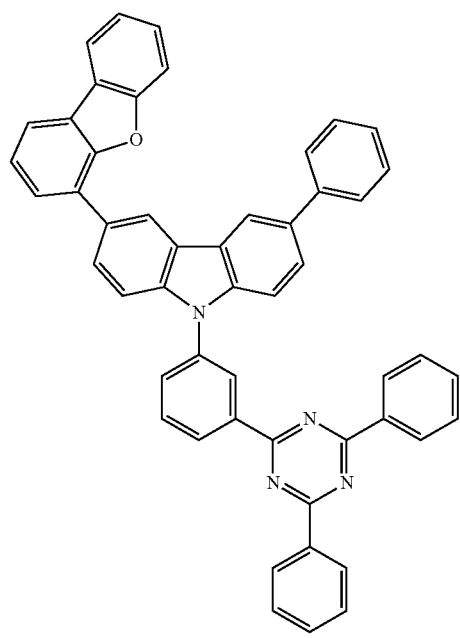
H2-245
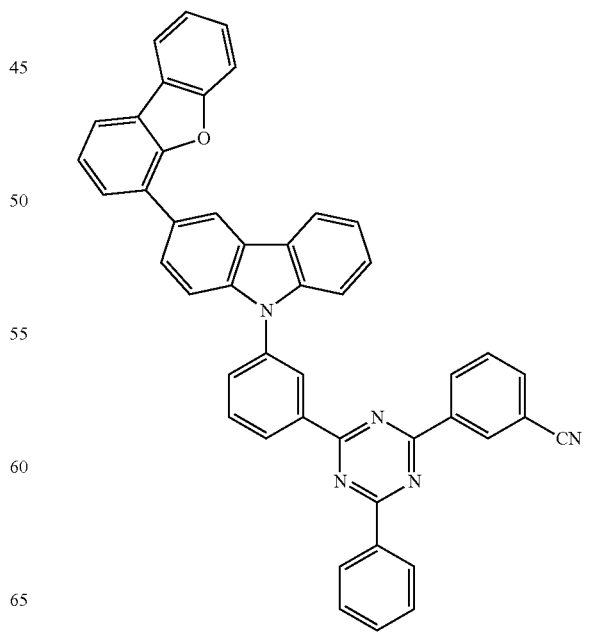

H2-246
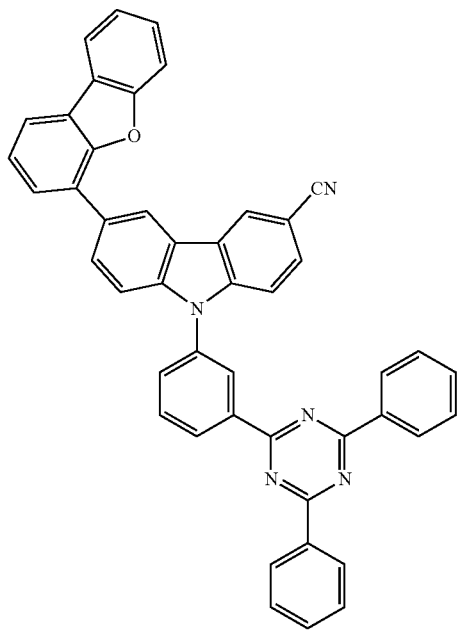
H2-247
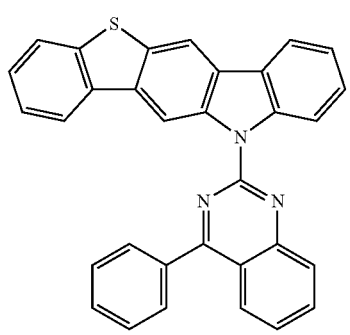
H2-248
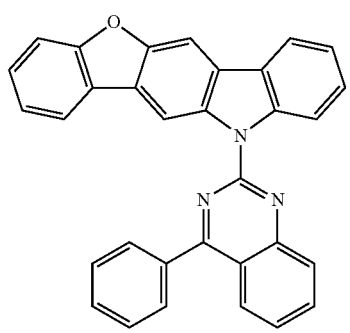
H2-249
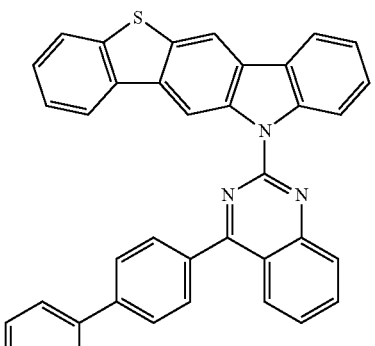
H2-250
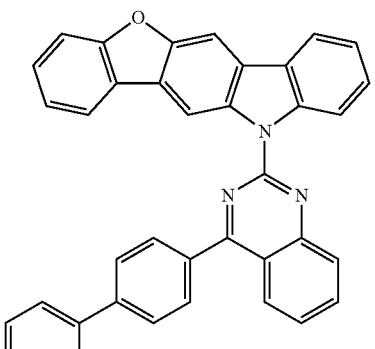
H2-251
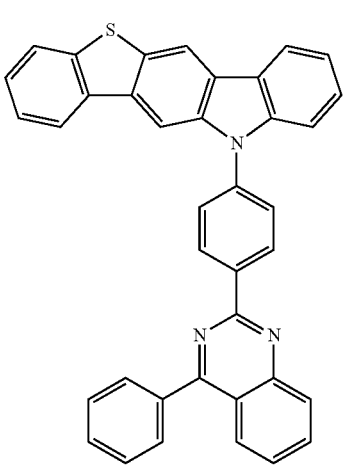

H2-252
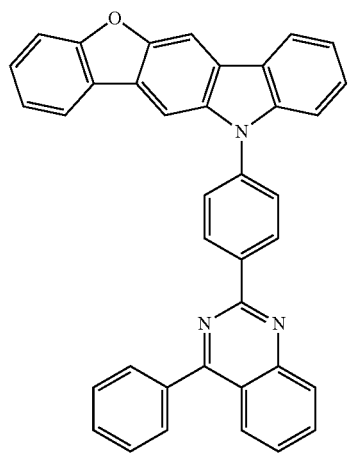
H2-255
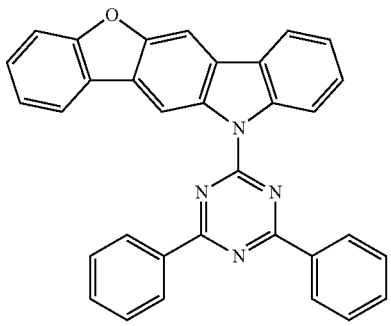
H2-253
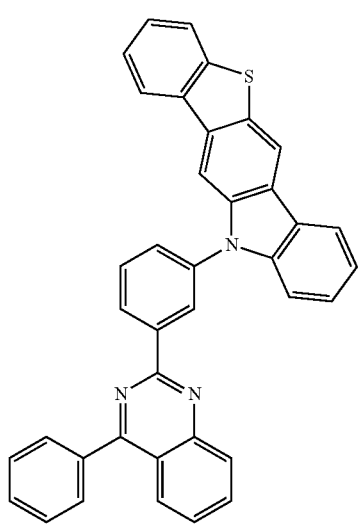
H2-256
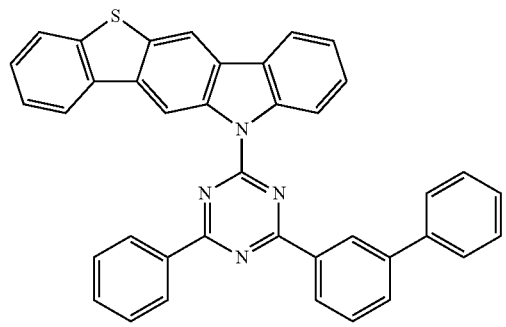
H2-257
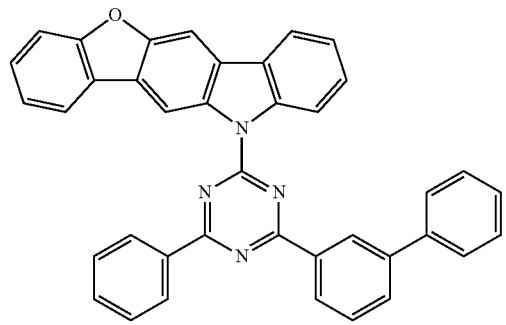
H2-254
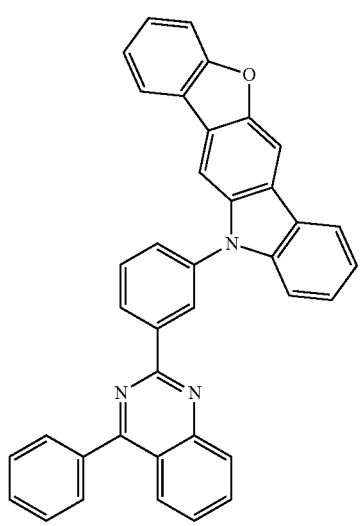
H2-258
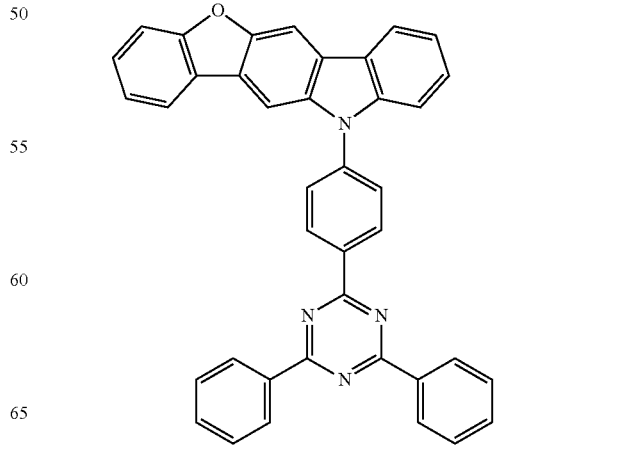

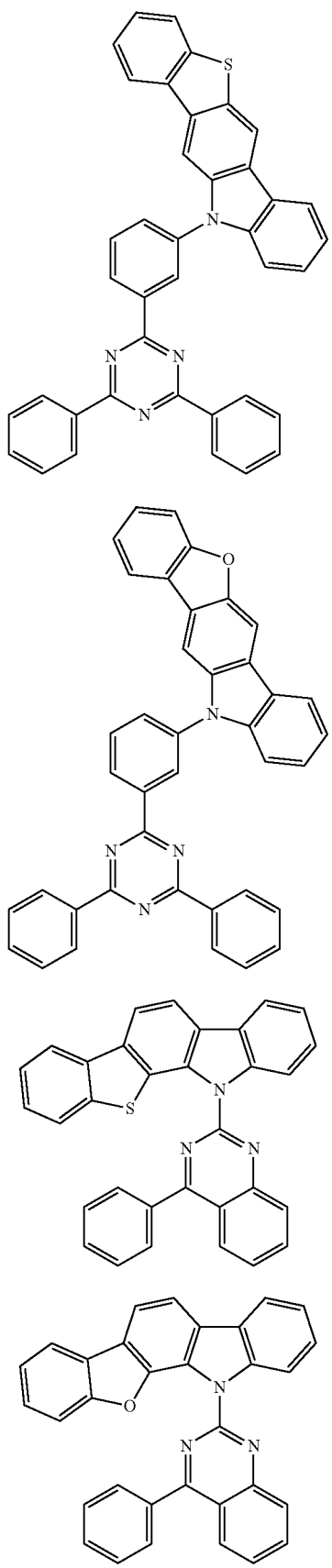
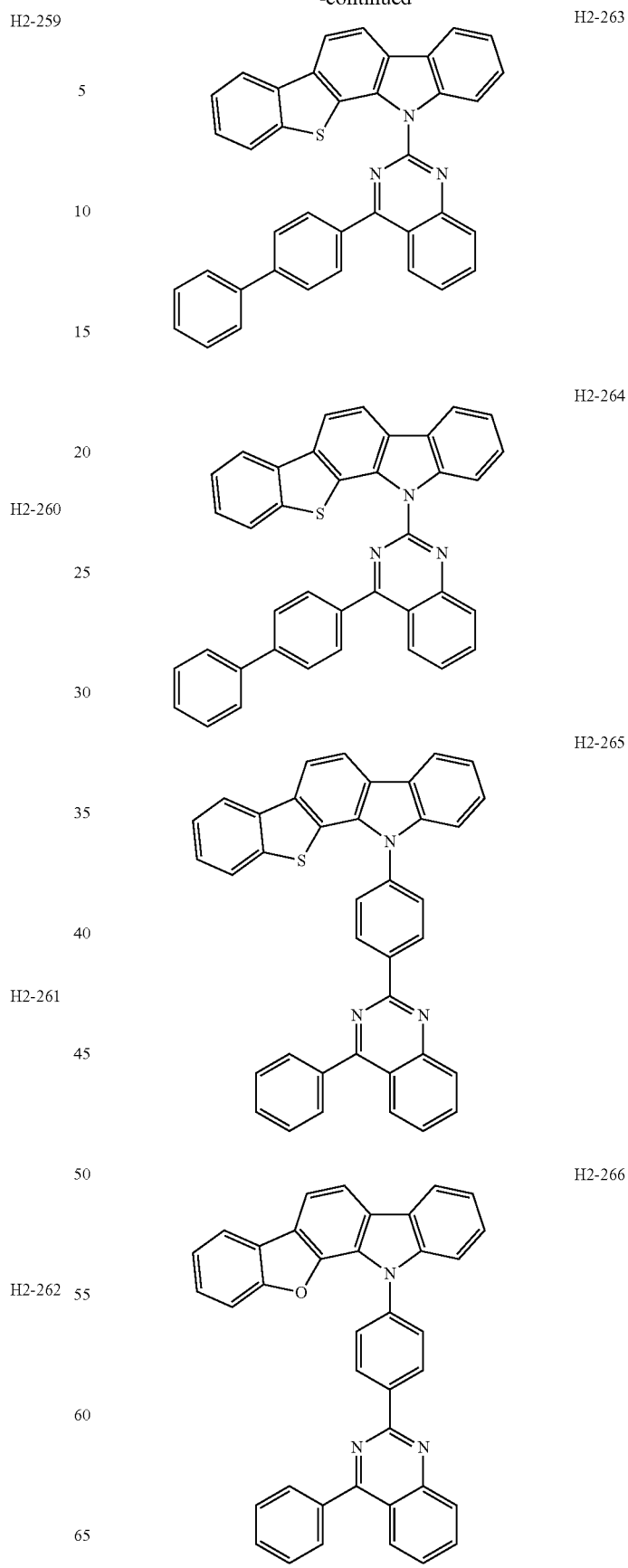

H2-267
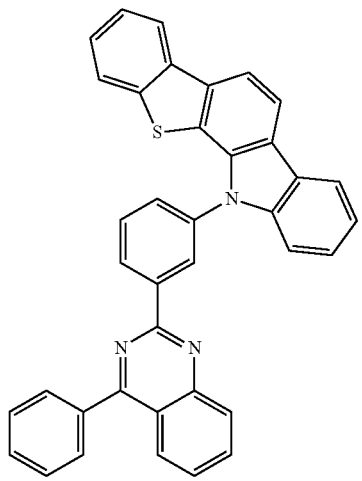
H2-268
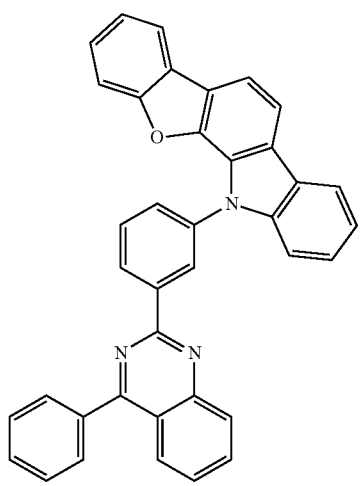
H2-269
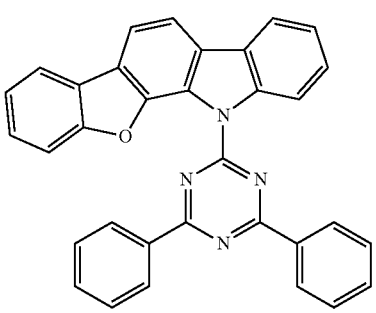
H2-270
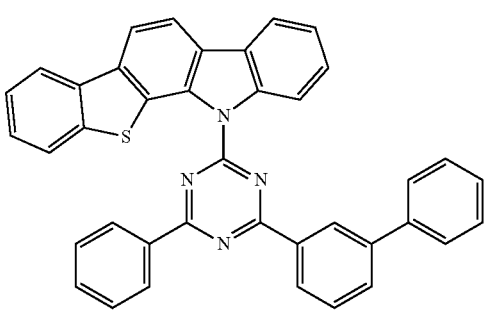
H2-271
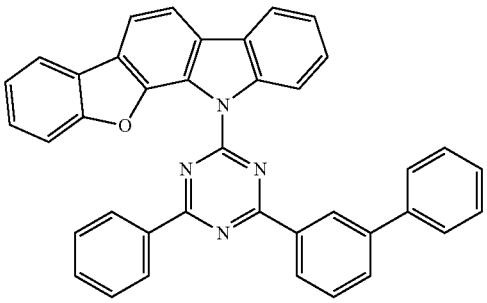
H2-272
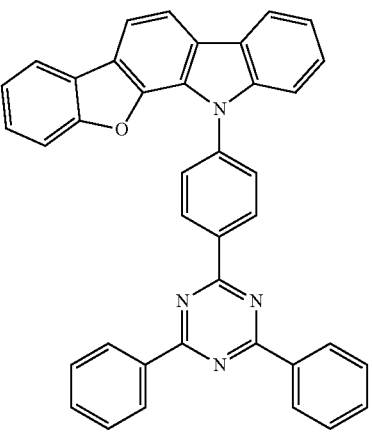
H2-273
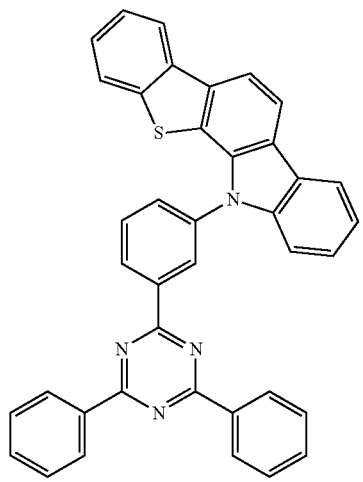

H2-274
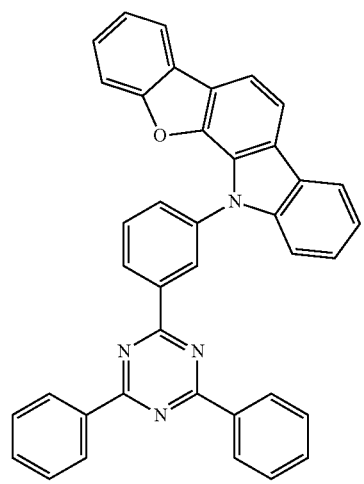
H2-275
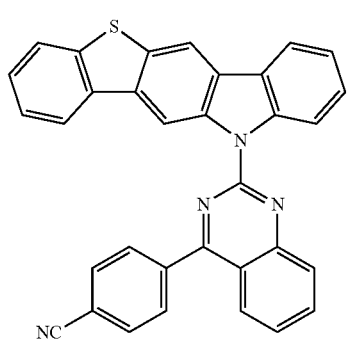
H2-276
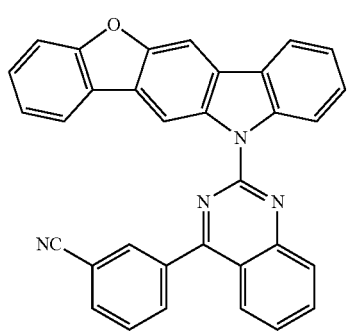
H2-277
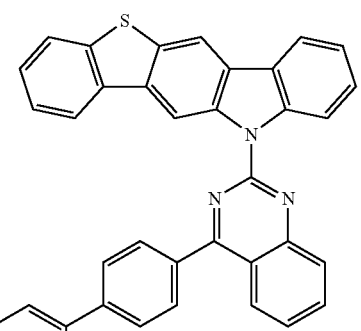
H2-278
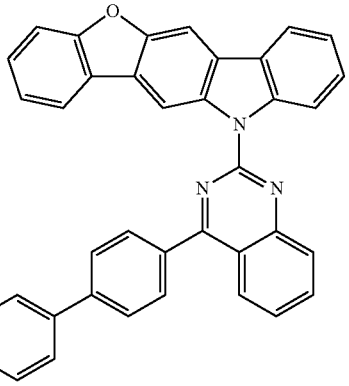
H2-279
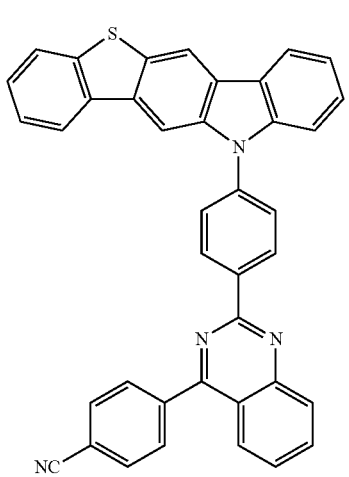
H2-280
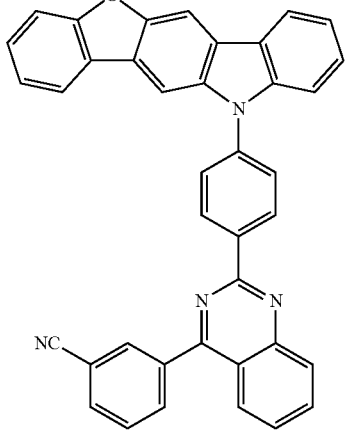

H2-281
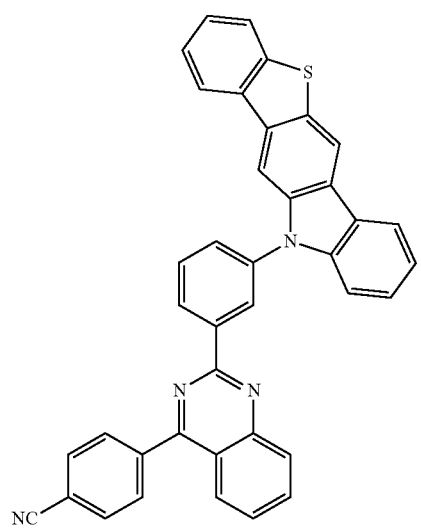
H2-282
H2-283
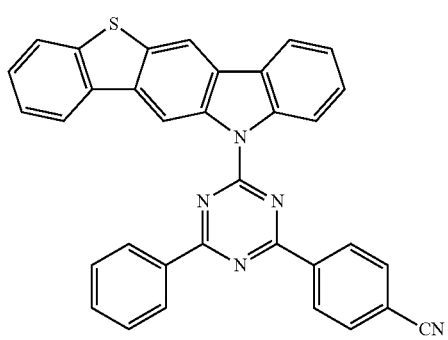
H2-284
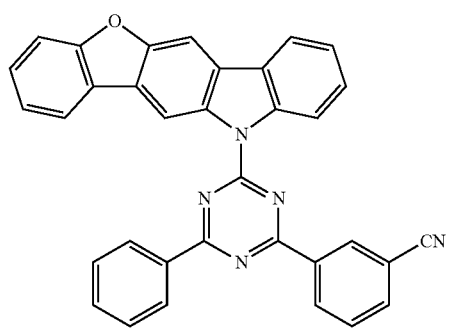
H2-285
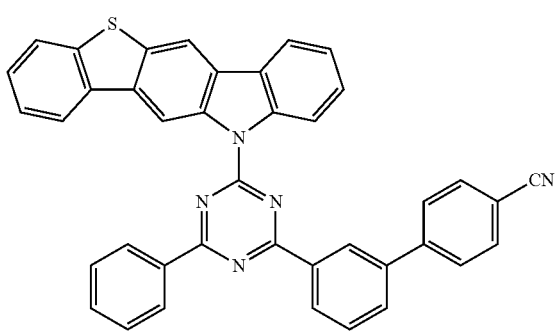
H2-286
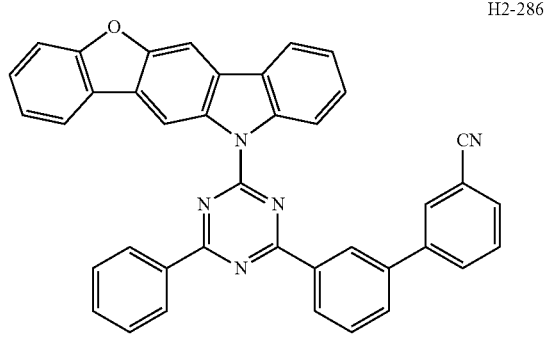
H2-287
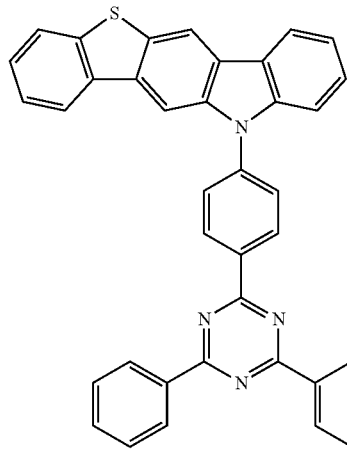

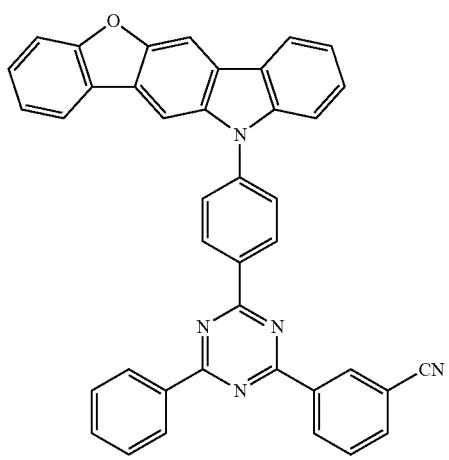
H2-288
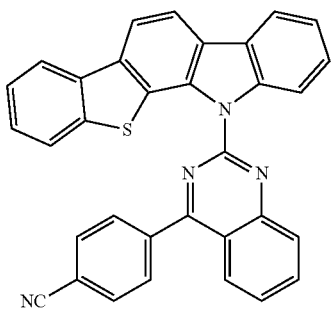
H2-291
H2-289
H2-292
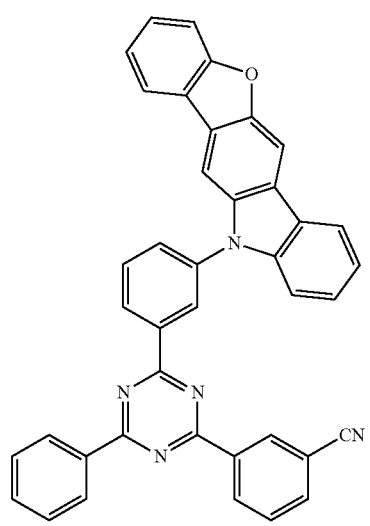
H2-290
H2-293
H2-294

H2-295
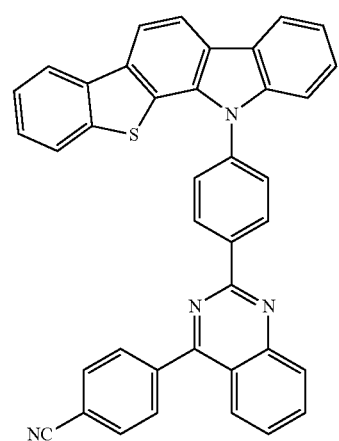
H2-296
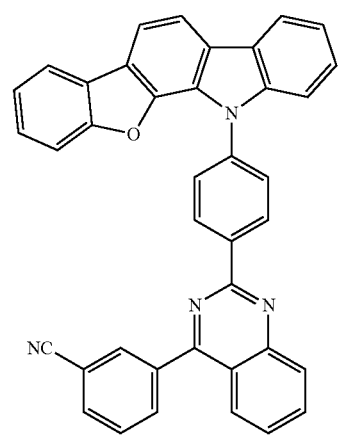
H2-297
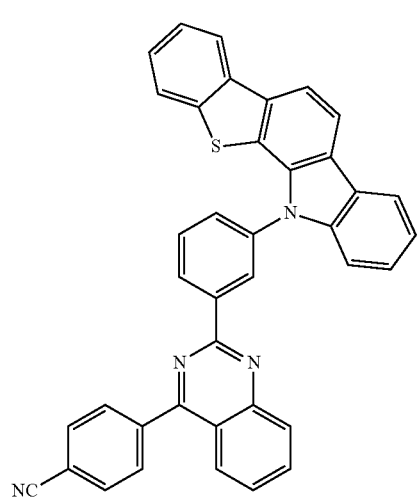
H2-298
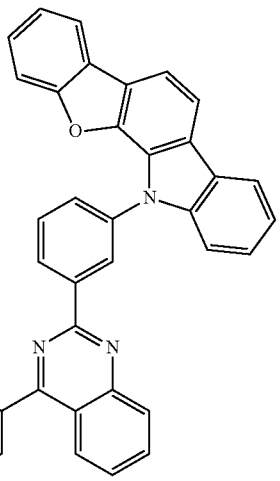
H2-299
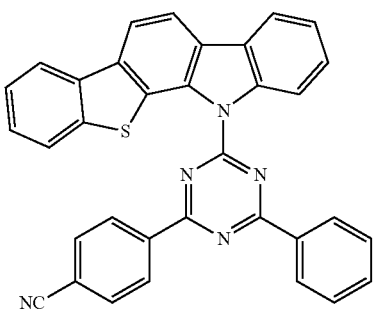
H2-300
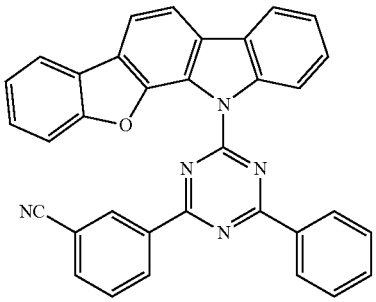
H2-301
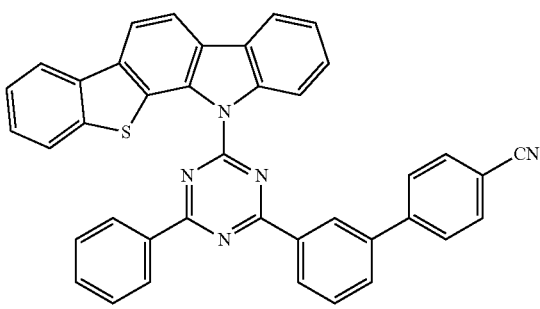

H2-302
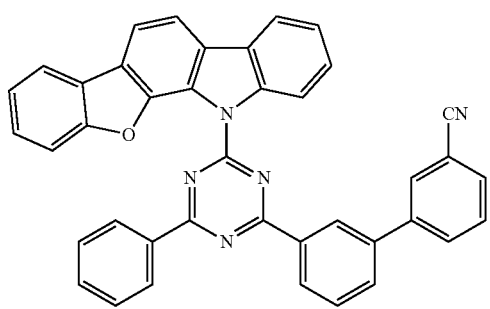
H2-303
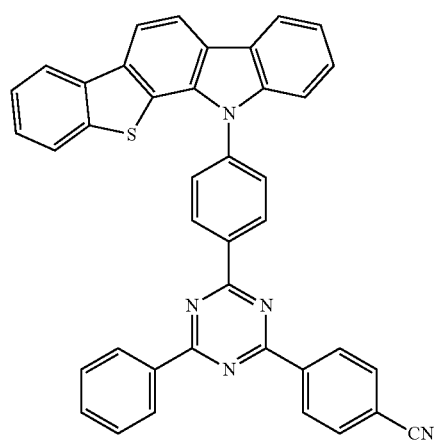
H2-304
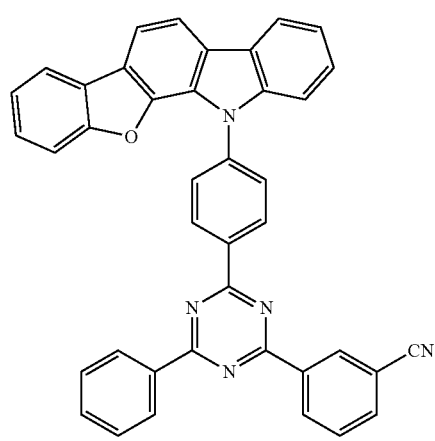
H2-305
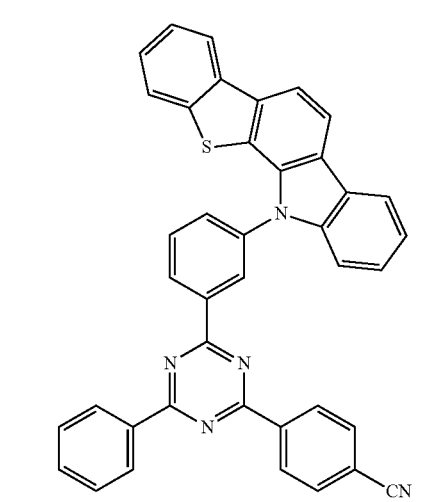
H2-306
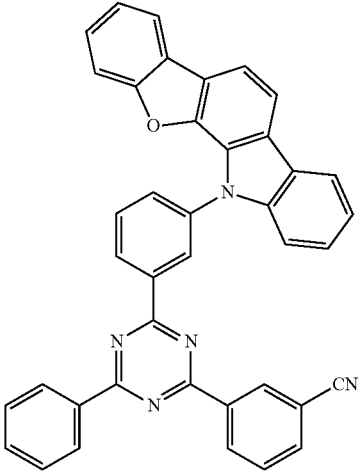
H2-307
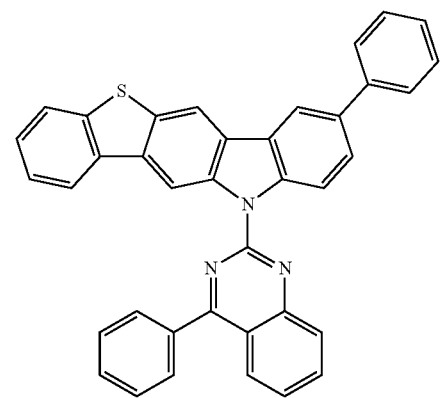
H2-308
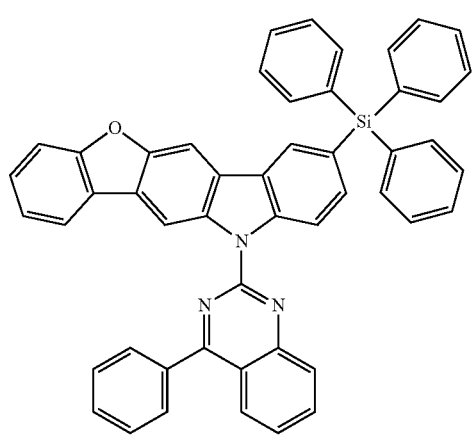

H2-309
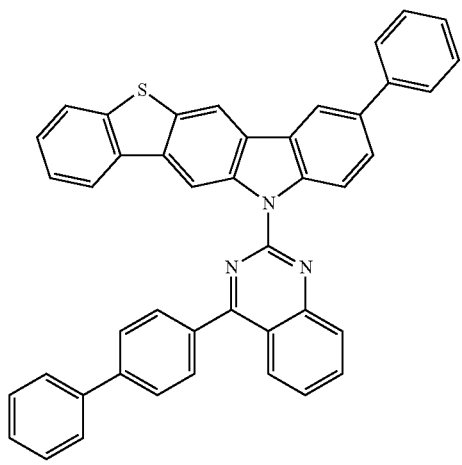
H2-310
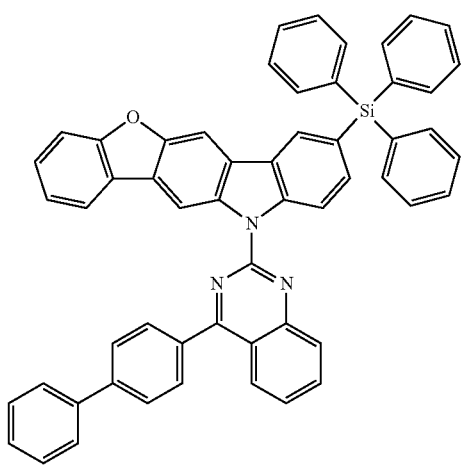
H2-311
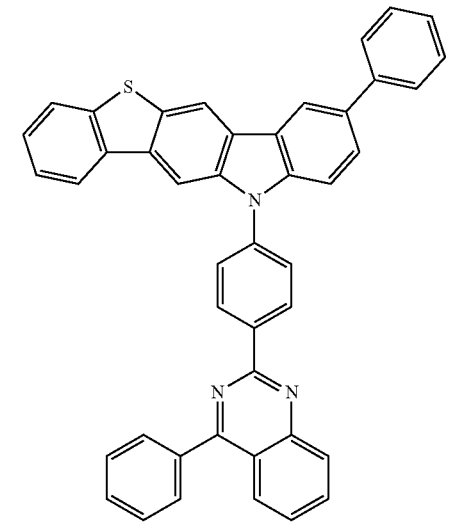
H2-312
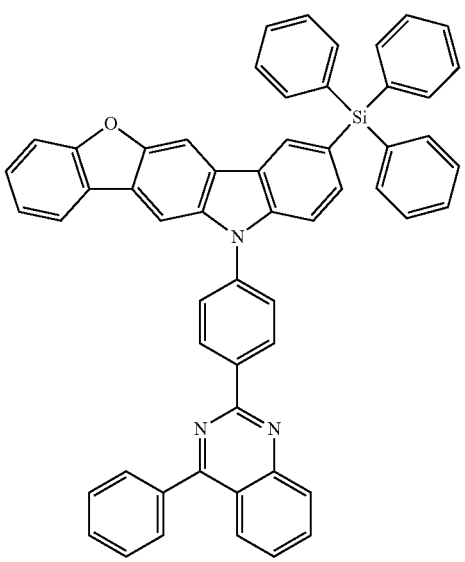
H2-313
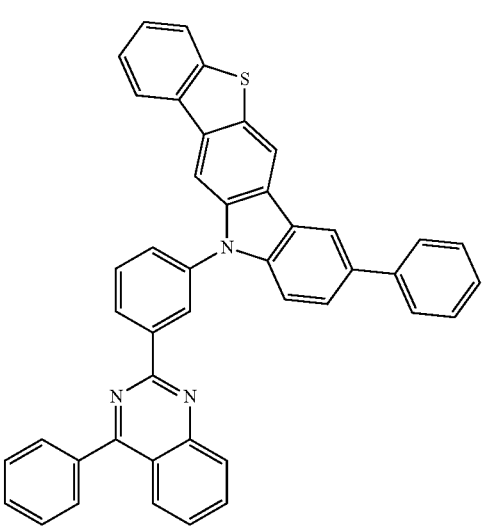
H2-314
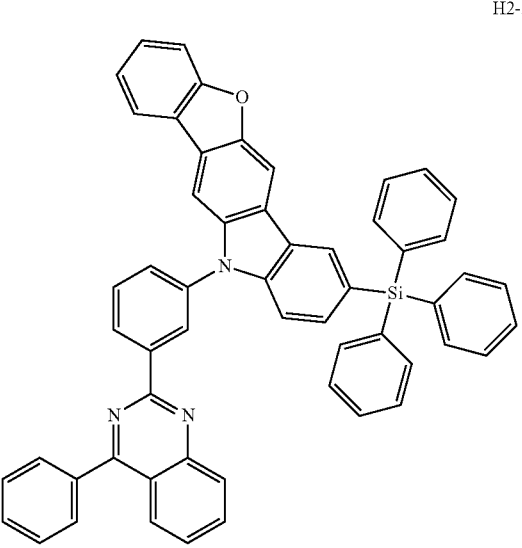

H2-315
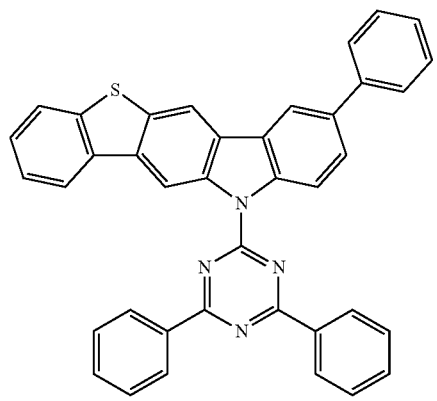
H2-318
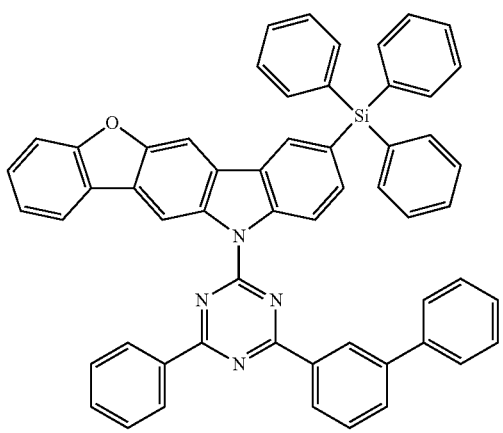
H2-316
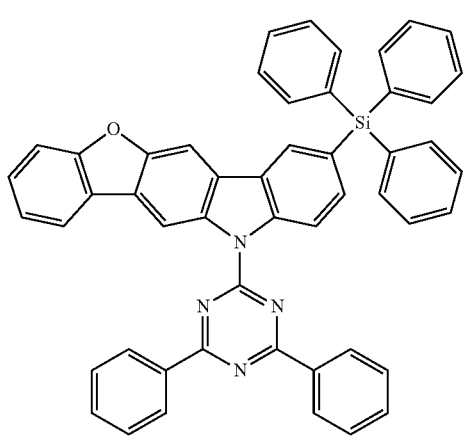
H2-319
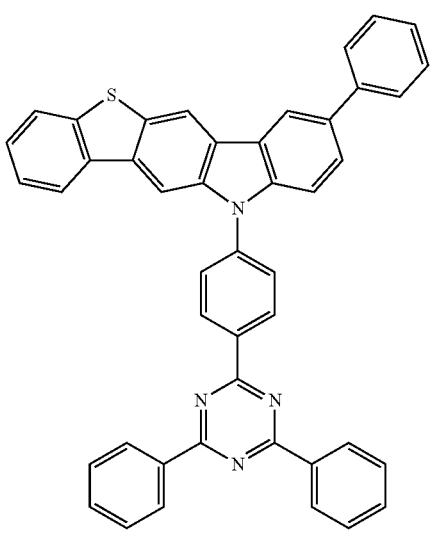
H2-317
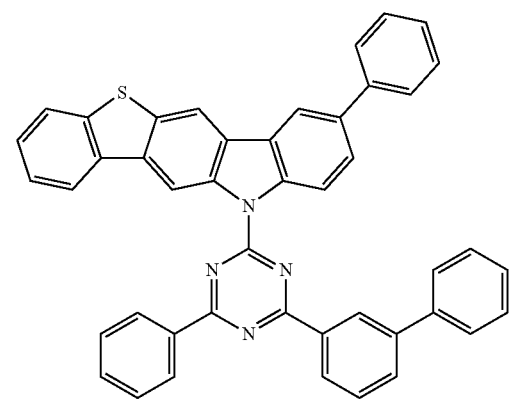
H2-320
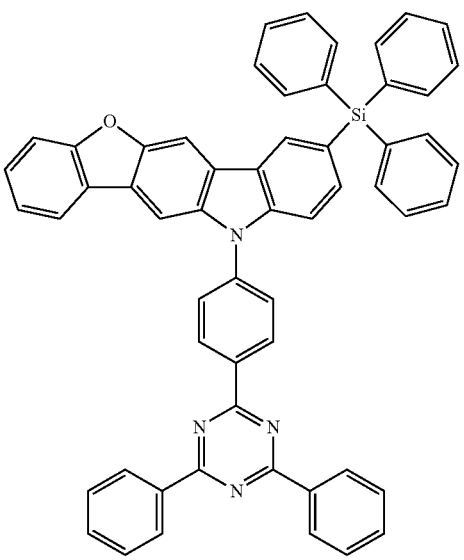

H2-321
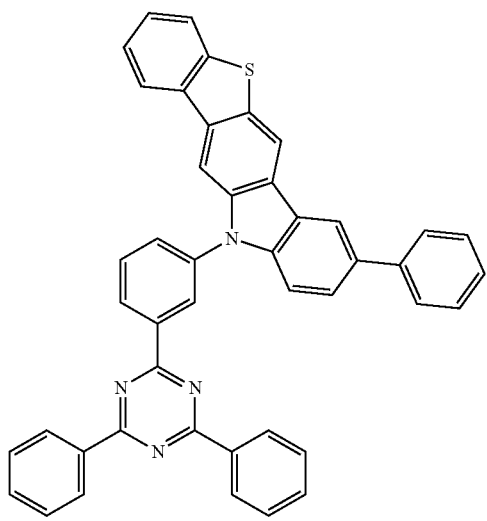
H2-322
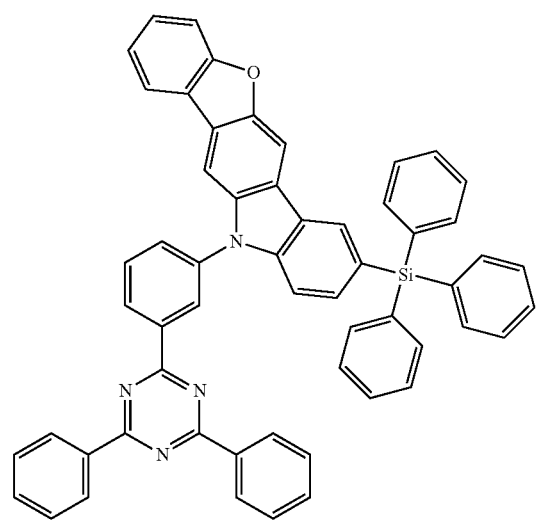
H2-323
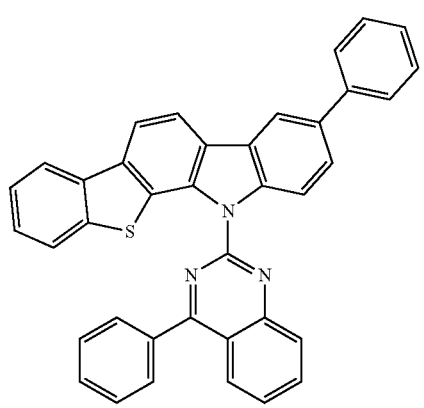
H2-324
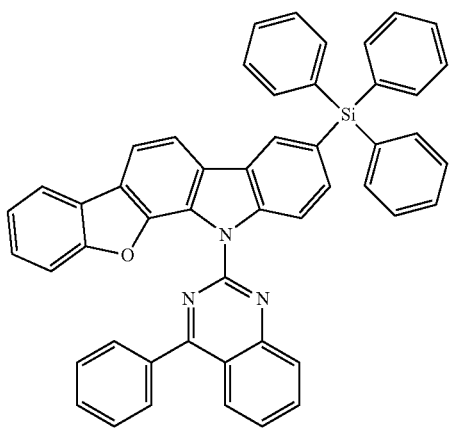
H2-325
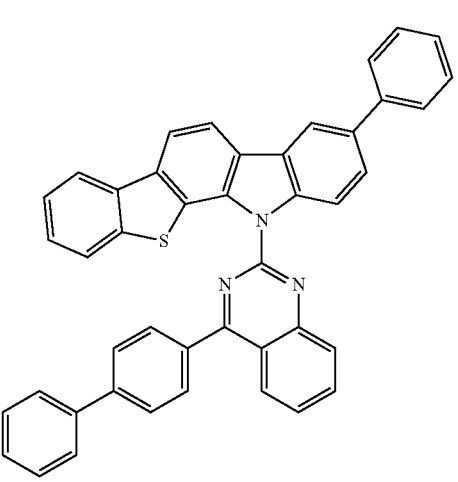
H2-326
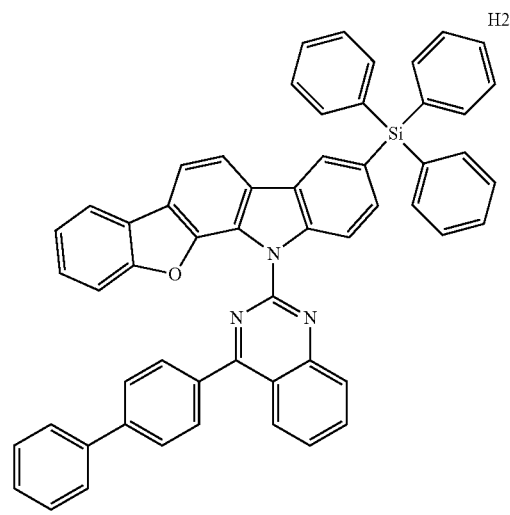

-continued
H2-327
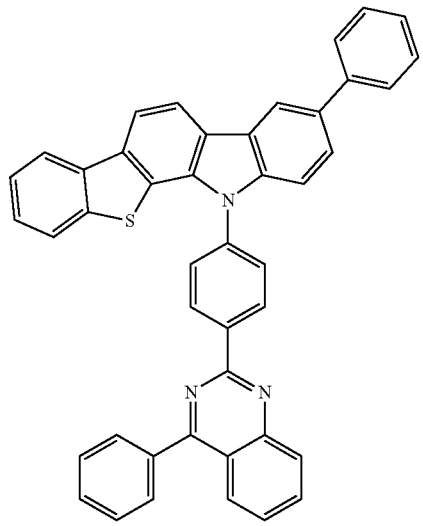
H2-328
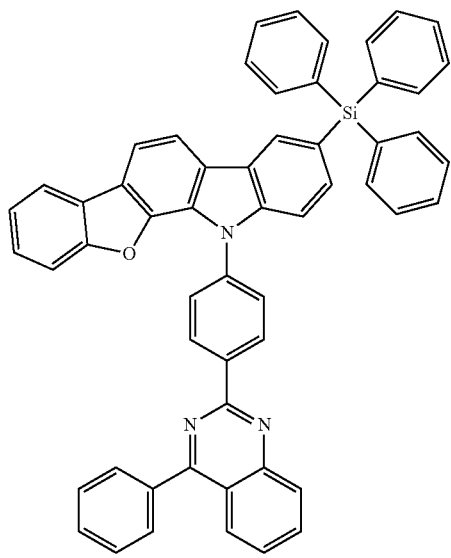
H2-329
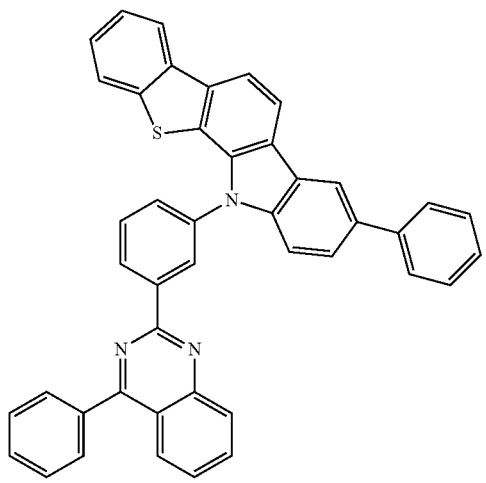
-continued
H2-330
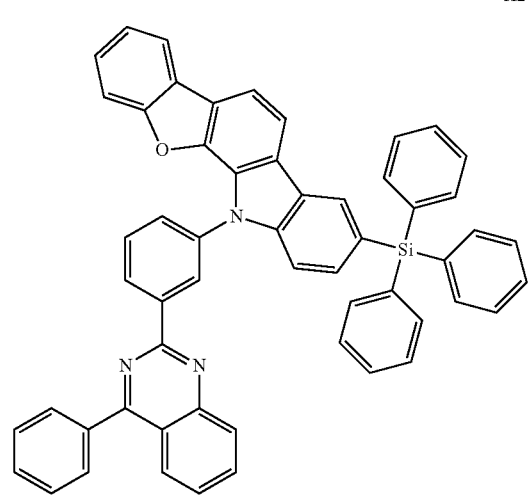
H2-331
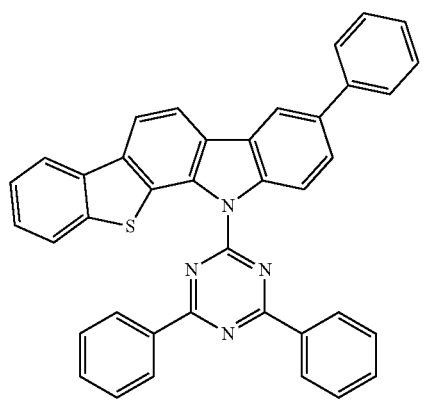
H2-332
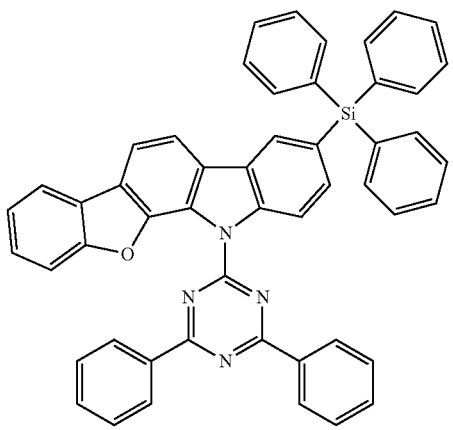

H2-333
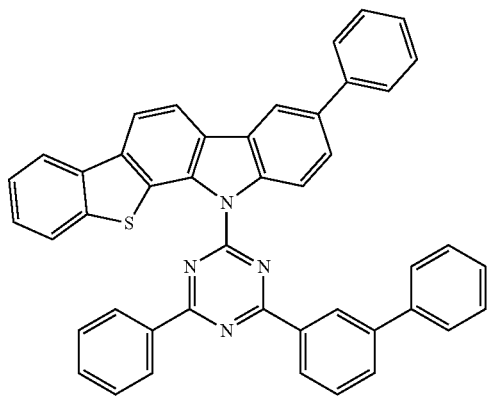
H2-334
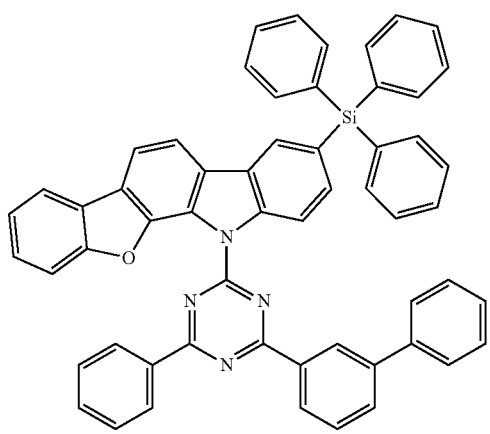
H2-335
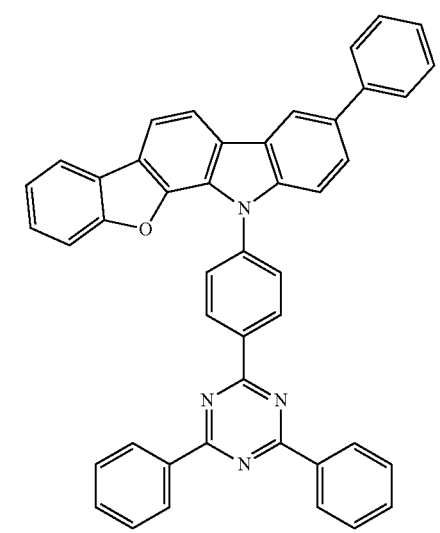
H2-336
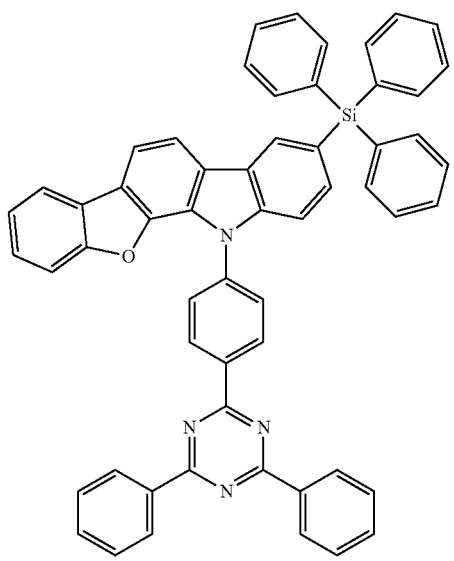
H2-337
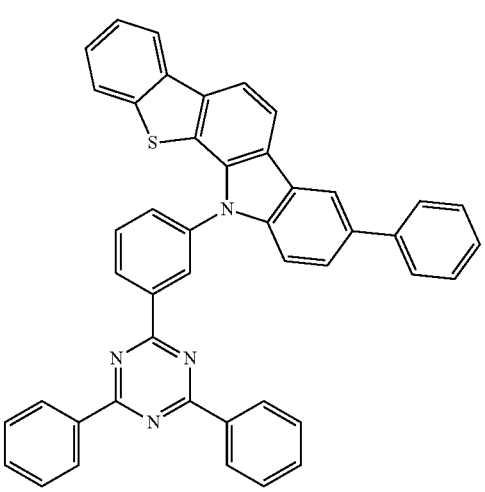
H2-338
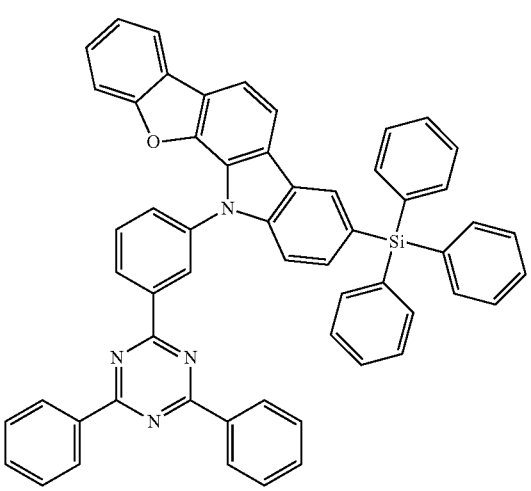

-continued
H2-339
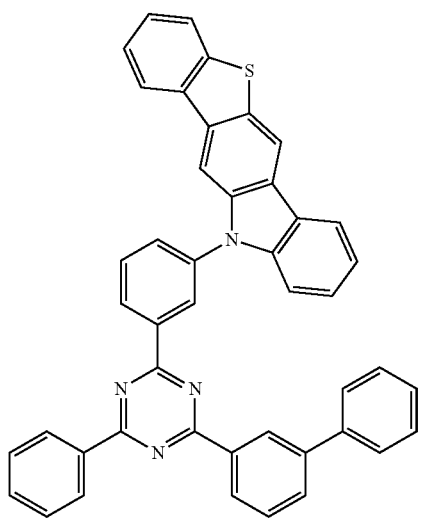
H2-340
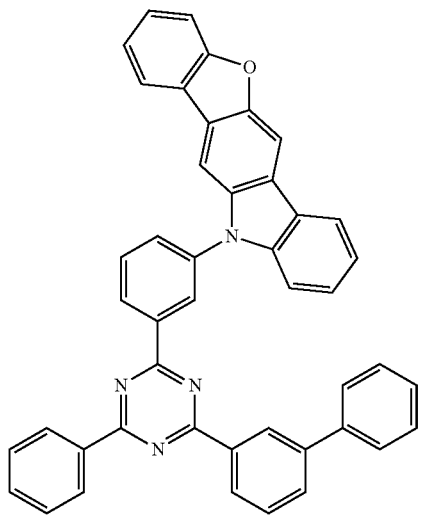
H2-341
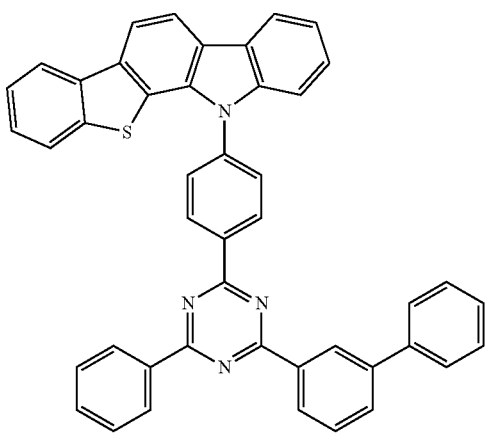
-continued
H2-342
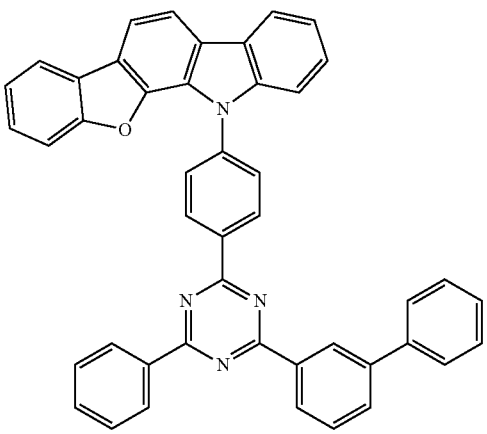
H2-343
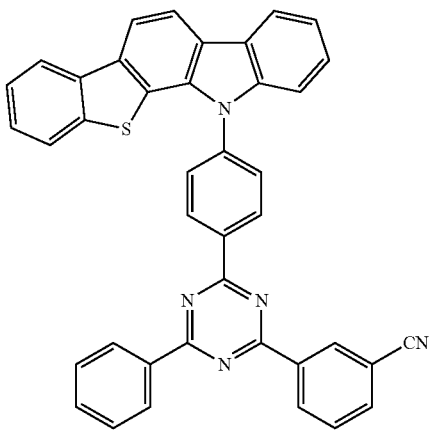
H2-344
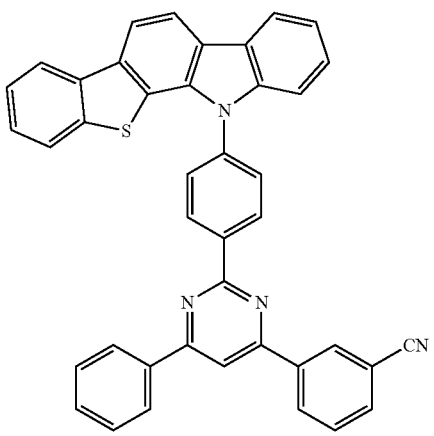

H2-345
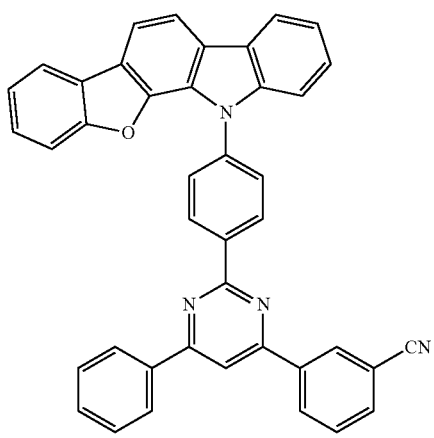
H2-346
H2-347
H2-348
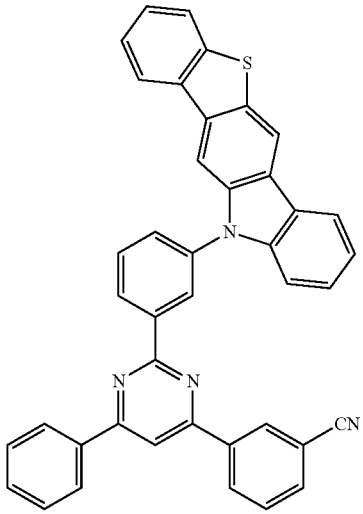
H2-349
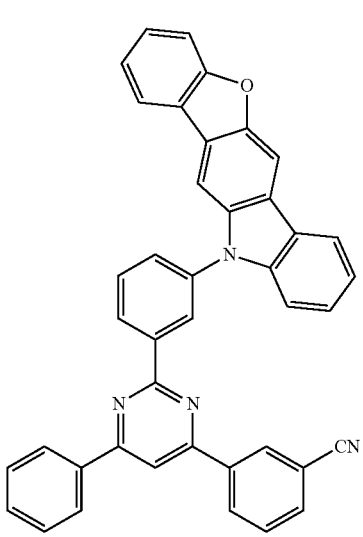
H2-350
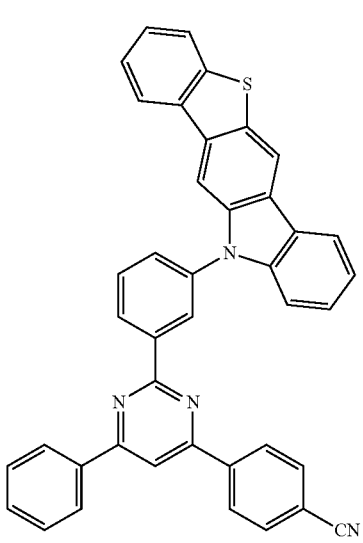

H2-351
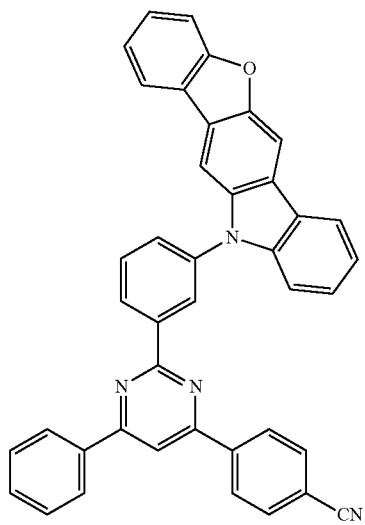
H2-354
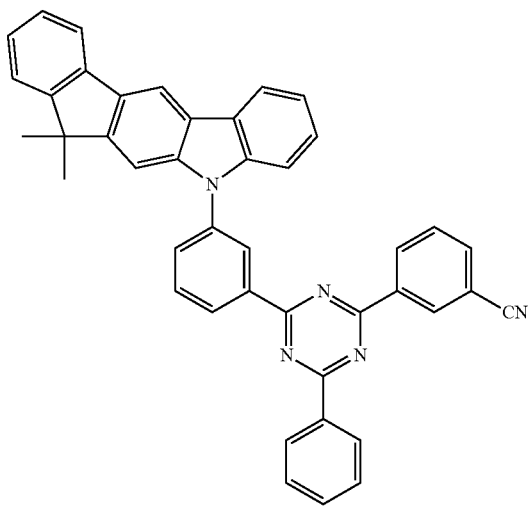
H2-352
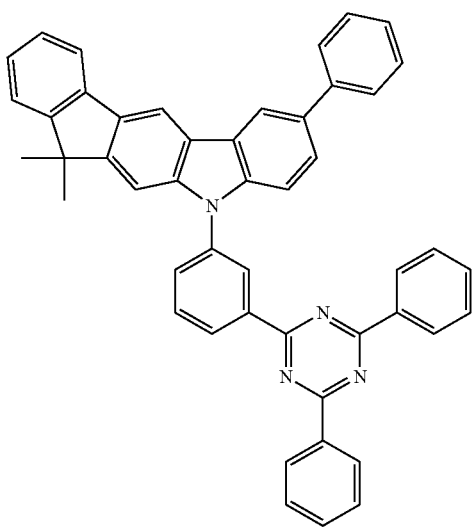
H2-355
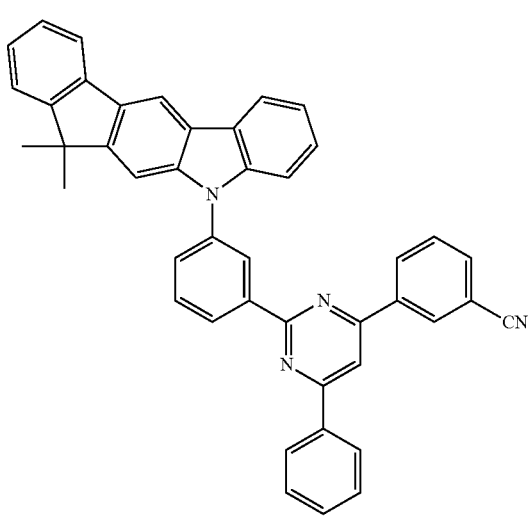
H2-353
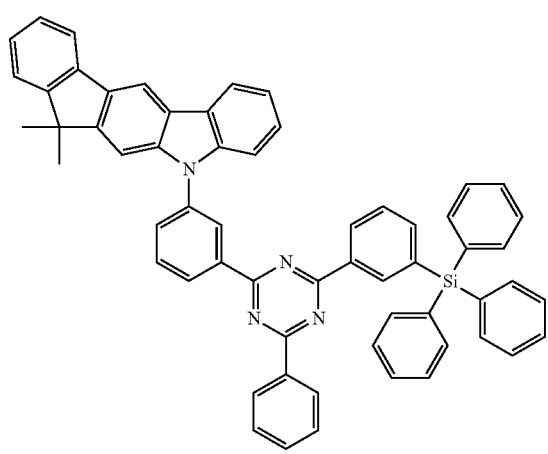
H2-356
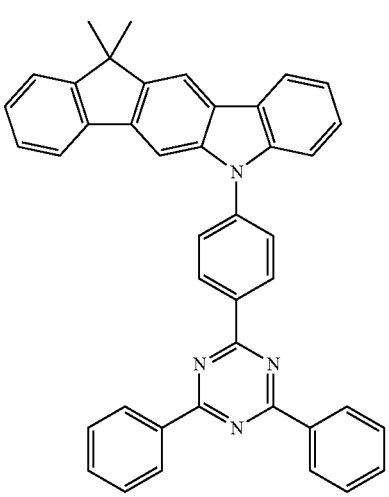

H2-357
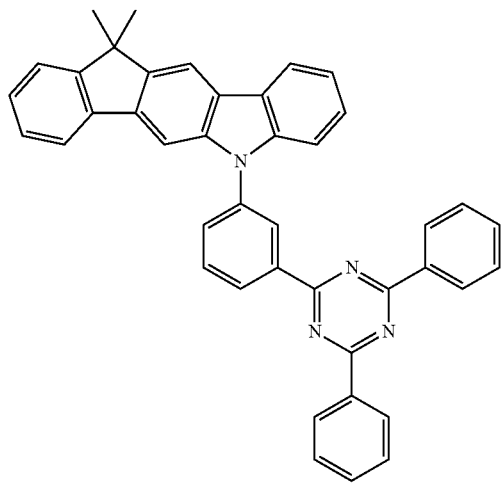
H2-358
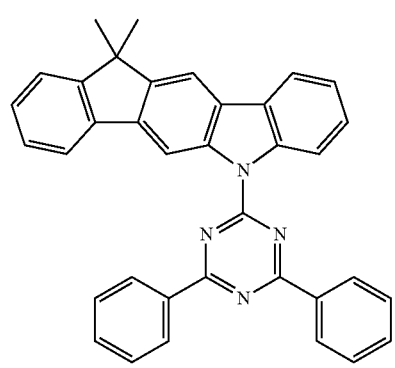
H2-359
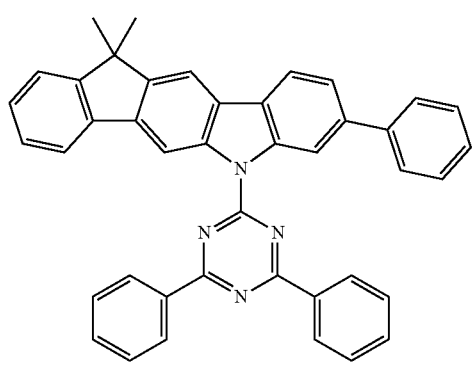
H2-360
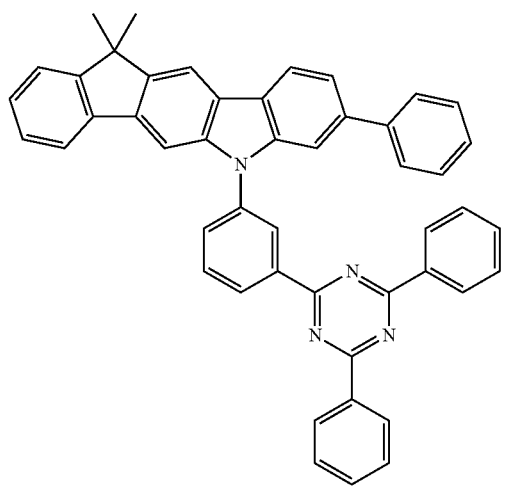
H2-361
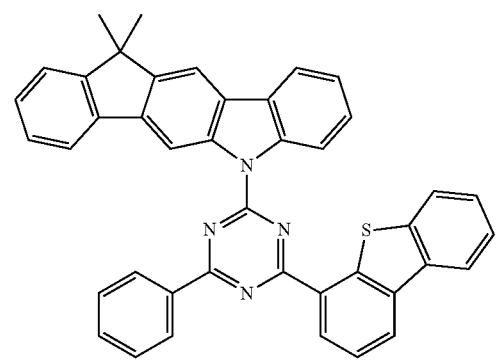
H2-362
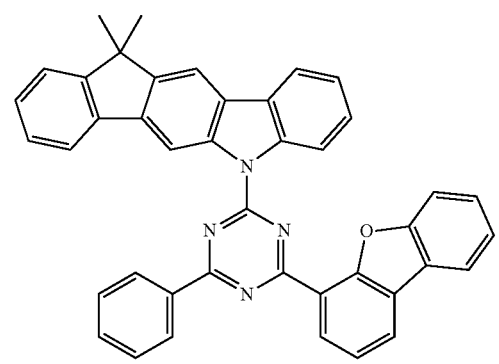
H2-363
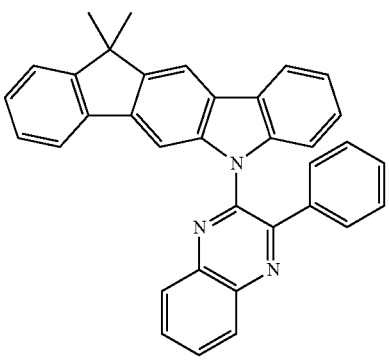

H2-364
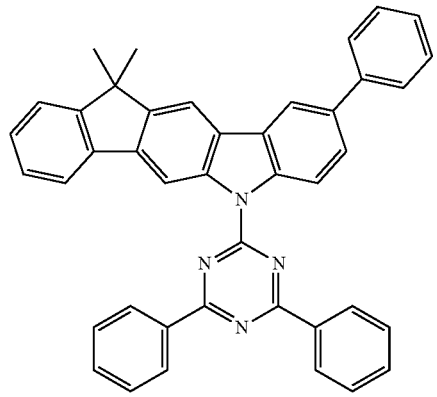
H2-365
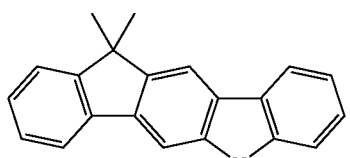
H2-366
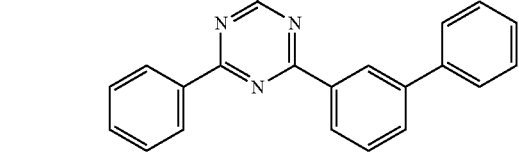
H2-367
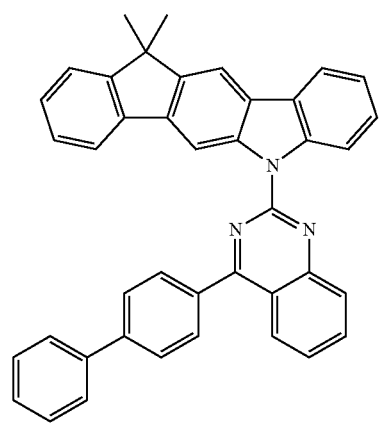
H2-368
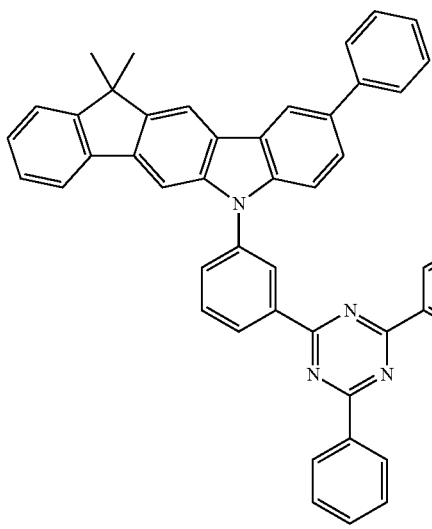
H2-369
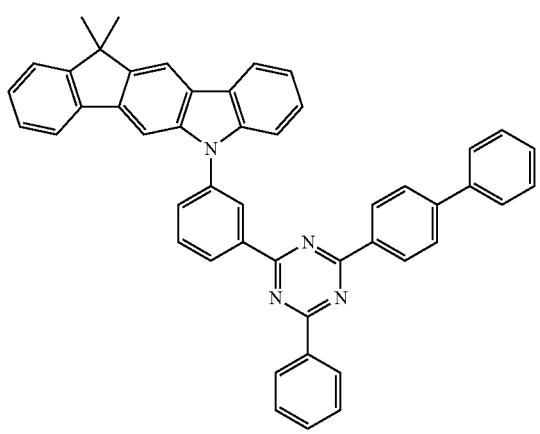
H2-370
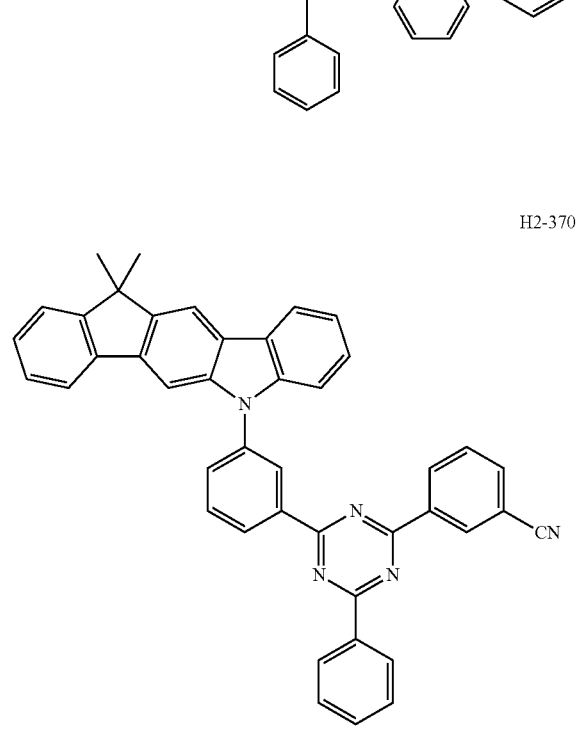

H2-371
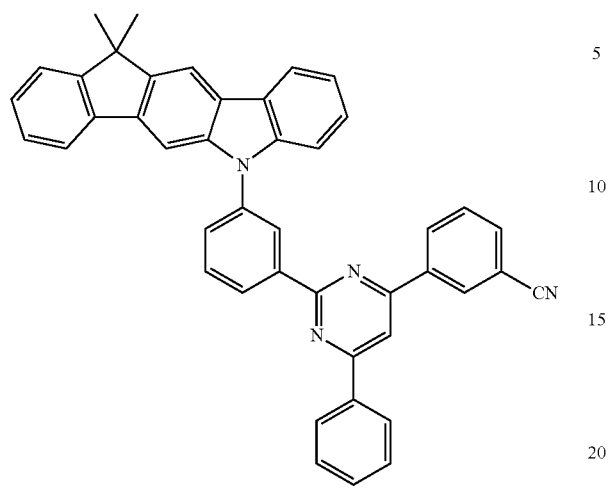
H2-372
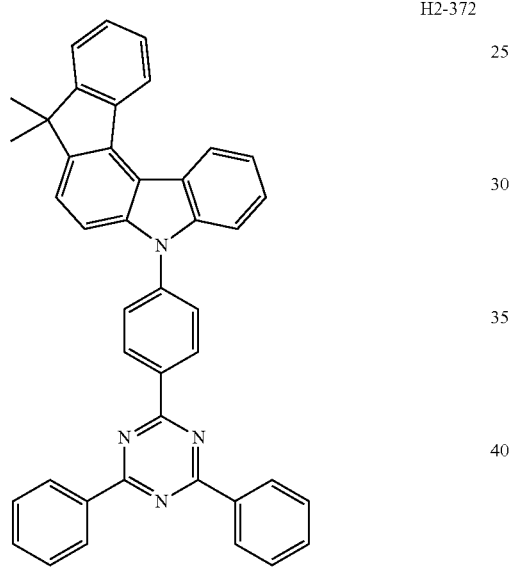
H2-373
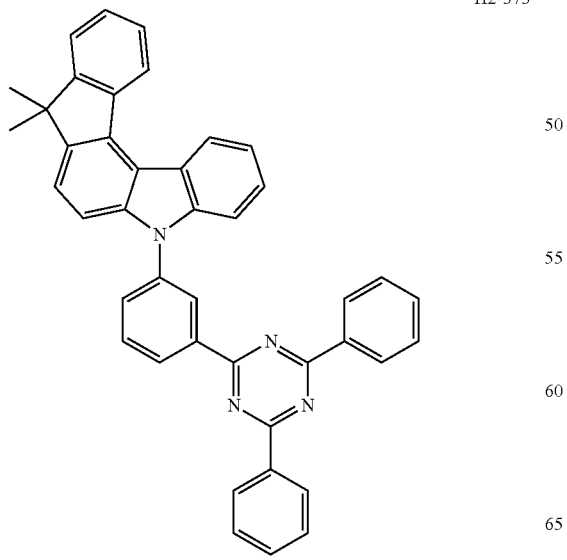
H2-374
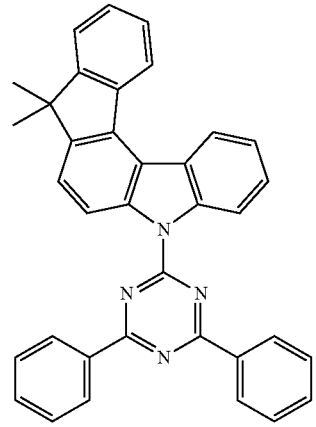
H2-375
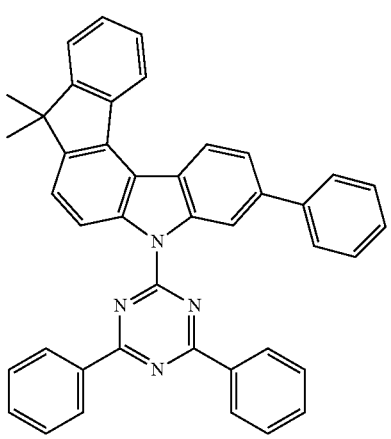
H2-376
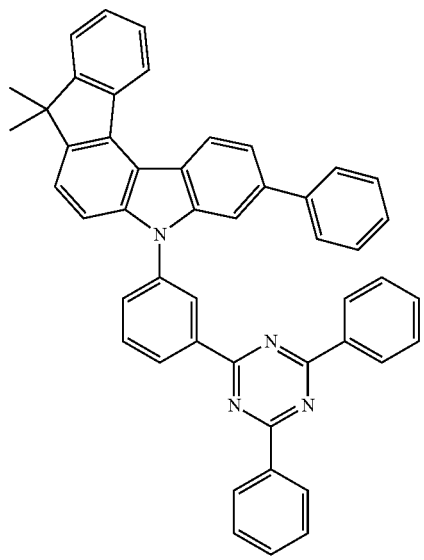

H2-377
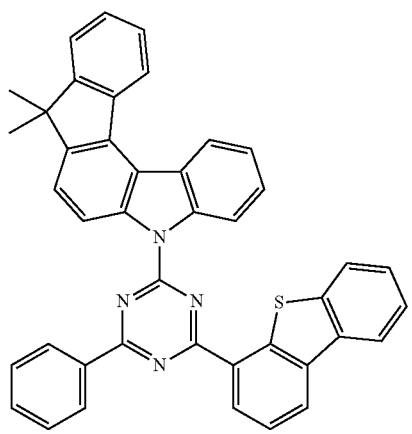
H2-378
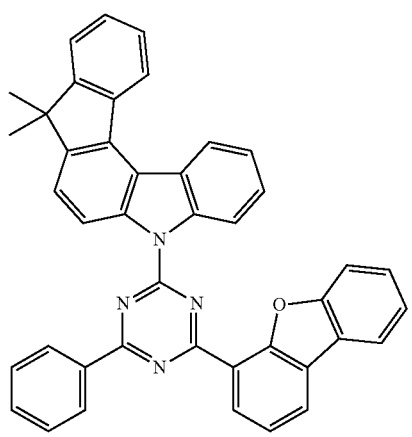
H2-379
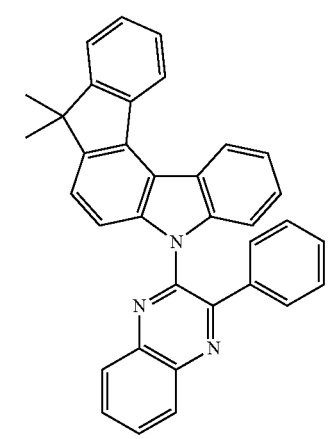
H2-380
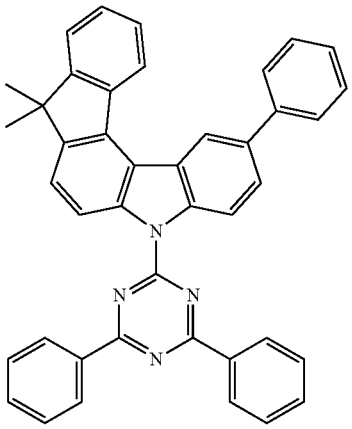
H2-381
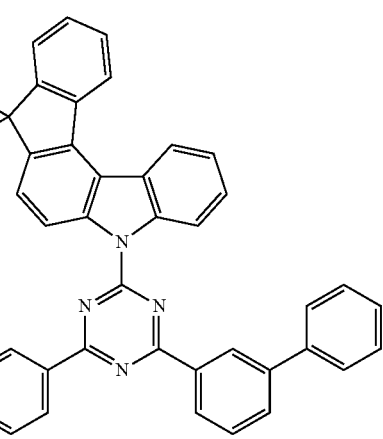
H2-382
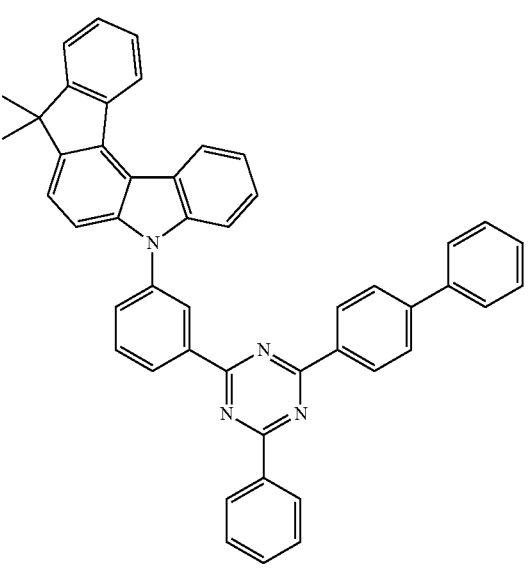

H2-383
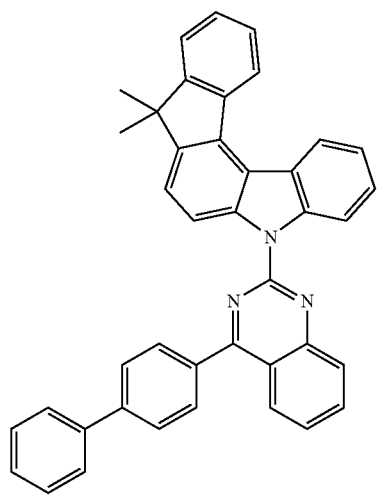
H2-384
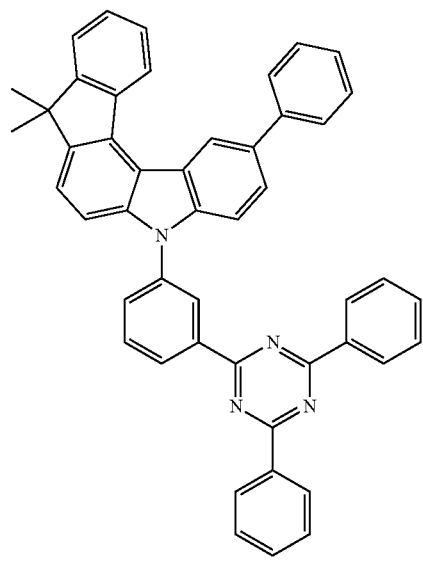
H2-385
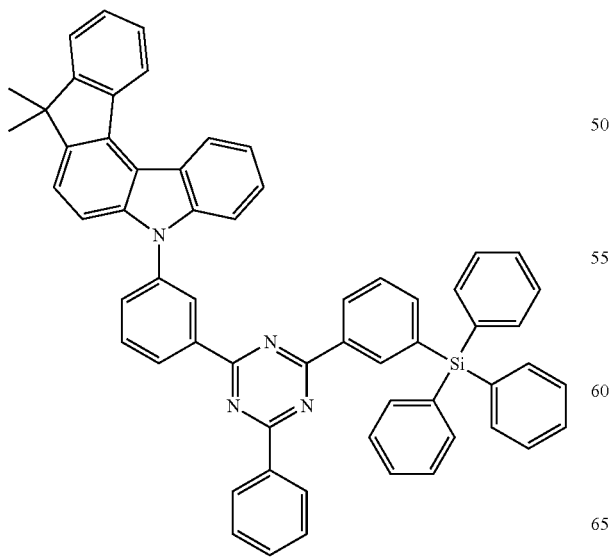
H2-386
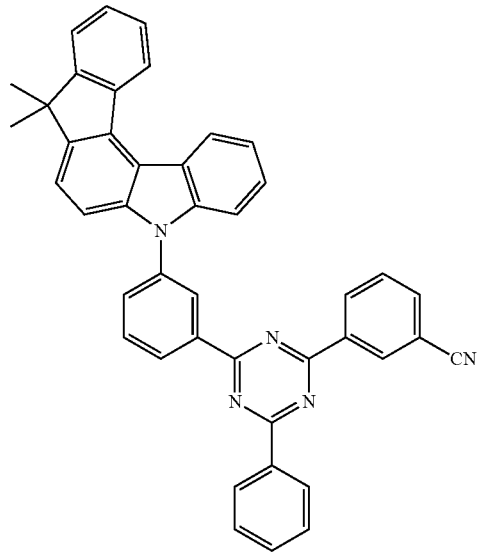
H2-387
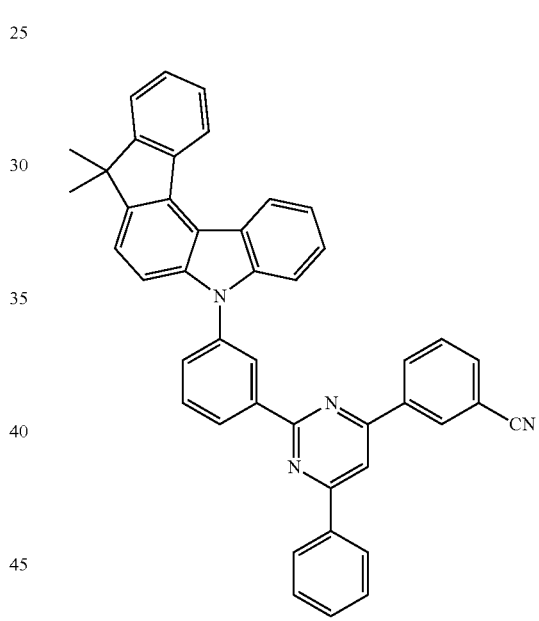
H2-388
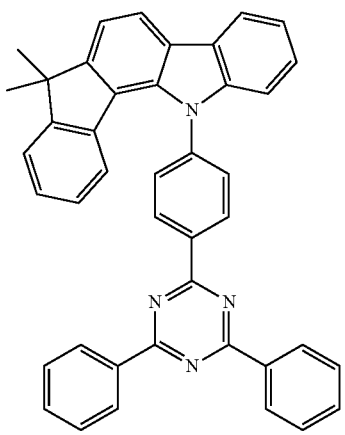

H2-389
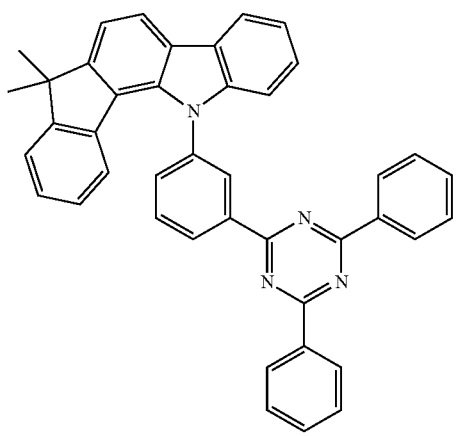
H2-390
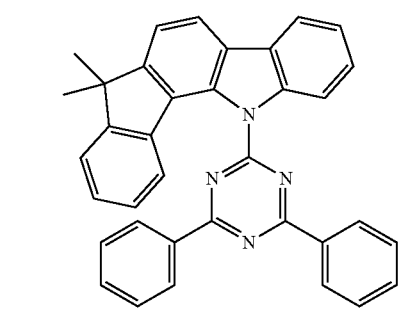
H2-391
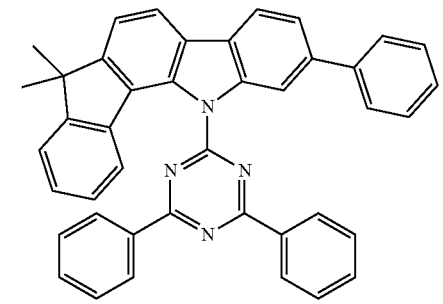
H2-392
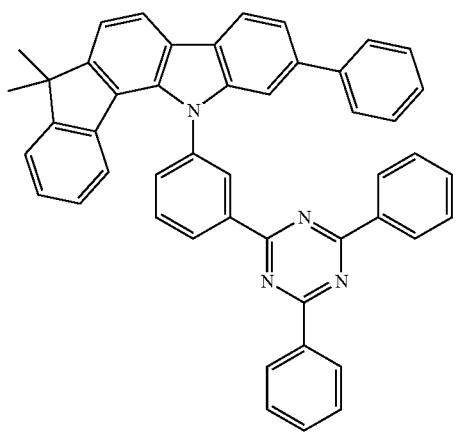
H2-393
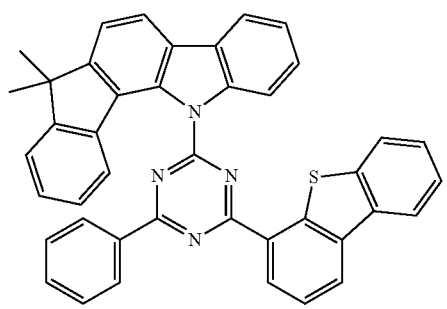
H394
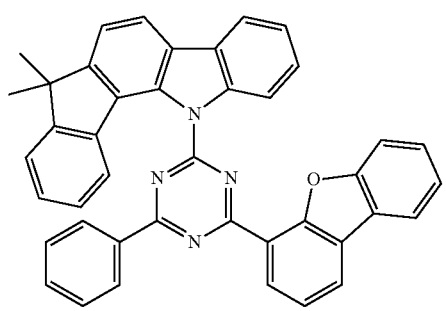
H2-395
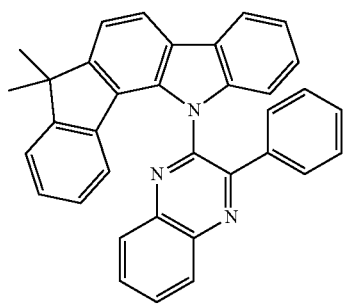
H2-396
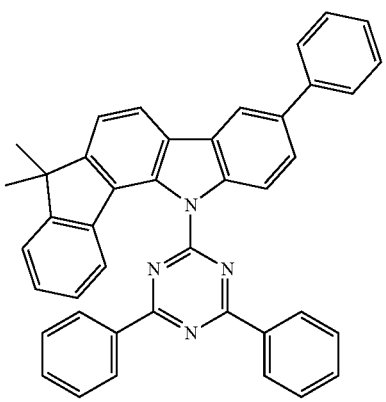
H2-397
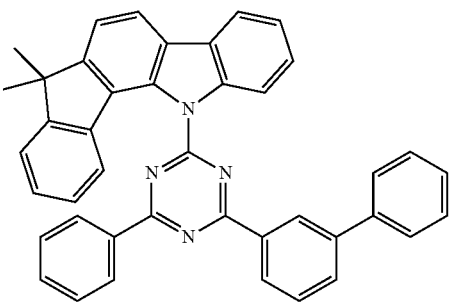

H2-398
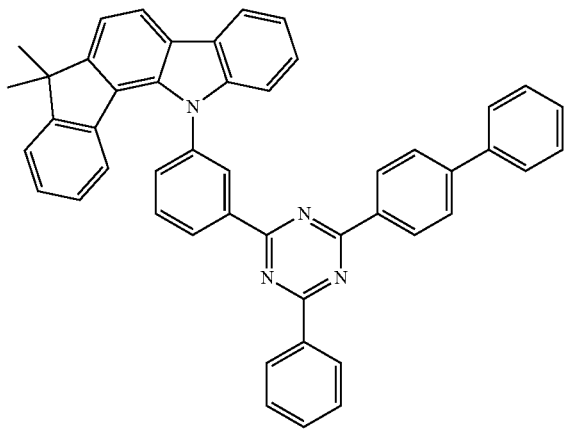
H2-401
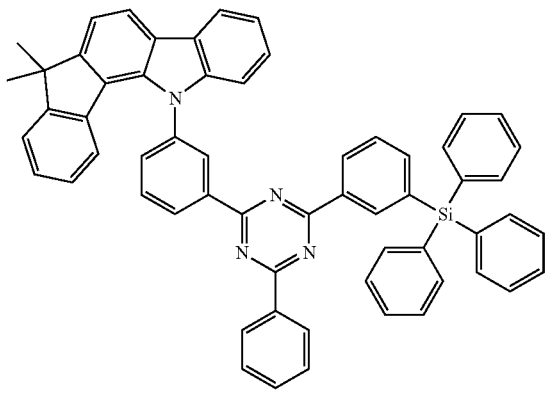
H2-399
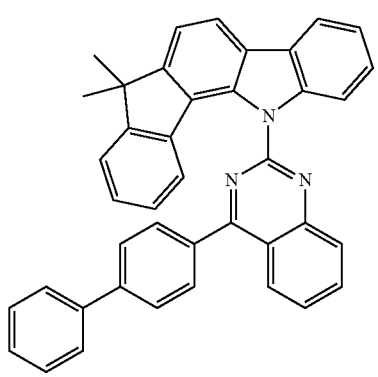
H2-402
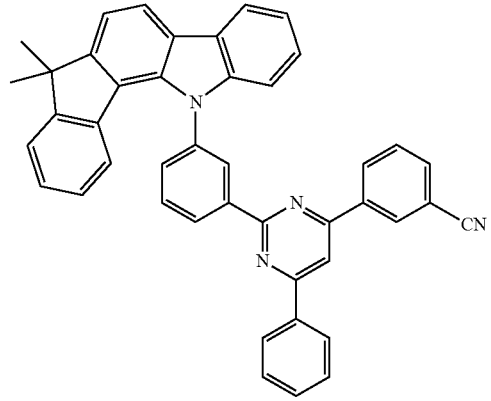
H2-400
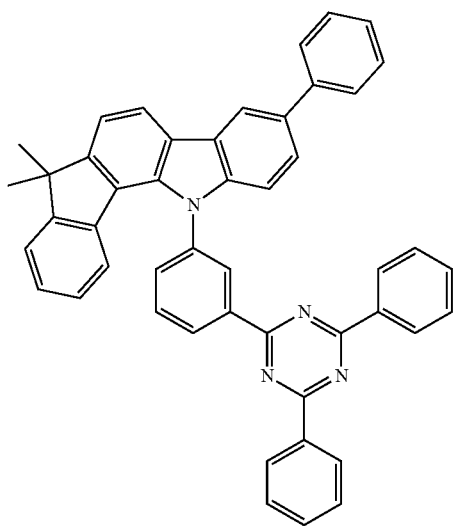
H2-403
H2-404
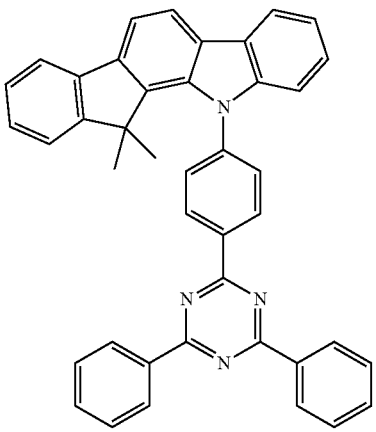

-continued
H2-405
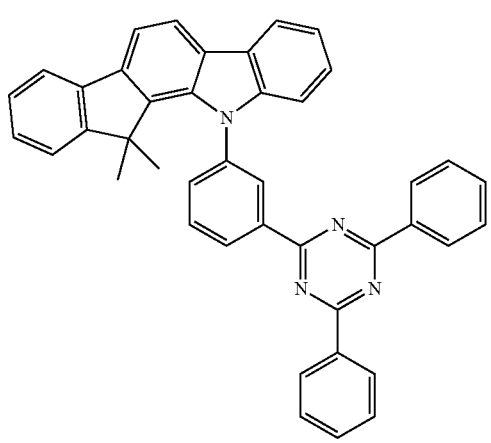
H2-406
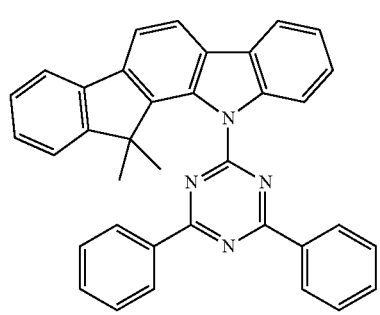
H2-407
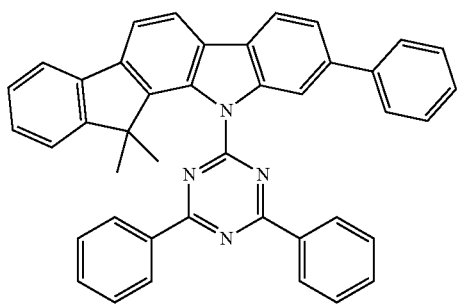
H2-408
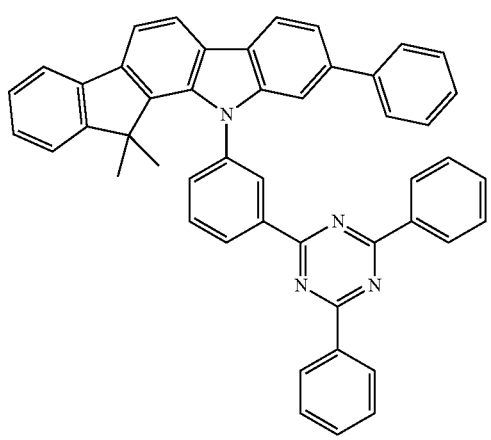
-continued
H2-409
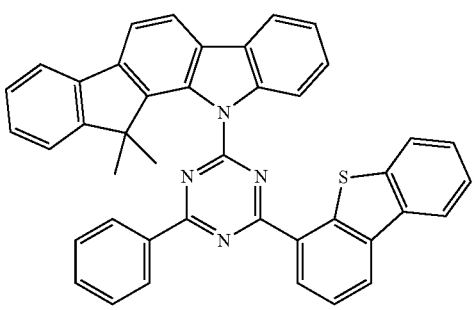
H2-410
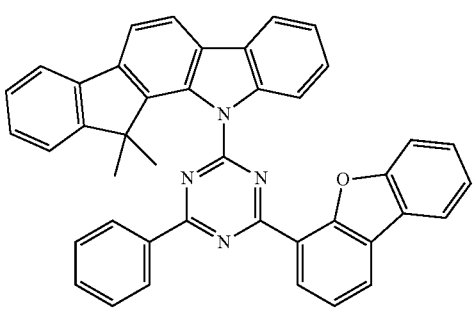
H2-411
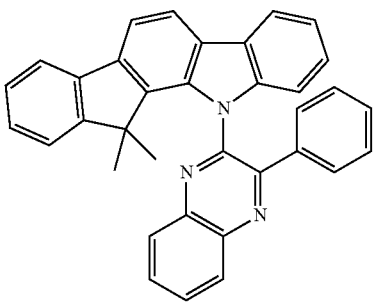
H2-412
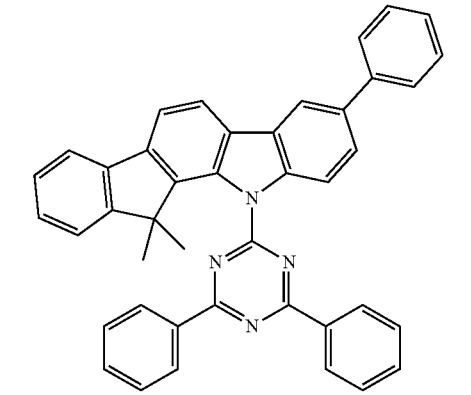
H2-413
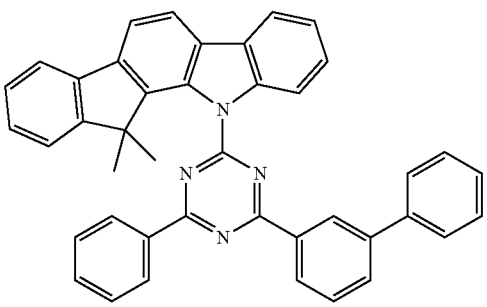

H2-414
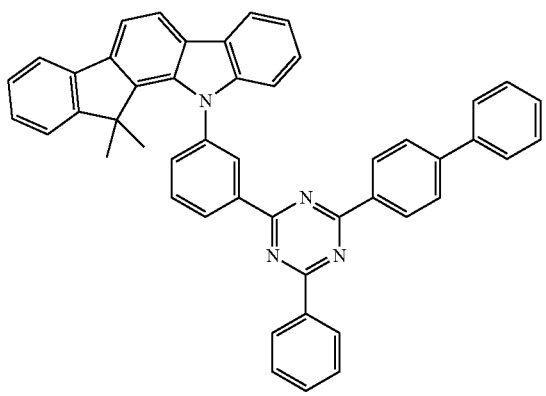
H2-417
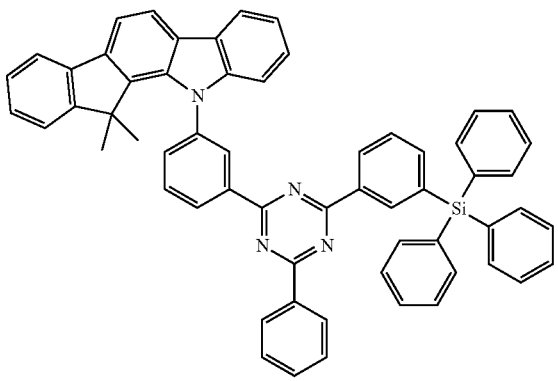
H2-415
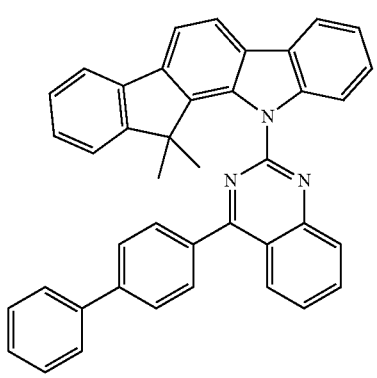
H2-418
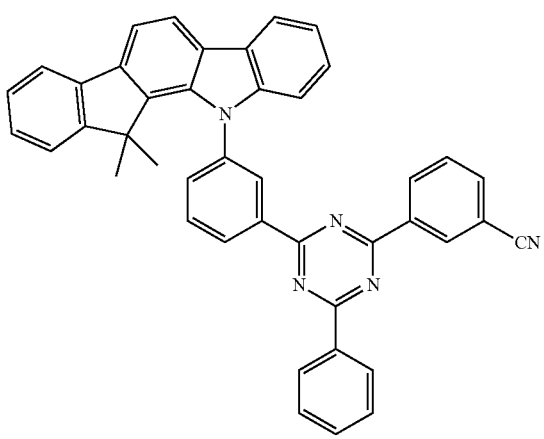
H2-416
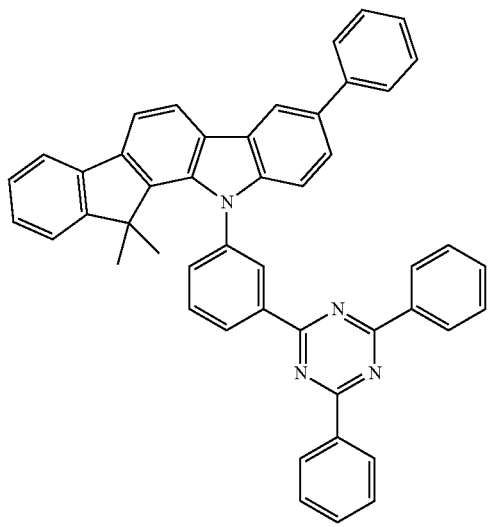
H2-419
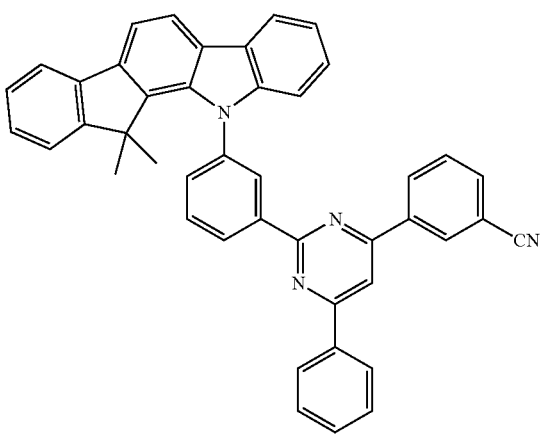

H2-420
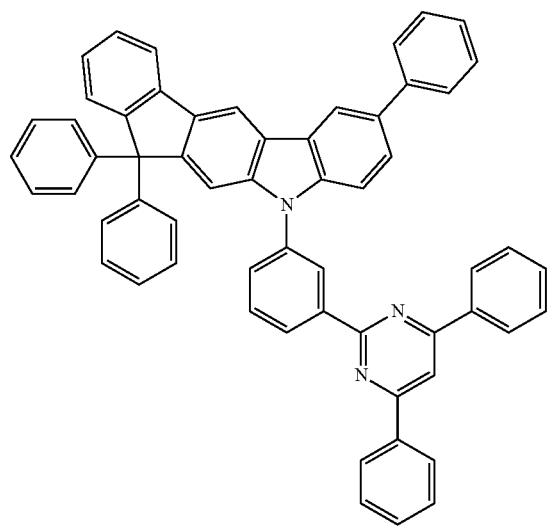
H2-421
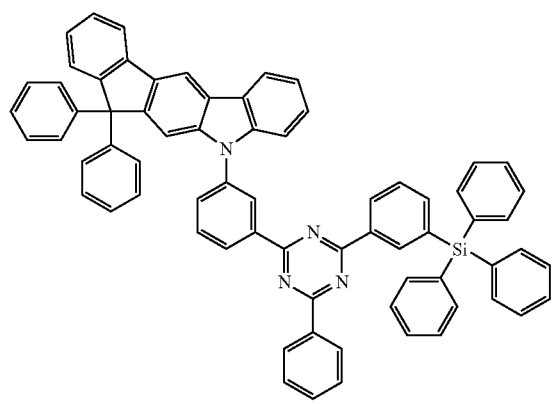
H2-422
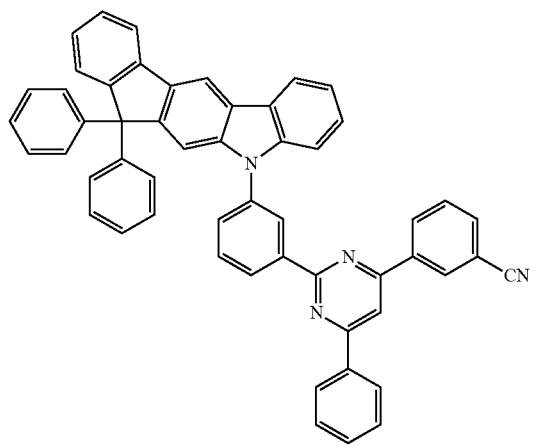
H2-423
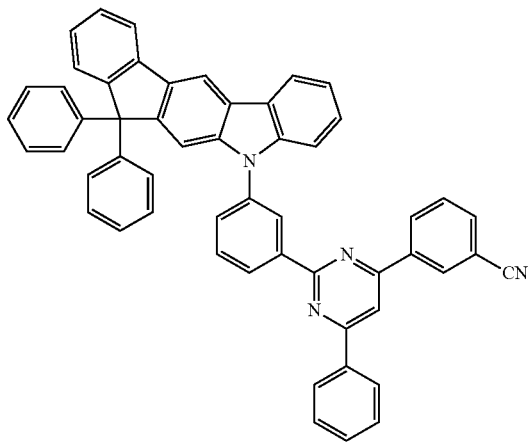
H2-424
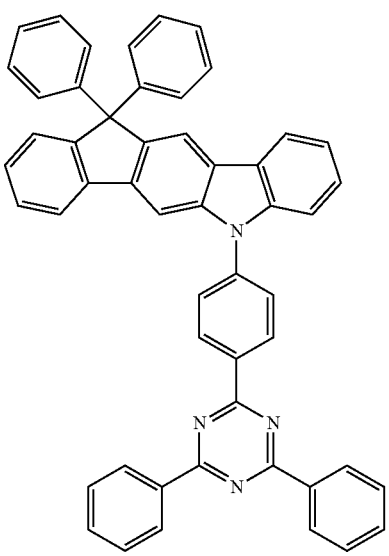
H2-425
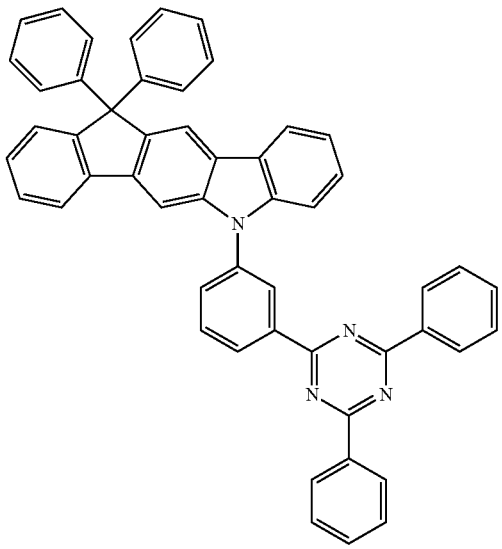

H2-426
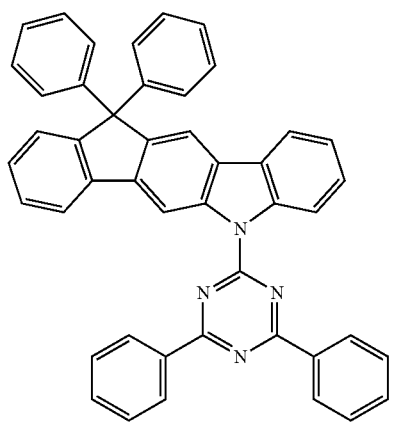
H2-427
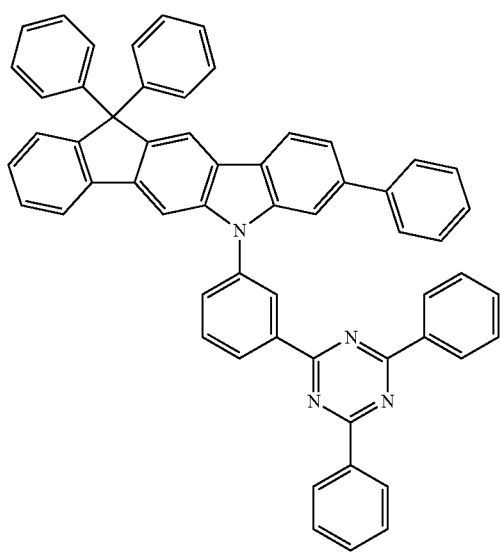
H2-428
H2-429
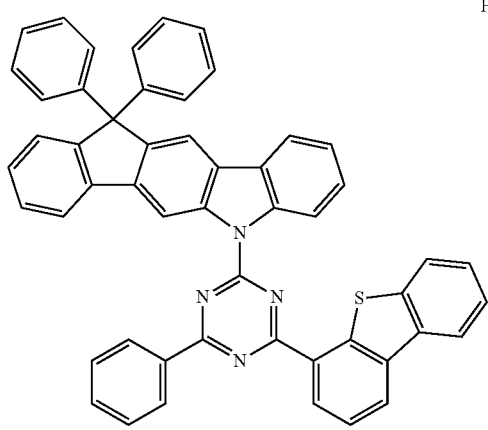
H2-430
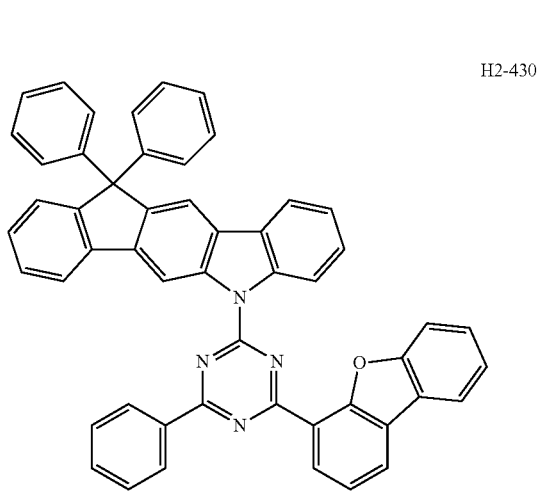
H2-431

H2-432
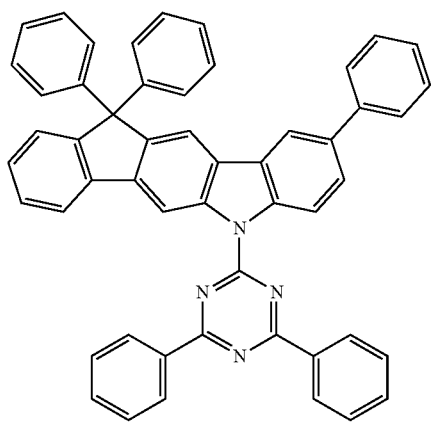
H2-435
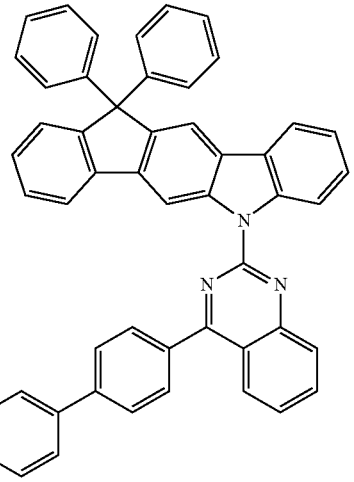
H2-433
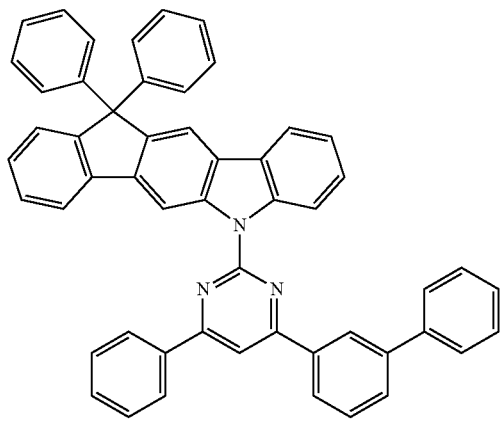
H2-436
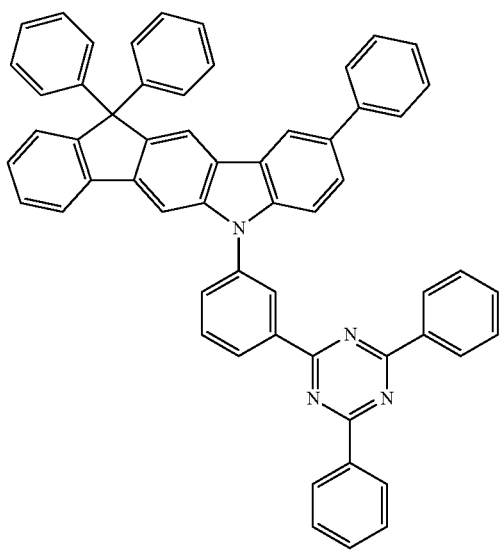
H2-434
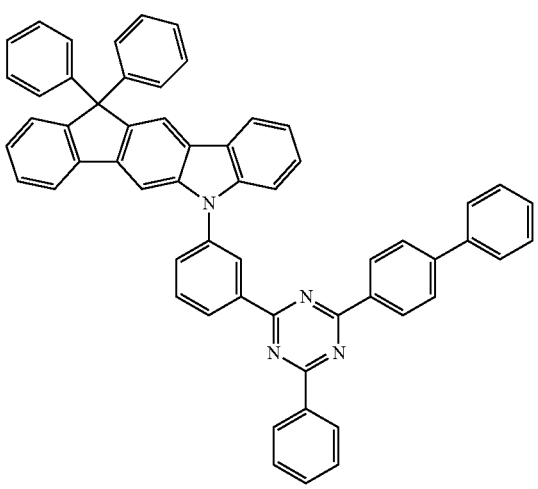
H2-437
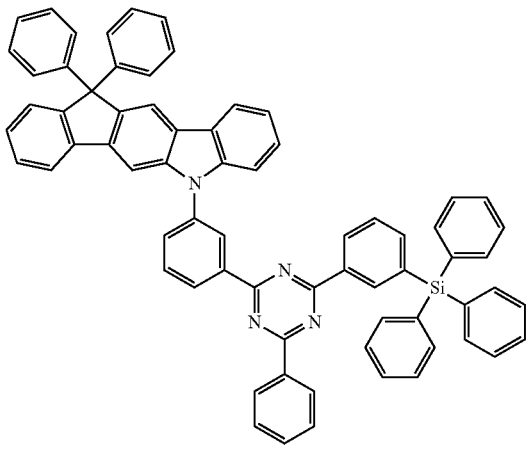

-continued
H2-438
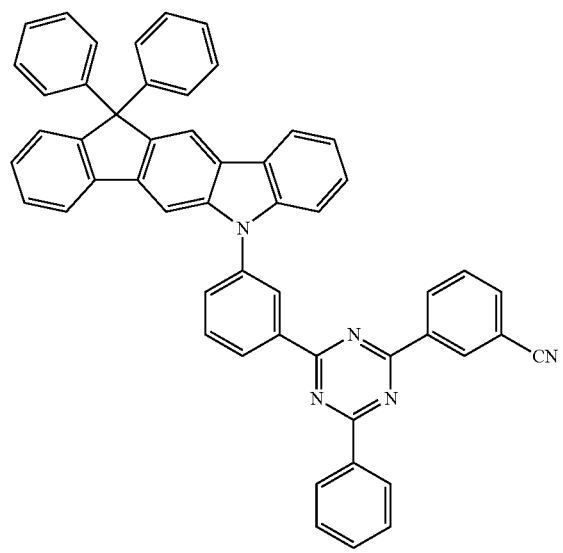
H2-440
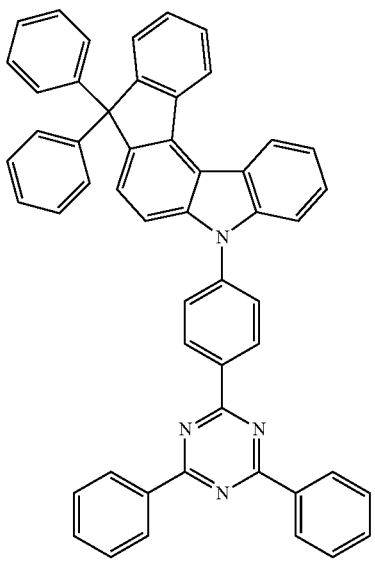
H2-441
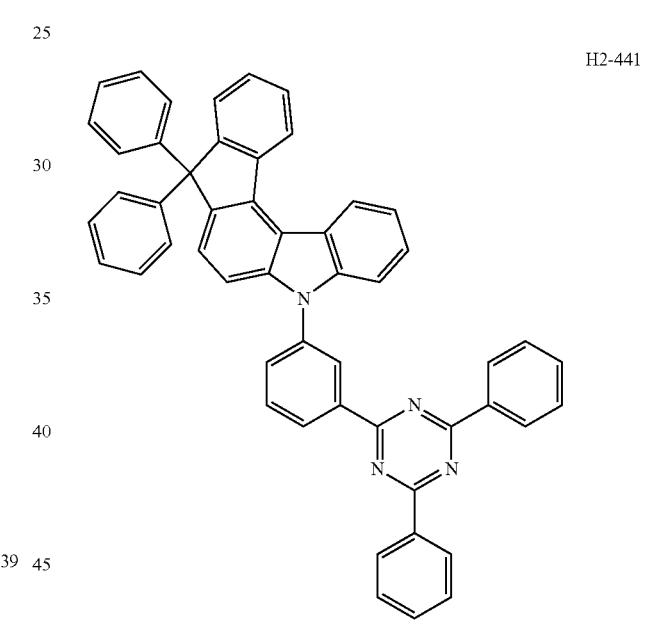
H2-439
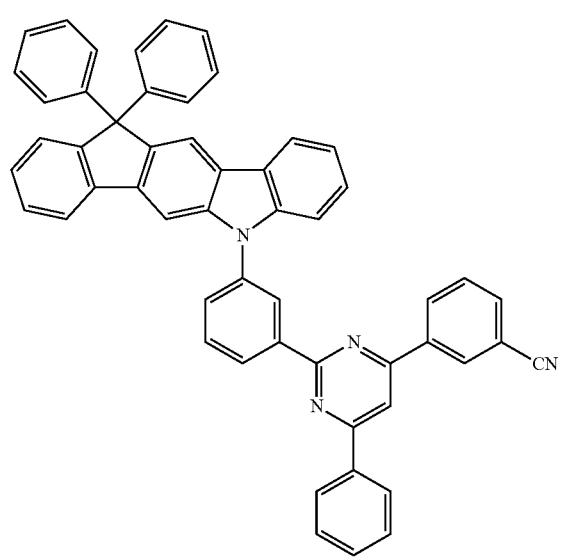
H2-442
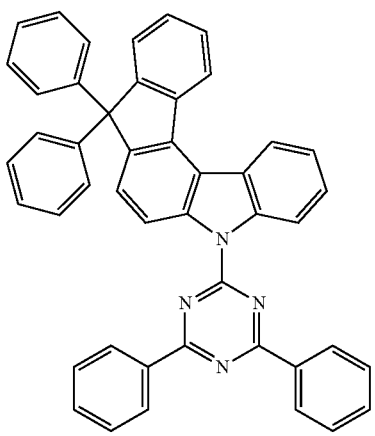

H2-443
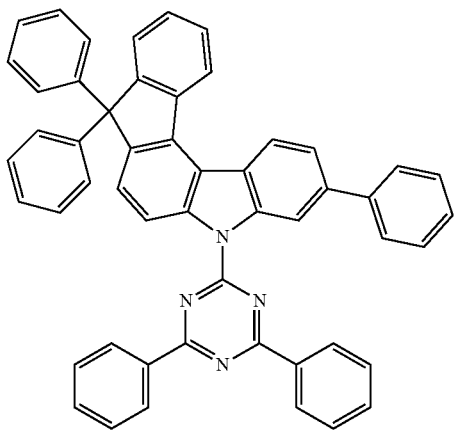
H2-444
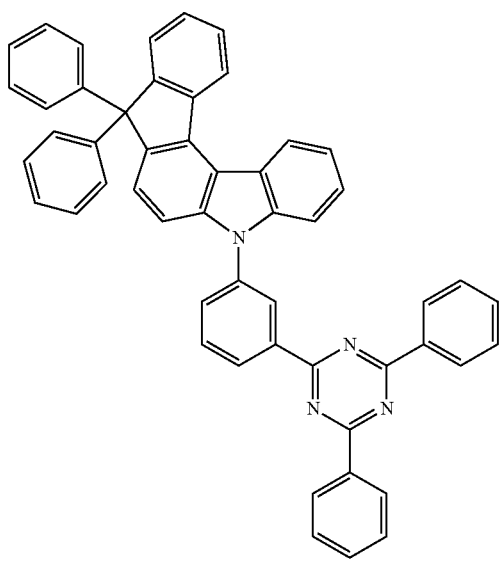
H2-445
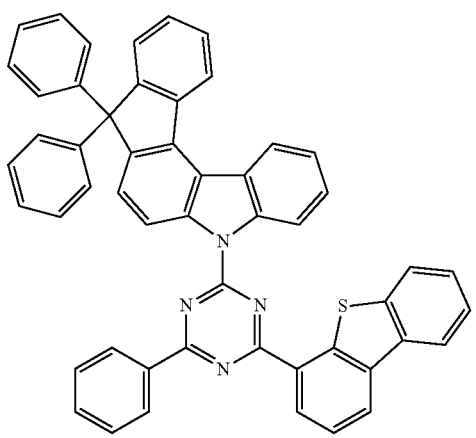
H2-446
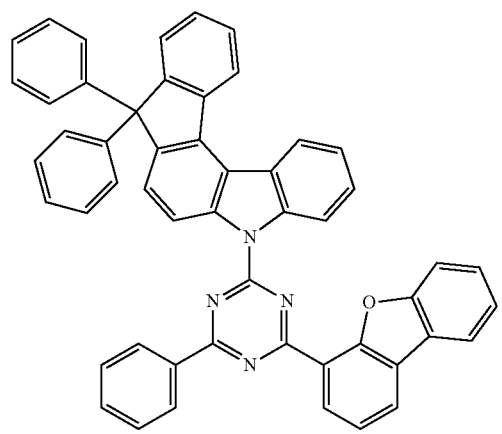
H2-447
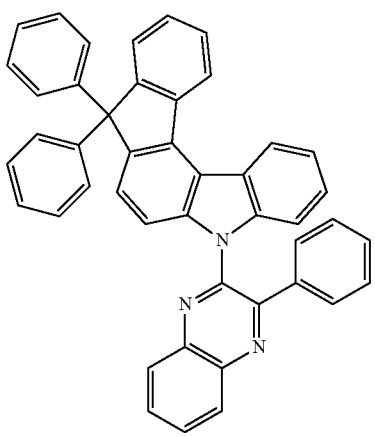
H2-448
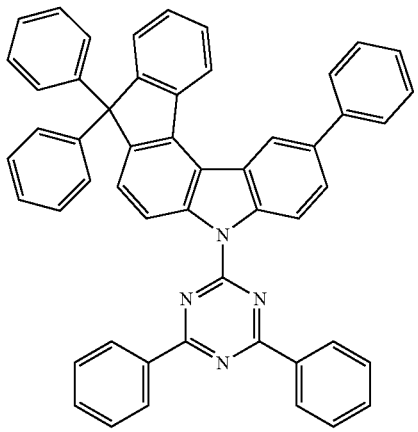

H2-449
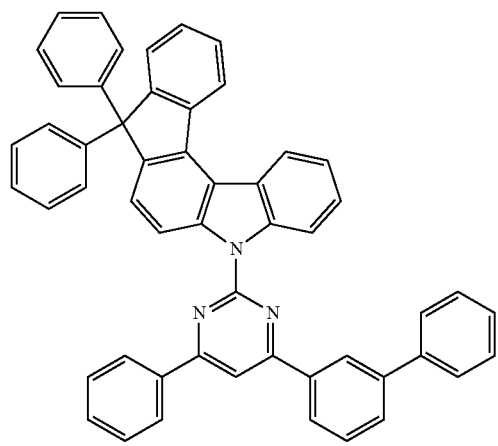
H2-450
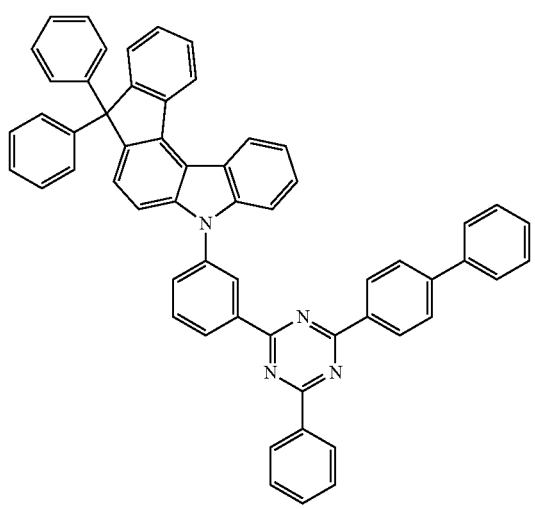
H2-451
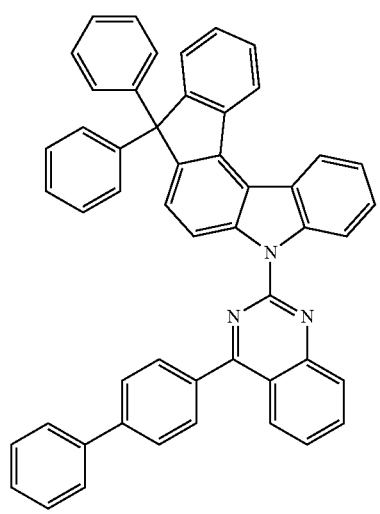
H2-452
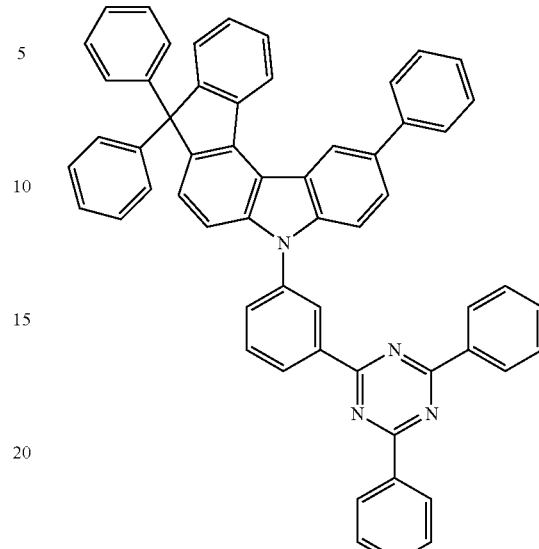
H2-453
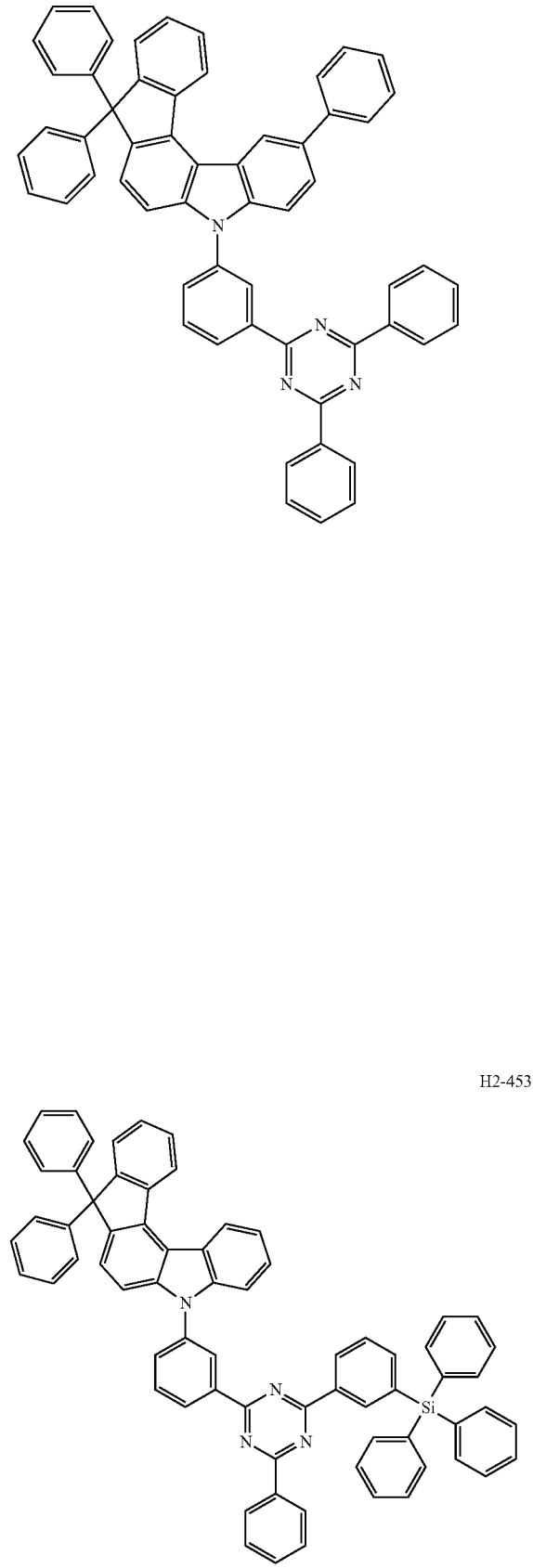

H2-454
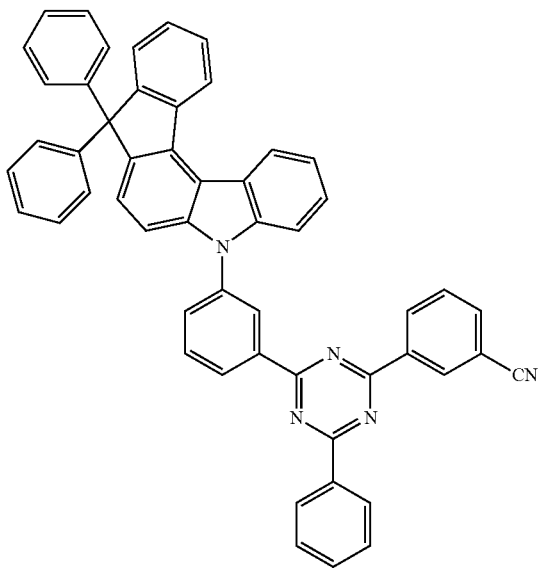
H2-455
H2-456
H2-457
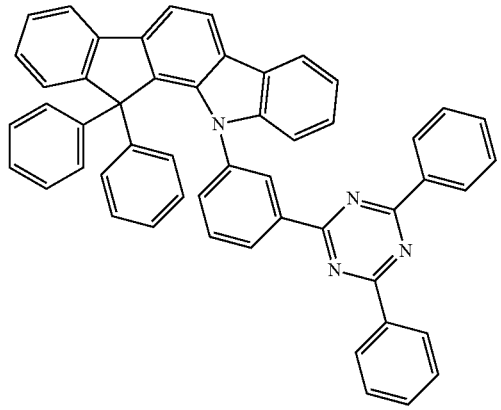
H2-458
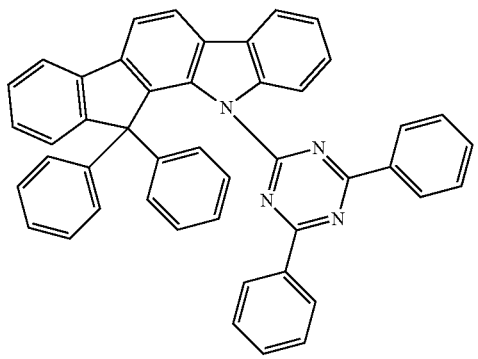
H2-459
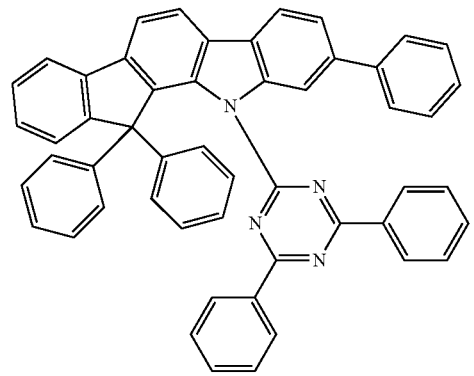
H2-460
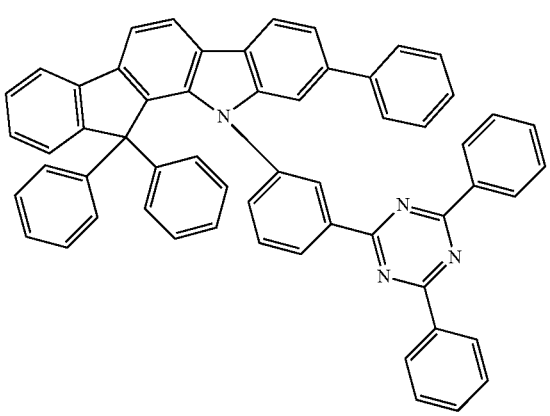

H2-461
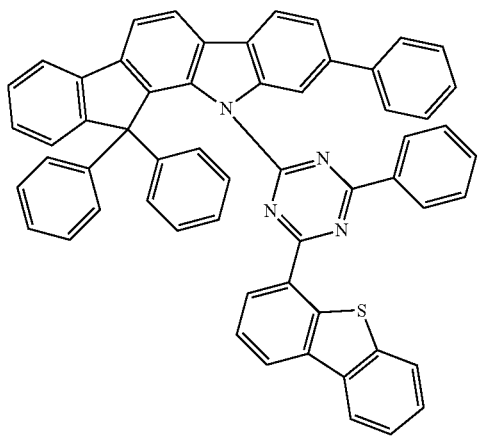
H2-464
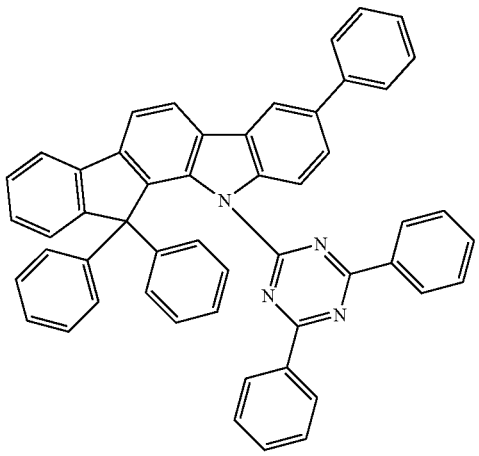
H2-462
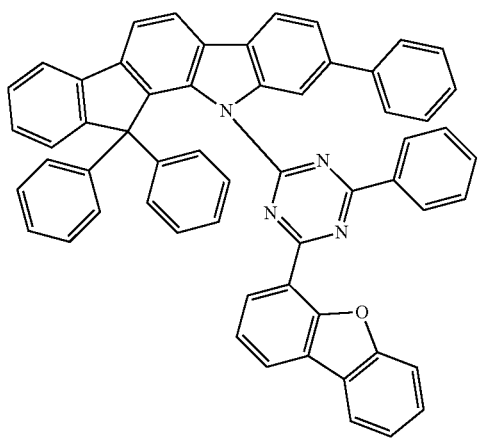
H2-465
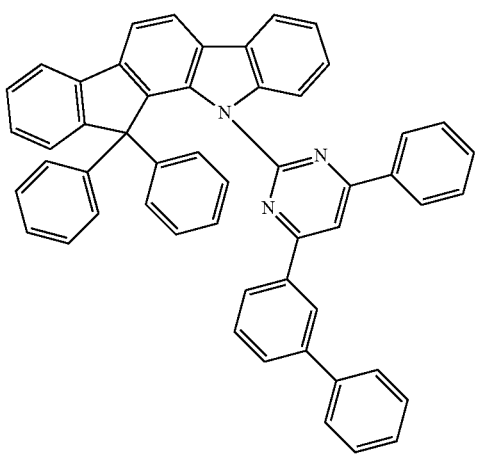
H2-463
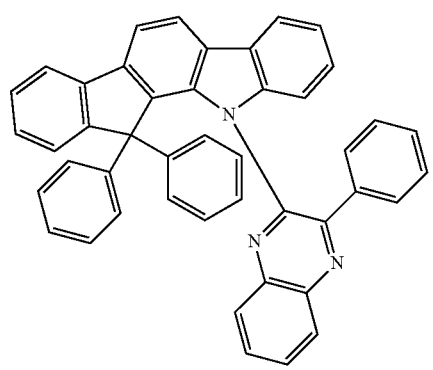
H2-466
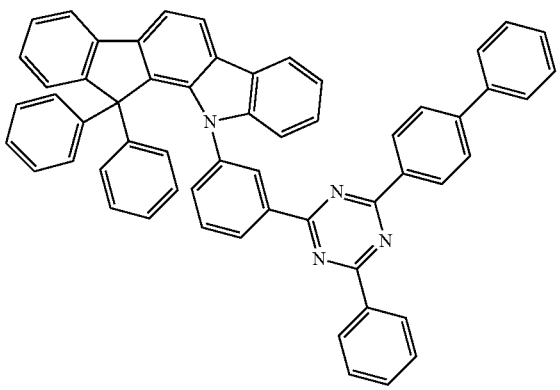

H2-467
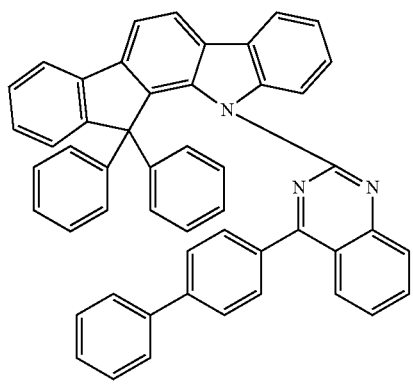
H2-468
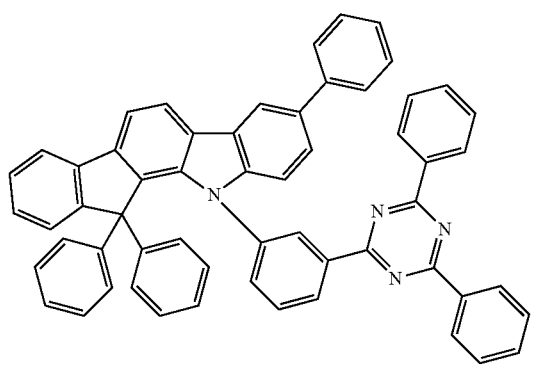
H2-469
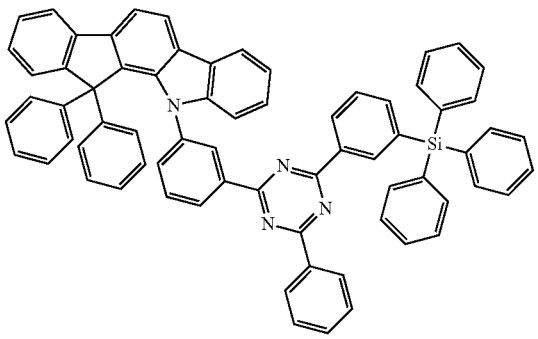
H2-470
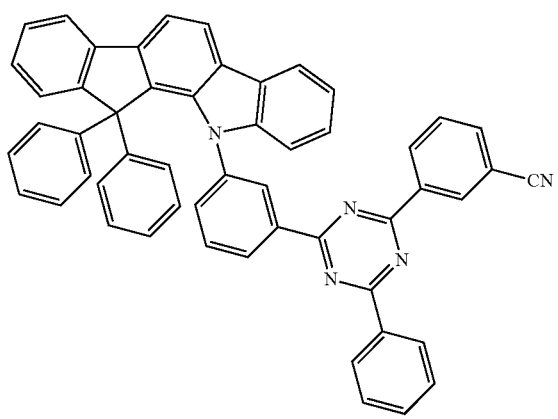
H2-471
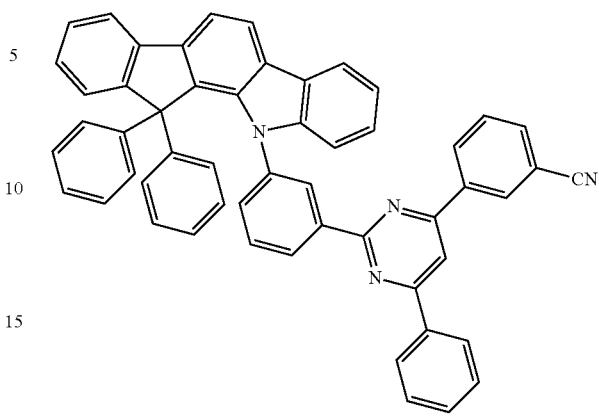
H2-472
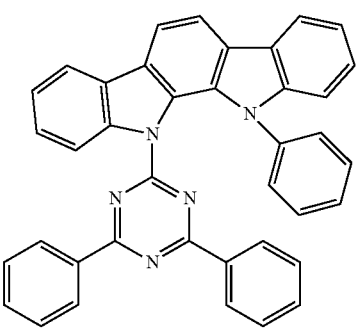
H2-473
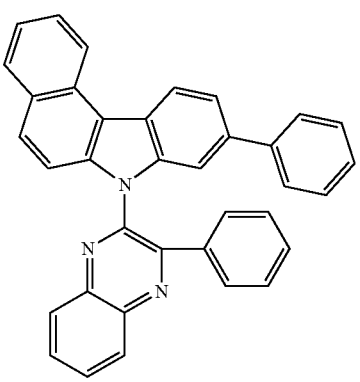
H2-474
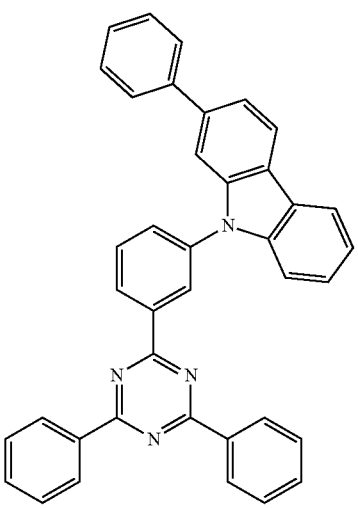

-continued
H2-475
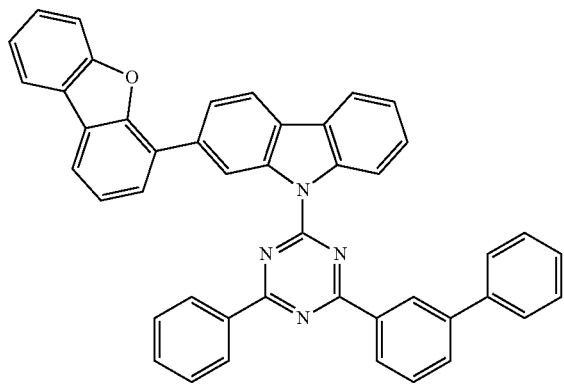
H2-476
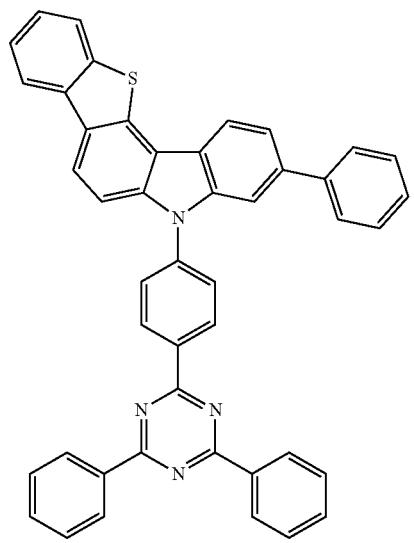
H2-477
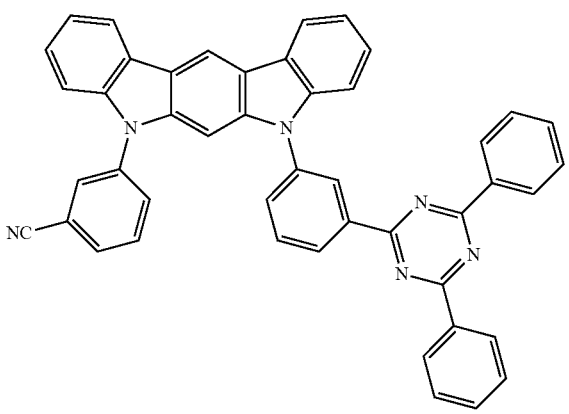
-continued
H2-478
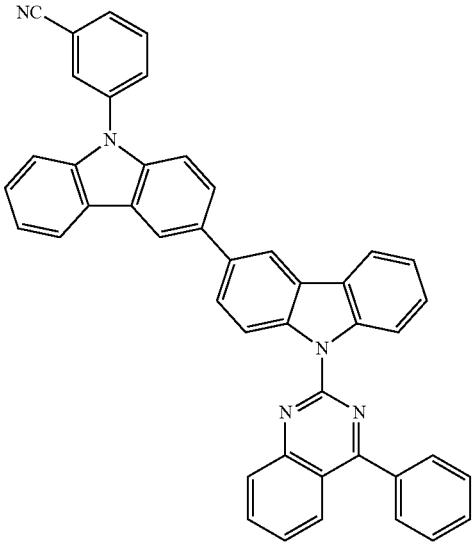
H2-479
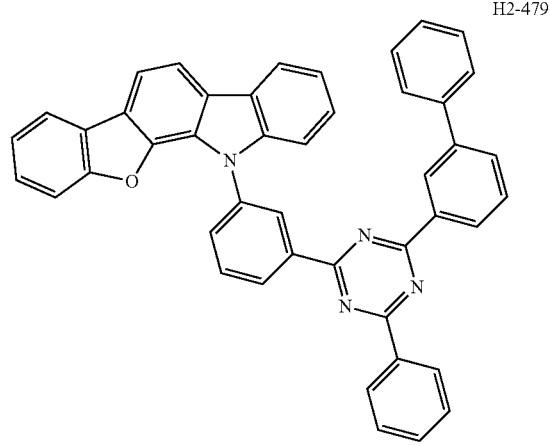
H2-480
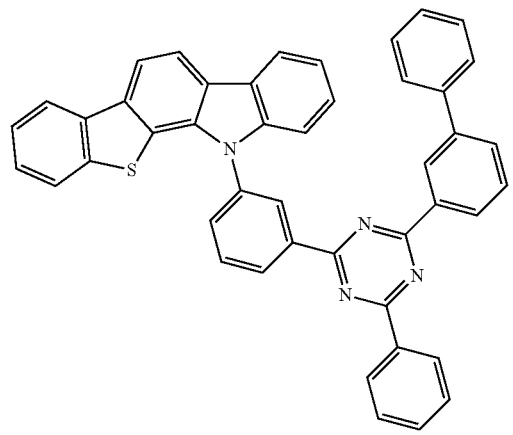

H2-481
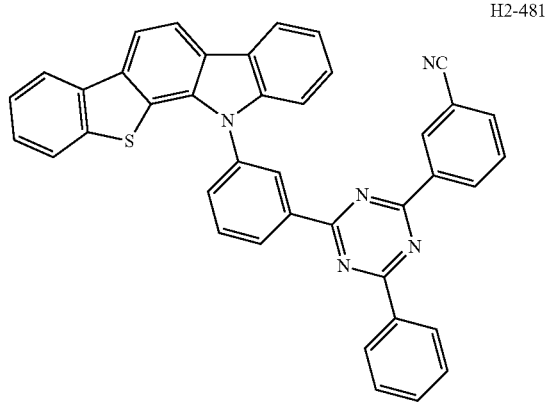
H2-484
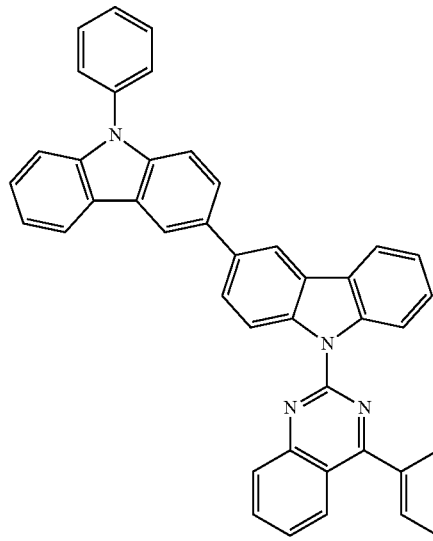
H2-482
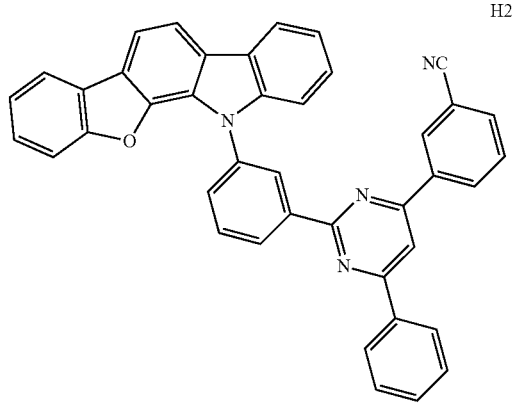
H2-485
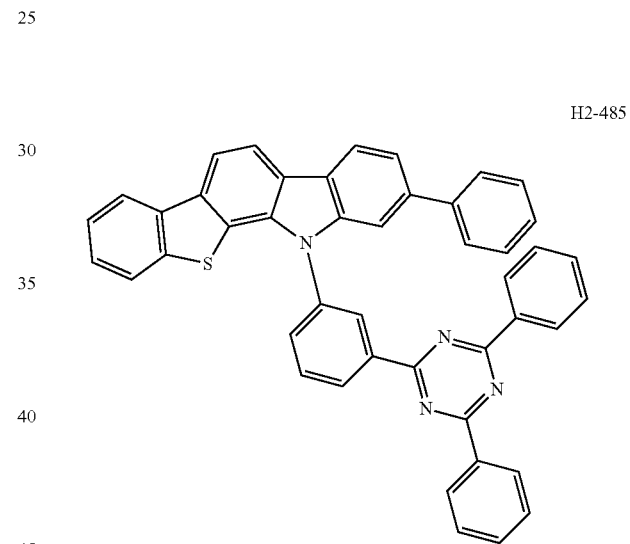
H2-483
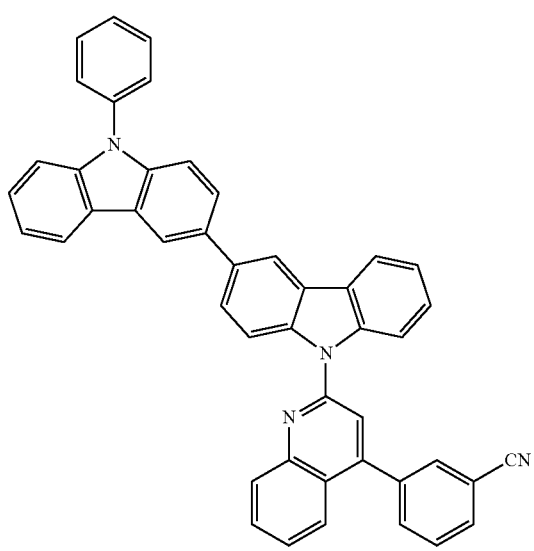
H2-486
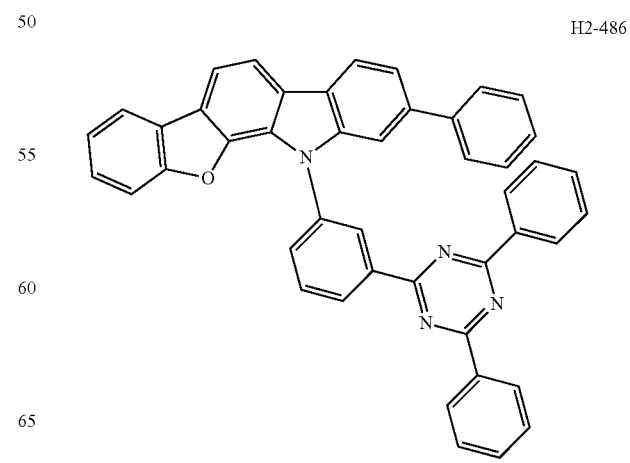

-continued
H2-487
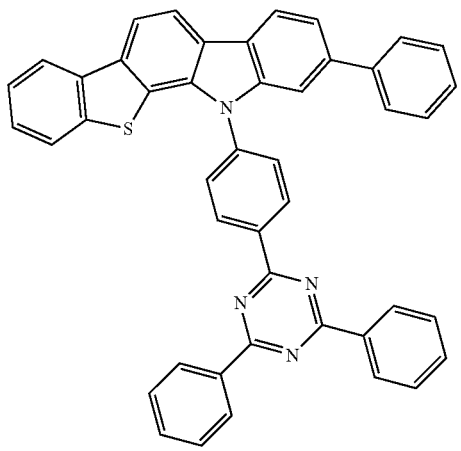
H2-490
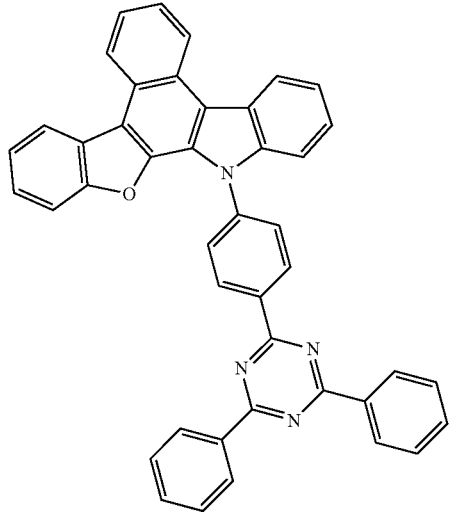
H2-488
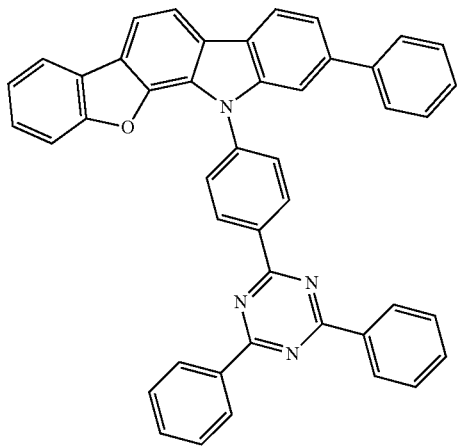
H2-491
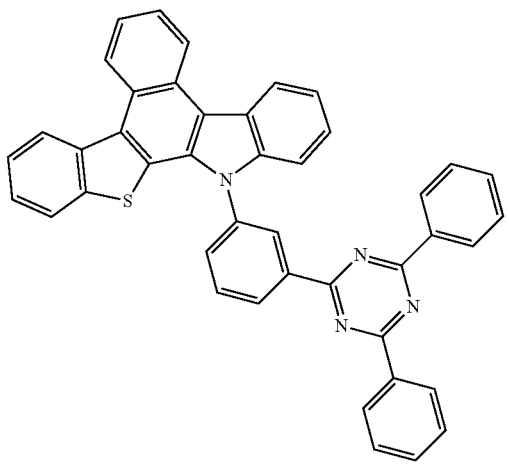
H2-489
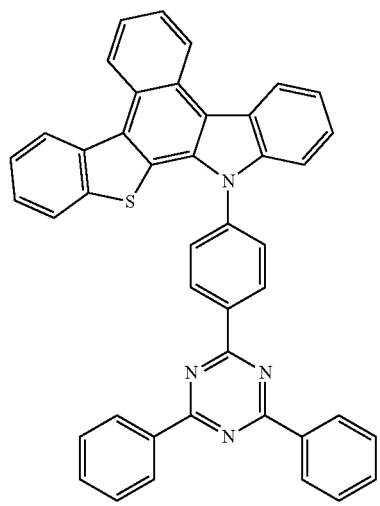
H2-492
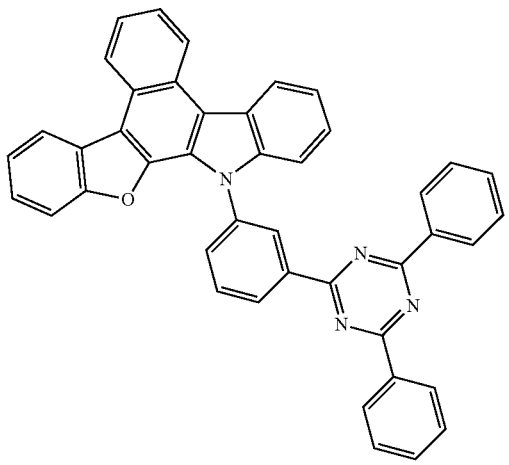

H2-493
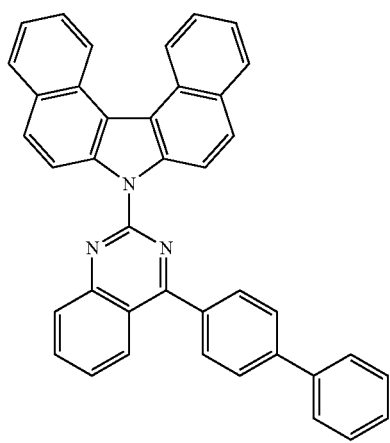
H2-494
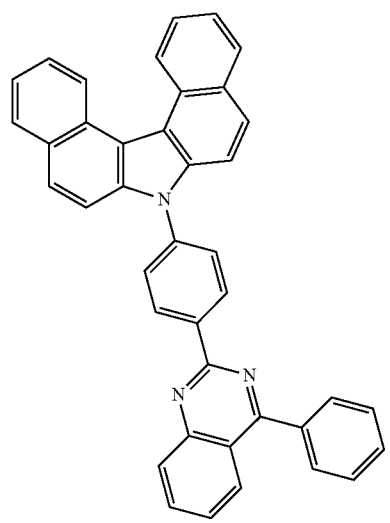
H2-495
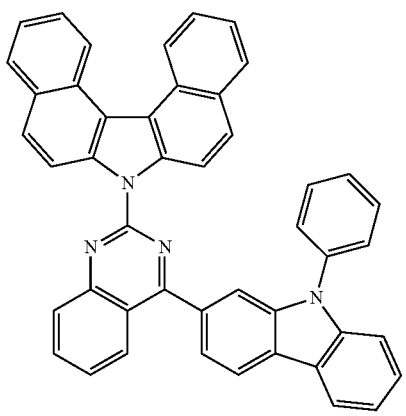
H2-496
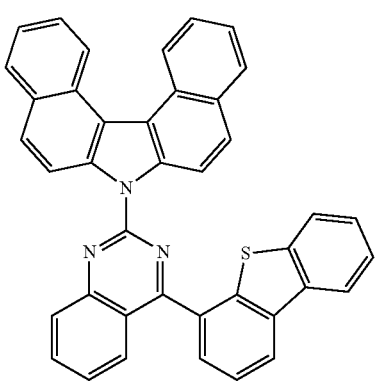
H2-497
H2-498
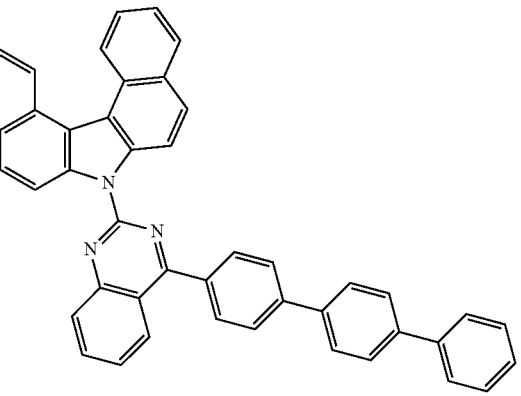

H2-499
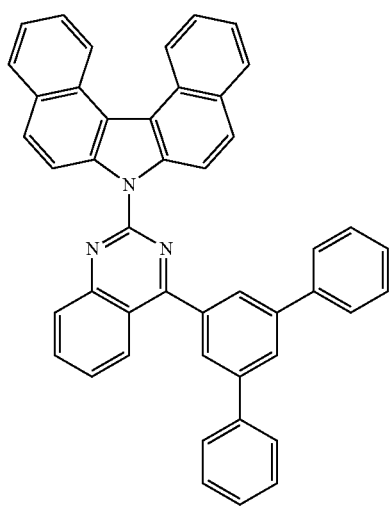
H2-502
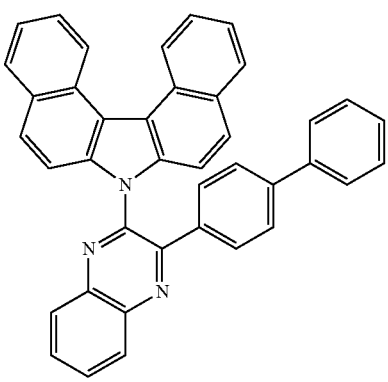
H2-500
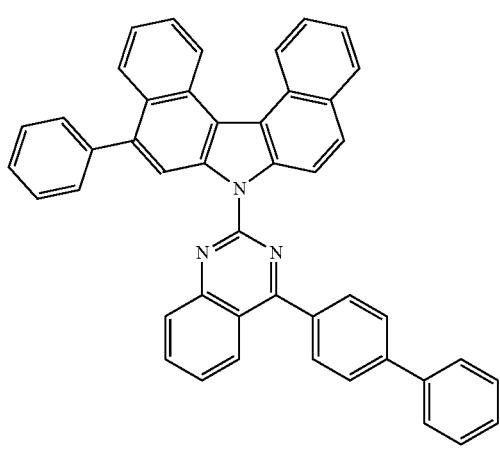
H2-503
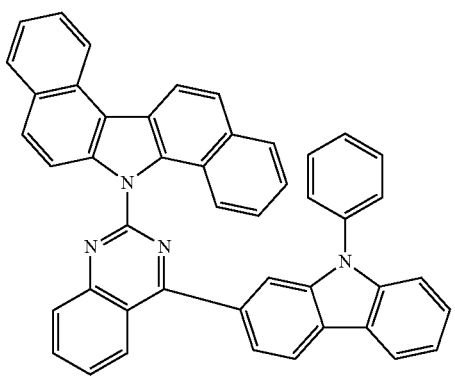
H2-501
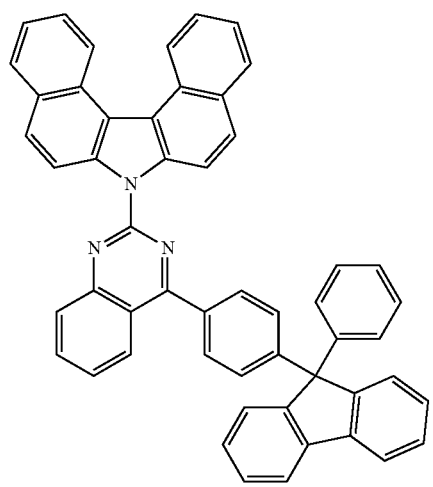
H2-504
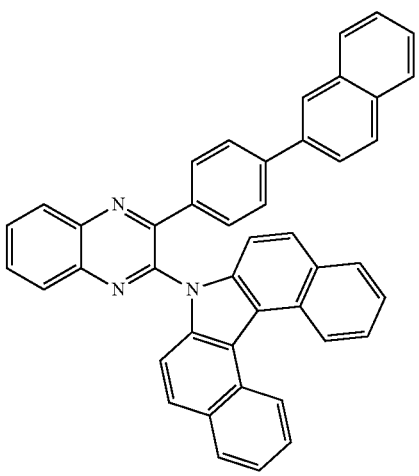

-continued
H2-505
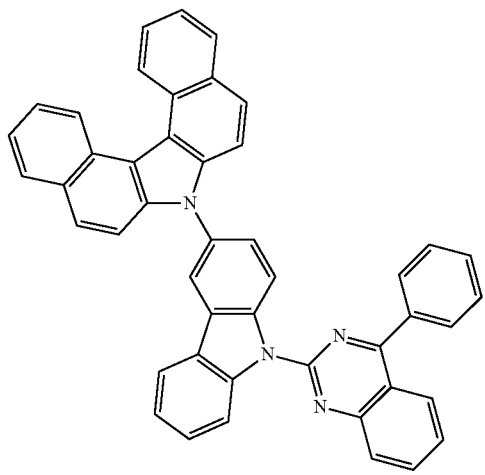
H2-506
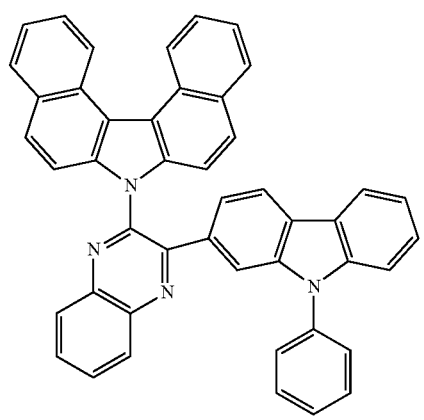
H2-507
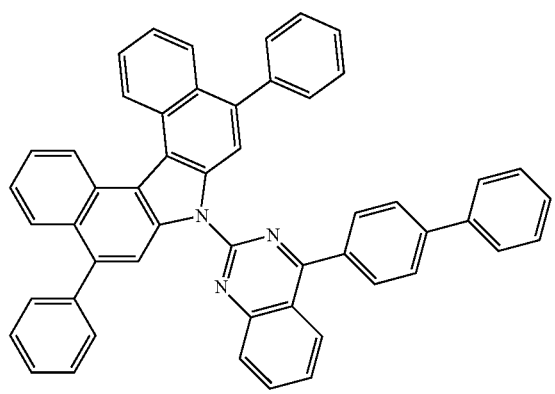
-continued
H2-508
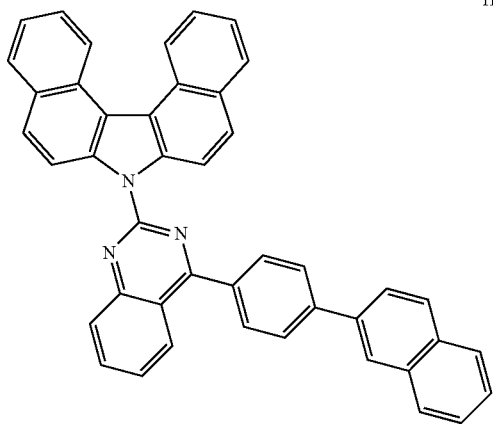
H2-509
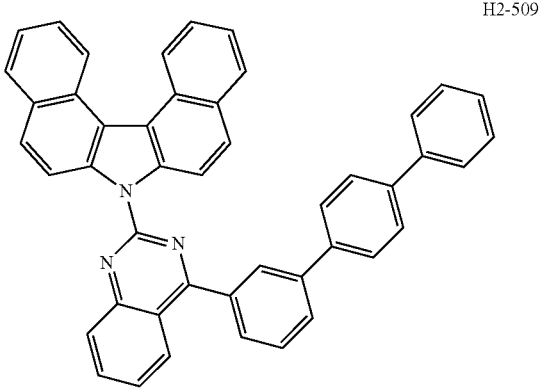
H2-510
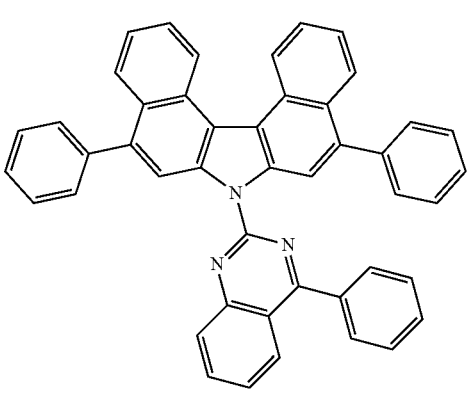
H2-511

205
-continued
H2-512
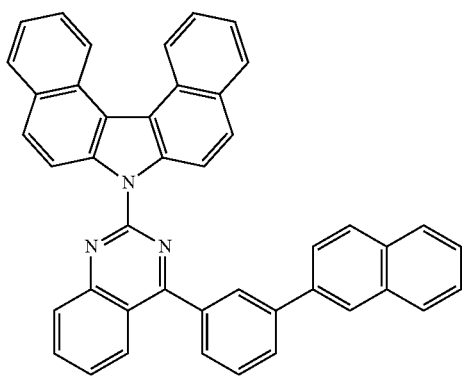
H2-513
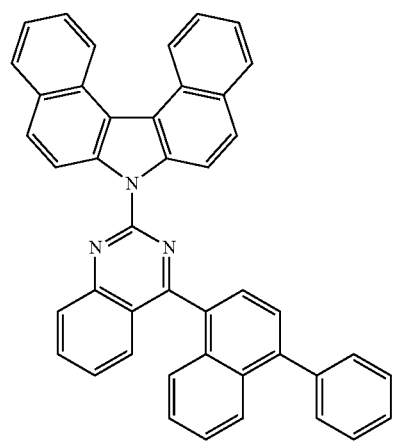
H2-514
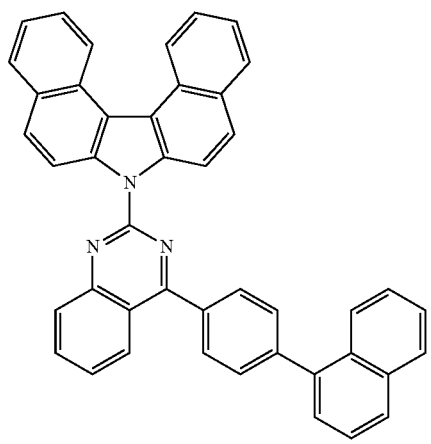
206
-continued
H2-515
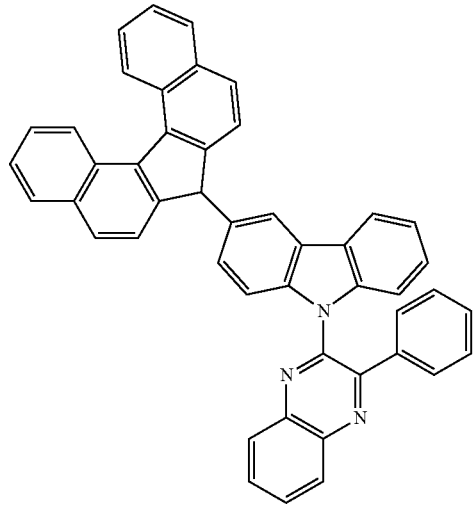
H2-516
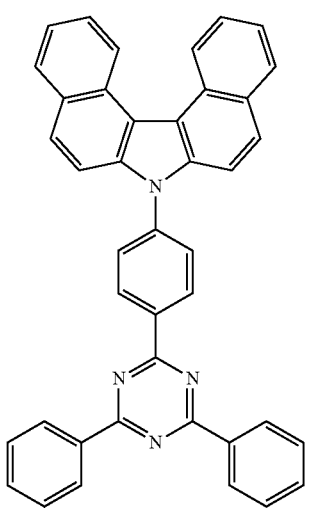
H2-517
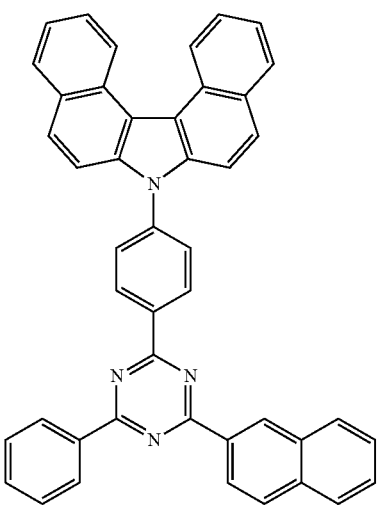

H2-518
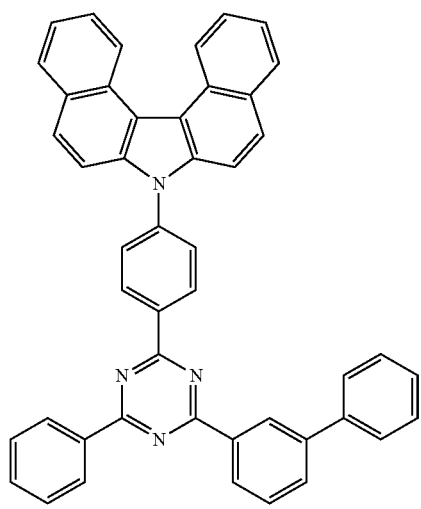
H2-519
H2-520
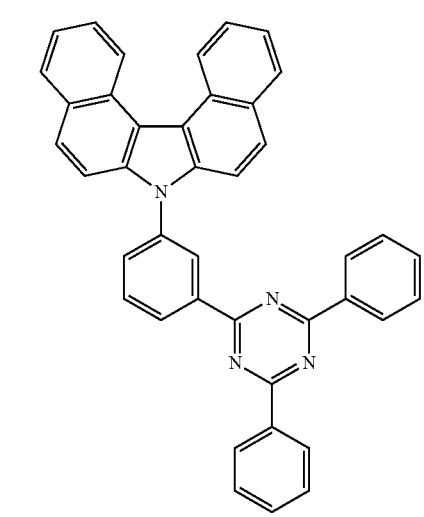
H2-521
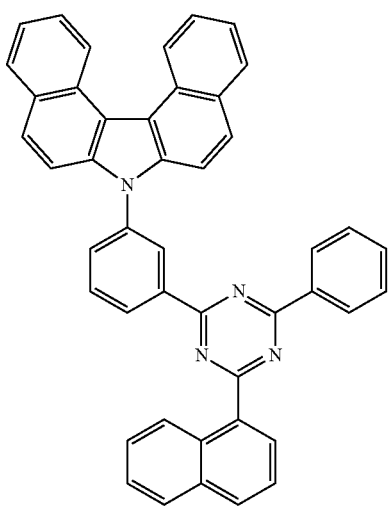
H2-522
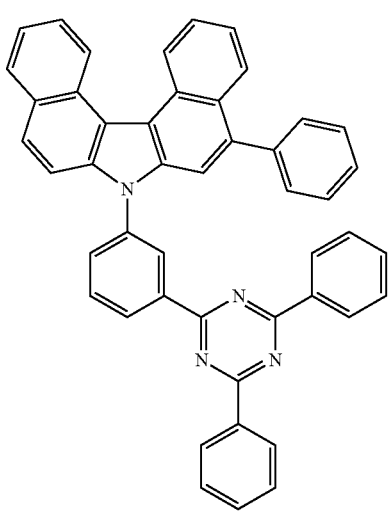
H2-523

H2-524

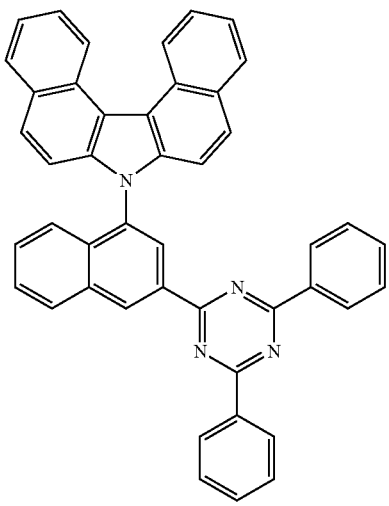

H2-525

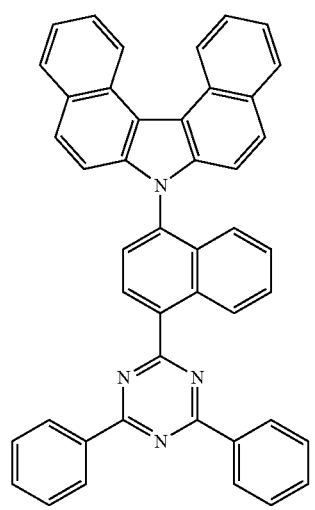

H2-526

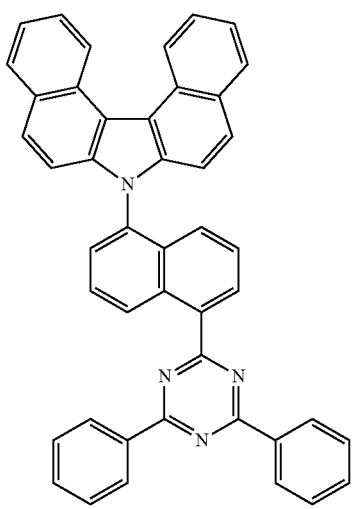

H2-527

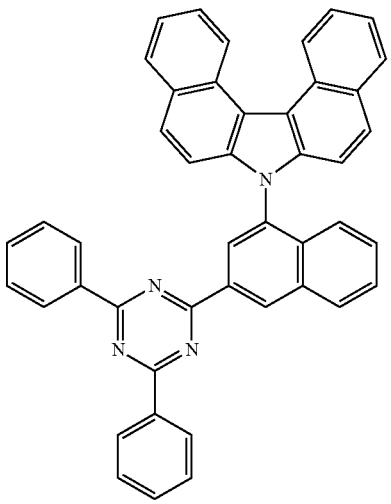

H2-528

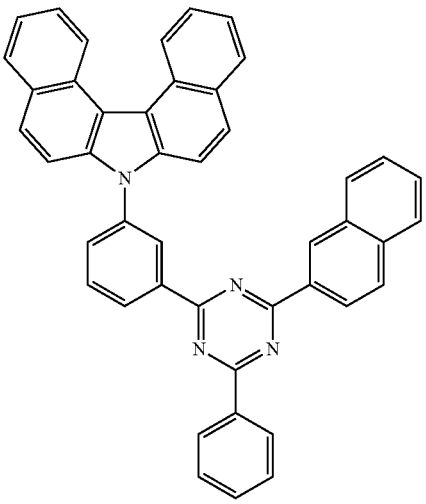

The dopant to be comprised in the organic electroluminescent device of the present disclosure is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

Preferably, the dopant to be comprised in the organic electroluminescent device of the present disclosure may be selected from the group consisting of compounds represented by the following formulae 101 to 103.

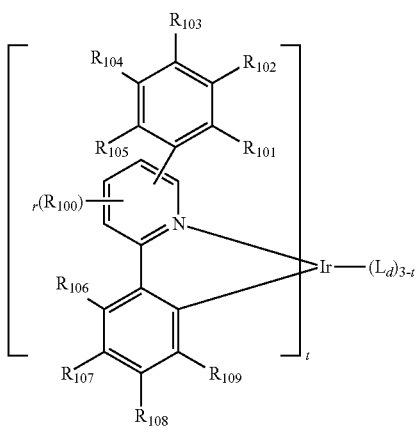

(101)

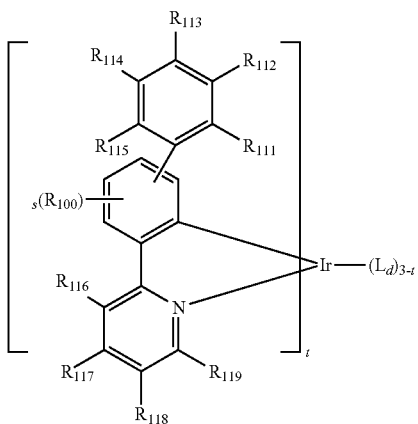

(102)

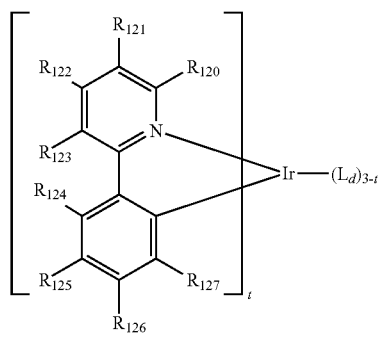

(103)

wherein L is selected from the following structures:

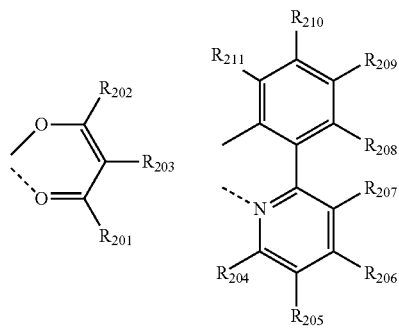

$R_{100}$ represents hydrogen, a substituted or unsubstituted (C1-C30)alkyl, or a substituted or unsubstituted (C3-C30) cycloalkyl; $R_{101}$ to $R_{109}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, or a substituted or unsubstituted (C1-C30)alkoxy; $R_{106}$ to $R_{109}$ may be linked to an adjacent substituent(s) to form a substituted or unsubstituted fused ring, for example, fluorene unsubstituted or substituted with alkyl, dibenzothiophene unsubstituted or substituted with alkyl, or dibenzofuran unsubstituted or substituted with alkyl; $R_{120}$ to $R_{123}$ may be linked to an adjacent substituent(s) to form a substituted or unsubstituted fused ring, for example, quinoline unsubstituted or substituted with alkyl or aryl; $R_{124}$ to $R_{127}$, each independently, represent hydrogen, deuterium, a halogen, a substituted or unsubstituted (C1-C30)alkyl, or a substituted or unsubstituted (C6-C30)aryl; $R_{124}$ to $R_{127}$ may be linked to an adjacent substituent(s) to form a substituted or unsubstituted fused ring, for example, fluorene unsubstituted or substituted with alkyl, dibenzothiophene unsubstituted or substituted with alkyl, or dibenzofuran unsubstituted or substituted with alkyl; $R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; $R_{208}$ to $R_{211}$ may be linked to an adjacent substituent(s) to form a substituted or unsubstituted fused ring, for example, fluorene unsubstituted or substituted with alkyl, dibenzothiophene unsubstituted or substituted with alkyl, or dibenzofuran unsubstituted or substituted with alkyl; r, s, and t, each independently, represent an integer of 1 to 3; where r or s is an integer of 2 or more, each of $R_{100}$ may be the same or different.

Specifically, the dopant material includes the following, but is not limited thereto.

D-1

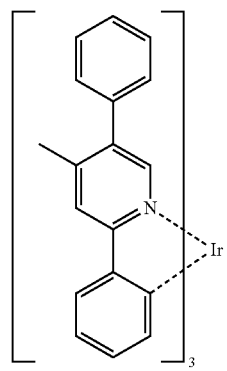

D-2

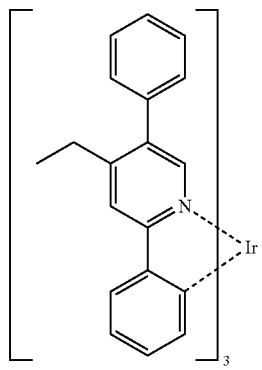

D-3
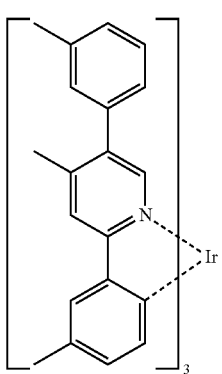
D-4
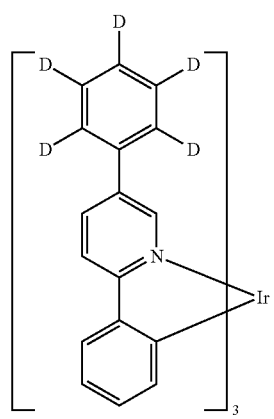
D-5
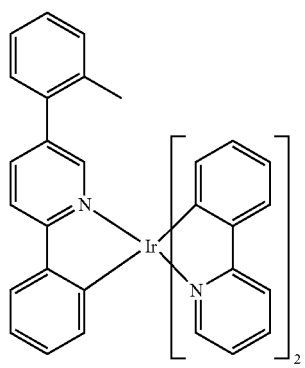
D-6
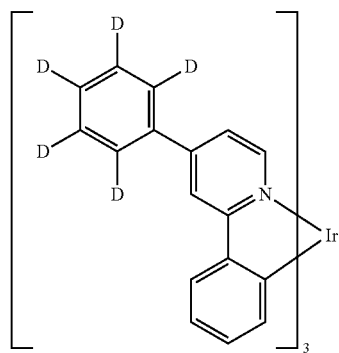
D-7
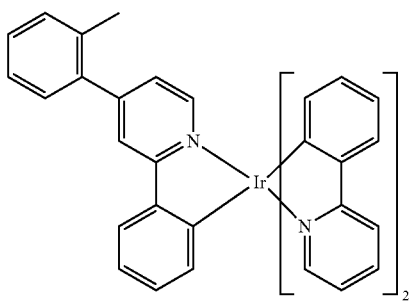
D-8
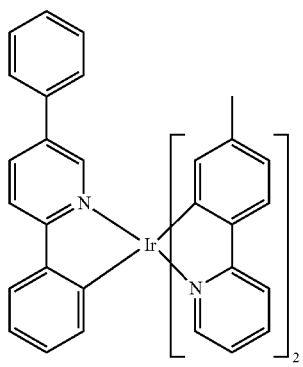
D-9
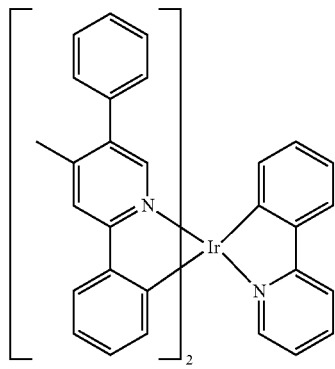
D-10
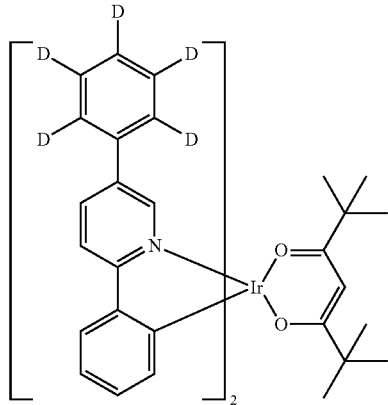

D-11
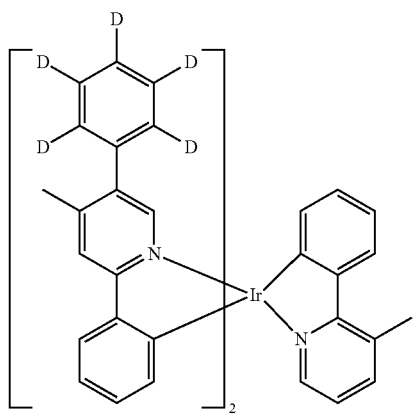
D-12
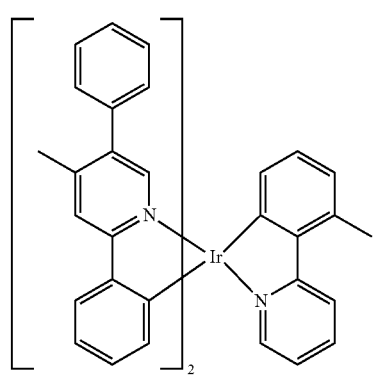
D-13
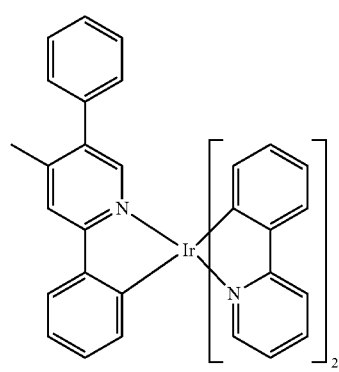
D-14
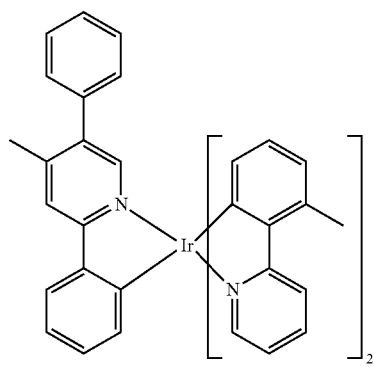
D-15
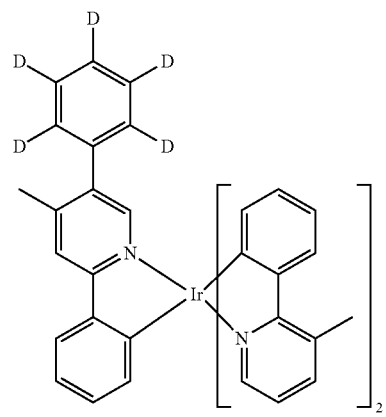
D-16
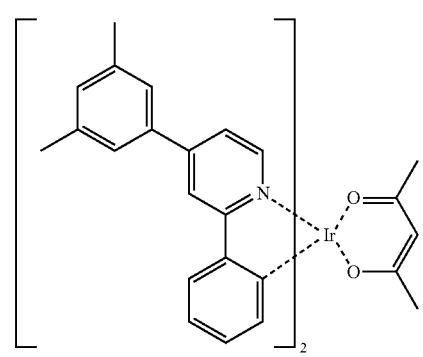
D-17
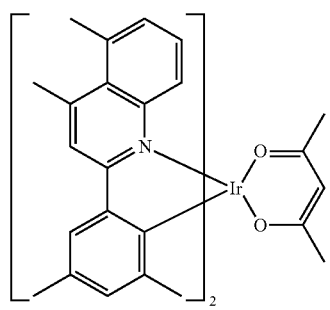
D-18
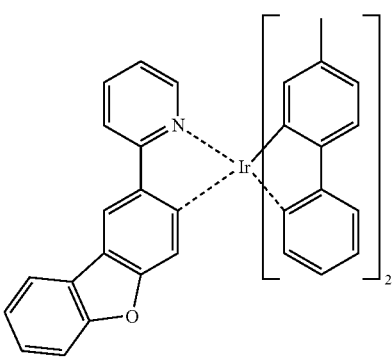

-continued
D-19
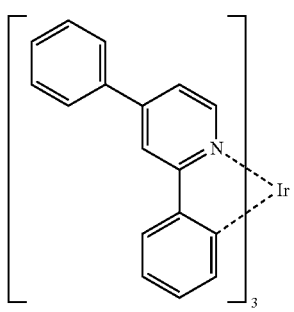
D-20
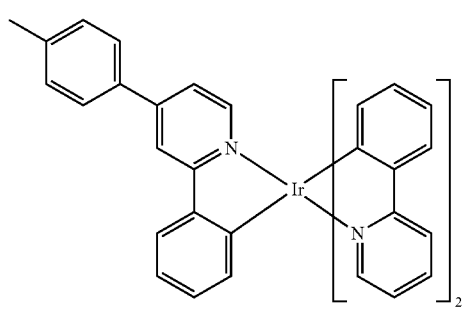
D-21
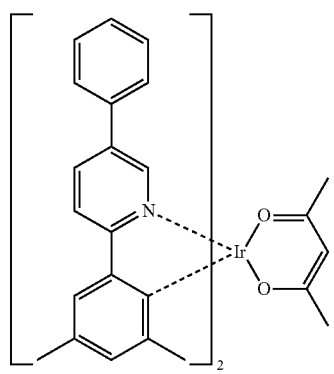
D-22
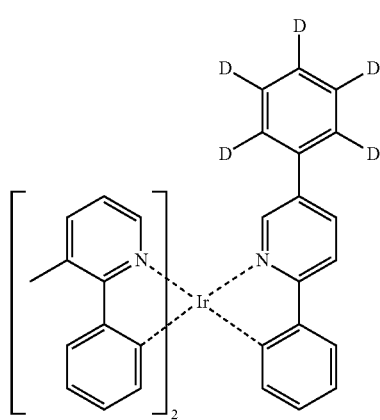
-continued
D-23
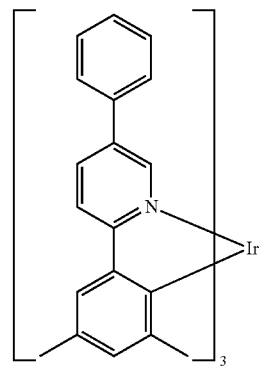
D-24
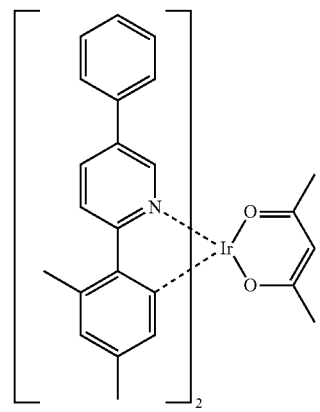
D-25
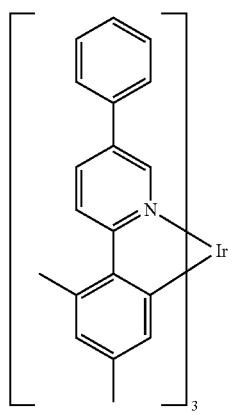
D-26
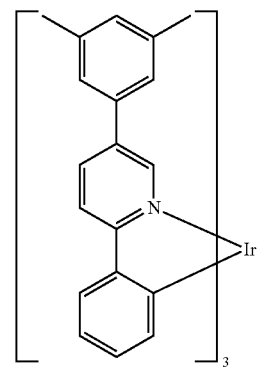

D-27
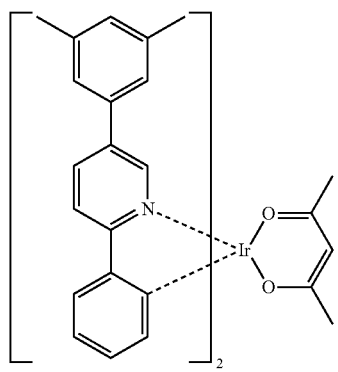
D-28
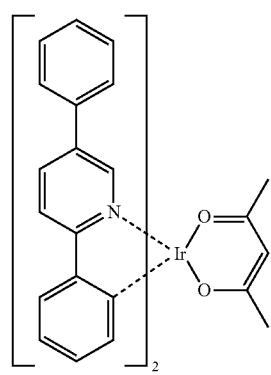
D-29
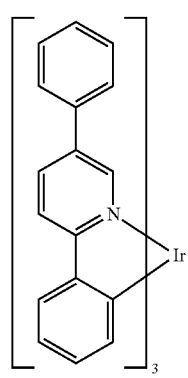
D-30
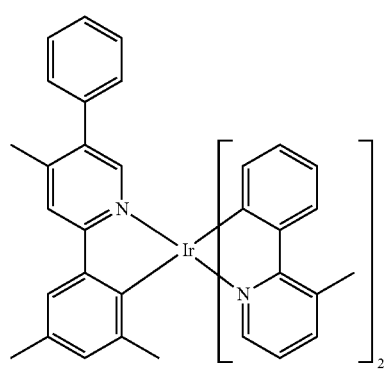
D-31
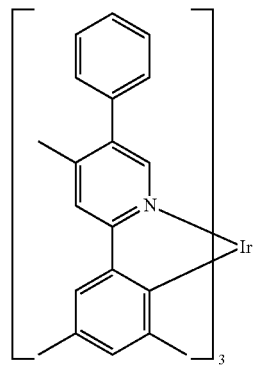
D-32
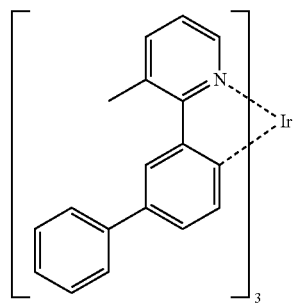
D-33
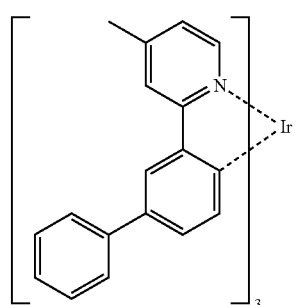
D-34
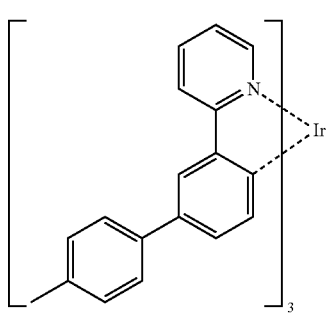
D-35
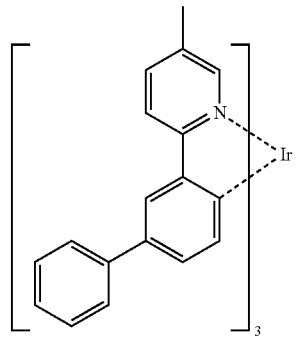

D-36 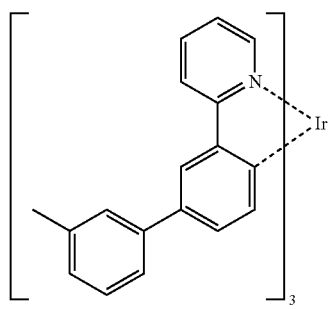
D-40 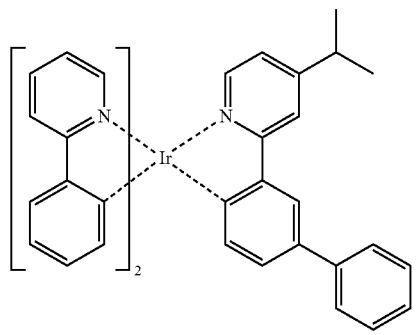
D-37 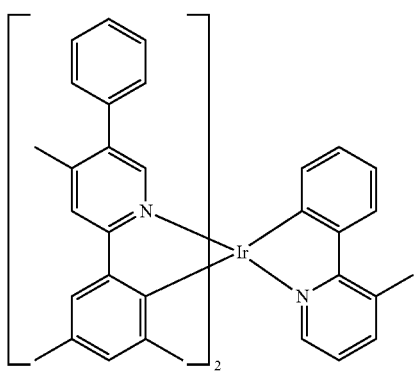
D-41 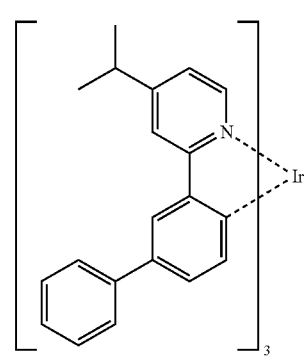
D-38 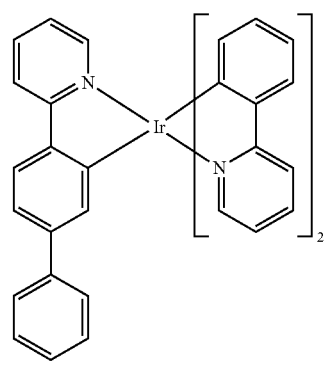
D-42 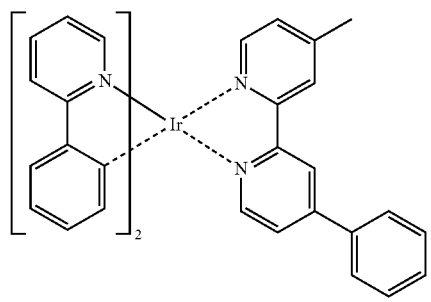
D-39 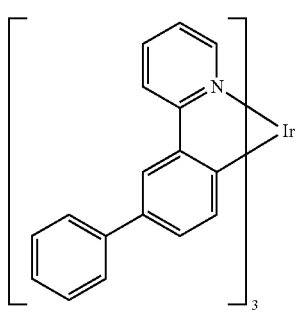
D-43 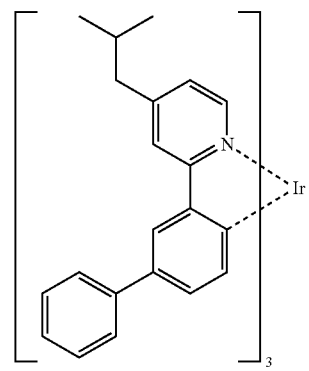

-continued
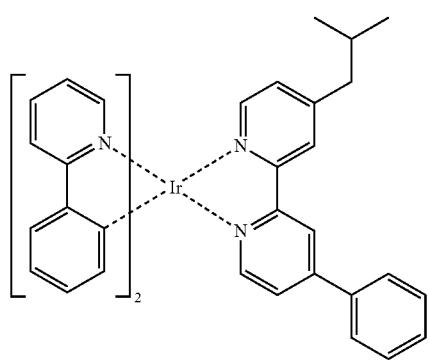 D-44
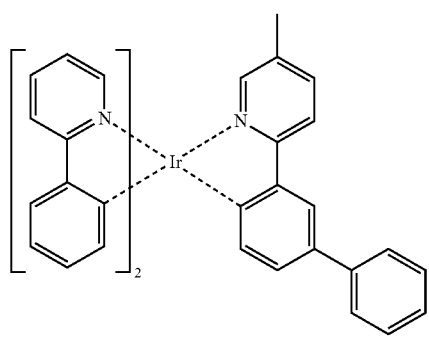 D-45
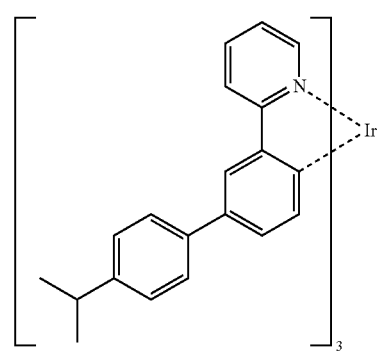 D-46
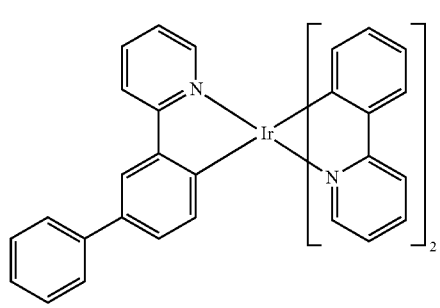 D-47
-continued
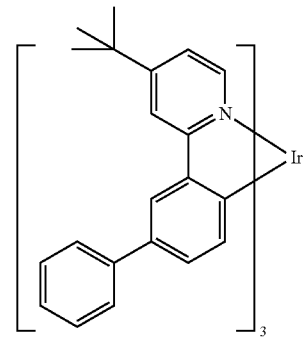 D-48
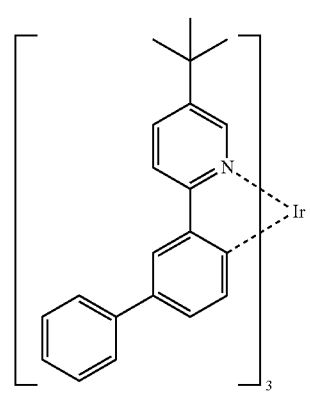 D-49
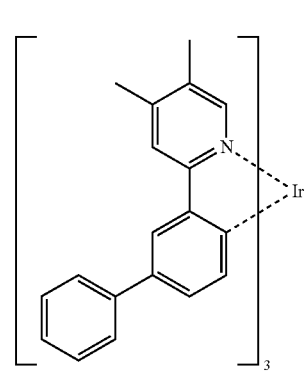 D-50
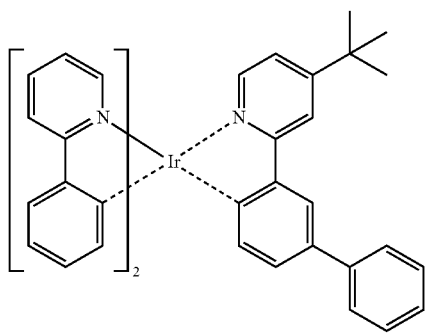 D-51

-continued
D-52
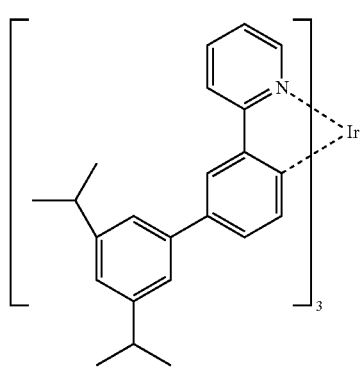
D-53
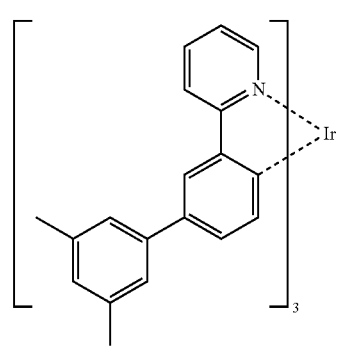
D-54
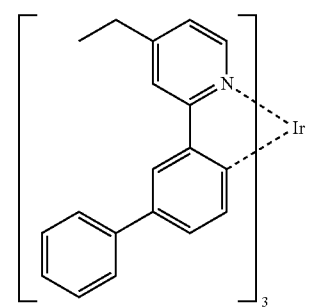
D-55
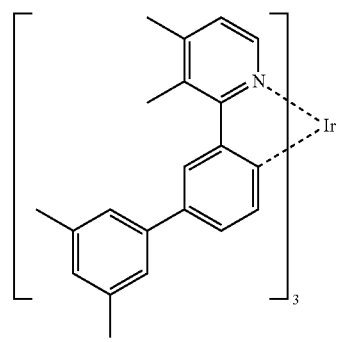
D-56
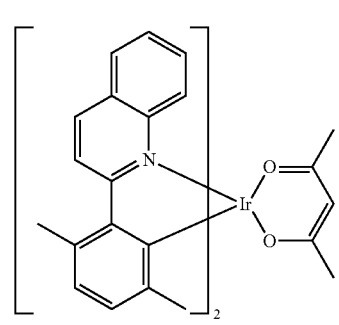
-continued
D-57
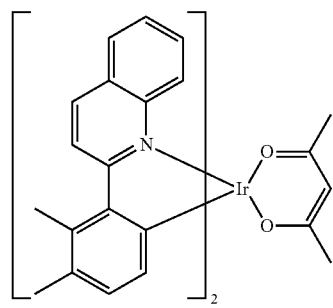
D-58
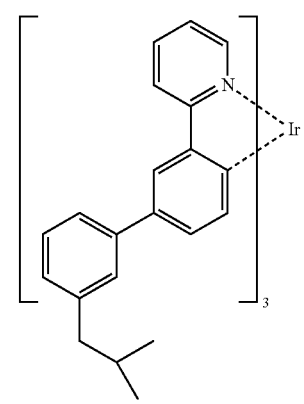
D-59
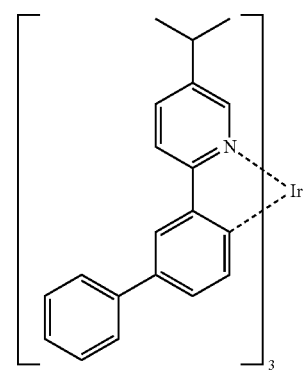
D-60
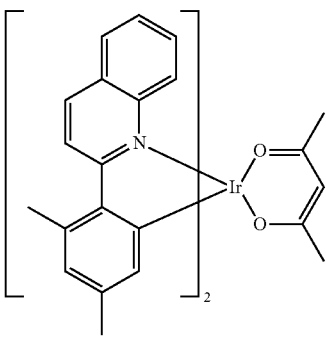

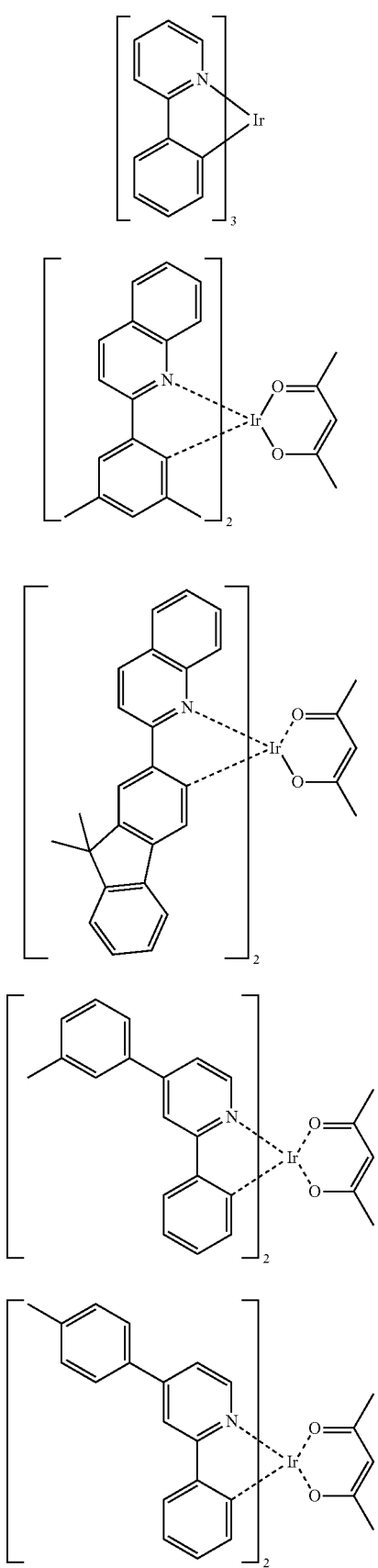
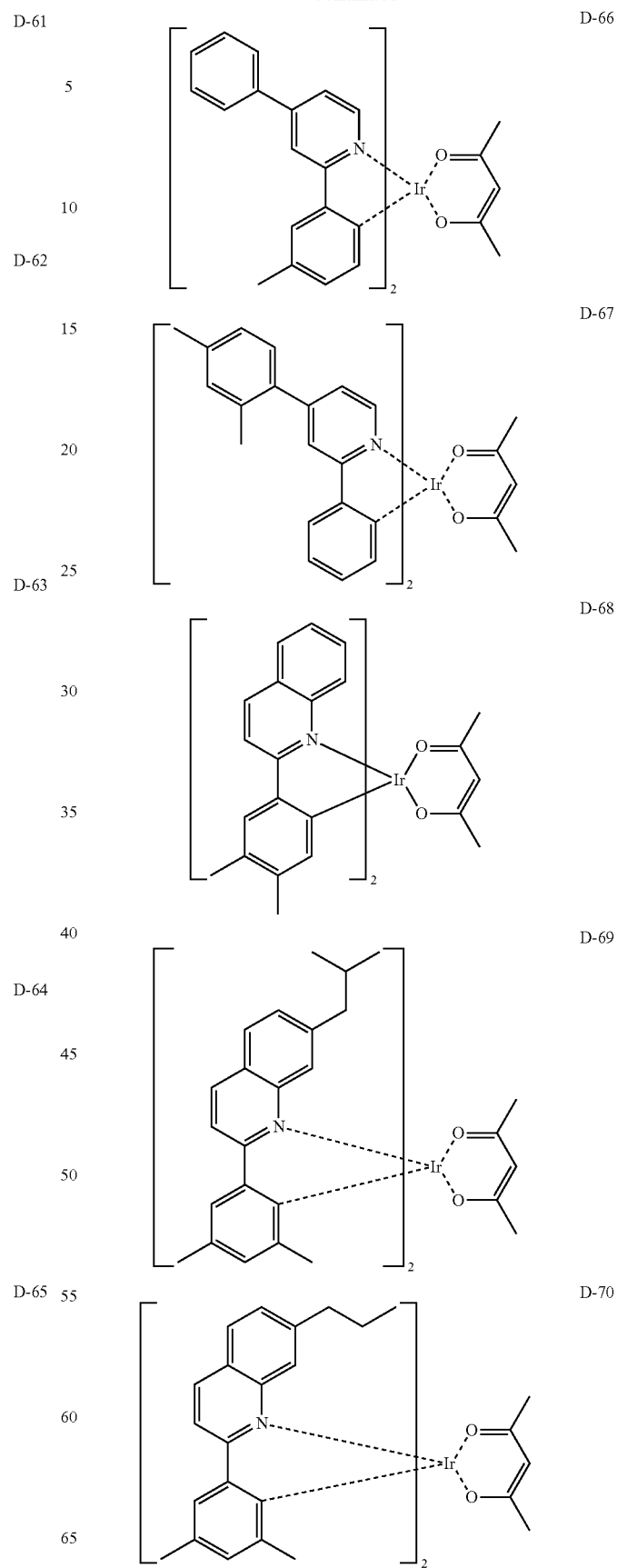

D-71
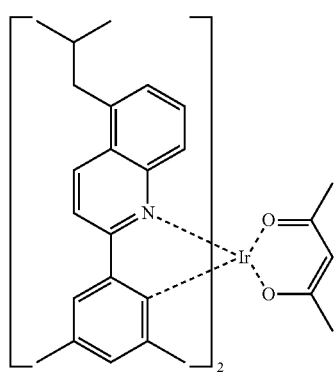
D-72
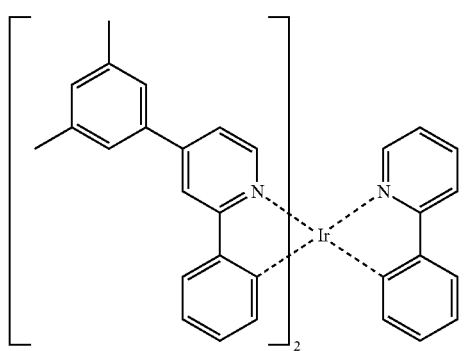
D-73
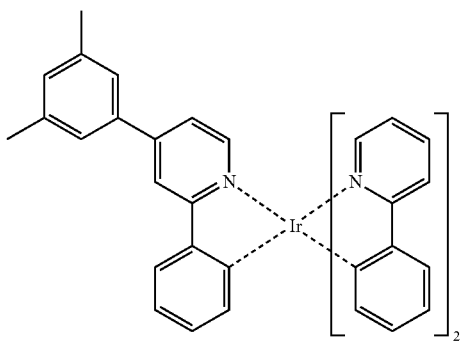
D-74
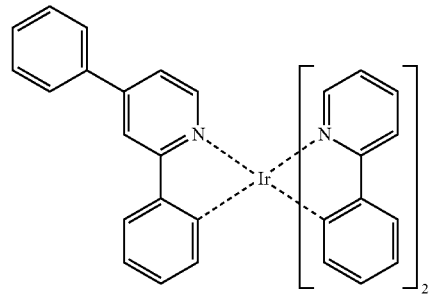
D-75
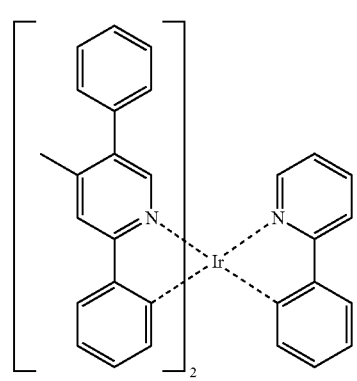
D-76
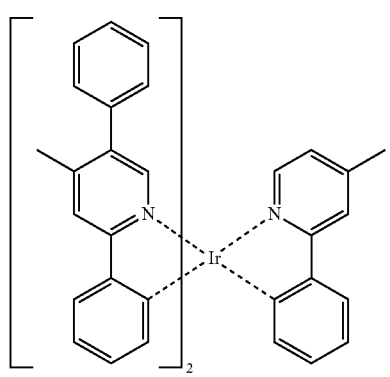
D-77
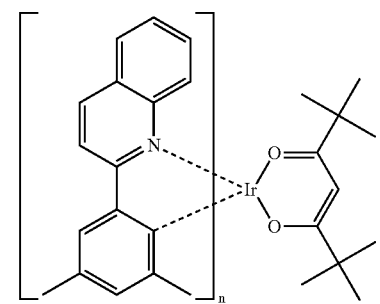
D-78

D-79
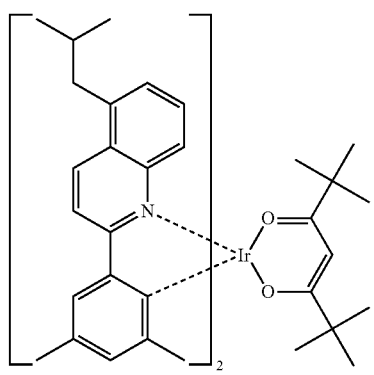
D-83
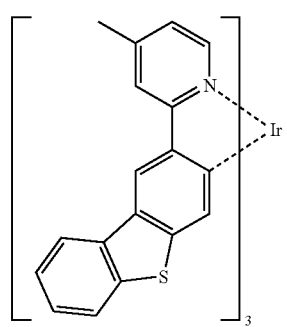
D-80
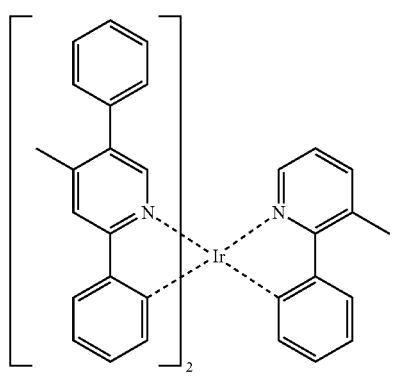
D-84
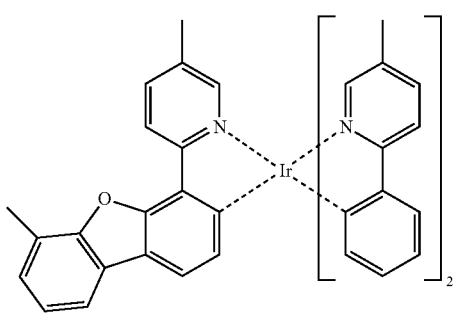
D-85
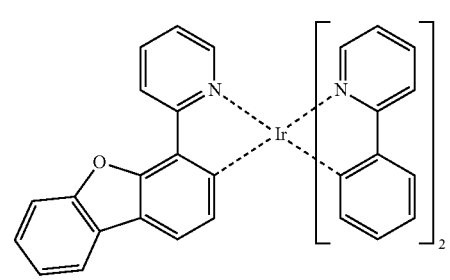
D-81
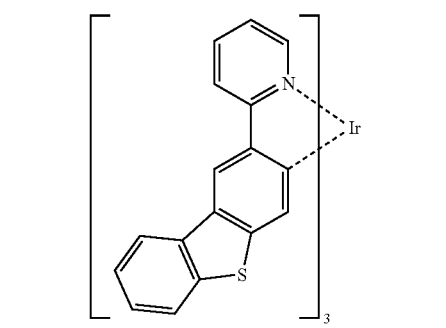
D-86
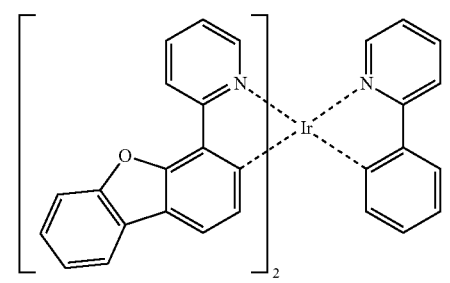
D-82
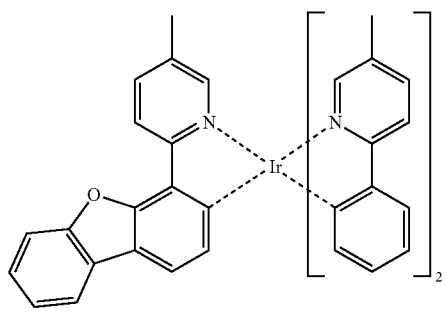
D-87
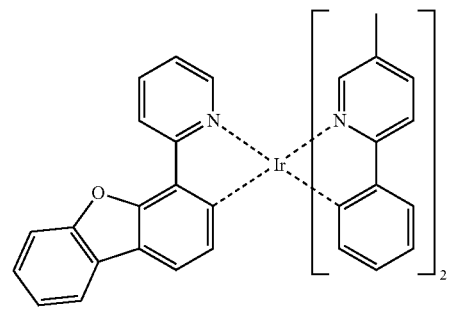

-continued
D-88
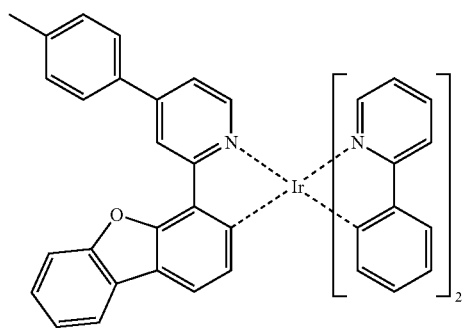
D-89
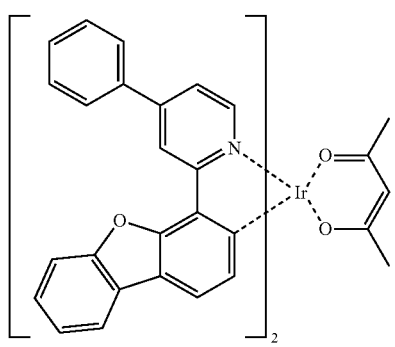
D-90
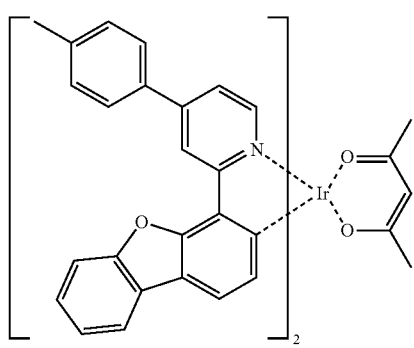
D-91
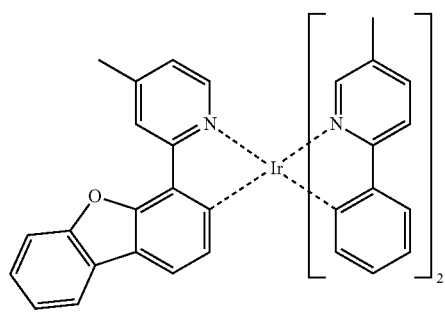
-continued
D-92
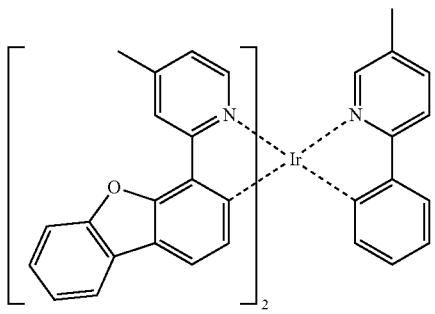
D-93
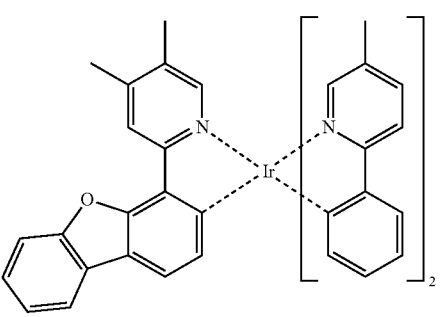
D-94
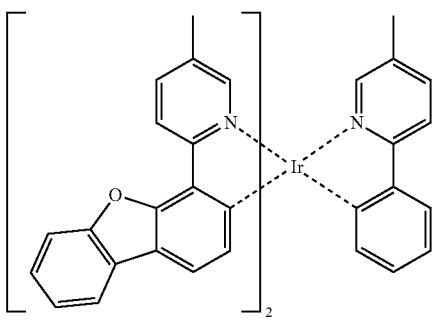
D-95
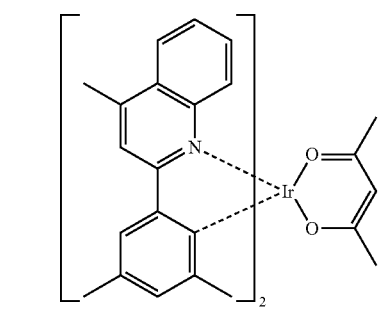
D-96
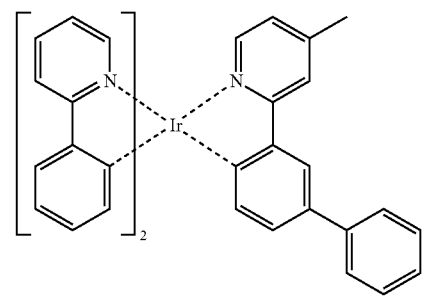

-continued
D-97
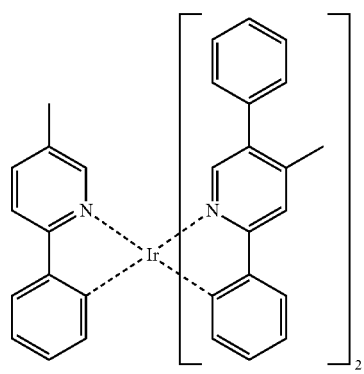
D-98
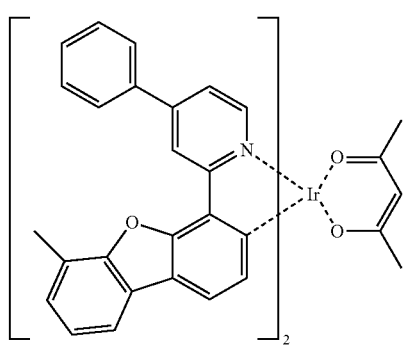
D-99
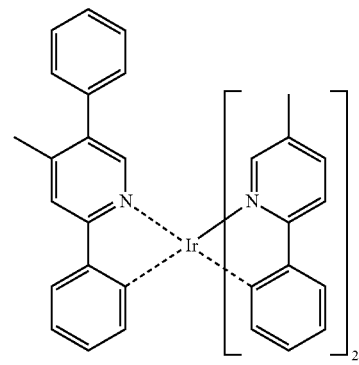
D-100
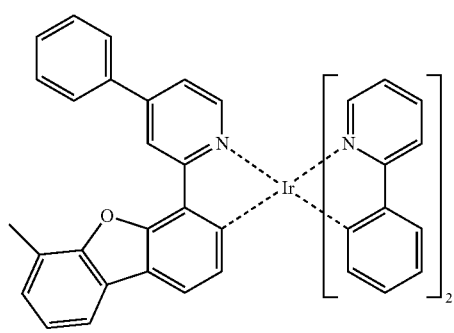
-continued
D-101
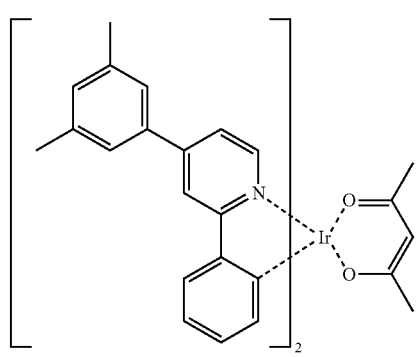
D-102
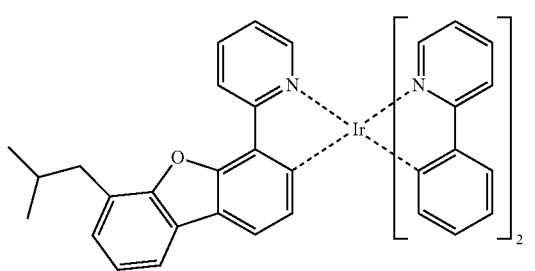
D-103
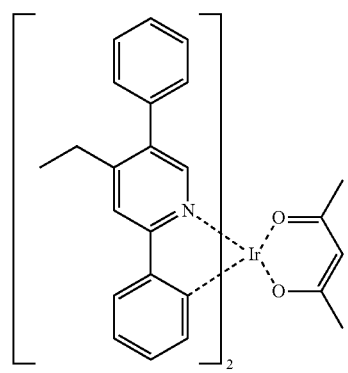
D-104
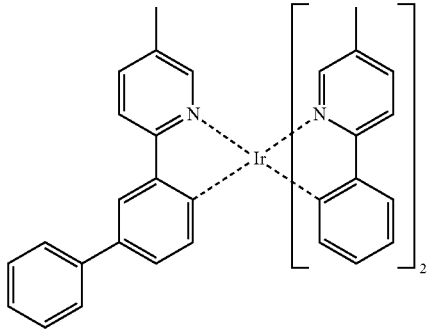

D-105
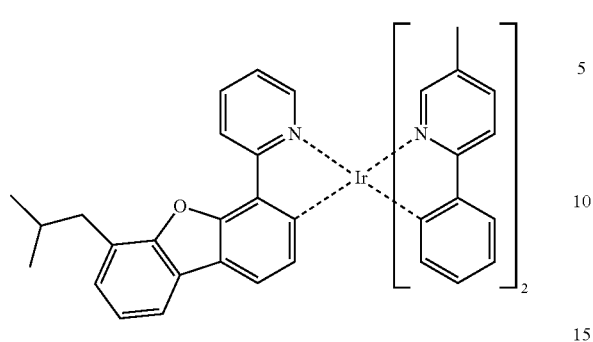
D-109
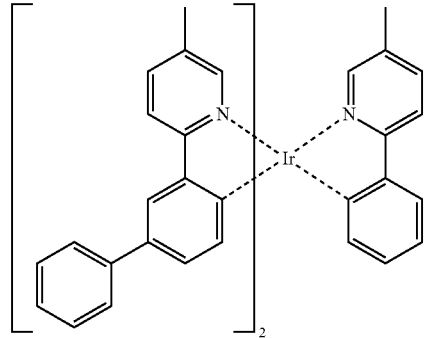
D-106
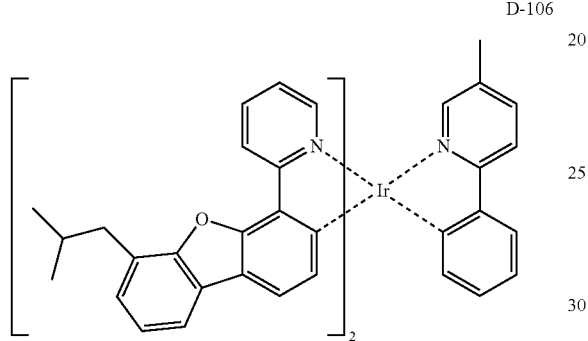
D-110
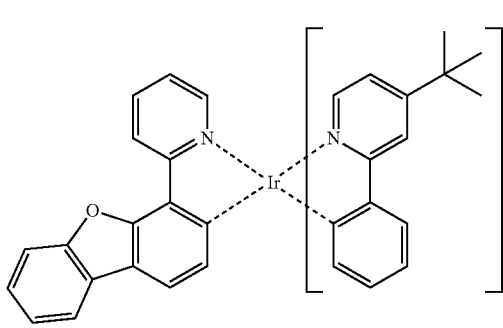
D-107
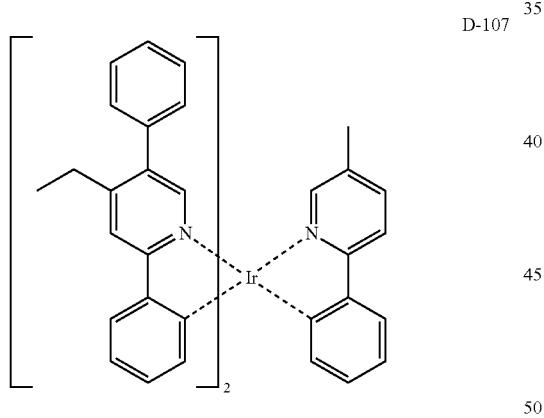
D-111
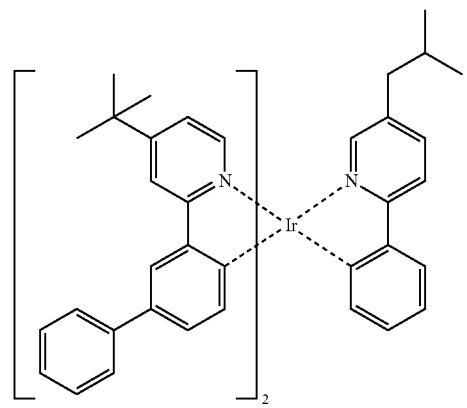
D-108
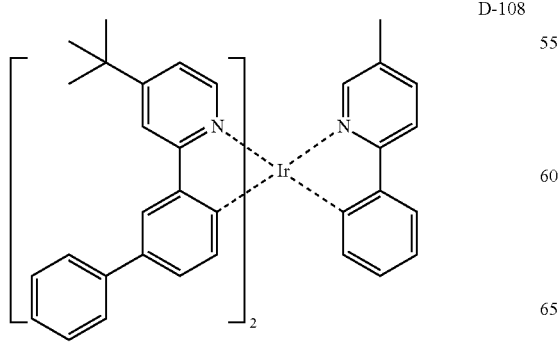
D-112
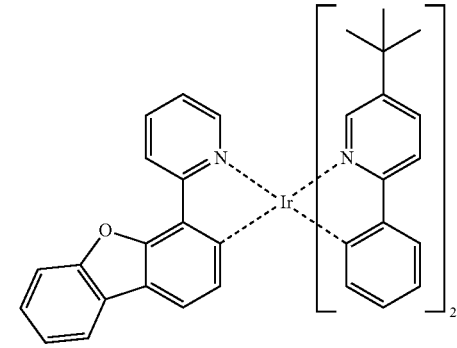

D-113
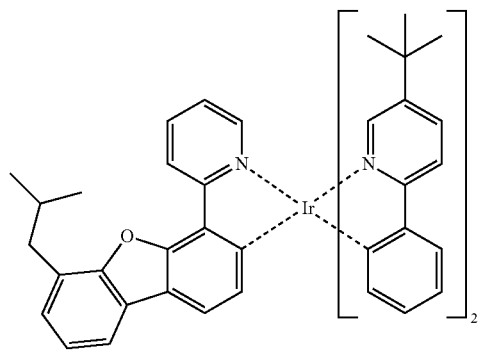
D-117
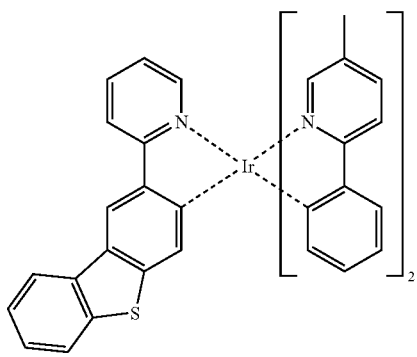
D-114
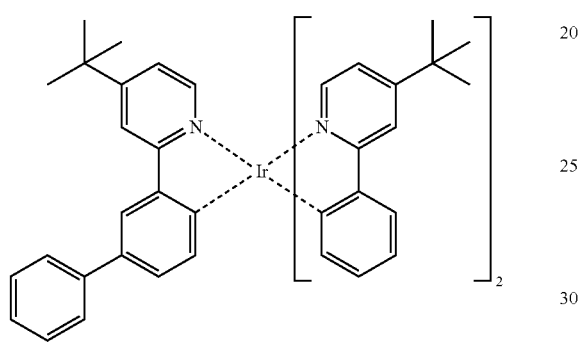
D-118
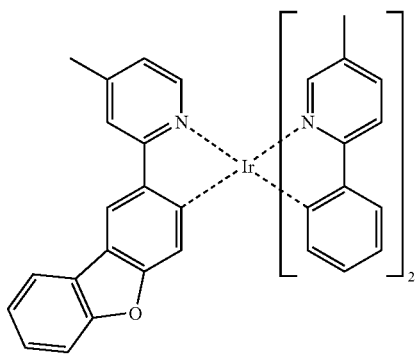
D-115
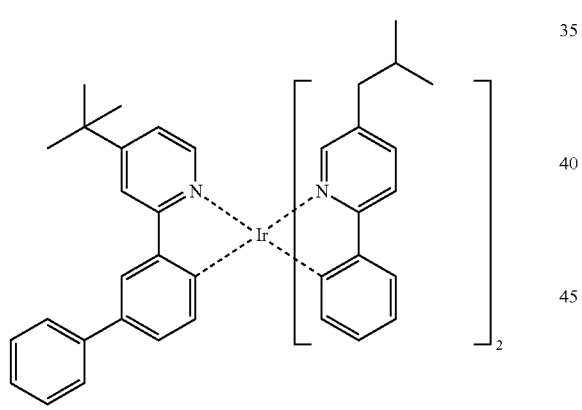
D-119
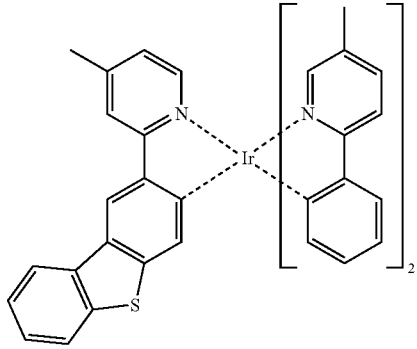
D-116
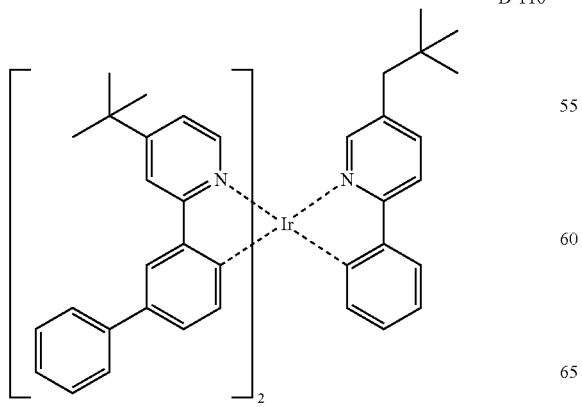
D-120
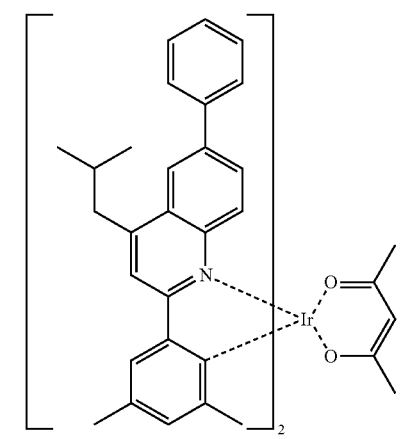

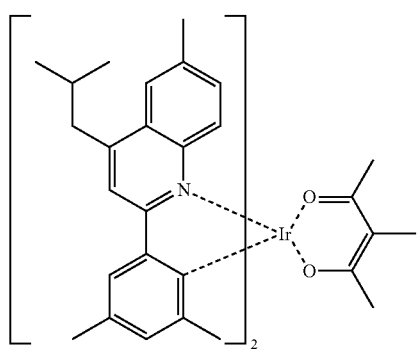
D-121
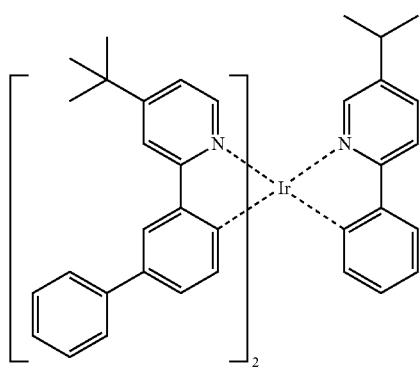
D-125
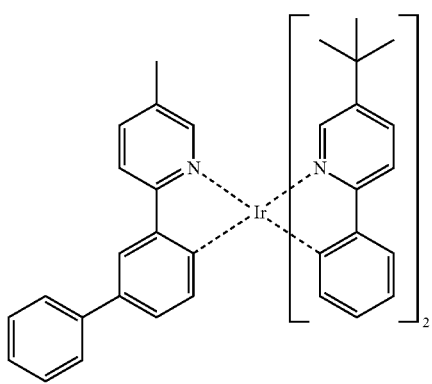
D-122
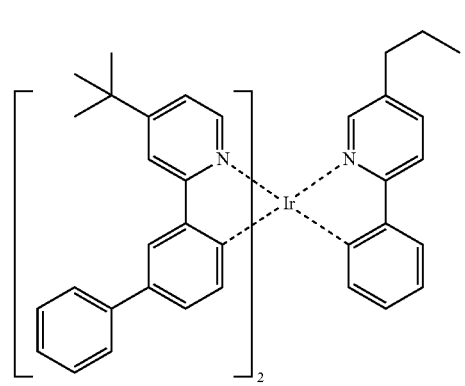
D-126
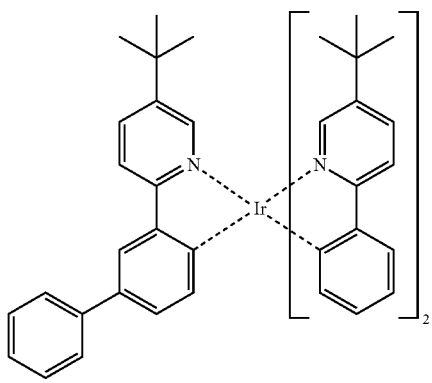
D-123
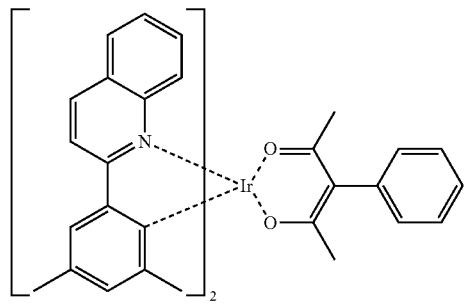
D-127
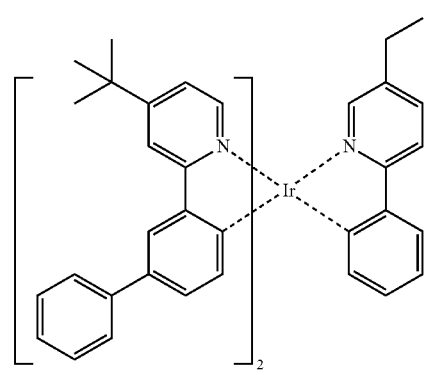
D-124
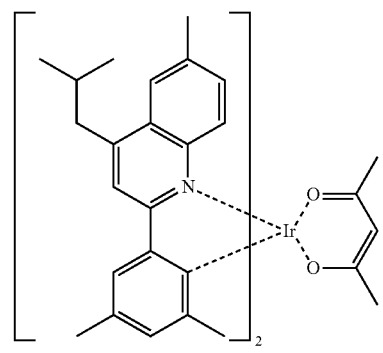
D-128

D-129
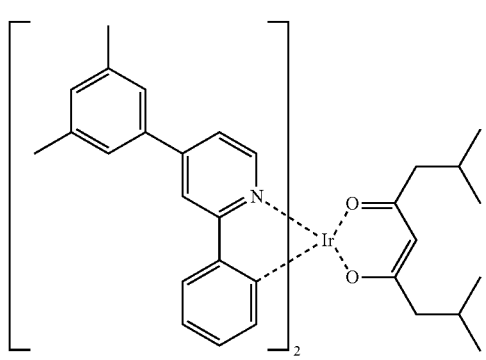
D-130
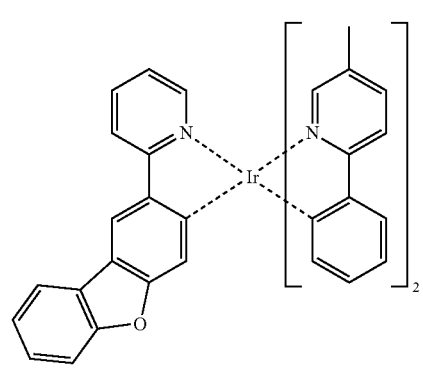
D-131
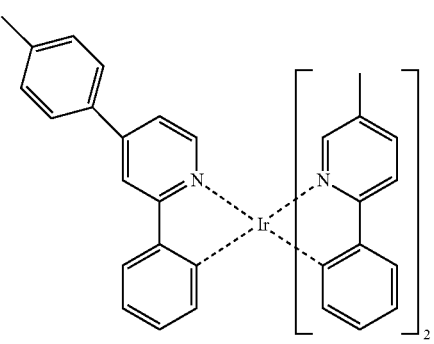
D-132
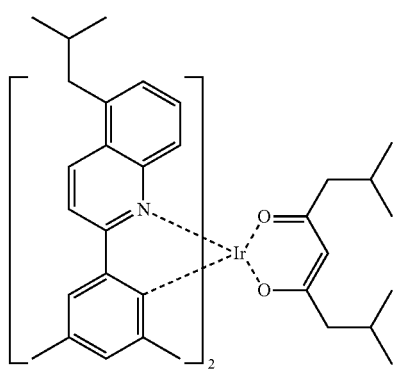
D-133
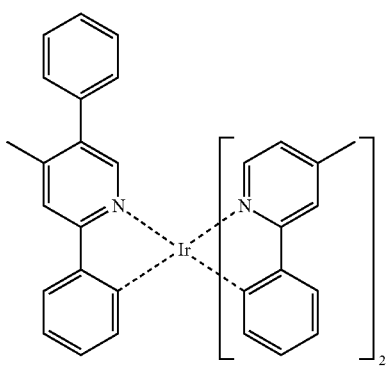
D-134
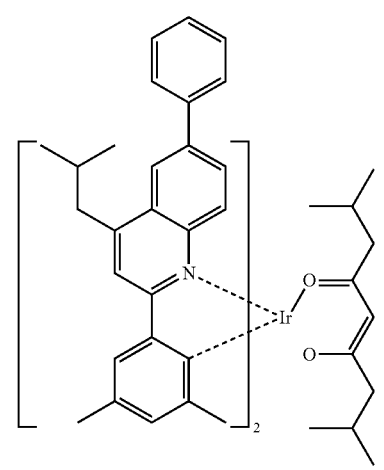
D-135
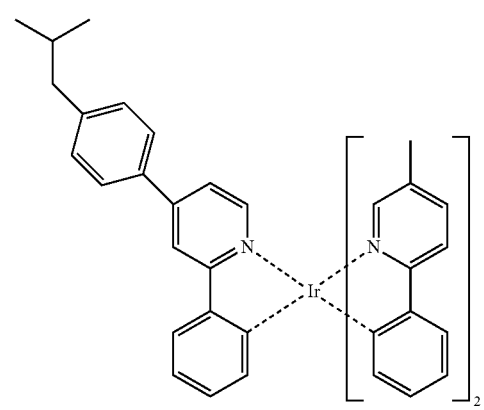
D-136
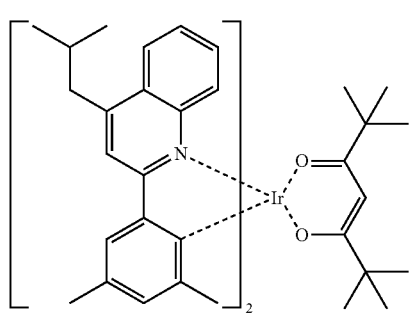

D-137
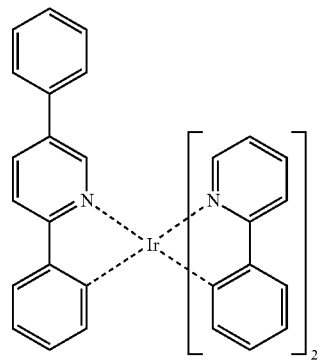
D-138
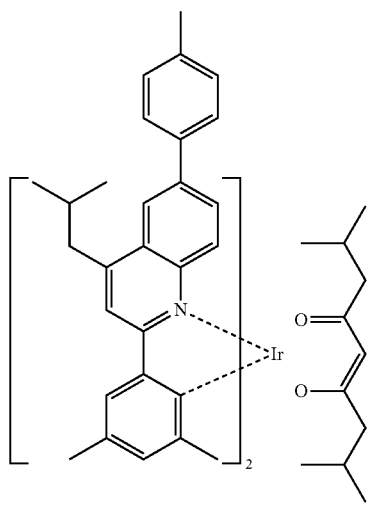
D-139
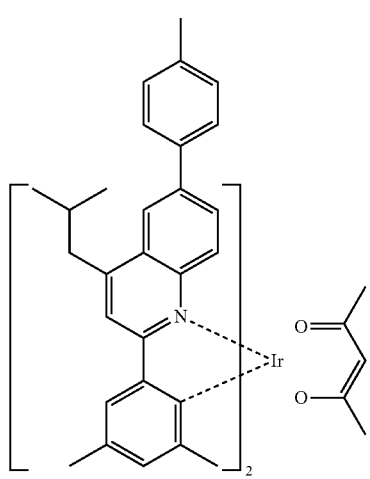
D-140
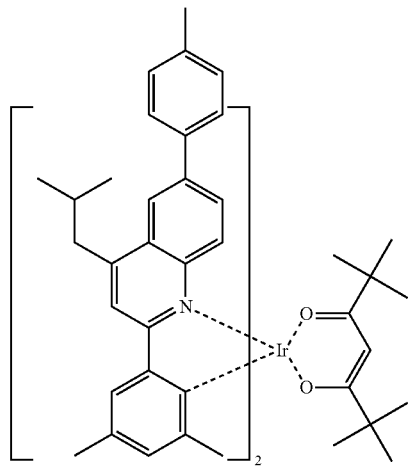
D-141
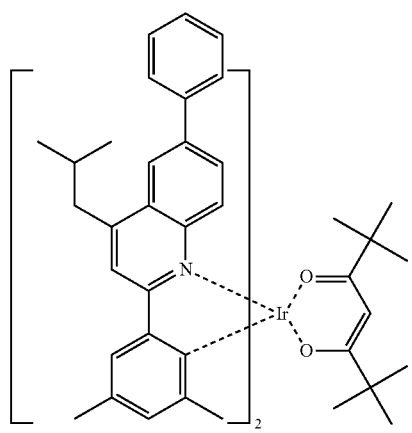
D-142
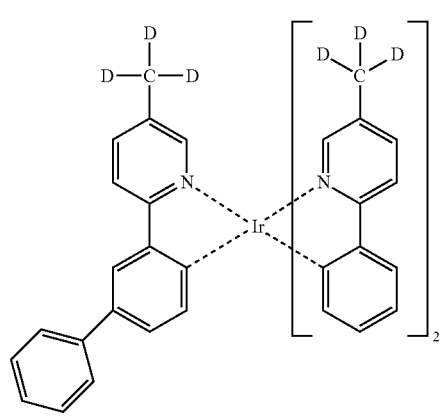
D-143
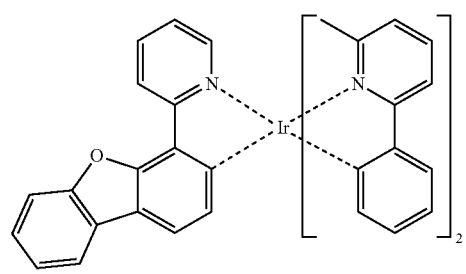

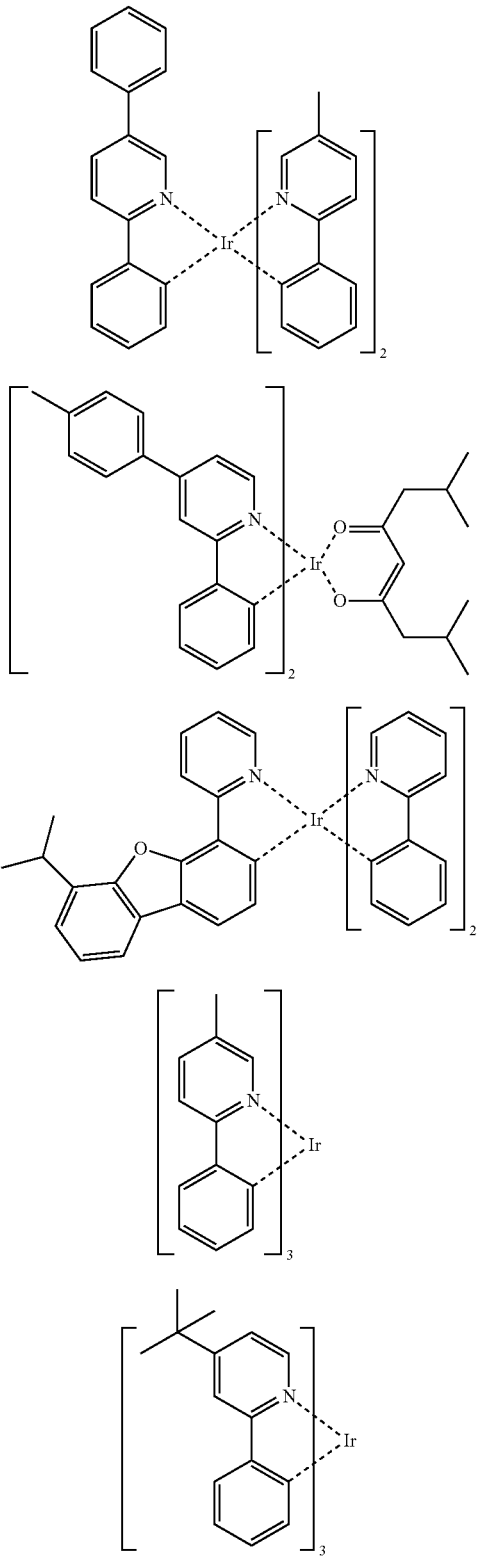

D-144
D-145
D-146
D-147
D-148

According to an additional aspect of the present disclosure, a mixture or composition for preparing an organic electroluminescent device is provided. The mixture or composition comprises the compound of the present disclosure. The mixture or composition may be used for preparing a light-emitting layer or a hole transport layer of an organic electroluminescent device. The mixture or composition for preparing a light-emitting layer of an organic electroluminescent device may be a mixture or composition for preparing a phosphorescent or fluorescent light-emitting layer, and specifically a phosphorescent red light-emitting layer of an organic electroluminescent device. Where the compound of the present disclosure is comprised in the mixture or composition for preparing a hole transport layer of an organic electroluminescent device, it may be comprised as a hole transport material. Where the compound of the present disclosure is comprised in the mixture or composition for preparing a light-emitting layer of an organic electroluminescent device, it may be comprised as a host material. Where the compound of the present disclosure is comprised as a host material, the mixture or composition may further comprise a second host material. The weight ratio between the first host material and the second host material is in the range of 1:99 to 99:1, and specifically 30:70 to 70:30.

The organic electroluminescent device of the present disclosure may comprise a first electrode, a second electrode, and at least one organic layer disposed between the first and second electrodes, wherein the organic layer may comprise a light-emitting layer or a hole transport layer, and the light-emitting layer or the hole transport layer may comprise the mixture or composition for an organic electroluminescent device of the present disclosure.

The organic electroluminescent device of the present disclosure may further comprise, in addition to the organic electroluminescent compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise a light-emitting layer and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the art, besides the compound of the present disclosure. If necessary, the organic electroluminescent device of the present disclosure may further comprise a yellow- or orange-light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X(1 \le X \le 2)$, $AlO_X(1 \le X \le 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

In the organic electroluminescent device of the present disclosure, two or more host compounds for a light-emitting layer may be co-evaporated or mixture-evaporated. Herein, a co-evaporation indicates a process for two or more materials to be deposited as a mixture, by introducing each of the two or more materials into respective crucible cells, and applying electric current to the cells for each of the materials to be evaporated. Herein, a mixture-evaporation indicates a process for two or more materials to be deposited as a mixture, by mixing the two or more materials in one crucible cell before the deposition, and applying electric current to the cell for the mixture to be evaporated.

A display system or a lighting system using the organic electroluminescent device of the present disclosure can be produced.

Hereinafter, the organic electroluminescent compound of the present disclosure, the preparation method of the compound, and the luminescent properties of the device will be explained in detail with reference to the following examples.

Example 1: Preparation of Compound H-1

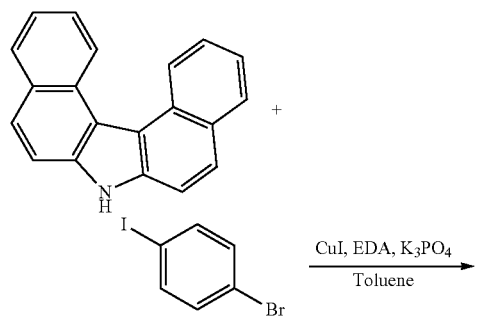

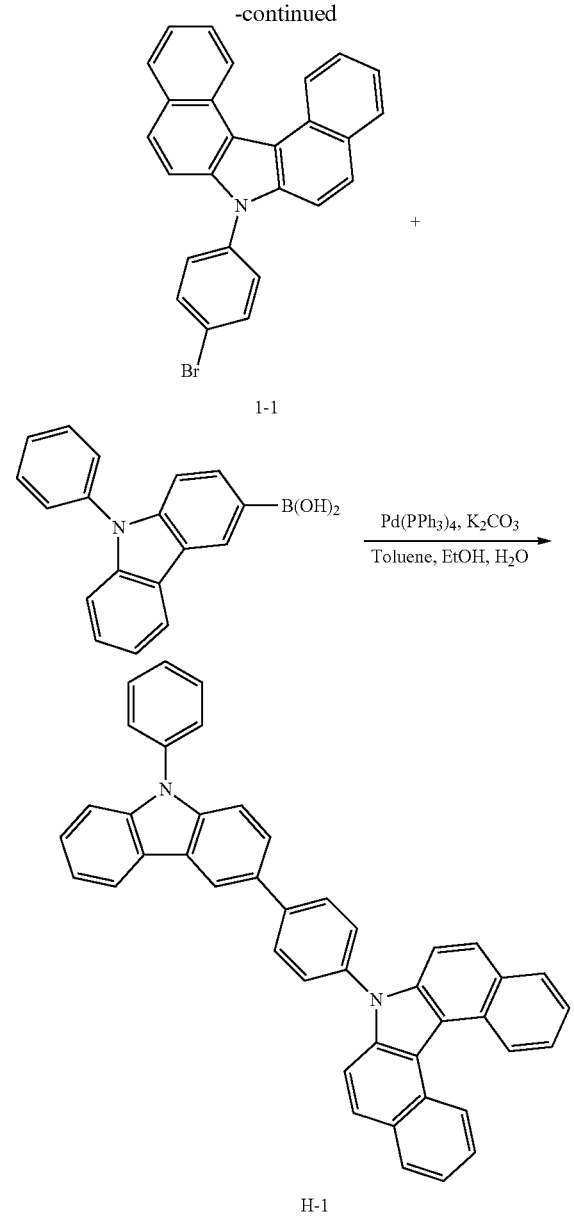

Preparation of Compound 1-1

After dissolving 7H-dibenzo[c,g]carbazole (10 g, 37.40 mmol), 1-bromo-4-iodobenzene (21 g, 74.80 mmol), CuI (3.6 g, 18.70 mmol), ethylenediamine (EDA) (5 mL, 74.80 mmol), and $K_3PO_4$ (20 g, 93.50 mmol) in toluene (200 mL) of a flask, the mixture was under reflux at 120° C. for 2 hours. After completion of the reaction, the mixture was filtered under reduced pressure with methylene chloride (MC), and subjected to column chromatography. Methanol was added to the resultant. The obtained solid was filtered under reduced pressure to obtain compound 1-1 (12.2 g, yield: 77%).

Preparation of Compound H-1

After dissolving compound 1-1 (8 g, 18.90 mmol), (9-phenyl-9H-carbazol-3-yl)boronic acid (6.6 g, 22.70 mmol), Pd(PPh$_3$)$_4$ (2.2 g, 1.89 mmol), and $K_2CO_3$ (7.8 g, 56.70 mmol) in toluene (100 mL), ethanol (50 mL), and $H_2O$ (50 mL), the mixture was under reflux at 120° C. for 4 hours. After completion of the reaction, the mixture was extracted with ethyl acetate (EA), dried with MgSO₄, and subjected to column chromatography. Methanol was added to the resultant. The obtained solid was filtered under reduced pressure, recrystallized with toluene, and filtered under reduced pressure to obtain compound H-1 (5.3 g, yield: 48%).

| Molecular Weight | UV | PL | Melting Point (M.P.) |
|---|---|---|---|
| 584.71 | 382 nm | 397 nm | 264.8° C. |

Example 2: Preparation of Compound H-55

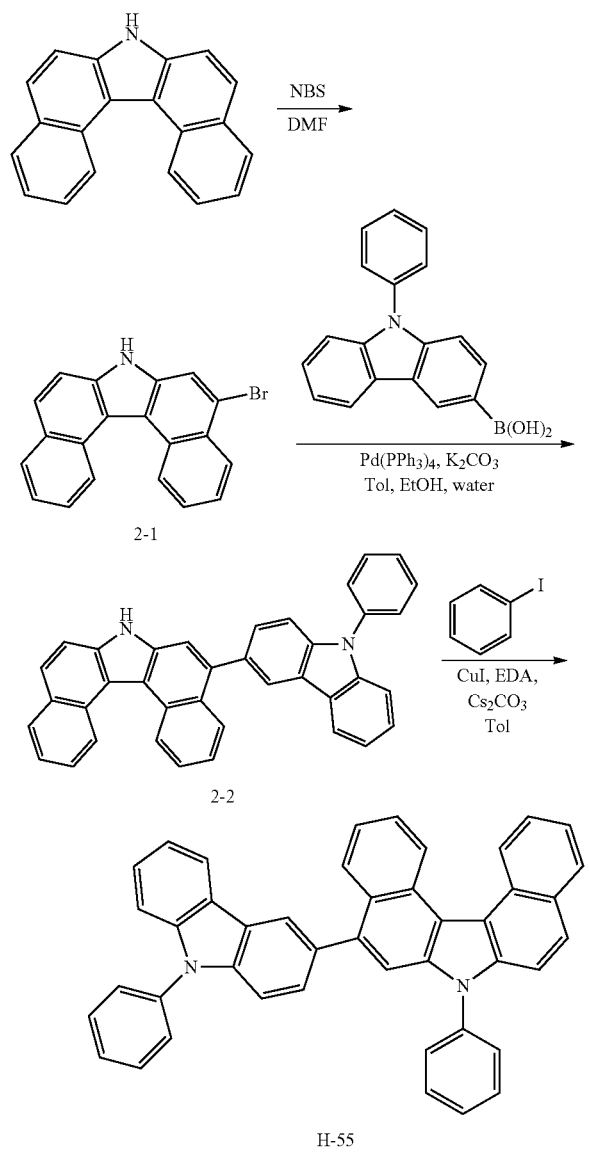

Preparation of Compound 2-1
After dissolving 7H-dibenzo[c,g]carbazole (50 g, 187 mmol) and N-bromosuccinimide (NBS) (31.6 g, 177 mmol) in dimethylformamide (DMF) (1 L) of a flask, the mixture was stirred at room temperature for 5 hours. After completion of the reaction, the mixture was extracted with EA, dried with MgSO₄, and subjected to column chromatography. Hexane was added to the resultant. The obtained solid was filtered under reduced pressure to obtain compound 2-1 (52 g, yield: 80%).

Preparation of Compound 2-2
After dissolving compound 2-1 (52 g, 150.2 mmol), (9-phenyl-9H-carbazol-3-yl)boronic acid (46.1 g, 150.2 mmol), Pd(PPh₃)₄ (8.7 g, 1.6 mmol), and K₂CO₃ (51.9 g, 375.5 mmol) in toluene (570 mL), ethanol (100 mL), and distilled water (190 mL), the mixture was under reflux at 120° C. for 4 hours. After completion of the reaction, the mixture was extracted with MC, dried with MgSO₄, and subjected to column chromatography. Hexane was added to the resultant. The obtained solid was filtered under reduced pressure to obtain compound 2-2 (62 g, yield: 71%).

Preparation of Compound H-55
After dissolving compound 2-2 (10.0 g, 19.66 mmol), iodobenzene (4.4 mL, 39.32 mmol), CuI (1.87 g, 9.83 mmol), EDA (1.32 mL, 19.66 mmol), and Cs₂CO₃ (16.0 g, 49.15 mmol) in toluene (100 mL), the mixture was under reflux at 130° C. for 5 hours. After completion of the reaction, the mixture was filtered under reduced pressure with MC, and subjected to column chromatography. Methanol was added to the resultant. The obtained solid was filtered under reduced pressure to obtain compound H-55 (7.6 g, yield: 66%).

| Molecular Weight | UV | PL | M.P. |
|---|---|---|---|
| 584.71 | 352 nm | 423 nm | 150° C. |

Example 3: Preparation of Compound H-56

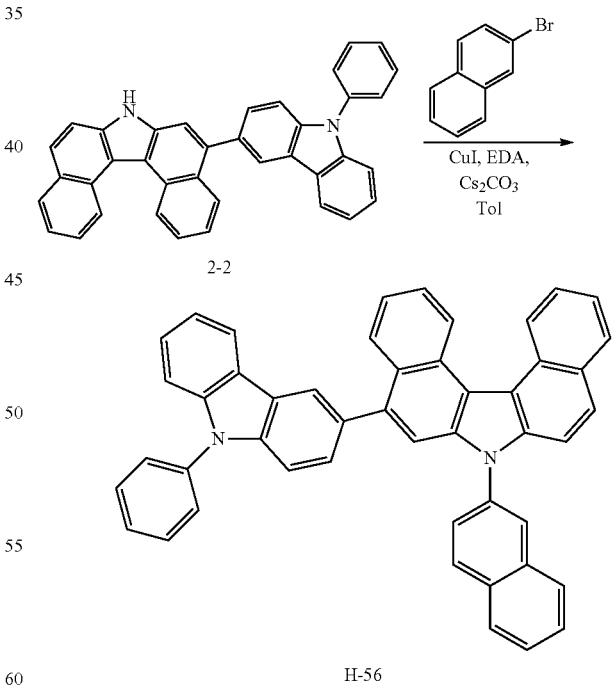

After dissolving compound 2-2 (10.0 g, 19.66 mmol), 2-bromonaphthalene (6.9 g, 33.4 mmol), CuI (1.87 g, 9.83 mmol), EDA (1.32 mL, 19.66 mmol), and Cs₂CO₃ (16.0 g, 49.15 mmol) in toluene (100 mL), the mixture was under reflux at 130° C. for 5 hours. After completion of the reaction, the mixture was filtered under reduced pressure with MC, and subjected to column chromatography. Methanol was added to the resultant. The obtained solid was filtered under reduced pressure to obtain compound H-56 (7.6 g, yield: 61%).

| Molecular Weight | UV | PL | M.P. |
|---|---|---|---|
| 634.77 | 334 nm | 421 nm | 140° C. |

Example 4: Preparation of Compound H-66

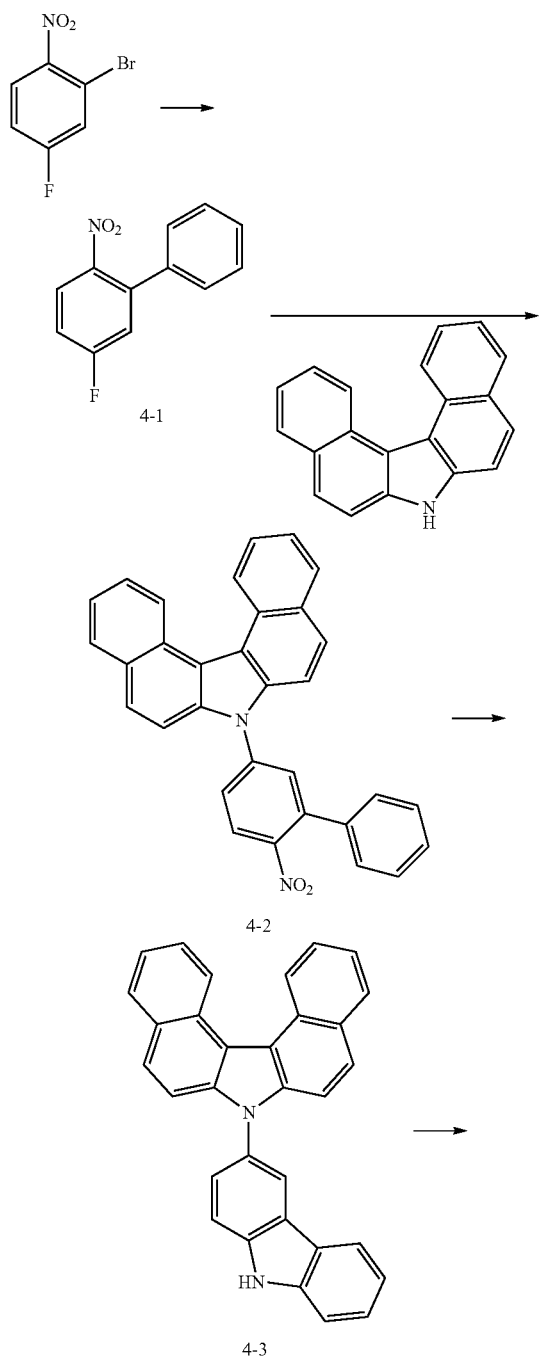

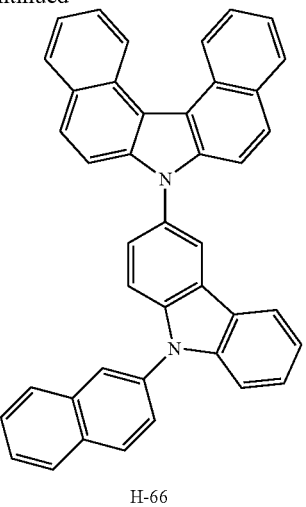

H-66

Preparation of Compound 4-1

After introducing 2-bromo-4-fluoro-1-nitrobenzene (50 g, 227.3 mmol), phenyl boronic acid (30.5 g, 250 mmol), Pd(PPh$_3$)$_4$ (13.1 g, 11.37 mmol), K$_2$CO$_3$ (62.8 g, 454.6 mmol), toluene (600 mL), ethanol (200 mL), and distilled water (200 mL) into a flask, the mixture was stirred under reflux for 6 hours. After cooling to room temperature, the mixture was extracted with EA and distilled water. The obtained organic layer was distilled under reduced pressure. The residue was subjected to column chromatography to obtain compound 4-1 (49 g, yield: 99%).

Preparation of Compound 4-2

After introducing 7H-dibenzo[c,g]carbazole (34.5 g, 128.9 mmol), compound 4-1 (28 g, 128.9 mmol), NaH (6.7 g, 167.6 mmol), and DMF (600 mL) into a flask, the mixture was stirred at 75° C. for 2 hours. After cooling to room temperature, MeOH (1 L) and purified water were added to the mixture. The obtained solid was filtered, and dried under reduced pressure to obtain compound 4-2 (52 g, yield: 86.8%).

Preparation of Compound 4-3

After introducing compound 4-2 (52 g, 111.9 mmol), PPh$_3$ (88 g, 335.8 mmol), and 1,2-dichlorobenzene (500 mL) into a flask, the mixture was stirred under reflux for 6 hours. The mixture was distilled to remove 1,2-dichlorobenzene (1,2-DCB). The residue was subjected to column chromatography to obtain compound 4-3 (39 g, yield: 75.9%).

Preparation of Compound H-66

After introducing compound 4-3 (7 g, 16.18 mmol), 2-bromonaphthalene (5.0 g, 24.27 mmol), Pd(OAc)$_2$ (365 mg, 1.6 mmol), P(t-Bu)$_3$ (1.6 mL, 3.2 mmol), NaOt-Bu (4.7 g, 48.54 mmol), and toluene (100 mL) into a flask, the mixture was stirred under reflux for 3 hours, cooled to room temperature, and extracted with ethyl acetate and purified water. The obtained organic layer was concentrated, and subjected to column chromatography to obtain compound H-66 (3.0 g, yield: 33.2%).

| Molecular Weight | UV | PL | M.P. |
|---|---|---|---|
| 558.67 | 378 nm | 397 nm | 250° C. |

Example 5: Preparation of Compound H-25

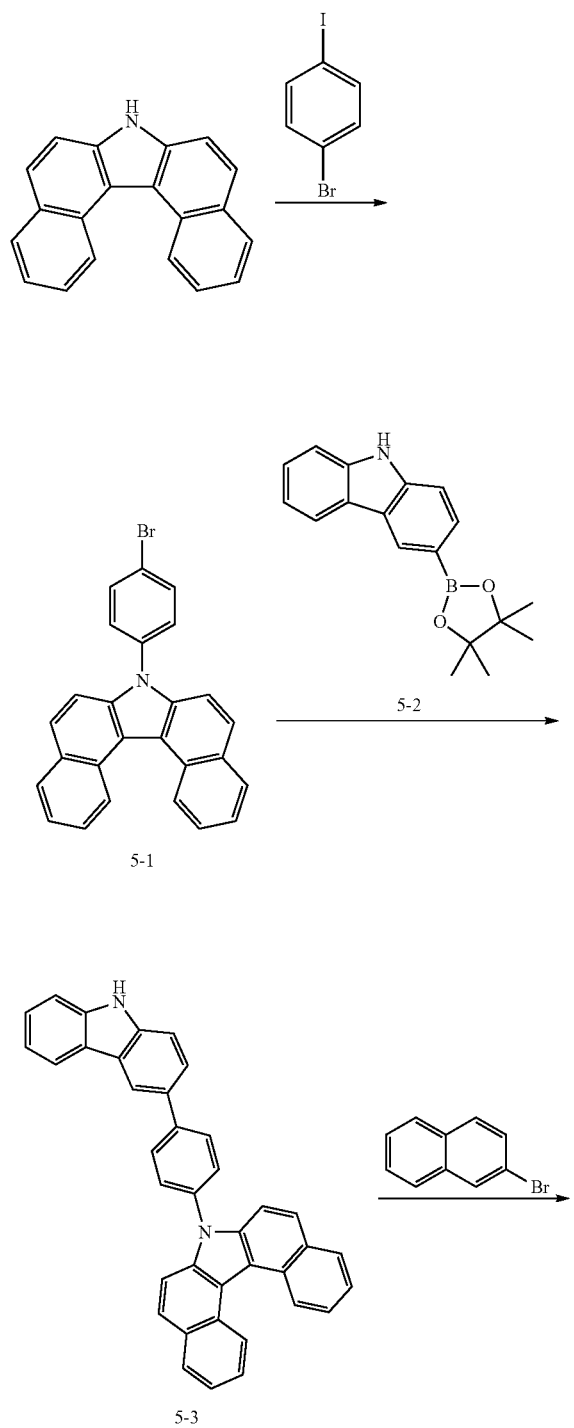

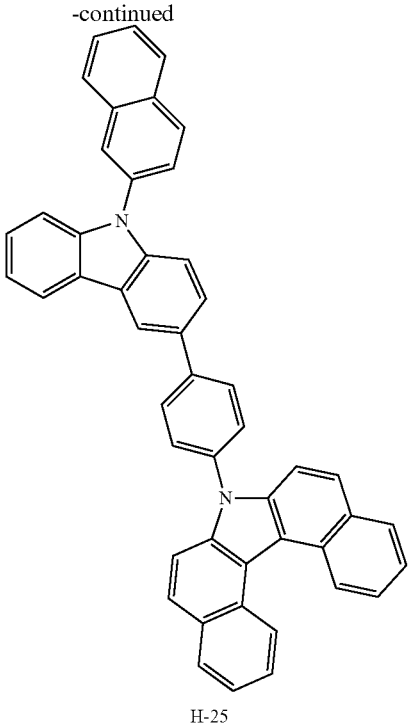

H-25

Preparation of Compound 5-1

After introducing 7H-dibenzo[c,g]carbazole (CAS: 194-59-2, 30 g, 112.2 mmol), 4-bromoiodobenzene (63 g, 224.4 mmol), copper(I) iodide (11 g, 56.1 mmol), ethylene diamine (13 mL, 224 mmol), potassium phosphate (48 g, 224.4 mmol), and toluene (600 mL) into a reaction vessel, the mixture was stirred at 140° C. for 3 hours. After completion of the reaction, the mixture was extracted with ethyl acetate, dried with magnesium sulfate, and dried by rotary evaporator to remove a solvent. The resultant was subjected to column chromatography to obtain compound 5-1 (33.7 g, yield: 71%).

Preparation of Compound 5-3

After introducing compound 5-1 (33.7 g, 79.8 mmol), compound 5-2 (CAS: 855738-89-5, 23.4 g, 79.8 mmol), tetrakis(triphenylphosphine)palladium (2.8 g, 2.39 mmol), potassium carbonate (22 g, 100 mmol), toluene (300 mL), water (100 mL), and ethanol (100 mL) into a reaction vessel, the mixture was stirred at 140° C. for 3 hours. After completion of the reaction, the mixture was cooled to room temperature, and filtered. The obtained solid was subjected to column chromatography to obtain compound 5-3 (28.5 g, yield: 70%).

Preparation of Compound H-25

After introducing compound 5-3 (14 g, 27.5 mmol), 2-bromonaphthalene (7.4 g. 36 mmol), tris(dibenzylideneacetone)dipalladium (1.2 g, 1.38 mmol), tri-tert-butylphosphine (50 wt % xylene, 1.1 mL, 2.75 mmol), sodium t-butoxide (5.3 g, 55 mmol), and toluene (200 mL) into a reaction vessel, the mixture was stirred at 140° C. overnight. After completion of the reaction, the mixture was added dropwise to methanol, and filtered. The obtained solid was subjected to column chromatography and recrystallized to obtain compound H-25 (2 g, yield: 11%).

| Molecular Weight | UV | PL | M.P. |
|---|---|---|---|
| 634.24 | 308 nm | 396 nm | 261° C. |

Example 6: Preparation of Compound H-34

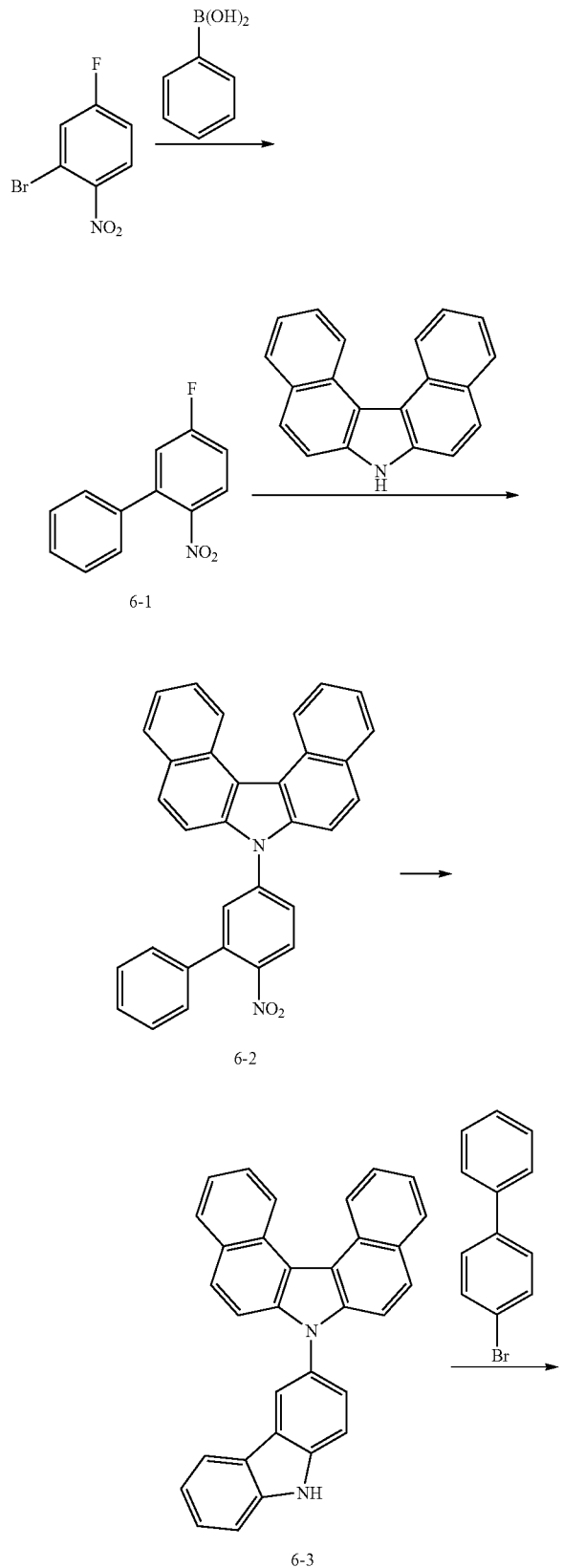

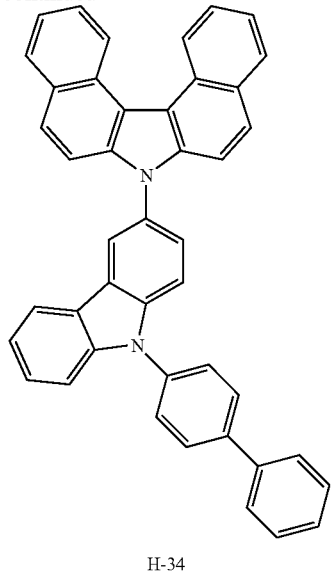

H-34

Preparation of Compound 6-1

After dissolving 2-bromo-4-fluoro-1-nitrobenzene (30 g, 136 mmol), phenylboronic acid (18.3 g, 150 mmol), Pd(PPh$_3$)$_4$ (6.3 g, 5.4 mmol), and Na$_2$CO$_3$ (36 g, 340 mmol) in toluene (680 mL), ethanol (170 mL), and distilled water (170 mL), the mixture was under reflux at 120° C. for 3 hours. After completion of the reaction, the mixture was extracted with MC, dried with MgSO$_4$, and subjected to column chromatography. Hexane was added to the resultant. The obtained solid was filtered under reduced pressure to obtain compound 6-1 (29 g, yield: 98%).

Preparation of Compound 6-2

A mixture of 7H-dibenzo[c,g]carbazole (35.7 g, 134 mmol), NaH (60% in dispersion oil) (6.9 g, 173 mmol), and DMF (900 mL) in a flask was slowly stirred at 0° C. for 30 minutes. Compound 6-1 was slowly added dropwise to the reaction mixture. The reaction mixture was stirred at room temperature overnight. After completion of the reaction, the mixture was added dropwise to water. The obtained solid was subjected to column chromatography. Hexane was added to the resultant. The obtained solid was filtered under reduced pressure to obtain compound 6-2 (41 g, yield: 66%).

Preparation of Compound 6-3

A mixture of compound 6-2 (41 g, 88 mmol), P(OEt)$_3$ (300 mL), and 1,2-DCB (300 mL) was under reflux at 180° C. for 12 hours. The reaction mixture was distilled under reduced pressure, and subjected to column chromatography. Hexane was added to the resultant. The obtained solid was filtered under reduced pressure to obtain compound 6-3 (21 g, yield: 55%).

Preparation of Compound H-34

After dissolving compound 6-3 (7 g, 16 mmol), 4-bromo-1,1'-biphenyl (5.6 g, 24 mmol), Pd(OAc)$_2$ (0.182 g, 0.8 mmol), P(t-Bu)$_3$ (0.76 mL, 1.6 mmol), and NaOtBu (2.3 g, 24 mmol) in o-xylene (80 mL), the mixture was under reflux at 150° C. for 12 hours. After completion of the reaction, the mixture was extracted with EA, dried with MgSO$_4$, and subjected to column chromatography. Hexane was added to the resultant. The obtained solid was filtered under reduced pressure, recrystallized with toluene, and filtered under reduced pressure to obtain compound H-34 (3.6 g, yield: 38%).

| Molecular Weight | UV | PL | M.P. |
|---|---|---|---|
| 584.71 | 382 nm | 399 nm | 263° C. |

Example 7: Preparation of Compound H-67

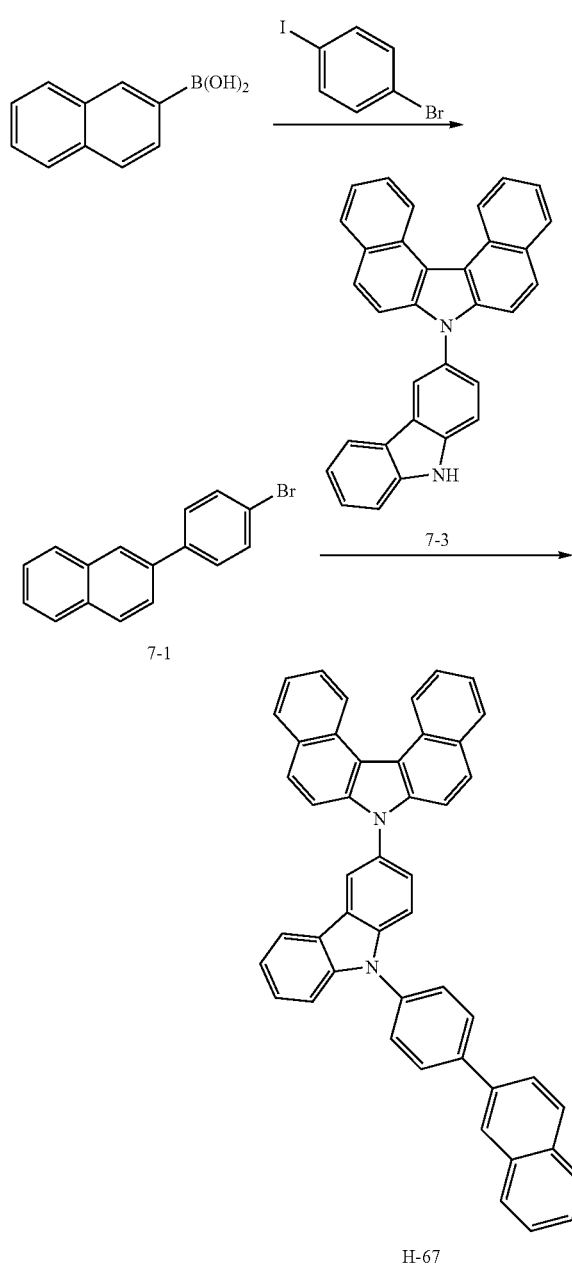

H-67

Preparation of Compound 7-1

After dissolving naphthalen-2-yl boronic acid (13.4 g, 77 mmol), 1-bromo-4-iodobenzene (20 g, 71 mmol), Pd(PPh$_3$)$_4$ (3.3 g, 21.8 mmol), and Na$_2$CO$_3$ (18.8 g, 177 mmol) in toluene (360 mL), ethanol (90 mL), and distilled water (90 mL) of a flask, the mixture was under reflux at 120° C. for 4 hours. After completion of the reaction, the mixture was extracted with MC, dried with MgSO$_4$, and subjected to column chromatography. Hexane was added to the resultant. The obtained solid was filtered under reduced pressure to obtain compound 7-1 (7 g, yield: 35%).

Preparation of Compound H-67

After dissolving compound 7-3 (7 g, 16 mmol), compound 7-1 (6.9 g, 24 mmol), Pd(OAc)$_2$ (0.182 g, 0.8 mmol), P(t-Bu)$_3$ (0.76 mL, 1.6 mmol), and NaOtBu (2.3 g, 24 mmol) in o-xylene (80 mL), the mixture was under reflux at 150° C. for 12 hours. After completion of the reaction, the mixture was extracted with EA, dried with MgSO$_4$, and subjected to column chromatography. Hexane was added to the resultant. The obtained solid was filtered under reduced pressure, recrystallized with toluene, and filtered under reduced pressure to obtain compound H-67 (3 g, yield: 29%).

| Molecular Weight | UV | PL | M.P. |
|---|---|---|---|
| 634.77 | 376 nm | 397 nm | 260° C. |

Example 8: Preparation of Compound H-68

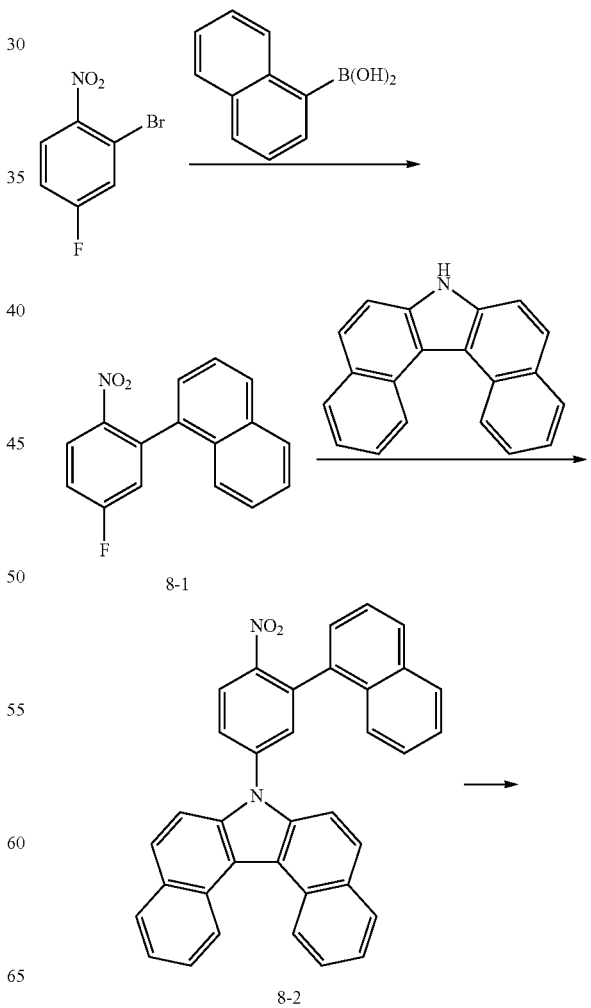

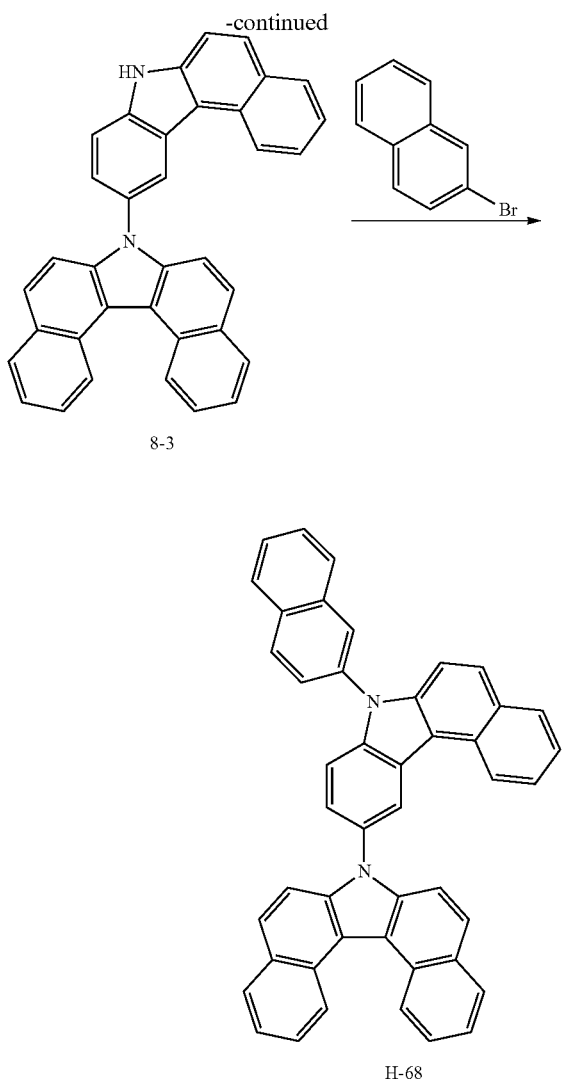

8-3

H-68

Preparation of Compound 1-1

After introducing 2-bromo-4-fluoro-1-nitrobenzene (30 g, 136.36 mmol), 1-naphthyl boronic acid (28 g, 163.64 mmol), tetrakis(triphenylphosphine)palladium (4.7 g, 4.09 mmol), potassium carbonate (47 g, 340.90 mmol), toluene (690 mL), and ethanol (170 mL) into a reaction vessel, distilled water (170 mL) was added thereto. The mixture was stirred at 120° C. for 4 hours. After completion of the reaction, the mixture was washed with distilled water, and extracted with ethyl acetate. The obtained organic layer was dried with magnesium sulfate, dried by rotary evaporator to remove a solvent, and subjected to column chromatography to obtain compound 8-1 (33 g, yield: 92%).

Preparation of Compound 8-2

After introducing 7H-dibenzo[c,g]carbazole (25 g, 115.10 mmol) and N,N-dimethylformamide (580 mL) into a reaction vessel, sodium hydride (6 g, 149.63 mmol) was slowly added dropwise to the mixture at 0° C. under nitrogen atmosphere. The mixture was stirred at 0° C. for 30 minutes, and compound 8-1 (32 g, 120.86 mmol) was slowly added dropwise thereto. After completion of the addition, the mixture was slowly warmed to room temperature, and additionally stirred for 4 hours. After completion of the reaction, methanol was added thereto to stop the reaction. The resultant was extracted with ethyl acetate. The obtained organic layer was dried with magnesium sulfate, dried by rotary evaporator to remove a solvent, and subjected to column chromatography to obtain compound 8-2 (35 g, yield: 59%).

Preparation of Compound 8-3

After introducing compound 8-2 (35 g, 68.02 mmol) and triethylphosphite (170 mL, 0.4M) to the reaction vessel, the mixture was stirred under reflux for 4 hours. After completion of the reaction, the mixture was distilled under reduced pressure to remove triethylphosphite, and subjected to column chromatography to obtain compound 8-3 (29 g, yield: 88%).

Preparation of Compound H-68

After introducing compound 8-3 (10 g, 20.72 mmol), 2-bromonaphthalene (6.4 g, 31.08 mmol), palladium(II) acetate (0.3 g, 1.04 mmol), tri-t-butyl phosphine (1 mL, 2.08 mmol), sodium tert-butoxide (3 g, 31.08 mmol), and o-xylene (105 mL) into a reaction vessel, the mixture was stirred under reflux for 4 hours. After completion of the reaction, the mixture was washed with distilled water, and extracted with ethyl acetate. The obtained organic layer was dried with magnesium sulfate, and then dried by rotary evaporator to remove a solvent. The resultant was subjected to column chromatography to obtain compound H-68 (2.5 g, yield: 20%).

| Molecular Weight | UV | PL | M.P. |
|---|---|---|---|
| 608.73 | 378 nm | 397 nm | 274° C. |

Example 9: Preparation of Compound H-35

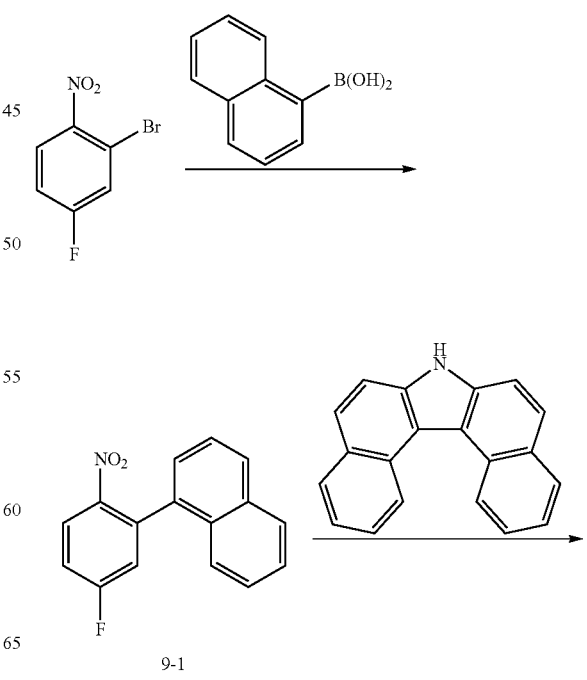

9-1

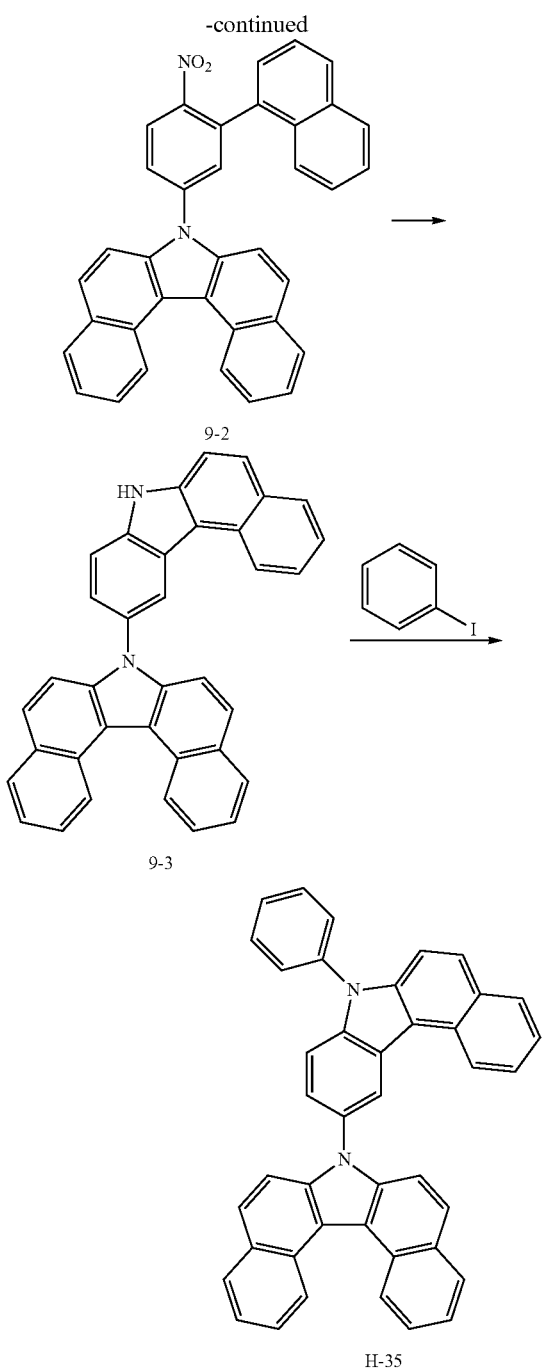

Preparation of Compound 1-1

After introducing 2-bromo-4-fluoro-1-nitrobenzene (30 g, 136.36 mmol), 1-naphthyl boronic acid (28 g, 163.64 mmol), tetrakis(triphenylphosphine)palladium (4.7 g, 4.09 mmol), potassium carbonate (47 g, 340.90 mmol), toluene (690 mL), and ethanol (170 mL) into a reaction vessel, distilled water (170 mL) was added thereto. The mixture was stirred at 120° C. for 4 hours. After completion of the reaction, the mixture was washed with distilled water, and extracted with ethyl acetate. The obtained organic layer was dried with magnesium sulfate, dried by rotary evaporator to remove a solvent, and subjected to column chromatography to obtain compound 9-1 (33 g, yield: 92%).

Preparation of Compound 9-2

After introducing 7H-dibenzo[c,g]carbazole (25 g, 115.10 mmol) and N,N-dimethylformamide (580 mL) into a reaction vessel, sodium hydride (6 g, 149.63 mmol) was slowly added dropwise to the mixture at 0° C. under nitrogen atmosphere. The mixture was stirred at 0° C. for 30 minutes, and compound 9-1 (32 g, 120.86 mmol) was slowly added dropwise thereto. After completion of the addition, the mixture was slowly warmed to room temperature, and additionally stirred for 4 hours. After completion of the reaction, methanol was added thereto to stop the reaction. The resultant was extracted with ethyl acetate. The obtained organic layer was dried with magnesium sulfate, dried by rotary evaporator to remove a solvent, and subjected to column chromatography to obtain compound 9-2 (35 g, yield: 59%).

Preparation of Compound 9-3

After introducing compound 9-2 (35 g, 68.02 mmol) and triethylphosphite (170 mL, 0.4M) into a reaction vessel, the mixture was stirred under reflux for 4 hours. After completion of the reaction, the mixture was distilled under reduced pressure to remove triethylphosphite, and subjected to column chromatography to obtain compound 9-3 (29 g, yield: 88%).

Preparation of Compound H-35

After introducing compound 9-3 (10 g, 20.72 mmol), iodobenzene (4 mL, 31.08 mmol), palladium(II) acetate (0.3 g, 1.04 mmol), tri-t-butylphosphine (1 mL, 2.08 mmol), sodium tert-butoxide (3 g, 31.08 mmol), and o-xylene (105 mL) into a reaction vessel, the mixture was stirred under reflux for 4 hours. After completion of the reaction, the mixture was washed with distilled water, and extracted with ethyl acetate. The obtained organic layer was dried with magnesium sulfate, and then dried by rotary evaporator to remove a solvent. The resultant was subjected to column chromatography to obtain compound H-35 (2.8 g, yield: 24%).

| Molecular Weight | UV | PL | M.P. |
| --- | --- | --- | --- |
| 558.67 | 378 nm | 397 nm | 292° C. |

[Device Example 1] OLED Using the Compound of the Present Disclosure

OLED was produced using the organic electroluminescent compound of the present disclosure as follows. A transparent electrode indium tin oxide (ITO) thin film (10 Ω/sq) on a glass substrate for an OLED (Geomatec) was subjected to an ultrasonic washing with acetone, ethanol, and distilled water sequentially, and was then stored in isopropanol. The ITO substrate was then mounted on a substrate holder of a vacuum vapor depositing apparatus. HI-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. HI-2 was then introduced into another cell of said vacuum vapor depositing apparatus, and evaporated by applying electric current to the cell, thereby forming a second hole injection layer having a thickness of 5 nm on the first hole injection layer. HT-1 was introduced into one cell of the vacuum vapor depositing apparatus, and evaporated by applying electric current to the cell, thereby forming a first hole transport layer having a thickness of 10 nm on the second hole injection layer. HT-3 was introduced into another cell of the vacuum vapor depositing apparatus, and evaporated by applying electric current to the cell, thereby forming a second hole transport layer having a thickness of 60 nm on the first hole transport layer. As a host material, a first host compound (H-1) and a second host compound (H2-41) were introduced into two cells of the vacuum vapor depositing apparatus, respectively. A dopant compound (D-71) was introduced into another cell. The two host materials were evaporated at a 1:1 rate, while the dopant was evaporated at a different rate from the host materials, so that the dopant was deposited in a doping amount of 3 wt % based on the total amount of the host and dopant to form a light-emitting layer having a thickness of 40 nm on the second hole transport layer. ET-1 and EI-1 were introduced into two cells of the vacuum vapor depositing apparatus, respectively, and evaporated at a 1:1 rate to form an electron transport layer having a thickness of 30 nm on the light-emitting layer. After depositing EI-1 as an electron injection layer having a thickness of 2 nm, an Al cathode having a thickness of 80 nm was then deposited by another vacuum vapor deposition apparatus on the electron injection layer to produce an OLED. The produced OLED showed a red emission having a luminance of 1,000 cd/m², and a current efficiency of 29.5 cd/A at a driving voltage of 3.5V. The minimum time taken to be reduced to 97% of the luminance at 5,000 nit was 114 hours.

-continued

HT-1

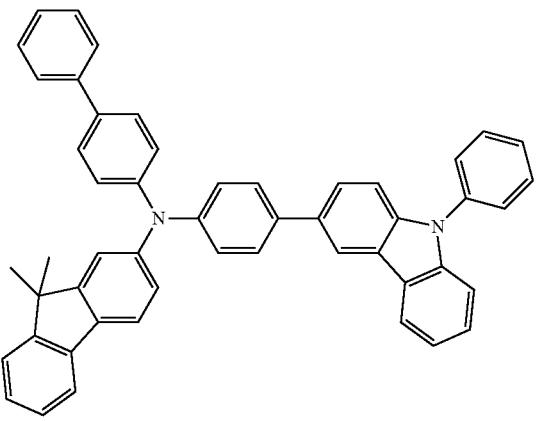

HT-3

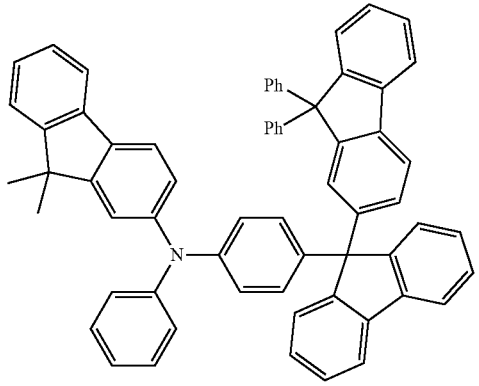

ET-1

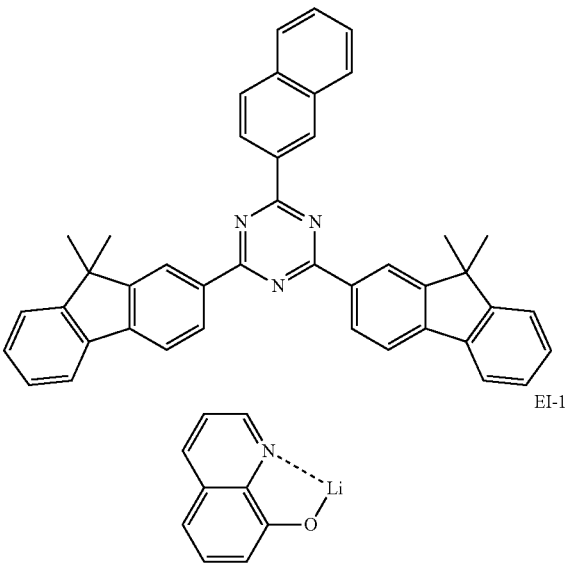

EI-1

HI-1

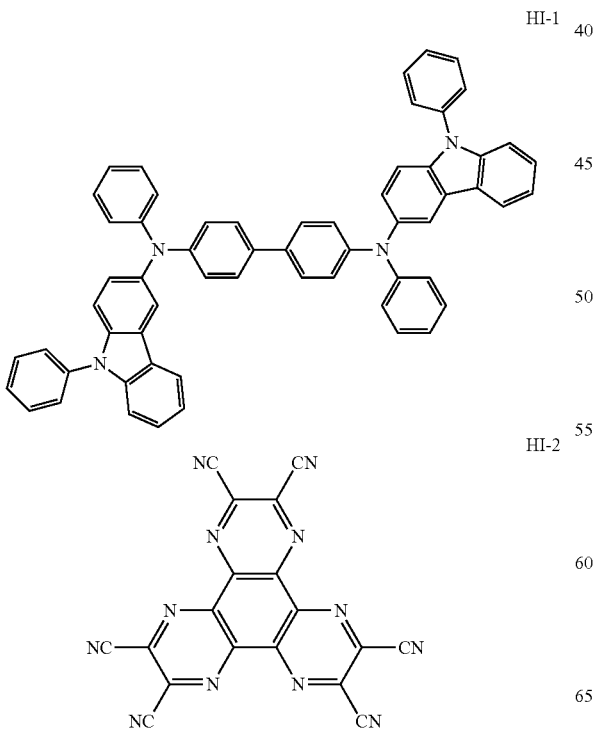

HI-2

[Device Example 2] OLED Using the Compound of the Present Disclosure

OLED was produced in the same manner as in Device Example 1, except that compound H-55 was used as a first host of the light-emitting material. The produced OLED showed a red emission having a luminance of 1,000 cd/m², and a current efficiency of 30.6 cd/A at a driving voltage of 3.6 V. The minimum time taken to be reduced to 97% of the luminance at 5,000 nit was 29 hours.

[Device Example 3] OLED Using the Compound of the Present Disclosure

OLED was produced in the same manner as in Device Example 1, except that compound H-56 was used as a first host of the light-emitting material. The produced OLED showed a red emission having a luminance of 1,000 cd/m$^2$, and a current efficiency of 29.2 cd/A at a driving voltage of 3.5 V. The minimum time taken to be reduced to 97% of the luminance at 5,000 nit was 12 hours.

[Device Example 4] OLED Using the Compound of the Present Disclosure

OLED was produced in the same manner as in Device Example 1, except that compound H-25 was used as a first host of the light-emitting material. The produced OLED showed a red emission having a luminance of 1,000 cd/m$^2$, and a current efficiency of 29.7 cd/A at a driving voltage of 3.5 V. The minimum time taken to be reduced to 97% of the luminance at 5,000 nit was 89 hours.

[Device Example 5] OLED Using the Compound of the Present Disclosure

OLED was produced in the same manner as in Device Example 1, except that compound H-66 was used as a first host of the light-emitting material. The produced OLED showed a red emission having a luminance of 1,000 cd/m$^2$, and a current efficiency of 29.9 cd/A at a driving voltage of 3.5 V. The minimum time taken to be reduced to 97% of the luminance at 5,000 nit was 167 hours.

[Device Example 6] OLED Using the Compound of the Present Disclosure

OLED was produced in the same manner as in Device Example 1, except that compound H-34 was used as a first host of the light-emitting material. The produced OLED showed a red emission having a luminance of 1,000 cd/m$^2$, and a current efficiency of 26.9 cd/A at a driving voltage of 3.4 V. The minimum time taken to be reduced to 97% of the luminance at 5,000 nit was 62 hours.

[Device Example 7] OLED Using the Compound of the Present Disclosure

OLED was produced in the same manner as in Device Example 1, except that compound H-34 and compound H2-528 were used as a first host and a second host of the light-emitting material, respectively. The produced OLED showed a red emission having a luminance of 1,000 cd/m$^2$, and a current efficiency of 30.0 cd/A at a driving voltage of 3.6 V. The minimum time taken to be reduced to 97% of the luminance at 5,000 nit was 58 hours.

[Device Example 8] OLED Using the Compound of the Present Disclosure

OLED was produced in the same manner as in Device Example 1, except that compound H-67 was used as a first host of the light-emitting material. The produced OLED showed a red emission having a luminance of 1,000 cd/m$^2$, and a current efficiency of 29.7 cd/A at a driving voltage of 3.5 V. The minimum time taken to be reduced to 97% of the luminance at 5,000 nit was 95 hours.

[Device Example 9] OLED Using the Compound of the Present Disclosure

OLED was produced in the same manner as in Device Example 1, except that compound H-35 was used as a first host of the light-emitting material. The produced OLED showed a red emission having a luminance of 1,000 cd/m$^2$, and a current efficiency of 28.6 cd/A at a driving voltage of 3.6 V. The minimum time taken to be reduced to 97% of the luminance at 5,000 nit was 95 hours.

[Device Example 10] OLED Using the Compound of the Present Disclosure

OLED was produced in the same manner as in Device Example 1, except that compound H-68 was used as a first host of the light-emitting material. The produced OLED showed a red emission having a luminance of 1,000 cd/m$^2$, and a current efficiency of 28.9 cd/A at a driving voltage of 3.6 V. The minimum time taken to be reduced to 97% of the luminance at 5,000 nit was 18 hours.

[Device Example 11] OLED Using the Compound of the Present Disclosure

OLED was produced in the same manner as in Device Example 1, except that a thickness of the first hole injection layer was 90 nm; compound H-1 was used to form the second hole transport layer instead of HT-3; compound H2-41 was used as a single host for the light-emitting layer; dopant compound D-71 was deposited in a doping amount of 2 wt % based on the total amount of the host and dopant; and a thickness of the electron transport layer was 35 nm. The produced OLED showed a red emission having a luminance of 1,000 cd/m$^2$, and a current efficiency of 27.2 cd/A at a driving voltage of 4.4 V.

[Device Example 12] OLED Using the Compound of the Present Disclosure

OLED was produced in the same manner as in Device Example 11, except that compound H-55 was used to form the second hole transport layer. The produced OLED showed a red emission having a luminance of 1,000 cd/m$^2$, and a current efficiency of 23.4 cd/A at a driving voltage of 3.8 V.

[Device Example 13] OLED Using the Compound of the Present Disclosure

OLED was produced in the same manner as in Device Example 11, except that compound H-56 was used to form the second hole transport layer. The produced OLED showed a red emission having a luminance of 1,000 cd/m$^2$, and a current efficiency of 23.3 cd/A at a driving voltage of 3.7 V.

[Device Example 14] OLED Using the Compound of the Present Disclosure

OLED was produced in the same manner as in Device Example 11, except that compound H-34 was used to form the second hole transport layer. The produced OLED showed a red emission having a luminance of 1,000 cd/m², and a current efficiency of 26.9 cd/A at a driving voltage of 4.2 V.

[Device Example 15] OLED Using the Compound of the Present Disclosure

OLED was produced in the same manner as in Device Example 11, except that compound H-67 was used to form the second hole transport layer. The produced OLED showed a red emission having a luminance of 1,000 cd/m², and a current efficiency of 27.1 cd/A at a driving voltage of 4.5 V.

[Device Example 16] OLED Using the Compound of the Present Disclosure

OLED was produced in the same manner as in Device Example 11, except that compound H-35 was used to form the second hole transport layer. The produced OLED showed a red emission having a luminance of 1,000 cd/m², and a current efficiency of 25.5 cd/A at a driving voltage of 3.6 V.

[Device Example 17] OLED Using the Compound of the Present Disclosure

OLED was produced in the same manner as in Device Example 11, except that compound H-68 was used to form the second hole transport layer. The produced OLED showed a red emission having a luminance of 1,000 cd/m², and a current efficiency of 26.9 cd/A at a driving voltage of 3.8 V.

[Comparative Example 1] OLED Using a Conventional Compound

OLED was produced in the same manner as in Device Example 1, except that compound 1 as shown below was used as a first host of the light-emitting material. The produced OLED showed a red emission having a luminance of 1,000 cd/m², and a current efficiency of 0.6 cd/A at a driving voltage of 7.8 V. Due to the low efficiency, lifespan cannot be measured.

compound 1

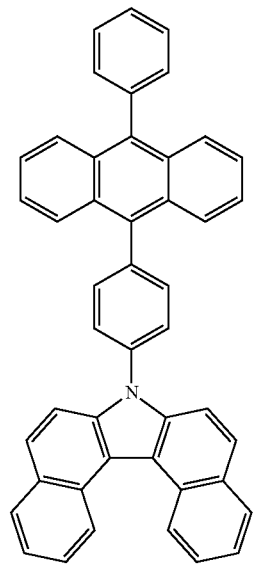

[Comparative Example 2] OLED Using a Conventional Compound

OLED was produced in the same manner as in Device Example 11, except that compound 1 as shown above was used to form the second hole transport layer. The produced OLED showed a red emission having a luminance of 1,000 cd/m², and a current efficiency of 10.2 cd/A at a driving voltage of 5.5 V.

The organic electroluminescent compounds of the present invention provide better luminous efficiency and longer lifespan than the conventional organic electroluminescent compounds. The device employing the organic electroluminescent compound of the present invention exhibits excellent luminous efficiency, in particular, excellent current/power efficiencies.

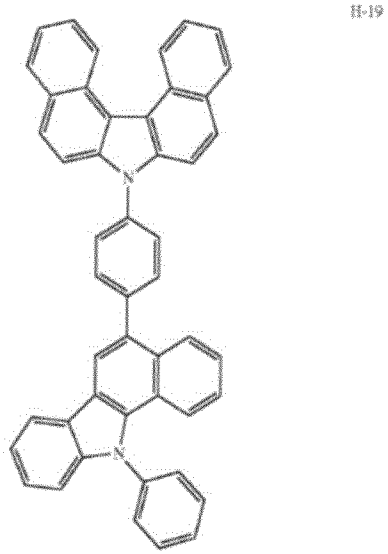

The invention claimed is:
1. An organic electroluminescent compound represented by the following formula 1:

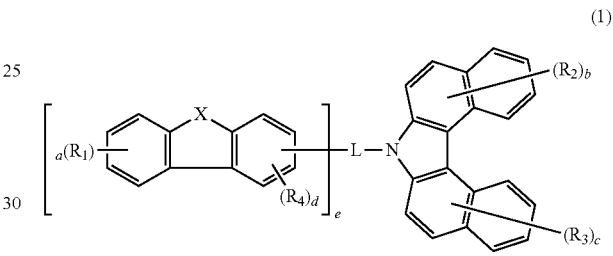

(1)

wherein
e represents 1;
X represents —NR$_{13}$—;
R$_{13}$ represents a substituted or unsubstituted phenyl, a substituted or unsubstituted naphthyl, a substituted or unsubstituted biphenyl, a substituted or unsubstituted phenyl-naphthyl, a substituted or unsubstituted naphthyl-phenyl, a substituted or unsubstituted anthracenyl, a substituted or unsubstituted phenanthrenyl, a substituted or unsubstituted terphenyl, a substituted or unsubstituted tetracenyl, a substituted or unsubstituted chrysenyl, a substituted or unsubstituted pyrenyl, a substituted or unsubstituted triphenylenyl, or a substituted or unsubstituted fluoranthenyl;
R$_1$ and R$_4$, each independently, represent hydrogen, a substituted or unsubstituted phenyl, a substituted or unsubstituted biphenyl, or a substituted or unsubstituted naphthyl, or may be linked to an adjacent substituent(s) to form a substituted or unsubstituted benzene or naphthalene ring;
L represents a single bond, or a substituted or unsubstituted (C6-C30)arylene;
R$_2$ and R$_3$, each independently, represent hydrogen, deuterium, a halogen, a cyano, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

a represents an integer of 0 to 4; where a is 2 or more, each of $R_1$ may be the same or different;

b and c, each independently, represent an integer of 0 to 6; where b or c is 2 or more, each of $R_2$ or $R_3$ may be the same or different;

d represents an integer of 0 to 3; where d is 2 or more, each of $R_4$ may be the same or different; and the heteroaryl contains at least one hetero atom selected from B, N, O, S, Si, and P.

2. The organic electroluminescent compound according to claim 1, wherein the compound represented by formula 1 is selected from the group consisting of:

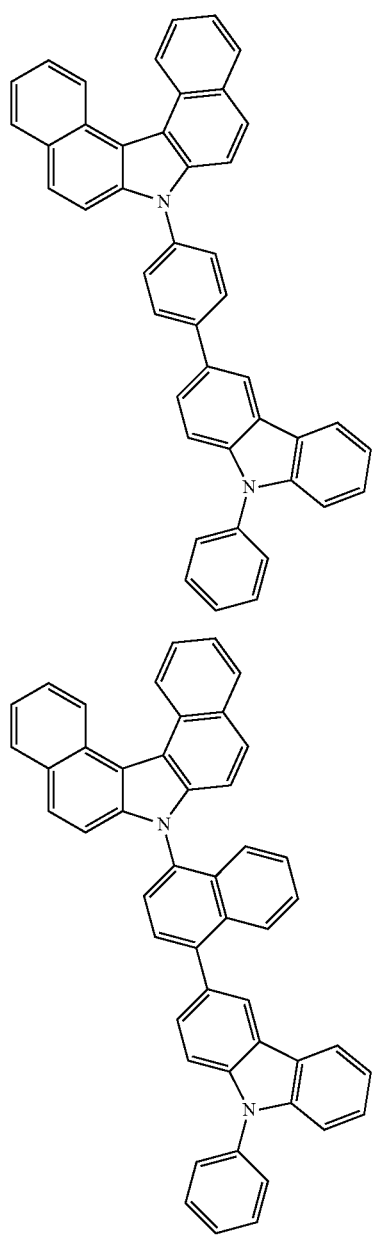

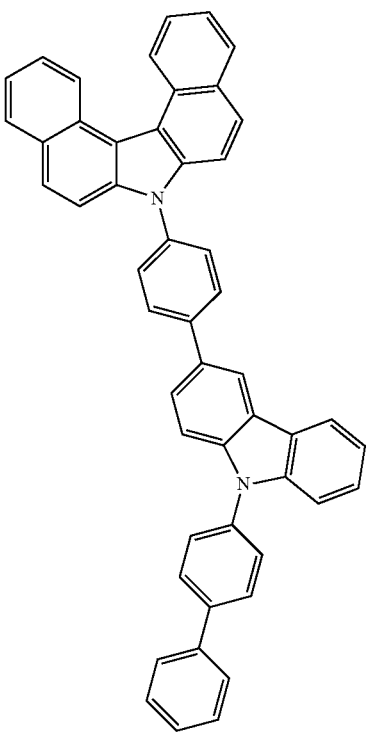

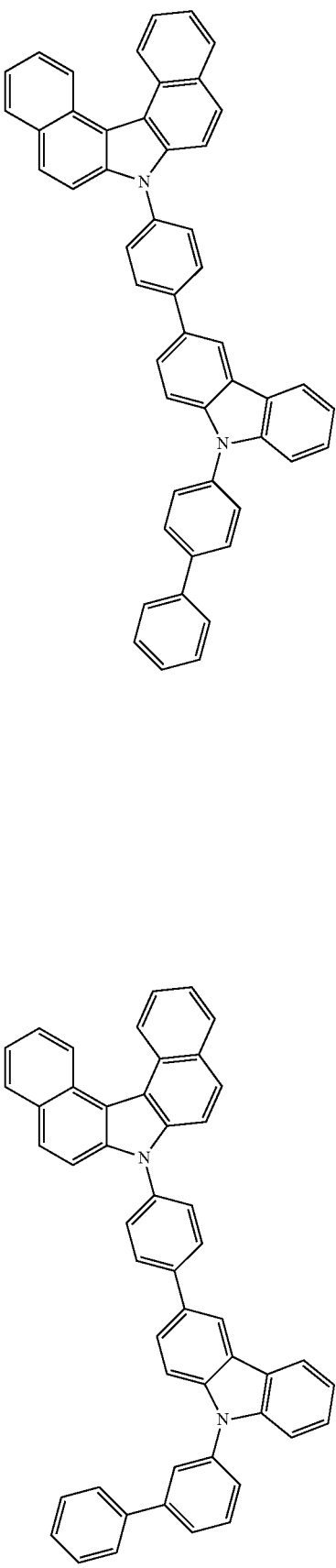

-continued
H-5
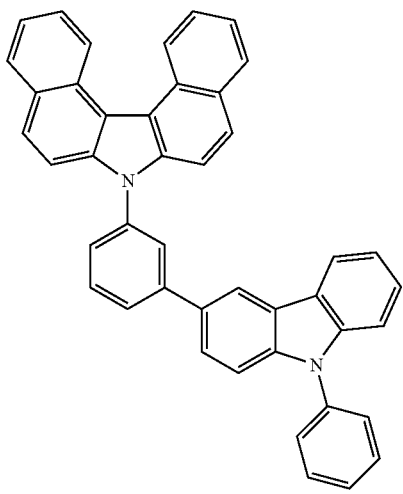
H-6
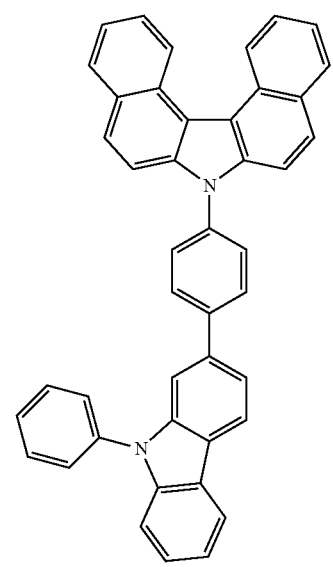
H-7
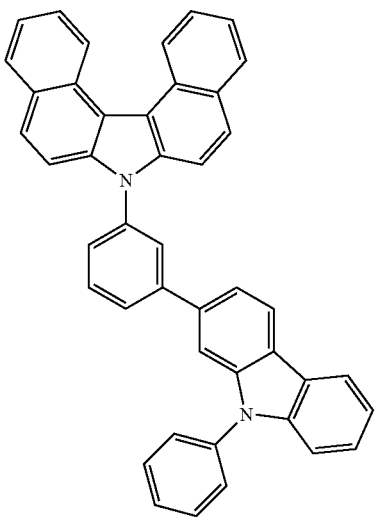
H-8
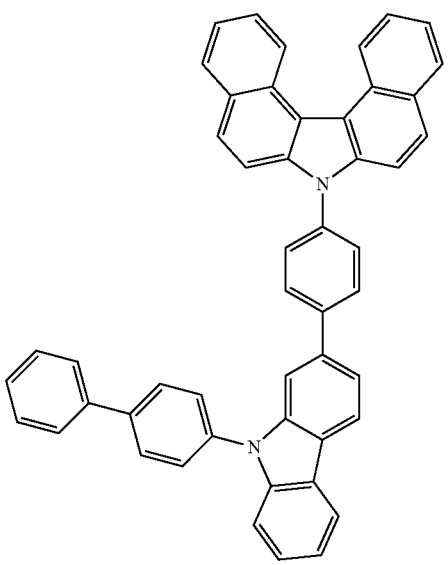
H-9
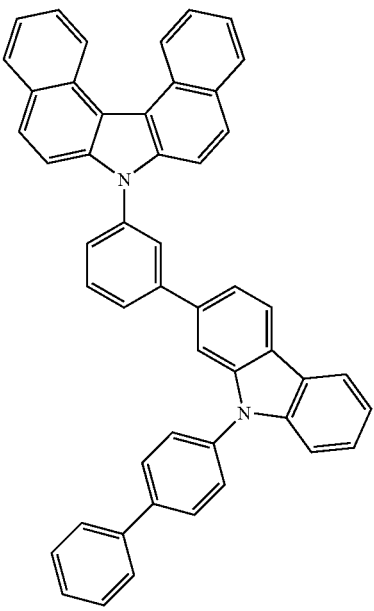

H-10
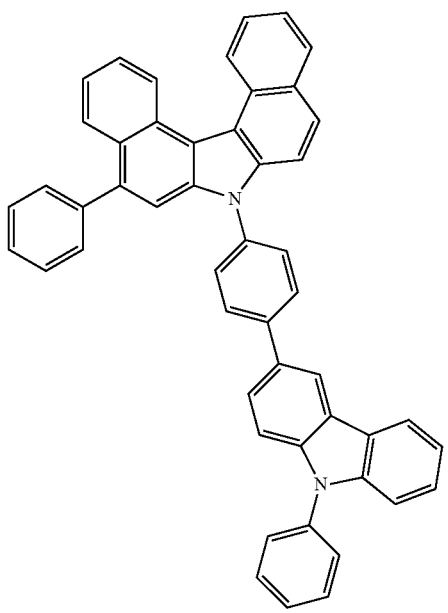
H-11
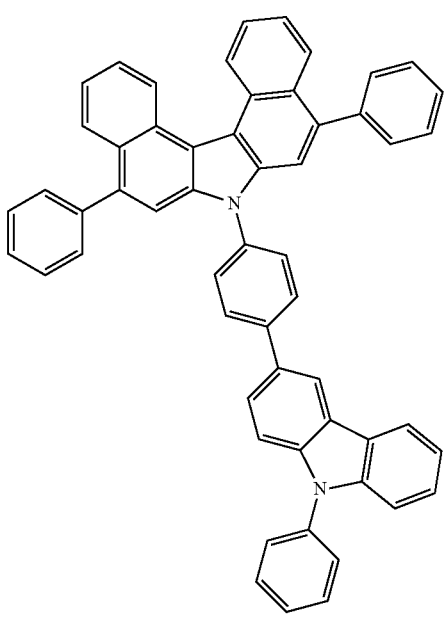
H-12
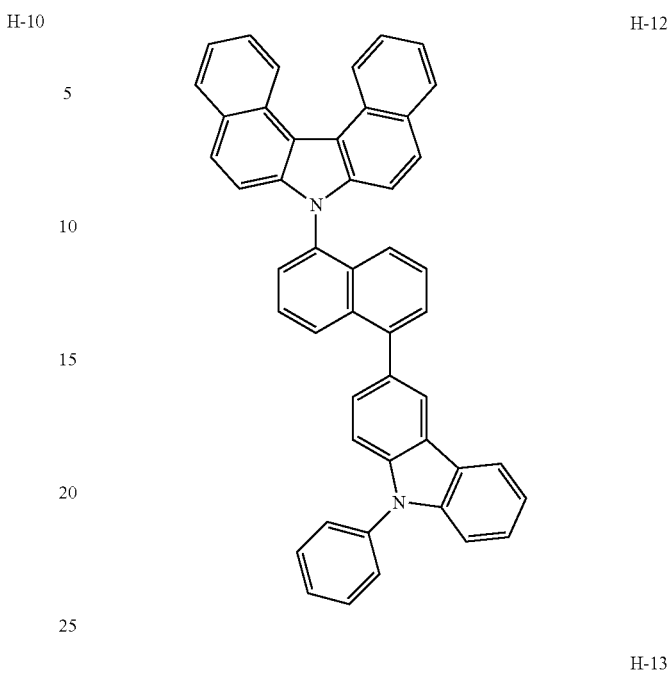
H-13
H-14
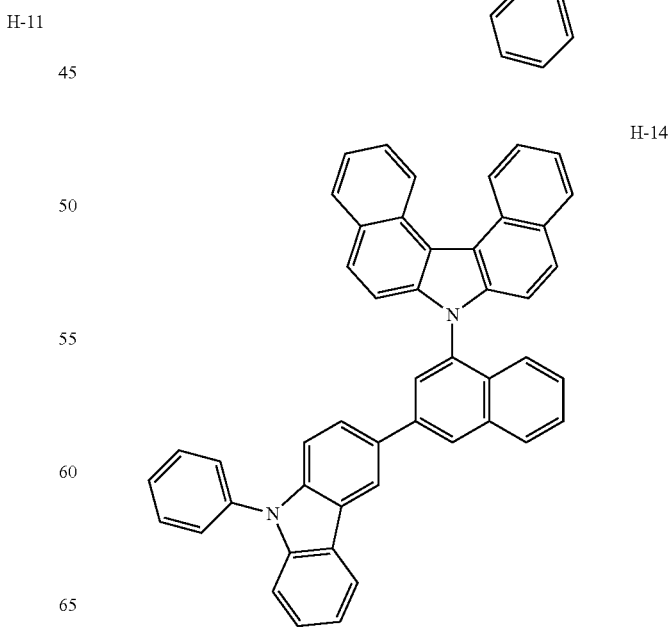

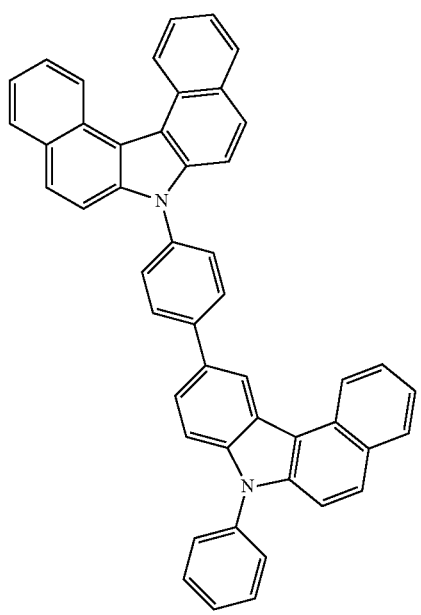
H-15
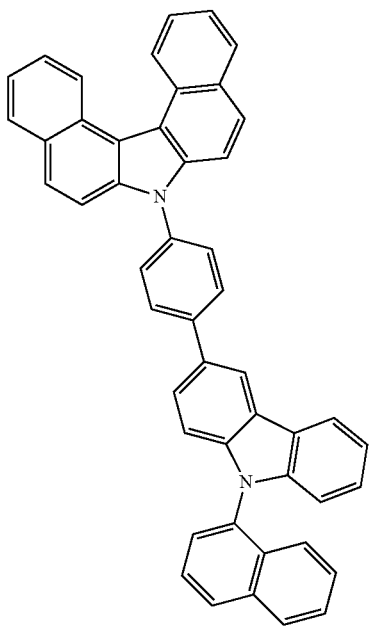
H-17
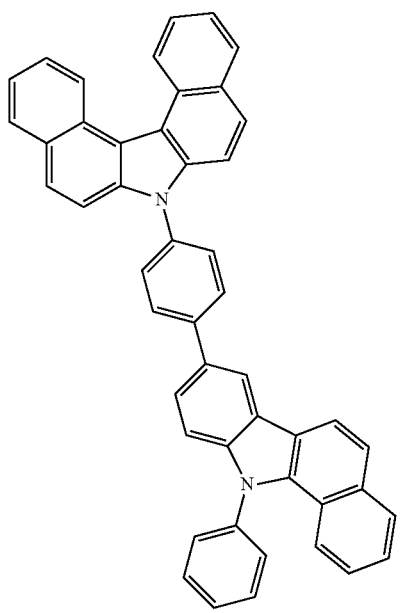
H-16
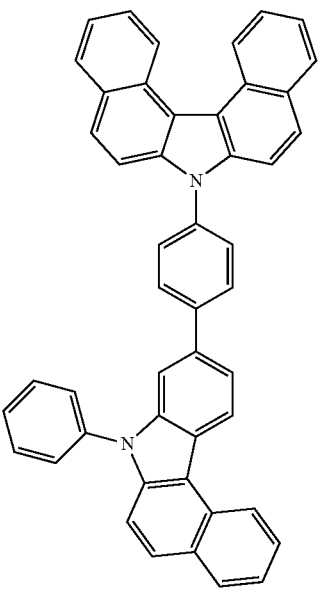
H-18

279
-continued
280
-continued
H-19
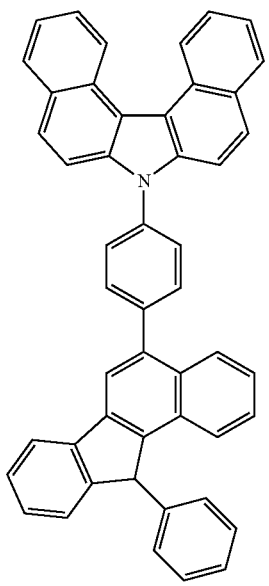
H-21
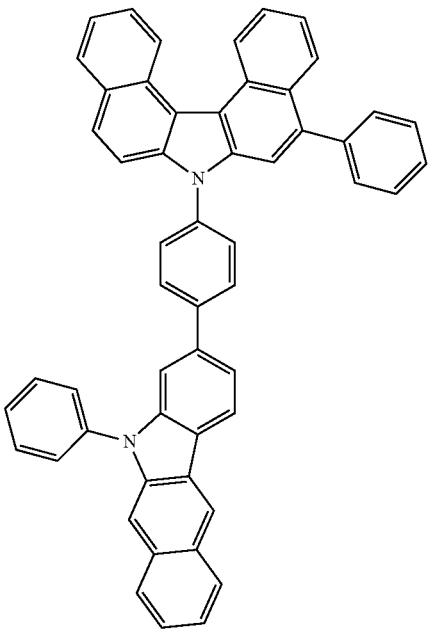
H-20
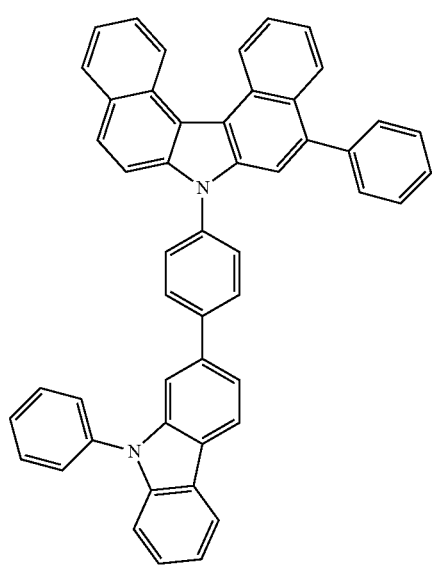
H-22
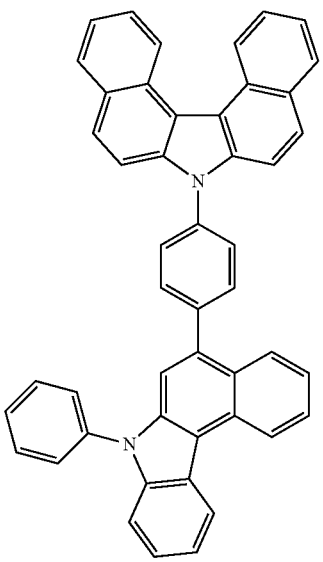

H-23
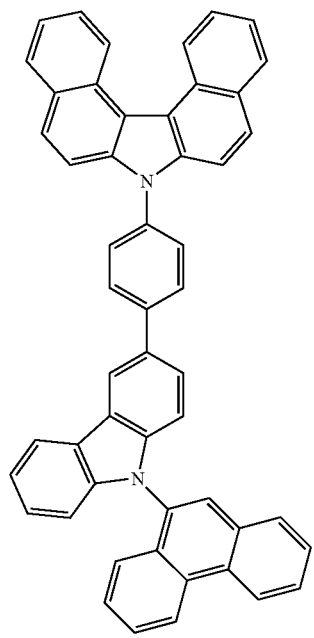
H-25
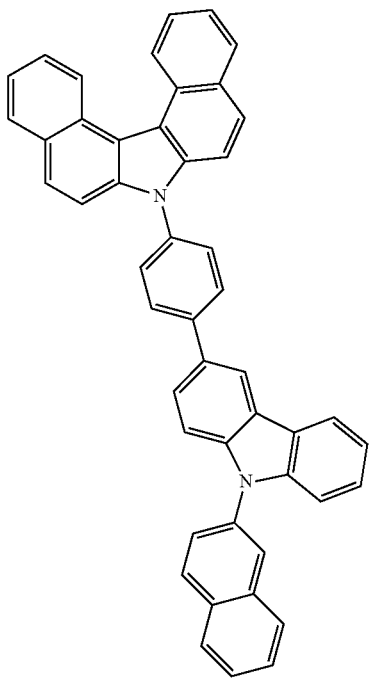
H-26
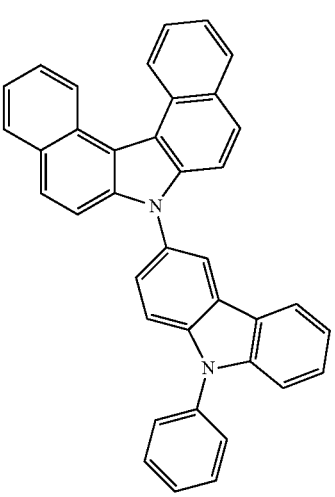
H-24
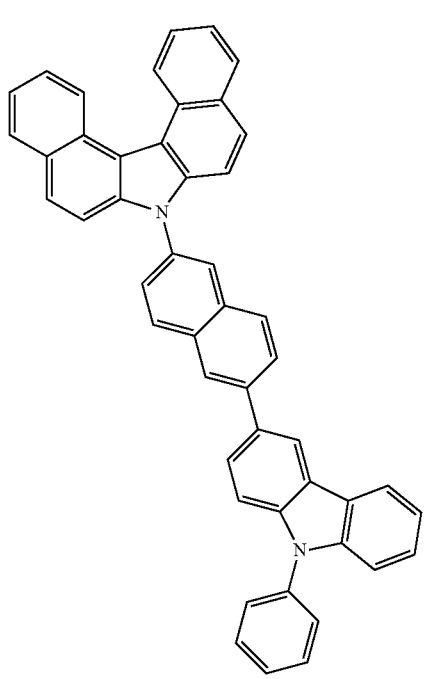
H-27
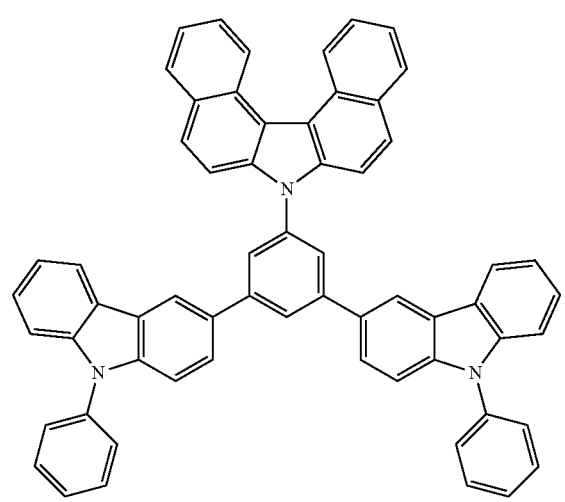

H-28
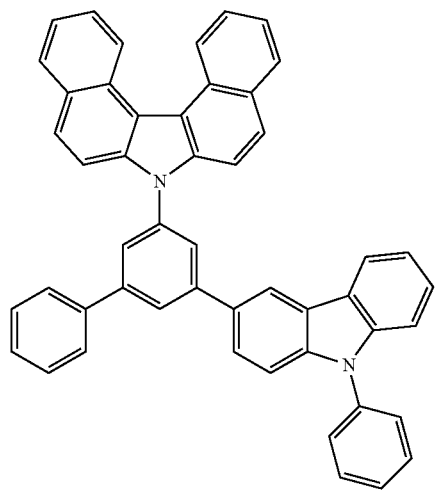
H-30
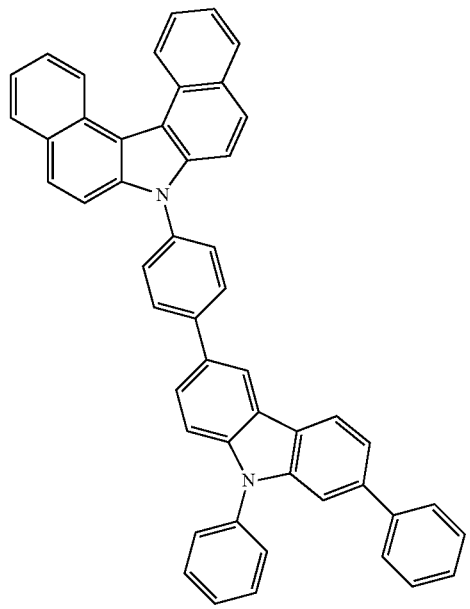
H-31
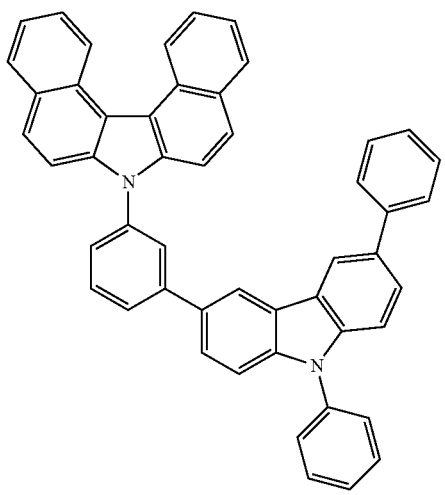
H-29
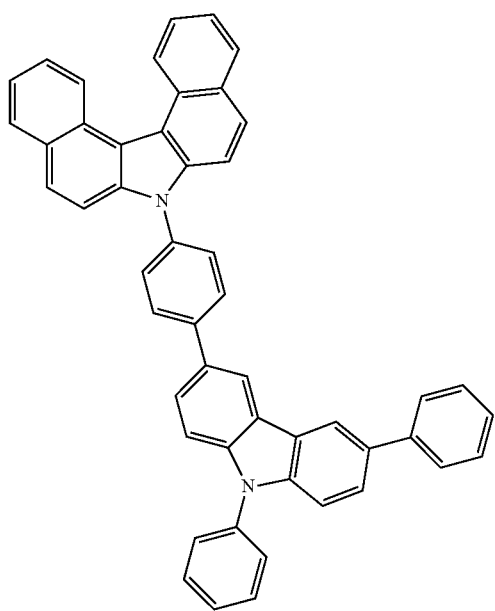
H-32
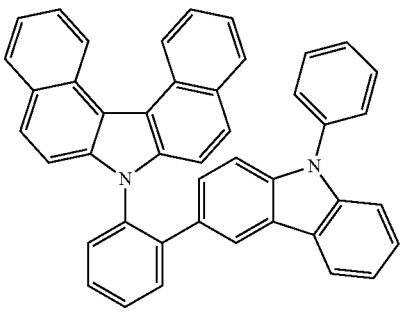

H-33
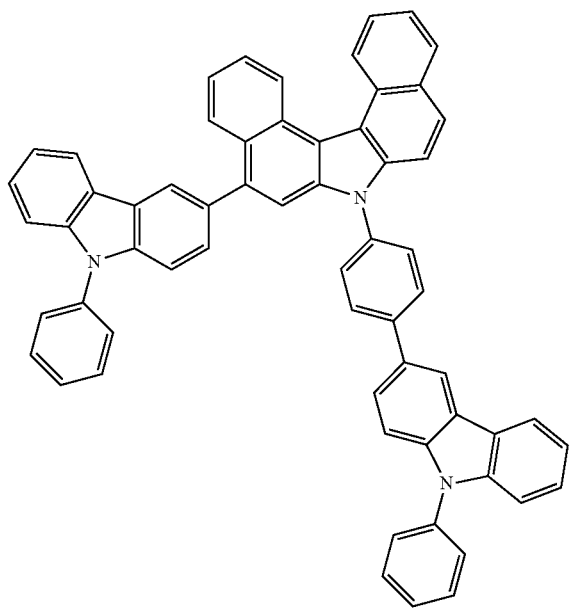
H-34
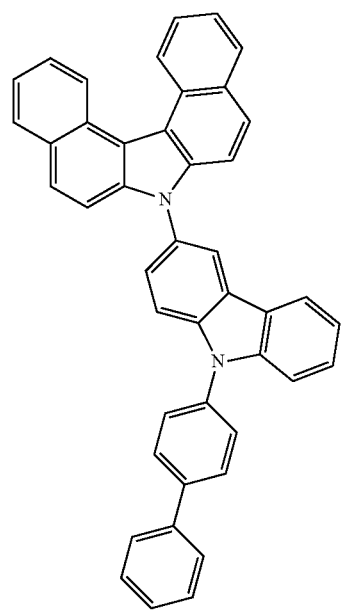
H-35
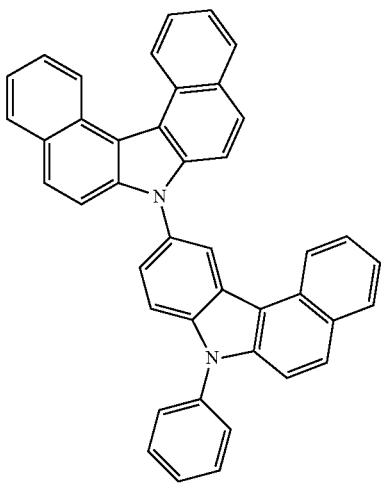
H-36
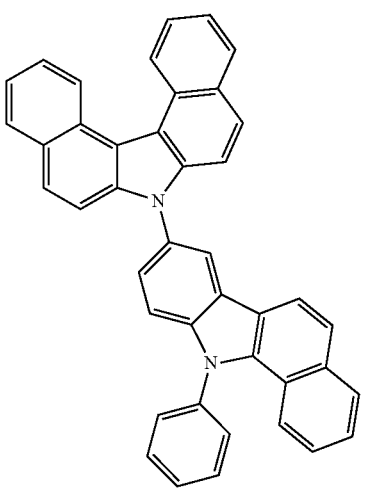
H-37
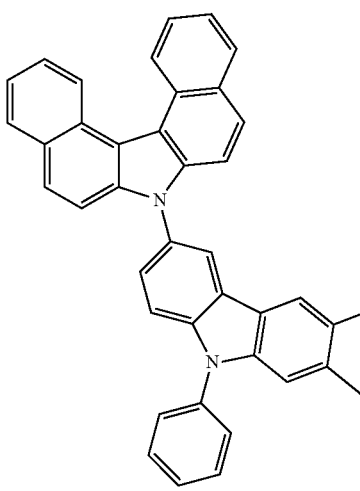
and H-65
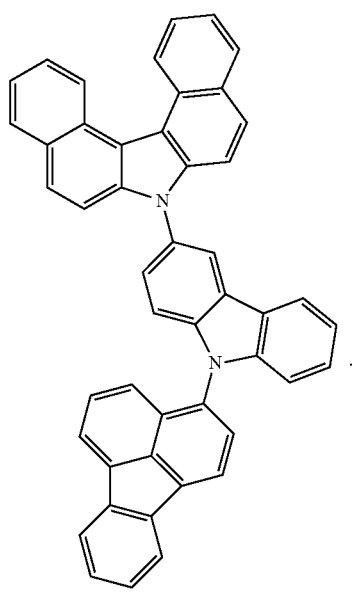
3. An organic electroluminescent material comprising the organic electroluminescent compound according to claim 1.
4. An organic electroluminescent device comprising the organic electroluminescent compound according to claim 1.
* * * * *

UNITED STATES PATENT AND TRADEMARK OFFICE
CERTIFICATE OF CORRECTION

| | |
|---|---|
| PATENT NO. | : 10,886,474 B2 |
| APPLICATION NO. | : 15/509590 |
| DATED | : January 5, 2021 |
| INVENTOR(S) | : Doo-Hyeon Moon et al. |

Page 1 of 2

It is certified that error appears in the above-identified patent and that said Letters Patent is hereby corrected as shown below:

In the Claims

Claim 2:
Compound H-13: Column 276, Lines 26-44. The omitted N should appear around Line 41, so that the correct structure for Compound H-13 is:

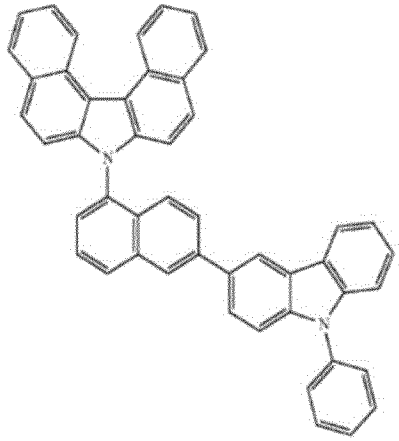

Signed and Sealed this
Twentieth Day of April, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)

Compound H-19: Column 279, Lines 1-24. The omitted N should appear around Line 21, so that the correct structure for Compound H-19 is: